(12) United States Patent
Tenniswood et al.

(10) Patent No.: US 11,661,633 B2
(45) Date of Patent: May 30, 2023

(54) METHODS FOR PREDICTING PROSTATE CANCER AND USES THEREOF

(71) Applicant: miR Scientific, LLC, Rensselaer, NY (US)

(72) Inventors: Martin Tenniswood, Rensselaer, NY (US); Albert Gregory DiRienzo, Rensselaer, NY (US); Wei-Lin Winnie Wang, Rensselaer, NY (US)

(73) Assignee: MIR SCIENTIFIC LLC, Rensselaer, NY (US)

( * ) Notice: Subject to any disclaimer, the term of this patent is extended or adjusted under 35 U.S.C. 154(b) by 0 days.

(21) Appl. No.: 16/819,070

(22) Filed: Mar. 14, 2020

(65) Prior Publication Data

US 2020/0291485 A1     Sep. 17, 2020

Related U.S. Application Data

(60) Provisional application No. 62/978,184, filed on Feb. 18, 2020, provisional application No. 62/819,325, filed on Mar. 15, 2019.

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 10,400,288 B2 | 9/2019 | Ronfeldt Thomsen et al. |
| 2014/0235469 A1 | 8/2014 | Shelton et al. |
| 2015/0337393 A1 | 11/2015 | Keller et al. |

FOREIGN PATENT DOCUMENTS

| | | |
|---|---|---|
| WO | WO 2014/085906 A1 | 6/2014 |
| WO | WO 2016/081941 A1 | 5/2016 |
| WO | WO 2017/214436 A1 | 12/2017 |

OTHER PUBLICATIONS

Baker. Journal of the National Cancer Institute, vol. 95, No. 7, Apr. 2, 2003 (Year: 2003).*
Slonin, Nature Genetics Supplement, vol. 32, Dec. 2002, pp. 502-508 (Year: 2002).*
Enard et al (Science. Apr. 12, 2002; 296(5566):340-43) (Year: 2002).*
Hoshikawa et al (Physiol Genomics vol. 12 2003) (Year: 2003).*
Cheung et al (Nature Genetics 2003 vol. 33 p. 422) (Year: 2003).*
Edgar et al., "Gene Expression Omnibus: NCBI gene expression and hybridization array data repository", *Nucleic Acid Res* (2002) 30:207.
Sapre et al., "Curated MicroRNAs in Urine and Blood Fail to Validate as Predictive Biomarkers for High-Risk Prostate Cancer", *PLoS ONE* (2014) 9(4): e91729. DOI:10.1371/journal.pone.0091729.
International Search Report for PCT Application No. PCT/US2020/022862 dated Aug. 4, 2020.
Martens-Uzunova et al., "Diagnostic and prognostic signatures from the small non-coding RNA transcriptome in prostate cancer", *Oncogene* (2012) 31: 978-991. DOI: 10.1038/onc.2011.304.
Endzeliņš et al., "Diagnostic, prognostic and predictive value of cell-free miRNAs in prostate cancer: a systematic review", *Molecular Cancer* (2016) 15:41. DOI 10.1186/s12943-016-0523-5.
Moustafa, et al., "Identification of microRNA signature and potential pathway targets in prostate cancer", *Experimental Biology and Medicine* (2017) 242:536-546. DOI: 10.1177/1535370216681554.
International Preliminary Report on Patentability dated Sep. 30, 2021 in respect of PCT Application No. PCT/US2020/022862.
Wang, W. L. W., Sorokin, I., Aleksic, I., Fisher, H., Kaufman Jr, R. P., Winer, A., . . . & Tenniswood, M. (2020). Expression of small noncoding RNAs in urinary exosomes classifies prostate cancer into indolent and aggressive disease. The Journal of Urology, 204(3), 466-475.
Mitchell, P. S., Parkin, R. K., Kroh, E. M., Fritz, B. R., Wyman, S. K., Pogosova-Agadjanyan, E. L., . . . & Tewari, M. (2008). Circulating microRNAs as stable blood-based markers for cancer detection. Proceedings of the National Academy of Sciences, 105(30), 10513-10518.

* cited by examiner

*Primary Examiner* — Katherine D Salmon
(74) *Attorney, Agent, or Firm* — Mark S. Cohen; Pearl Cohen Zedek Latzer Baratz LLP

(57) ABSTRACT

The present invention relates to compositions and methods for diagnosing, prognosing, monitoring, and treating a patient with prostate cancer. In particular, the invention relates to the use of miRNA and snoRNA as expression signatures for identifying a clinically significant prostate cancer.

8 Claims, 10 Drawing Sheets
(8 of 10 Drawing Sheet(s) Filed in Color)
Specification includes a Sequence Listing.

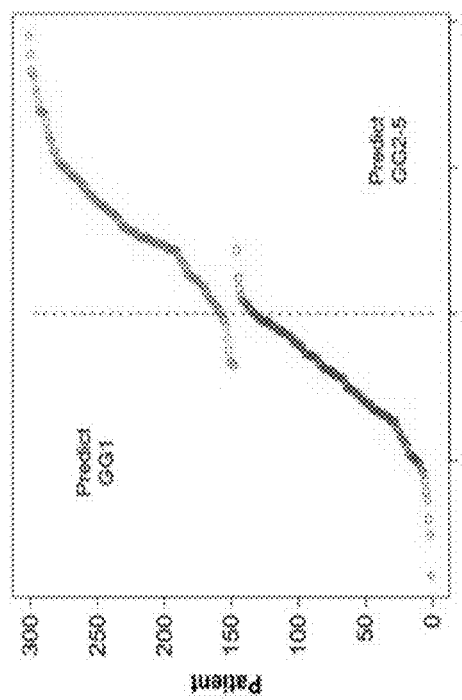
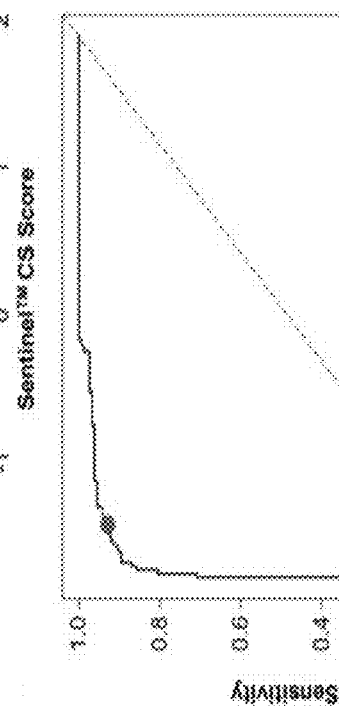
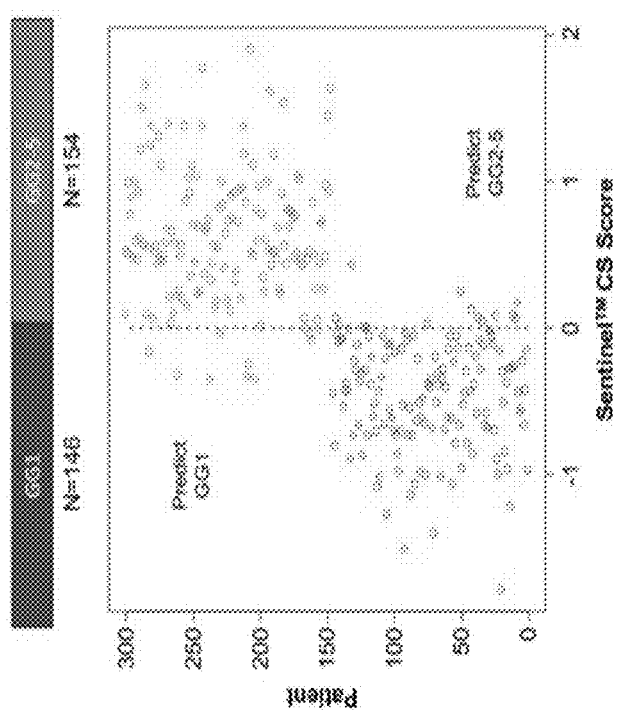
FIG. 9B
FIG. 9C
FIG. 9A

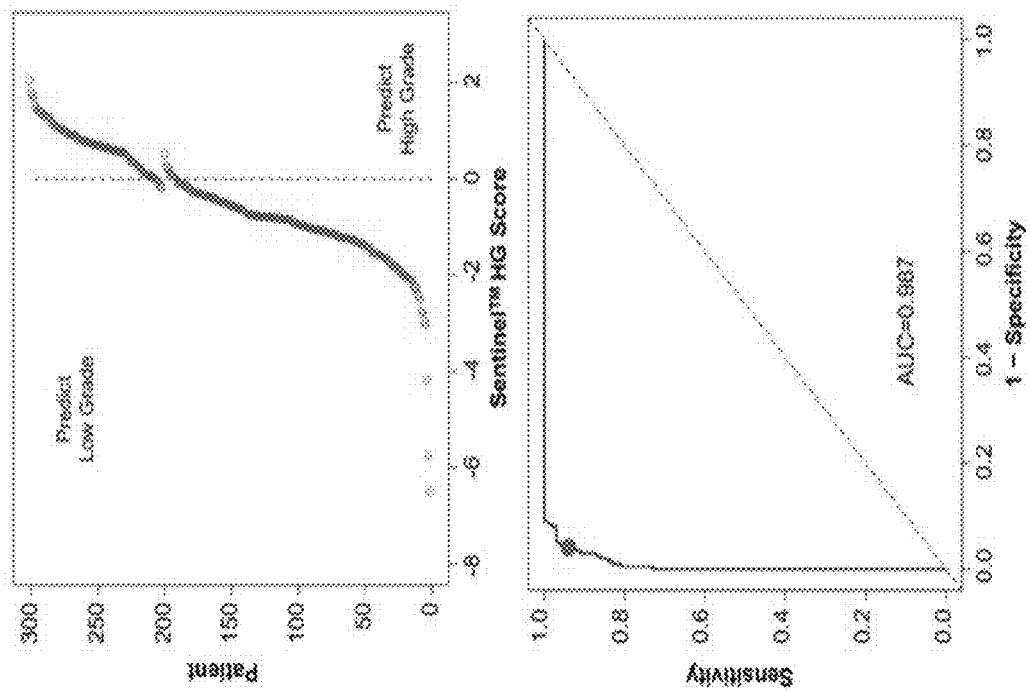
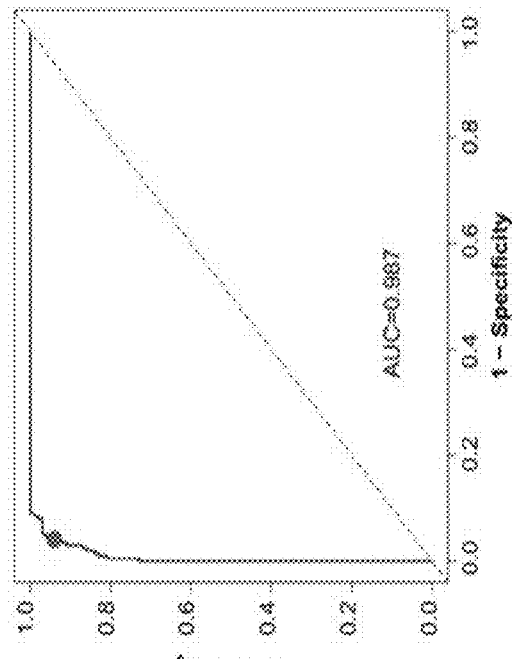
FIG. 10B
FIG. 10C
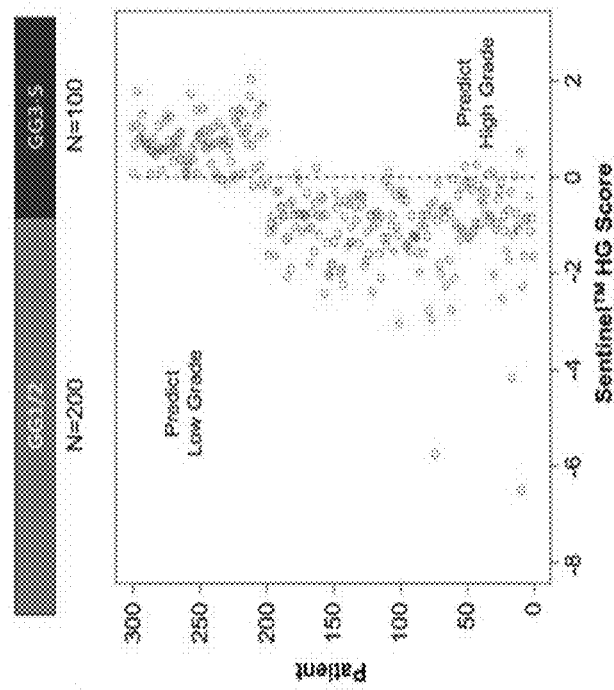
FIG. 10A

SEQUENCE LISTING

<160> NUMBER OF SEQ ID NOS: 840

<210> SEQ ID NO 1
<211> LENGTH: 22
<212> TYPE: RNA
<213> ORGANISM: Homo sapiens

<400> SEQUENCE: 1
caaaaaccgg caauuacuuu ug                                        22

<210> SEQ ID NO 2
<211> LENGTH: 65
<212> TYPE: RNA
<213> ORGANISM: Homo sapiens

<400> SEQUENCE: 2
gagaaugggg ggacagaugg agaggacaca ggcuggcacu gagguccccu ccacuuuccu    60
ccuag                                                            65

<210> SEQ ID NO 3
<211> LENGTH: 86

```
<212> TYPE: RNA
<213> ORGANISM: Homo sapiens

<400> SEQUENCE: 3
gagggaaagc aggccaaccu cgaggaucuc cccagccuug gcguucaggu gcugaggaga    60
ucgucgaggu uggccugcuu ccccuc                                         86

<210> SEQ ID NO 4
<211> LENGTH: 82
<212> TYPE: RNA
<213> ORGANISM: Homo sapiens

<400> SEQUENCE: 4
ggauugtggg gggucgcucu aggcaccgca gcacugugcu ggggauguug cagcugccug    60
ggagugacuu cacacagucc uc                                             82

<210> SEQ ID NO 5
<211> LENGTH: 84
<212> TYPE: RNA
<213> ORGANISM: Homo sapiens

<400> SEQUENCE: 5
auuagguugg uauaaaauua auugcaguuu uugucauuac uuucaauagc aaaaacugca    60
guuacuuuug caccaaugua auac                                           84

<210> SEQ ID NO 6
<211> LENGTH: 22
<212> TYPE: RNA
<213> ORGANISM: Homo sapiens

<400> SEQUENCE: 6
ugagguagua gguugugugg uu                                             22

<210> SEQ ID NO 7
<211> LENGTH: 75
<212> TYPE: RNA
<213> ORGANISM: Homo sapiens

<400> SEQUENCE: 7
uggaccaaug augugaaugg aaugcaucug aauaaaaauu augaucaauc aguuuuugga    60
acaacugagg uccac                                                     75

<210> SEQ ID NO 8
<211> LENGTH: 96
<212> TYPE: RNA
<213> ORGANISM: Homo sapiens

<400> SEQUENCE: 8
agauaaaucu auagacaaaa uacaaucccg gacaacaaga agcuccuaua gcuccuguag    60
cuucuugugc ucuaggauug uauuuuguuu auauau                              96

<210> SEQ ID NO 9
<211> LENGTH: 21
<212> TYPE: RNA
<213> ORGANISM: Homo sapiens

<400> SEQUENCE: 9
cacauuacac ggucgaccuc u                                              21

<210> SEQ ID NO 10
```

```
<211> LENGTH: 17
<212> TYPE: RNA
<213> ORGANISM: Homo sapiens

<400> SEQUENCE: 10 ugggggcucag cgaguuu                                                        17

<210> SEQ ID NO 11
<211> LENGTH: 93
<212> TYPE: RNA
<213> ORGANISM: Homo sapiens

<400> SEQUENCE: 11
uaaguguaaa cuuaaggacu gucuuuucua agccugugcc uugccuuucc uuuggcacag          60
gcuuagaaaa gacagucuuu aaguuuacac uuc                                      93

<210> SEQ ID NO 12
<211> LENGTH: 63
<212> TYPE: RNA
<213> ORGANISM: Homo sapiens

<400> SEQUENCE: 12
gaaggccucu gcaggguuug cuugagguua cuccuuccu gucaacccug uucuggaguc          60
ugu                                                                       63

<210> SEQ ID NO 13
<211> LENGTH: 22
<212> TYPE: RNA
<213> ORGANISM: Homo sapiens

<400> SEQUENCE: 13
gaucccuuua ucuguccucu ag                                                  22

<210> SEQ ID NO 14
<211> LENGTH: 22
<212> TYPE: RNA
<213> ORGANISM: Homo sapiens

<400> SEQUENCE: 14
uuggguuuuc ucuucaaucc ag                                                  22

<210> SEQ ID NO 15
<211> LENGTH: 21
<212> TYPE: RNA
<213> ORGANISM: Homo sapiens

<400> SEQUENCE: 15
cuuagauuag aggauauugu u                                                   21

<210> SEQ ID NO 16
<211> LENGTH: 18
<212> TYPE: RNA
<213> ORGANISM: Homo sapiens

<400> SEQUENCE: 16 cagcccccaca gccucaga                                                      18

<210> SEQ ID NO 17
<211> LENGTH: 67
<212> TYPE: RNA
<213> ORGANISM: Homo sapiens
```

```
<400> SEQUENCE: 17
uacaggccgg ggcuuugggu gagggacccc cggagucugu cacggcucua ccccaacucu    60
gccccag                                                              67

<210> SEQ ID NO 18
<211> LENGTH: 134
<212> TYPE: RNA
<213> ORGANISM: Homo sapiens

<400> SEQUENCE: 18
uugcacagug aacacccaag ugugcuuuau aguucccuug gcuuugaccc ugugcuagag    60
cauugccugc ucuucccuc ugcauuaaaa ggaauauuua uccuuuuaaa uguauucaga   120
aagccagcac auua                                                    134

<210> SEQ ID NO 19
<211> LENGTH: 65
<212> TYPE: RNA
<213> ORGANISM: Homo sapiens

<400> SEQUENCE: 19
cuccucuggg ggugggggc ugggcguggu ggacagcgau gcaucccucg ccuucucacc    60
cucag                                                                65

<210> SEQ ID NO 20
<211> LENGTH: 67
<212> TYPE: RNA
<213> ORGANISM: Homo sapiens

<400> SEQUENCE: 20
guggcacuca aacugugggg gcacuuucug cucucuggug aaagugccgc caucuuuuga    60
guguuac                                                              67

<210> SEQ ID NO 21
<211> LENGTH: 79
<212> TYPE: RNA
<213> ORGANISM: Homo sapiens

<400> SEQUENCE: 21
cugacuccag ugccaggcc aggggcagac aguggacaga gaacagugcc caagaccacu    60
ggacuuggag ucaggacau                                                 79

<210> SEQ ID NO 22
<211> LENGTH: 22
<212> TYPE: RNA
<213> ORGANISM: Homo sapiens

<400> SEQUENCE: 22
uggggaggug uggagucagc au                                             22

<210> SEQ ID NO 23
<211> LENGTH: 103
<212> TYPE: RNA
<213> ORGANISM: Homo sapiens

<400> SEQUENCE: 23
augaccugug aaaccaaggg cuccuaaugc uaugaccaaa gacugaagcu cucuaugaga    60
ugccagccac ucaauagugc acuuuuucug agaagauaua aga                    103
```

```
<210> SEQ ID NO 24
<211> LENGTH: 103
<212> TYPE: RNA
<213> ORGANISM: Homo sapiens

<400> SEQUENCE: 24
gugucggcug uggcgugacu gucccucugu gucccccacu aggcccacug cucaguggag      60
cguggaggac gaggaggagg ccguccacga gcaaugccag cau                       103

<210> SEQ ID NO 25
<211> LENGTH: 22
<212> TYPE: RNA
<213> ORGANISM: Homo sapiens

<400> SEQUENCE: 25
gugugcggaa augcuucugc ua                                              22

<210> SEQ ID NO 26
<211> LENGTH: 110
<212> TYPE: RNA
<213> ORGANISM: Homo sapiens

<400> SEQUENCE: 26
ugaguuuuga gguugcuuca gugaacauuc aacgcugucg gugaguuugg aauuaaaauc      60
aaaaccaucg accguugauu guacccuaug gcuaaccauc aucuacucca                110

<210> SEQ ID NO 27
<211> LENGTH: 22
<212> TYPE: RNA
<213> ORGANISM: Homo sapiens

<400> SEQUENCE: 27
cagcagcaau ucauguuuug aa                                              22

<210> SEQ ID NO 28
<211> LENGTH: 82
<212> TYPE: RNA
<213> ORGANISM: Homo sapiens

<400> SEQUENCE: 28
gacaggauuc caguacaggu cucucauuuc cuucaugauu aggaauacua cuuugaaaug      60
agagaccugu acuguaucug uu                                              82

<210> SEQ ID NO 29
<211> LENGTH: 19
<212> TYPE: RNA
<213> ORGANISM: Homo sapiens

<400> SEQUENCE: 29
agagcuggcu gaagggcag                                                  19

<210> SEQ ID NO 30
<211> LENGTH: 22
<212> TYPE: RNA
<213> ORGANISM: Homo sapiens

<400> SEQUENCE: 30
ugcccuaaau gccccuucug gc                                              22

<210> SEQ ID NO 31
<211> LENGTH: 102
```

```
<212> TYPE: RNA
<213> ORGANISM: Homo sapiens

<400> SEQUENCE: 31
uuauuuuugu aguugaugaa ugugcugauu ggguauucuc gugugugugu gaggugccac      60
ccucaaacuu uguuaugaug uuggcacauu acccaucuga ua                       102

<210> SEQ ID NO 32
<211> LENGTH: 22
<212> TYPE: RNA
<213> ORGANISM: Homo sapiens

<400> SEQUENCE: 32
auggccagag cucacacaga gg                                              22

<210> SEQ ID NO 33
<211> LENGTH: 21
<212> TYPE: RNA
<213> ORGANISM: Homo sapiens

<400> SEQUENCE: 33
cgagccucaa gcaagggacu u                                               21

<210> SEQ ID NO 34
<211> LENGTH: 23
<212> TYPE: RNA
<213> ORGANISM: Homo sapiens

<400> SEQUENCE: 34
ugccccaccu gcugaccacc cuc                                             23

<210> SEQ ID NO 35
<211> LENGTH: 70
<212> TYPE: RNA
<213> ORGANISM: Homo sapiens

<400> SEQUENCE: 35
aaagugagug augaauaguu cuguggcaua ugaaucauua auuugauua aacccuaaac      60 ucugaagucc                                                            70

<210> SEQ ID NO 36
<211> LENGTH: 21
<212> TYPE: RNA
<213> ORGANISM: Homo sapiens

<400> SEQUENCE: 36
caacaccagu cgaugggcug u                                               21

<210> SEQ ID NO 37
<211> LENGTH: 104
<212> TYPE: RNA
<213> ORGANISM: Homo sapiens

<400> SEQUENCE: 37
auccuuuugu gguucauaag caugaugauc agguuuucag gcauaugugu acgaugugcc      60
uccuucaaac uuuguuagga ugcuaccacg cuacccaucu gacu                     104

<210> SEQ ID NO 38
<211> LENGTH: 23
<212> TYPE: RNA
<213> ORGANISM: Homo sapiens
```

```
<400> SEQUENCE: 38
agaacucuug cagucuuaga ugu                                   23

<210> SEQ ID NO 39
<211> LENGTH: 58
<212> TYPE: RNA
<213> ORGANISM: Homo sapiens

<400> SEQUENCE: 39
ugcuggcuca uuucauaugu gugcugagaa aauucacaca uaugaaguga gccagcac    58

<210> SEQ ID NO 40
<211> LENGTH: 67
<212> TYPE: RNA
<213> ORGANISM: Homo sapiens

<400> SEQUENCE: 40
gugcauauga uggaaaaguu uuaaucuccu gacacuugug augucuucaa aggaaccacu  60
gaugcac                                                     67

<210> SEQ ID NO 41
<211> LENGTH: 87
<212> TYPE: RNA
<213> ORGANISM: Homo sapiens

<400> SEQUENCE: 41
accgcaggga aaugaggga cuuuuggggg cagauguguu uccauccac uaucauaaug    60 ccccuaaaaa uccuuauugc ucuugca                               87

<210> SEQ ID NO 42
<211> LENGTH: 71
<212> TYPE: RNA
<213> ORGANISM: Homo sapiens

<400> SEQUENCE: 42
uggaucaaug augaccacug guggcguaug agucauaugu gaugaauacg ugucuggaac  60
ucugaggucc a                                                71

<210> SEQ ID NO 43
<211> LENGTH: 88
<212> TYPE: RNA
<213> ORGANISM: Homo sapiens

<400> SEQUENCE: 43
ugaguuuugg gaugagaccc uggaauaagu gcuggacaca gugccugaau cagacugugg  60
aaauauuaau guauuuuauu uuuacuua                              88

<210> SEQ ID NO 44
<211> LENGTH: 77
<212> TYPE: RNA
<213> ORGANISM: Homo sapiens

<400> SEQUENCE: 44
uuccagcccg aggccucugu gacgucacgg ugucugcggg aggagaccau gacgucacag  60
aggcuucgcg cucugag                                          77

<210> SEQ ID NO 45
<211> LENGTH: 21
<212> TYPE: RNA
<213> ORGANISM: Homo sapiens
```

```
-continued

<400> SEQUENCE: 45
ccuguugaag uguaaucccc a                                             21

<210> SEQ ID NO 46
<211> LENGTH: 71
<212> TYPE: RNA
<213> ORGANISM: Homo sapiens

<400> SEQUENCE: 46
uggaucgaug gugacuguug auggcauaug acucacauau gaugaguacg uaucuggaac   60
ucugaggucu g                                                        71

<210> SEQ ID NO 47
<211> LENGTH: 98
<212> TYPE: RNA
<213> ORGANISM: Homo sapiens

<400> SEQUENCE: 47
auccuuuugu acuugguaag caugaugauu ggguuuuuau gcuuauauau gagacaugcu   60
ugucucaaau cuuguuacag cacauuaccc uuccuacu                           98

<210> SEQ ID NO 48
<211> LENGTH: 21
<212> TYPE: RNA
<213> ORGANISM: Homo sapiens

<400> SEQUENCE: 48
ucuaguaaga guggcagucg a                                             21

<210> SEQ ID NO 49
<211> LENGTH: 71
<212> TYPE: RNA
<213> ORGANISM: Homo sapiens

<400> SEQUENCE: 49
ggcucaaucu cugguccugc agccuucugc cuuuggcuuu cugaagcgag cugaacuaga   60
gauugggccc a                                                        71

<210> SEQ ID NO 50
<211> LENGTH: 103
<212> TYPE: RNA
<213> ORGANISM: Homo sapiens

<400> SEQUENCE: 50
guccuuuugu aguccauaag cauggugauu ugguuucaug cucauguguc agauaugcuu   60
cccucaaacc uuguuacagc aucaucacau uaccuguuug aug                    103

<210> SEQ ID NO 51
<211> LENGTH: 75
<212> TYPE: RNA
<213> ORGANISM: Homo sapiens

<400> SEQUENCE: 51
uucuuacaaa ucuaaaugug cuuugaugca aguauauuug aaucccuuuc caucugauaa   60
cugagcaaaa uaaua                                                    75

<210> SEQ ID NO 52
<211> LENGTH: 22
<212> TYPE: RNA
```

```
<213> ORGANISM: Homo sapiens

<400> SEQUENCE: 52
uaauacuguc ugguaaaacc gu                                              22

<210> SEQ ID NO 53
<211> LENGTH: 22
<212> TYPE: RNA
<213> ORGANISM: Homo sapiens

<400> SEQUENCE: 53
aacaauaucc uggugcugag ug                                              22

<210> SEQ ID NO 54
<211> LENGTH: 19
<212> TYPE: RNA
<213> ORGANISM: Homo sapiens

<400> SEQUENCE: 54
aggugugucu guagagucc                                                  19

<210> SEQ ID NO 55
<211> LENGTH: 20
<212> TYPE: RNA
<213> ORGANISM: Homo sapiens

<400> SEQUENCE: 55
cuacaaaggg aagcccuuuc                                                 20

<210> SEQ ID NO 56
<211> LENGTH: 75
<212> TYPE: RNA
<213> ORGANISM: Homo sapiens

<400> SEQUENCE: 56
gucagaugau uugaauugau aagcugaugu ucugugaggu acaaaaguua auagcauguu     60
agaguucuga uggca                                                      75

<210> SEQ ID NO 57
<211> LENGTH: 22
<212> TYPE: RNA
<213> ORGANISM: Homo sapiens

<400> SEQUENCE: 57
caaucacuaa cuccacugcc au                                              22

<210> SEQ ID NO 58
<211> LENGTH: 20
<212> TYPE: RNA
<213> ORGANISM: Homo sapiens

<400> SEQUENCE: 58
aaaacugcag uuacuuuugc                                                 20

<210> SEQ ID NO 59
<211> LENGTH: 215
<212> TYPE: RNA
<213> ORGANISM: Homo sapiens

<400> SEQUENCE: 59
aaaauuauac uuucagcaau caucucuaua guuguuacu agagaagcuu cugugaaugu      60
guagagcacc ggaaaccaca aggcaaaggc ucagcauucu cuccuaagcg cgaagcuggc    120
```

```
uccuggucuu gguuggccgc aacugccauu ugccauugau gaucauucuu cucuuccugu    180
gguagaggaa gagggagaga augcaguuug agugg                              215

<210> SEQ ID NO 60
<211> LENGTH: 104
<212> TYPE: RNA
<213> ORGANISM: Homo sapiens

<400> SEQUENCE: 60
auccuucugu aguucgugag caugaugauu gggugcucac acacauaugu gagauguacc    60
acccucaaac cuuguuacaa ugucagcaca uuacccaucu gacc                    104

<210> SEQ ID NO 61
<211> LENGTH: 21
<212> TYPE: RNA
<213> ORGANISM: Homo sapiens

<400> SEQUENCE: 61
agagaagaag aucagccugc a                                             21

<210> SEQ ID NO 62
<211> LENGTH: 82
<212> TYPE: RNA
<213> ORGANISM: Homo sapiens

<400> SEQUENCE: 62
uuuuuuuguu gcuugucuug guuuuaugcc uuuuaugugc cuugauauaa aaggcauaaa    60
accaagacaa gcaacagaaa aa                                            82

<210> SEQ ID NO 63
<211> LENGTH: 60
<212> TYPE: RNA
<213> ORGANISM: Homo sapiens

<400> SEQUENCE: 63
gagcaggcga ggcugggcug aacccgugggg ugaggagugc agcccagcug aggccucugc    60

<210> SEQ ID NO 64
<211> LENGTH: 21
<212> TYPE: RNA
<213> ORGANISM: Homo sapiens

<400> SEQUENCE: 64
cugaccuaug aauugacagc c                                             21

<210> SEQ ID NO 65
<211> LENGTH: 22
<212> TYPE: RNA
<213> ORGANISM: Homo sapiens

<400> SEQUENCE: 65
acuuuaacau ggaagugcuu uc                                            22

<210> SEQ ID NO 66
<211> LENGTH: 23
<212> TYPE: RNA
<213> ORGANISM: Homo sapiens

<400> SEQUENCE: 66
ugucacucgg cucggcccac uac                                           23
```

-continued

```
<210> SEQ ID NO 67
<211> LENGTH: 22
<212> TYPE: RNA
<213> ORGANISM: Homo sapiens

<400> SEQUENCE: 67
ccuggcauau uugguauaac uu                                                  22

<210> SEQ ID NO 68
<211> LENGTH: 22
<212> TYPE: RNA
<213> ORGANISM: Homo sapiens

<400> SEQUENCE: 68
ugucaguuug ucaaauaccc ca                                                  22

<210> SEQ ID NO 69
<211> LENGTH: 104
<212> TYPE: RNA
<213> ORGANISM: Homo sapiens

<400> SEQUENCE: 69
auccuguuau gauucauaag caugaugacu gaguuucac acuccugugu gagaugugcc          60
ucccucuaac cuuauuacaa cauugacauc uuacucauuu gaca                         104

<210> SEQ ID NO 70
<211> LENGTH: 22
<212> TYPE: RNA
<213> ORGANISM: Homo sapiens

<400> SEQUENCE: 70
aacccguaga uccgaacuug ug                                                  22

<210> SEQ ID NO 71
<211> LENGTH: 22
<212> TYPE: RNA
<213> ORGANISM: Homo sapiens

<400> SEQUENCE: 71
cguguucaca gcggaccuug au                                                  22

<210> SEQ ID NO 72
<211> LENGTH: 72
<212> TYPE: RNA
<213> ORGANISM: Homo sapiens

<400> SEQUENCE: 72
cuaaaacaau gucaauaguu uucaucaaca gcaguugaac cuaguaagug ucgauacuuu         60
gggucugagu gg                                                             72

<210> SEQ ID NO 73
<211> LENGTH: 23
<212> TYPE: RNA
<213> ORGANISM: Homo sapiens

<400> SEQUENCE: 73
agugccugag ggaguaagag ccc                                                 23

<210> SEQ ID NO 74
<211> LENGTH: 131
<212> TYPE: RNA
<213> ORGANISM: Homo sapiens
```

```
<400> SEQUENCE: 74
cccuccuaca aaggcauguc uauaguuccu ugucuuugga cauguaagaa uuggaggcaa      60
agaaaugugg acuuggagaa aucuggggcc agcuugcucu ccgcaggcuc aagaucaacc     120
aucccacaua g                                                          131

<210> SEQ ID NO 75
<211> LENGTH: 23
<212> TYPE: RNA
<213> ORGANISM: Homo sapiens

<400> SEQUENCE: 75
ugugcuugcu cgucccgccc gca                                              23

<210> SEQ ID NO 76
<211> LENGTH: 22
<212> TYPE: RNA
<213> ORGANISM: Homo sapiens

<400> SEQUENCE: 76
ugggaaagag aaagaacaag ua                                               22

<210> SEQ ID NO 77
<211> LENGTH: 22
<212> TYPE: RNA
<213> ORGANISM: Homo sapiens

<400> SEQUENCE: 77
uuaacuccuu ucacacccau gg                                               22

<210> SEQ ID NO 78
<211> LENGTH: 22
<212> TYPE: RNA
<213> ORGANISM: Homo sapiens

<400> SEQUENCE: 78
uaccugggag acugagguug ga                                               22

<210> SEQ ID NO 79
<211> LENGTH: 65
<212> TYPE: RNA
<213> ORGANISM: Homo sapiens

<400> SEQUENCE: 79 cguaaugau guugcucaaa uaucugaccu gaaaugauua uauagaccaa uuuaauacug       60
aagaa                                                                  65

<210> SEQ ID NO 80
<211> LENGTH: 133
<212> TYPE: RNA
<213> ORGANISM: Homo sapiens

<400> SEQUENCE: 80
uagcaagccu ccagcgugcu ugggucugcg gugacccuau gcauuccuuc agugcuugcu      60
agaacaguuu ugaaacgguu ugaggccuug cccugcucca uccagagcaa gguauagaa      120 auuucagaca aug                                                        133

<210> SEQ ID NO 81
<211> LENGTH: 20
<212> TYPE: RNA
```

<213> ORGANISM: Homo sapiens

<400> SEQUENCE: 81 auaugggutuu acuaguuggu        20

<210> SEQ ID NO 82
<211> LENGTH: 86
<212> TYPE: RNA
<213> ORGANISM: Homo sapiens

<400> SEQUENCE: 82
aaccuaugua ucauaucaca uuggguuuuc augcucaugu gugagaagug ccucuuucaa        60
accuuguucu gacacauuau cuuaca        86

<210> SEQ ID NO 83
<211> LENGTH: 20
<212> TYPE: RNA
<213> ORGANISM: Homo sapiens

<400> SEQUENCE: 83
ugggcugcug agaaggggca        20

<210> SEQ ID NO 84
<211> LENGTH: 75
<212> TYPE: RNA
<213> ORGANISM: Homo sapiens

<400> SEQUENCE: 84
guuuaaagaa uacgugaauu uucacuguca caaauucaaa uaaagugaga guggaauuca        60
caguauuuaa ggaau        75

<210> SEQ ID NO 85
<211> LENGTH: 82
<212> TYPE: RNA
<213> ORGANISM: Homo sapiens

<400> SEQUENCE: 85
cugacuuuuu uagggaguag aagggugggg agcaugaaca auguuucuca cucccuaccc        60
cuccacuccc caaaaaaguc ag        82

<210> SEQ ID NO 86
<211> LENGTH: 20
<212> TYPE: RNA
<213> ORGANISM: Homo sapiens

<400> SEQUENCE: 86
ucugguccug gacaggaggc        20

<210> SEQ ID NO 87
<211> LENGTH: 141
<212> TYPE: RNA
<213> ORGANISM: Homo sapiens

<400> SEQUENCE: 87
ggucucuugu gucggcaccu ggguggcuug ccgcccacac aaccaaauua aaaaauaaca        60
cagaagggua agguaagucu ccauuaaacc caggaaagag acuggaaaac uccucuuugg        120
agccugucua uagucacagg u        141

<210> SEQ ID NO 88
<211> LENGTH: 87

```
<212> TYPE: RNA
<213> ORGANISM: Homo sapiens

<400> SEQUENCE: 88
agcgguggcc agugucauuu uugugauguu gcagcuagua auaugagccc aguugcauag     60
ucacaaaagu gaucauugga aacugug                                        87

<210> SEQ ID NO 89
<211> LENGTH: 20
<212> TYPE: RNA
<213> ORGANISM: Homo sapiens

<400> SEQUENCE: 89
aggaggacaa guguggggau                                                20

<210> SEQ ID NO 90
<211> LENGTH: 22
<212> TYPE: RNA
<213> ORGANISM: Homo sapiens

<400> SEQUENCE: 90
agcaaaauaa gcaaauggaa aa                                             22

<210> SEQ ID NO 91
<211> LENGTH: 67
<212> TYPE: RNA
<213> ORGANISM: Homo sapiens

<400> SEQUENCE: 91
cugguccauu ucccugccau ucccuuggcu ucaauuuacu cccagggcug gcagugacau     60
gggucaa                                                              67

<210> SEQ ID NO 92
<211> LENGTH: 22
<212> TYPE: RNA
<213> ORGANISM: Homo sapiens

<400> SEQUENCE: 92
agaaagggug gcaauaccuc uu                                             22

<210> SEQ ID NO 93
<211> LENGTH: 97
<212> TYPE: RNA
<213> ORGANISM: Homo sapiens

<400> SEQUENCE: 93
uauuaugcca ugacauugug ucaauaugcg augaugaguu gugauggcac agcgucauca     60
cguggugacg caacaucaug acguaagacg ucacaac                              97

<210> SEQ ID NO 94
<211> LENGTH: 60
<212> TYPE: RNA
<213> ORGANISM: Homo sapiens

<400> SEQUENCE: 94
ucggcuaagg aaguccugug cucaguuuug uagcaucaaa acuaggauuu cucuuguuac     60

<210> SEQ ID NO 95
<211> LENGTH: 99
<212> TYPE: RNA
<213> ORGANISM: Homo sapiens
```

```
<400> SEQUENCE: 95
uggcggccug ggcgggagcg cgcgggcggg gccggccccg cugccuggaa uuaacccgc      60 ugugcuugcu cgucccgccc gcagcccuag cggcgucg                            99

<210> SEQ ID NO 96
<211> LENGTH: 104
<212> TYPE: RNA
<213> ORGANISM: Homo sapiens

<400> SEQUENCE: 96 auccuuugu aauacauaag cauaaugauu ggguuuuuau guucacaugu uugauaugcc      60
ucccucaaau ccucuuauga ugucggcaca uuacccaucu gagg                    104

<210> SEQ ID NO 97
<211> LENGTH: 18
<212> TYPE: RNA
<213> ORGANISM: Homo sapiens

<400> SEQUENCE: 97
ugaggcgggg gggcgagc                                                  18

<210> SEQ ID NO 98
<211> LENGTH: 66
<212> TYPE: RNA
<213> ORGANISM: Homo sapiens

<400> SEQUENCE: 98
agggcugggc uggcagggca agugcugcag aucuuugucu aagcagcccc ugccuuggau    60
cuccca                                                               66

<210> SEQ ID NO 99
<211> LENGTH: 22
<212> TYPE: RNA
<213> ORGANISM: Homo sapiens

<400> SEQUENCE: 99
aguuugggau ggagagagga ga                                             22

<210> SEQ ID NO 100
<211> LENGTH: 22
<212> TYPE: RNA
<213> ORGANISM: Homo sapiens

<400> SEQUENCE: 100
agcgagguug cccuuuguau au                                             22

<210> SEQ ID NO 101
<211> LENGTH: 17
<212> TYPE: RNA
<213> ORGANISM: Homo sapiens

<400> SEQUENCE: 101
uaagugcuuc caugcuu                                                   17

<210> SEQ ID NO 102
<211> LENGTH: 22
<212> TYPE: RNA
<213> ORGANISM: Homo sapiens

<400> SEQUENCE: 102
uaggggcagc agaggaccug gg                                             22
```

<210> SEQ ID NO 103
<211> LENGTH: 20
<212> TYPE: RNA
<213> ORGANISM: Homo sapiens

<400> SEQUENCE: 103
ccuccugccc uccuugcugu                                                     20

<210> SEQ ID NO 104
<211> LENGTH: 72
<212> TYPE: RNA
<213> ORGANISM: Homo sapiens

<400> SEQUENCE: 104
acuccaugau gaacccaaaa ugccaaguau augacugaac uuacaaguga uaccaucuua         60
cgacugaaga gu                                                             72

<210> SEQ ID NO 105
<211> LENGTH: 90
<212> TYPE: RNA
<213> ORGANISM: Homo sapiens

<400> SEQUENCE: 105
augcuuuugu aguucguaag caugaugauu ggguuucuu gcucuuguau gagaugugcc          60
uccgucauac cuuggaaacc ugacuugaaa                                          90

<210> SEQ ID NO 106
<211> LENGTH: 21
<212> TYPE: RNA
<213> ORGANISM: Homo sapiens

<400> SEQUENCE: 106
uuggagggug uggaagacau c                                                   21

<210> SEQ ID NO 107
<211> LENGTH: 20
<212> TYPE: RNA
<213> ORGANISM: Homo sapiens

<400> SEQUENCE: 107
aaguccugcu ucuguugcag                                                     20

<210> SEQ ID NO 108
<211> LENGTH: 75
<212> TYPE: RNA
<213> ORGANISM: Homo sapiens

<400> SEQUENCE: 108
gcagugccuu acucagaaag gugccaguca cuuacacuac augucacugu guccuuucug         60
cguagaguaa ggcuc                                                          75

<210> SEQ ID NO 109
<211> LENGTH: 110
<212> TYPE: RNA
<213> ORGANISM: Homo sapiens

<400> SEQUENCE: 109
acaagggbuc uaauuucacu acauccccuc caauauuugg uaucuuuccu uucuaaaaa          60 aauagccagc cuagugagug ugaaguggca ucucaaugug guuugauuu                     110

```
<210> SEQ ID NO 110
<211> LENGTH: 139
<212> TYPE: RNA
<213> ORGANISM: Homo sapiens

<400> SEQUENCE: 110
ugcacugcgu gguaucugca cucagcaguu uacuccugcu agggguuca aaggucagug        60 ccauagaaau ccaguaucug guuucauugg uuuucuuggc uuugugcuug uuaaaccugg      120
uauuucuauu gauacagca                                                   139

<210> SEQ ID NO 111
<211> LENGTH: 100
<212> TYPE: RNA
<213> ORGANISM: Homo sapiens

<400> SEQUENCE: 111
auacuuuugu aggucauaag cugaggauug gguuucaug cucuugugug agauaugcuu        60
cucucaaacc uucugaccug ggcacauuac ccagcuaaug                            100

<210> SEQ ID NO 112
<211> LENGTH: 189
<212> TYPE: RNA
<213> ORGANISM: Homo sapiens

<400> SEQUENCE: 112
uuucuauagu uuauuaccag aaaaguuucu cagaaugugu agagcacugg aaaccaugag        60
gaagaggcau agcguucucu cuugagcauc aaguuggcug uuggguugc uuugcugcaa       120 acgccauuug ucauugucuu ccuugucuuc cuuuaggaga guaagaggga gaggacacag      180
ucuggguag                                                              189

<210> SEQ ID NO 113
<211> LENGTH: 22
<212> TYPE: RNA
<213> ORGANISM: Homo sapiens

<400> SEQUENCE: 113
cacccccugu uccuggccc ac                                                 22

<210> SEQ ID NO 114
<211> LENGTH: 80
<212> TYPE: RNA
<213> ORGANISM: Homo sapiens

<400> SEQUENCE: 114
gcucugauuu acuucugucc ggcaugguga acagcaggau uggcuguagc uguucucuuu        60
gccaaggaca gaucugaucu                                                   80

<210> SEQ ID NO 115
<211> LENGTH: 22
<212> TYPE: RNA
<213> ORGANISM: Homo sapiens

<400> SEQUENCE: 115
gguucccucu ccaaaugugu cu                                                22

<210> SEQ ID NO 116
<211> LENGTH: 84
<212> TYPE: RNA
<213> ORGANISM: Homo sapiens
```

-continued

<400> SEQUENCE: 116
ggccaguguu gagaggcgga gacuugggca auugcuggac gcugcccugg gcauugcacu    60
ugucucgguc ugacagugcc ggcc                                          84

<210> SEQ ID NO 117
<211> LENGTH: 106
<212> TYPE: RNA
<213> ORGANISM: Homo sapiens

<400> SEQUENCE: 117
auccuuuugu aguucauaaa ugugauaauu gggguuucac gugcauguau gagaugucug    60
agucccucaa accuuguuac aacauuggua cauuacccau uuuacc                  106

<210> SEQ ID NO 118
<211> LENGTH: 20
<212> TYPE: RNA
<213> ORGANISM: Homo sapiens

<400> SEQUENCE: 118
gauauucaga ggcuaggugg                                               20

<210> SEQ ID NO 119
<211> LENGTH: 22
<212> TYPE: RNA
<213> ORGANISM: Homo sapiens

<400> SEQUENCE: 119
cuauacaguc uacugucuuu cc                                            22

<210> SEQ ID NO 120
<211> LENGTH: 21
<212> TYPE: RNA
<213> ORGANISM: Homo sapiens

<400> SEQUENCE: 120
uuccuucugu ugucugugca g                                             21

<210> SEQ ID NO 121
<211> LENGTH: 65
<212> TYPE: RNA
<213> ORGANISM: Homo sapiens

<400> SEQUENCE: 121
gacauguggg guuugcugua gacauuucag auaacucggg auucguagc uuccuggcaa    60 cuuug                                                               65

<210> SEQ ID NO 122
<211> LENGTH: 107
<212> TYPE: RNA
<213> ORGANISM: Homo sapiens

<400> SEQUENCE: 122
auccuuuugu aguuuauaag cgugaugacu ggguuucac gugcaugugu gaaaugugcc    60
uuccccaagc cuuguuauga ccucauugga acauuacccc uuugaca               107

<210> SEQ ID NO 123
<211> LENGTH: 21
<212> TYPE: RNA
<213> ORGANISM: Homo sapiens

```
<400> SEQUENCE: 123
caccgacucu gucuccugca g                                              21

<210> SEQ ID NO 124
<211> LENGTH: 19
<212> TYPE: RNA
<213> ORGANISM: Homo sapiens

<400> SEQUENCE: 124
ggccuuguuc cugucccca                                                 19

<210> SEQ ID NO 125
<211> LENGTH: 22
<212> TYPE: RNA
<213> ORGANISM: Homo sapiens

<400> SEQUENCE: 125
ucugccaucc ucccuccccu ac                                             22

<210> SEQ ID NO 126
<211> LENGTH: 23
<212> TYPE: RNA
<213> ORGANISM: Homo sapiens

<400> SEQUENCE: 126
uugggauggu aggaccagag ggg                                            23

<210> SEQ ID NO 127
<211> LENGTH: 92
<212> TYPE: RNA
<213> ORGANISM: Homo sapiens

<400> SEQUENCE: 127
uuaguuccag ccuccuggcu caccuggaac cauuucuccu gggaagcaug guagccagga    60
gaguggauuc caggugguga gggcuuggua cu                                  92

<210> SEQ ID NO 128
<211> LENGTH: 23
<212> TYPE: RNA
<213> ORGANISM: Homo sapiens

<400> SEQUENCE: 128
caacggaauc ccaaaagcag cug                                            23

<210> SEQ ID NO 129
<211> LENGTH: 25
<212> TYPE: RNA
<213> ORGANISM: Homo sapiens

<400> SEQUENCE: 129
ggcggaggga aguagguccg uuggu                                          25

<210> SEQ ID NO 130
<211> LENGTH: 22
<212> TYPE: RNA
<213> ORGANISM: Homo sapiens

<400> SEQUENCE: 130
uaguucuucc cuuugcccaa uu                                             22

<210> SEQ ID NO 131
<211> LENGTH: 65
```

```
<212> TYPE: RNA
<213> ORGANISM: Homo sapiens

<400> SEQUENCE: 131 cguuaaugc uaaucgugau aggguuuuu gccuccaacu gacuccuaca uauuagcauu    60
aacag                                                              65

<210> SEQ ID NO 132
<211> LENGTH: 24
<212> TYPE: RNA
<213> ORGANISM: Homo sapiens

<400> SEQUENCE: 132
cccggacagg cguucgugcg acgu                                         24

<210> SEQ ID NO 133
<211> LENGTH: 103
<212> TYPE: RNA
<213> ORGANISM: Homo sapiens

<400> SEQUENCE: 133
auccuuuugu aguucaucag ugucaugagu ggguuuucac gcacaugugu caaauaugcc    60
ucccucaaac uguuacguca uuggcauauu accugacgug aag                    103

<210> SEQ ID NO 134
<211> LENGTH: 23
<212> TYPE: RNA
<213> ORGANISM: Homo sapiens

<400> SEQUENCE: 134
ccggggcaga uugguguagg gug                                          23

<210> SEQ ID NO 135
<211> LENGTH: 23
<212> TYPE: RNA
<213> ORGANISM: Homo sapiens

<400> SEQUENCE: 135
ucagcaccag gauauuguug gag                                          23

<210> SEQ ID NO 136
<211> LENGTH: 22
<212> TYPE: RNA
<213> ORGANISM: Homo sapiens

<400> SEQUENCE: 136
ucaaguaguu ucaugauaaa gg                                           22

<210> SEQ ID NO 137
<211> LENGTH: 22
<212> TYPE: RNA
<213> ORGANISM: Homo sapiens

<400> SEQUENCE: 137
ugcucagguu gcacagcugg ga                                           22

<210> SEQ ID NO 138
<211> LENGTH: 73
<212> TYPE: RNA
<213> ORGANISM: Homo sapiens
```

```
<400> SEQUENCE: 138
ugaaucaaug gugaccacug guggcauaua agucauggau gaugaauaug agaagaaaag      60
aaucuagguu uuu                                                        73

<210> SEQ ID NO 139
<211> LENGTH: 111
<212> TYPE: RNA
<213> ORGANISM: Homo sapiens

<400> SEQUENCE: 139
auccuuuugu gguucauccg ccugaugauu ggguuuucau gcagacgugu gagcugugcc     60
ucccucaagc cuuguuacaa cauccgacau ccgcacauua ccugucugau g              111

<210> SEQ ID NO 140
<211> LENGTH: 111
<212> TYPE: RNA
<213> ORGANISM: Homo sapiens

<400> SEQUENCE: 140
ccacgguccu aguuaaaaag gcacauuccu agacccugcc ucagaacuac ugaacagagu     60 cacuggugu ggaguccagg aaucugcauu uuuacccccua ucgccccgc c              111

<210> SEQ ID NO 141
<211> LENGTH: 24
<212> TYPE: RNA
<213> ORGANISM: Homo sapiens

<400> SEQUENCE: 141
ccucacccag cucucuggcc cucu                                            24

<210> SEQ ID NO 142
<211> LENGTH: 22
<212> TYPE: RNA
<213> ORGANISM: Homo sapiens

<400> SEQUENCE: 142
aaucauacag ggacauccag uu                                              22

<210> SEQ ID NO 143
<211> LENGTH: 97
<212> TYPE: RNA
<213> ORGANISM: Homo sapiens

<400> SEQUENCE: 143
uagccaguca gaaaugagcu uauucauaaa agugcaguau ggugaaguca aucuguaauu     60
uuauguauaa gcuagucucu gauugaaaca ugcagca                              97

<210> SEQ ID NO 144
<211> LENGTH: 22
<212> TYPE: RNA
<213> ORGANISM: Homo sapiens

<400> SEQUENCE: 144
acugggaaga ggagcugagg ga                                              22

<210> SEQ ID NO 145
<211> LENGTH: 79
<212> TYPE: RNA
<213> ORGANISM: Homo sapiens
```

```
<400> SEQUENCE: 145
ccgggacuuu gugggugucug accccacuug gaucacgccg acaacacugg ucuugaaguc    60
agaacccgca aaguccugg                                                  79

<210> SEQ ID NO 146
<211> LENGTH: 72
<212> TYPE: RNA
<213> ORGANISM: Homo sapiens

<400> SEQUENCE: 146
cugccucuga ugaagccugu guugguaggg acaucugaga guaaugauga augccaaccg    60
cucugauggu gg                                                         72

<210> SEQ ID NO 147
<211> LENGTH: 21
<212> TYPE: RNA
<213> ORGANISM: Homo sapiens

<400> SEQUENCE: 147
ugauauguuu gauauugggu u                                               21

<210> SEQ ID NO 148
<211> LENGTH: 81
<212> TYPE: RNA
<213> ORGANISM: Homo sapiens

<400> SEQUENCE: 148 aguuggugg ggagccauga gauaagagca ccuccuagag aauguugaac uaaaggugcc     60
cucucuggcu ccuccccaaa g                                               81

<210> SEQ ID NO 149
<211> LENGTH: 99
<212> TYPE: RNA
<213> ORGANISM: Homo sapiens

<400> SEQUENCE: 149
auucuuaaau gaaugaugaa auaccaaaaa gaaaaauaag caaagaacag auaacagaaa    60
gaagcacagc aaauacaaca uaauacugac aguaaaaau                            99

<210> SEQ ID NO 150
<211> LENGTH: 75
<212> TYPE: RNA
<213> ORGANISM: Homo sapiens

<400> SEQUENCE: 150
auggauuuga uugaaugauu cucccauuuc cacauggaga guggagccca gagaauuguu    60
uaaucaugua uccau                                                      75

<210> SEQ ID NO 151
<211> LENGTH: 24
<212> TYPE: RNA
<213> ORGANISM: Homo sapiens

<400> SEQUENCE: 151
gcugguuuca uauggugguu uaga                                            24

<210> SEQ ID NO 152
<211> LENGTH: 62
<212> TYPE: RNA
<213> ORGANISM: Homo sapiens
```

-continued

<400> SEQUENCE: 152
gggggugggg cuagugaugc aggacgcugg ggacuggaga aguccugccu gacccugucc    60
ca                                                                   62

<210> SEQ ID NO 153
<211> LENGTH: 143
<212> TYPE: RNA
<213> ORGANISM: Homo sapiens

<400> SEQUENCE: 153
aagcauggca cacuggaugg gcguucugcu ucucuuuaaa gagcauggau uuauccauac    60
caugugacau gaaugaaaug aggaguuuuc agggcugcca accucuuggu uaagguucug   120
uguaguauau uucuccuaca aua                                           143

<210> SEQ ID NO 154
<211> LENGTH: 72
<212> TYPE: RNA
<213> ORGANISM: Homo sapiens

<400> SEQUENCE: 154
uggaccaaug augagaauau gucaugaacc aaggaauaug auuaauccaa uucuguguac    60
uggaggguca aa                                                        72

<210> SEQ ID NO 155
<211> LENGTH: 21
<212> TYPE: RNA
<213> ORGANISM: Homo sapiens

<400> SEQUENCE: 155
agaaguggcu aauaauauug a                                              21

<210> SEQ ID NO 156
<211> LENGTH: 69
<212> TYPE: RNA
<213> ORGANISM: Homo sapiens

<400> SEQUENCE: 156
uagcccaggg cuuggagugg ggcaagguug uuggugauau ggcuuccucu cccuuccugc    60
ccuggcuag                                                            69

<210> SEQ ID NO 157
<211> LENGTH: 23
<212> TYPE: RNA
<213> ORGANISM: Homo sapiens

<400> SEQUENCE: 157
acggaauaug uauacggaau aua                                            23

<210> SEQ ID NO 158
<211> LENGTH: 79
<212> TYPE: RNA
<213> ORGANISM: Homo sapiens

<400> SEQUENCE: 158
auuaauaugg aagggagaag agcuuuaaug cucugaaaau gacuccaauc auuaaagcuc    60
uucucccuuc cauauuaau                                                 79

<210> SEQ ID NO 159

```
<211> LENGTH: 76
<212> TYPE: RNA
<213> ORGANISM: Homo sapiens

<400> SEQUENCE: 159
gccaacugca gaucauggga cugucucagc cccauaugua ucgaaggcu gagaagucccc    60 augauccgca cuuggc                                                    76

<210> SEQ ID NO 160
<211> LENGTH: 22
<212> TYPE: RNA
<213> ORGANISM: Homo sapiens

<400> SEQUENCE: 160 agugggugg gacccagcug uu                                              22

<210> SEQ ID NO 161
<211> LENGTH: 22
<212> TYPE: RNA
<213> ORGANISM: Homo sapiens

<400> SEQUENCE: 161
aagcugccag uugaagaacu gu                                             22

<210> SEQ ID NO 162
<211> LENGTH: 23
<212> TYPE: RNA
<213> ORGANISM: Homo sapiens

<400> SEQUENCE: 162
cccuucccuc acucuucucu cag                                            23

<210> SEQ ID NO 163
<211> LENGTH: 133
<212> TYPE: RNA
<213> ORGANISM: Homo sapiens

<400> SEQUENCE: 163
ucccaucucu uaaauaaaaa gauuuuuuuu uuaagaaguu guacaugugc aauggcugca    60
aacagcagcu uccuuggcag ugugugcagc cuguuucuug uauggguugc ucuaagggac   120
cuuggagaca ggc                                                      133

<210> SEQ ID NO 164
<211> LENGTH: 20
<212> TYPE: RNA
<213> ORGANISM: Homo sapiens

<400> SEQUENCE: 164 gggcugggc gcggggaggu                                                 20

<210> SEQ ID NO 165
<211> LENGTH: 17
<212> TYPE: RNA
<213> ORGANISM: Homo sapiens

<400> SEQUENCE: 165
gccggacaag agggagg                                                   17

<210> SEQ ID NO 166
<211> LENGTH: 134
<212> TYPE: RNA
<213> ORGANISM: Homo sapiens
```

```
<400> SEQUENCE: 166
ucaucaggug ggauaauccu uaccuguucc ucguuuugga gggcagauag aacaggauaa      60
uuggaguuug caugauccau gauuaauguc ucuguguaau caggacuugc aaacucugau     120
uguucauauc ugau                                                      134

<210> SEQ ID NO 167
<211> LENGTH: 21
<212> TYPE: RNA
<213> ORGANISM: Homo sapiens

<400> SEQUENCE: 167
uucacagugg cuaaguuccg c                                               21

<210> SEQ ID NO 168
<211> LENGTH: 22
<212> TYPE: RNA
<213> ORGANISM: Homo sapiens

<400> SEQUENCE: 168 acugggagc agaaggagaa cc                                               22

<210> SEQ ID NO 169
<211> LENGTH: 19
<212> TYPE: RNA
<213> ORGANISM: Homo sapiens

<400> SEQUENCE: 169
uugaucucgg aagcuaagc                                                  19

<210> SEQ ID NO 170
<211> LENGTH: 50
<212> TYPE: RNA
<213> ORGANISM: Homo sapiens

<400> SEQUENCE: 170
cuucucuuuc caguucuucc cagaauuggg aaaagcuggg uugagagggu                 50

<210> SEQ ID NO 171
<211> LENGTH: 65
<212> TYPE: RNA
<213> ORGANISM: Homo sapiens

<400> SEQUENCE: 171
uauuguugug gguggcaga agucuguuuu cuucaugguu uucugaccuu ugccucuccc       60
cucag                                                                 65

<210> SEQ ID NO 172
<211> LENGTH: 22
<212> TYPE: RNA
<213> ORGANISM: Homo sapiens

<400> SEQUENCE: 172
caaggagacg ggaacaugga gc                                              22

<210> SEQ ID NO 173
<211> LENGTH: 81
<212> TYPE: RNA
<213> ORGANISM: Homo sapiens
```

```
<400> SEQUENCE: 173 aucucaggccg guccugcaga gaggaagccc uuccaauacc uguaagcaga agggcuuccu    60
cucugcagga ccggccugaa u                                              81

<210> SEQ ID NO 174
<211> LENGTH: 104
<212> TYPE: RNA
<213> ORGANISM: Homo sapiens

<400> SEQUENCE: 174 aucuuuugu gguucacaag ugugaugauu agguuuucag acucaugugu gagacaugcc     60
uuccucaaac cuucuuaugc uaucagcaca uaaucuggcu gaca                    104

<210> SEQ ID NO 175
<211> LENGTH: 23
<212> TYPE: RNA
<213> ORGANISM: Homo sapiens

<400> SEQUENCE: 175
uaaauuucac cuuucugaga agg                                            23

<210> SEQ ID NO 176
<211> LENGTH: 139
<212> TYPE: RNA
<213> ORGANISM: Homo sapiens

<400> SEQUENCE: 176
gagcuuccag gaucacccu gcagagggc uaauauucug ccagcuucgg aaagggaggg      60
gaagcaagcc uggcagaggc acccauucca uucccagcuu gcuuaguagc uggccauggg  120
aagacacugu gcaacacug                                                139

<210> SEQ ID NO 177
<211> LENGTH: 69
<212> TYPE: RNA
<213> ORGANISM: Homo sapiens

<400> SEQUENCE: 177
ucuuagugau gaaaacuuug uccaguucug cuaaugacuu uaagugauga uaaacuaugu    60
cugagggga                                                            69

<210> SEQ ID NO 178
<211> LENGTH: 140
<212> TYPE: RNA
<213> ORGANISM: Homo sapiens

<400> SEQUENCE: 178
auccaaggcg auucccucuc caaggggaca ucuagugccc cucucaggaa aguagcaacu    60
uggaauagaa ucuggcaugc cuaaggucuu ugaggaacag ggaugcuuau uuccucugcc  120
uuccuuggcu gccuacauag                                               140

<210> SEQ ID NO 179
<211> LENGTH: 22
<212> TYPE: RNA
<213> ORGANISM: Homo sapiens

<400> SEQUENCE: 179
agcucugcug cucacuggca gu                                             22
```

```
<210> SEQ ID NO 180
<211> LENGTH: 133
<212> TYPE: RNA
<213> ORGANISM: Homo sapiens

<400> SEQUENCE: 180
uagcaagccu ccagcgugcu ugggucugca gugacccgu ggauccuac agggcuugcc      60 agaacaguuu ugaaaugguu ugaggccuug ccgugcucca guagagcaa gguuauagaa    120 auuucagaca aug                                                      133

<210> SEQ ID NO 181
<211> LENGTH: 20
<212> TYPE: RNA
<213> ORGANISM: Homo sapiens

<400> SEQUENCE: 181
ucacucucac cuugcuuugc                                                20

<210> SEQ ID NO 182
<211> LENGTH: 94
<212> TYPE: RNA
<213> ORGANISM: Homo sapiens

<400> SEQUENCE: 182
uggaucgaug augacuuuca uacaugcauu ccuuggaaag cugaacaaaa ugagugaaaa    60
cucuauaccg ucauccucgu cgaacugagg ucca                                94

<210> SEQ ID NO 183
<211> LENGTH: 96
<212> TYPE: RNA
<213> ORGANISM: Homo sapiens

<400> SEQUENCE: 183
ccugaagagg ugcaugaagc cugguccugc ccucacuggg aacccccuuc ccucugggua    60
ccagacagaa uucuaugcac uuccuggag gcucca                               96

<210> SEQ ID NO 184
<211> LENGTH: 23
<212> TYPE: RNA
<213> ORGANISM: Homo sapiens

<400> SEQUENCE: 184
gcgaggaccc cucggggucu gac                                            23

<210> SEQ ID NO 185
<211> LENGTH: 211
<212> TYPE: RNA
<213> ORGANISM: Homo sapiens

<400> SEQUENCE: 185
aagacucuac ucucagggcu cauuucuguc auucaauacu agagaaguuu cucugaaugu    60
uuagagcacu ggaaaccaaa cggaggaggc gggcauucuu uccugagcau gcagccagcu   120
cauaguguug uuuuguugca gcugccgcuu gccauugaug auccuucuuc ucuuccuuca   180
ggggaguaag gagacgacgc ggucuuagug g                                  211

<210> SEQ ID NO 186
<211> LENGTH: 23
<212> TYPE: RNA
<213> ORGANISM: Homo sapiens
```

```
<400> SEQUENCE: 186
ucuaaagacu agacuucgcu aug                                              23

<210> SEQ ID NO 187
<211> LENGTH: 137
<212> TYPE: RNA
<213> ORGANISM: Homo sapiens

<400> SEQUENCE: 187
aagacuacac uuucagggau aauuucuaua guucauuacu agagaaguuu cucugaaugu      60
guagagcacc auaaaauaca uuuuauuuuu uauuugagac agggucucac ucugucaccc     120
aagcuggagu gcagugg                                                   137

<210> SEQ ID NO 188
<211> LENGTH: 86
<212> TYPE: RNA
<213> ORGANISM: Homo sapiens

<400> SEQUENCE: 188
ccugccugca gaaaggagcu auccacucca ggguccuuu cuucugagag cuggacacuu       60
guugggauga ccugccugca gguagg                                          86

<210> SEQ ID NO 189
<211> LENGTH: 22
<212> TYPE: RNA
<213> ORGANISM: Homo sapiens

<400> SEQUENCE: 189
auucucucug gaucccaugg au                                              22

<210> SEQ ID NO 190
<211> LENGTH: 68
<212> TYPE: RNA
<213> ORGANISM: Homo sapiens

<400> SEQUENCE: 190
cucaggcuca guggugcaug cuuauagucc cagccacucu ggaggcugaa ggaagauggc     60
uugagccu                                                              68

<210> SEQ ID NO 191
<211> LENGTH: 27
<212> TYPE: RNA
<213> ORGANISM: Homo sapiens

<400> SEQUENCE: 191
uggucuguuc auucucucuu uuuggcc                                         27

<210> SEQ ID NO 192
<211> LENGTH: 96
<212> TYPE: RNA
<213> ORGANISM: Homo sapiens

<400> SEQUENCE: 192
auccuucugu ggcugauaug ugugaugagg ggguuuucac acucuugcgu gggacgugca     60
accucuuuag aacagguggca cauuaccugu ccuaca                              96

<210> SEQ ID NO 193
<211> LENGTH: 84
<212> TYPE: RNA
```

<213> ORGANISM: Homo sapiens

<400> SEQUENCE: 193
gcguacagug ccuuucucaa ggaggugucg uuuaugugaa cuaaaauaua aauuucaccu    60
uucugagaag aguaauguac agca                                          84

<210> SEQ ID NO 194
<211> LENGTH: 20
<212> TYPE: RNA
<213> ORGANISM: Homo sapiens

<400> SEQUENCE: 194
ucuuuucuuu gagacucacu                                               20

<210> SEQ ID NO 195
<211> LENGTH: 23
<212> TYPE: RNA
<213> ORGANISM: Homo sapiens

<400> SEQUENCE: 195
uugggaggga agacagcugg aga                                           23

<210> SEQ ID NO 196
<211> LENGTH: 69
<212> TYPE: RNA
<213> ORGANISM: Homo sapiens

<400> SEQUENCE: 196
auguaauaau guucaucaaa ugucugaccu gaaaugagca guagacaag uuaauuuaac     60 acugaagaa                                                           69

<210> SEQ ID NO 197
<211> LENGTH: 96
<212> TYPE: RNA
<213> ORGANISM: Homo sapiens

<400> SEQUENCE: 197
gcuccaguaa caucuuaaag uaaauaugca ccaaaauuac uuuugguaaa uacaguuuug    60
gugcauauuu acuuuaggau guuacuggag cuccca                             96

<210> SEQ ID NO 198
<211> LENGTH: 142
<212> TYPE: RNA
<213> ORGANISM: Homo sapiens

<400> SEQUENCE: 198
cugcagccua uuaagccaac ugaguuccuu uccucauggg ggggcccagu gugcaauggc    60
ugcaaacagc agcuuccuug guaguguaug cagccugugu guuguauugu augggguugcu  120 cuaagggacc cuggagacag uc                                            142

<210> SEQ ID NO 199
<211> LENGTH: 22
<212> TYPE: RNA
<213> ORGANISM: Homo sapiens

<400> SEQUENCE: 199
agcuacaguu acuuuugcac ca                                            22

<210> SEQ ID NO 200
<211> LENGTH: 22

<212> TYPE: RNA
<213> ORGANISM: Homo sapiens

<400> SEQUENCE: 200
agacaguagu ucuugccugg uu                                              22

<210> SEQ ID NO 201
<211> LENGTH: 22
<212> TYPE: RNA
<213> ORGANISM: Homo sapiens

<400> SEQUENCE: 201
gggaggugug aucucacacu cg                                              22

<210> SEQ ID NO 202
<211> LENGTH: 22
<212> TYPE: RNA
<213> ORGANISM: Homo sapiens

<400> SEQUENCE: 202
aacucacgaa guauaccgaa gu                                              22

<210> SEQ ID NO 203
<211> LENGTH: 19
<212> TYPE: RNA
<213> ORGANISM: Homo sapiens

<400> SEQUENCE: 203
ucugaggugg aacagcagc                                                  19

<210> SEQ ID NO 204
<211> LENGTH: 22
<212> TYPE: RNA
<213> ORGANISM: Homo sapiens

<400> SEQUENCE: 204
ggauuccugg aaauacuguu cu                                              22

<210> SEQ ID NO 205
<211> LENGTH: 211
<212> TYPE: RNA
<213> ORGANISM: Homo sapiens

<400> SEQUENCE: 205
aauuguauac uuucagggau cauuccauag guuguuacua gagaaguuuu uuuagaugug      60
uagaacacug gaaaccacga ggaggaggcg cagcauucuc ucuugaccau gaagccggcu     120 cuuggguguug uuucauugca acugucauuu gccaugaug aucguucucu uccucuggga    180
gaguaagagg gagaggacac aguuugagug g                                   211

<210> SEQ ID NO 206
<211> LENGTH: 102
<212> TYPE: RNA
<213> ORGANISM: Homo sapiens

<400> SEQUENCE: 206
auccauuugu aguucagaaa caugacuauu gucuuuucaa gcuuauauga gaucuggcuc      60
ccucaauccu ugcuaugaua ucaguacauu accugucuga ug                       102

<210> SEQ ID NO 207
<211> LENGTH: 77
<212> TYPE: RNA

<213> ORGANISM: Homo sapiens

<400> SEQUENCE: 207
cucuugguau gaacaucugu guguucaugu cucucugugc acaggggacg agagucacug    60
augucuguag cugagac    77

<210> SEQ ID NO 208
<211> LENGTH: 82
<212> TYPE: RNA
<213> ORGANISM: Homo sapiens

<400> SEQUENCE: 208
gggucaauga ugagaaccuu auauuguucu gaagagaggu gaugacuuaa aaaucaugcu    60
caauaggauu acgcugaggc cc    82

<210> SEQ ID NO 209
<211> LENGTH: 22
<212> TYPE: RNA
<213> ORGANISM: Homo sapiens

<400> SEQUENCE: 209
auagugguug ugaauuuacc uu    22

<210> SEQ ID NO 210
<211> LENGTH: 23
<212> TYPE: RNA
<213> ORGANISM: Homo sapiens

<400> SEQUENCE: 210
acuccauuug uuuugaugau gga    23

<210> SEQ ID NO 211
<211> LENGTH: 23
<212> TYPE: RNA
<213> ORGANISM: Homo sapiens

<400> SEQUENCE: 211
auacacauac acgcaacaca cau    23

<210> SEQ ID NO 212
<211> LENGTH: 69
<212> TYPE: RNA
<213> ORGANISM: Homo sapiens

<400> SEQUENCE: 212
accaccagug augaguugaa uacugcccca gucugaucaa caugcgugaa agauauuuuc    60
ugagcugug    69

<210> SEQ ID NO 213
<211> LENGTH: 22
<212> TYPE: RNA
<213> ORGANISM: Homo sapiens

<400> SEQUENCE: 213
ucgcgguuug ugccagauga cg    22

<210> SEQ ID NO 214
<211> LENGTH: 22
<212> TYPE: RNA
<213> ORGANISM: Homo sapiens

```
<400> SEQUENCE: 214
ugucuuacuc ccucaggcac au                                              22

<210> SEQ ID NO 215
<211> LENGTH: 85
<212> TYPE: RNA
<213> ORGANISM: Homo sapiens

<400> SEQUENCE: 215
ggcuguggag gcaccaguau uucugaaauu cuuuuuucug aaauucuuca ggaaggauuu     60
cagaaauacu ggugucccga cagcc                                           85

<210> SEQ ID NO 216
<211> LENGTH: 67
<212> TYPE: RNA
<213> ORGANISM: Homo sapiens

<400> SEQUENCE: 216
gcaugacucu ucaaccucag gacuugcaga auuaauggaa ugcugccua agguuguuga     60 guguguc                                                               67

<210> SEQ ID NO 217
<211> LENGTH: 21
<212> TYPE: RNA
<213> ORGANISM: Homo sapiens

<400> SEQUENCE: 217
auuugugcuu ggcucuguca c                                               21

<210> SEQ ID NO 218
<211> LENGTH: 70
<212> TYPE: RNA
<213> ORGANISM: Homo sapiens

<400> SEQUENCE: 218
auacaugaug acuuacaugg acucucauuc agcuaaugac uugcugcuga aacauggaaa     60
ucugauuuuu                                                            70

<210> SEQ ID NO 219
<211> LENGTH: 22
<212> TYPE: RNA
<213> ORGANISM: Homo sapiens

<400> SEQUENCE: 219
uuccugggcu ucuccucugu ag                                              22

<210> SEQ ID NO 220
<211> LENGTH: 22
<212> TYPE: RNA
<213> ORGANISM: Homo sapiens

<400> SEQUENCE: 220
caggaugugg ucaaguguug uu                                              22

<210> SEQ ID NO 221
<211> LENGTH: 73
<212> TYPE: RNA
<213> ORGANISM: Homo sapiens
```

```
<400> SEQUENCE: 221
ccagagaugg gaaggccuuc cggugauuau cacagccaug ccuuuaccuc cagaaggccu    60
uuccaucucu guc                                                      73

<210> SEQ ID NO 222
<211> LENGTH: 20
<212> TYPE: RNA
<213> ORGANISM: Homo sapiens

<400> SEQUENCE: 222
gagacagguu caugcugcua                                               20

<210> SEQ ID NO 223
<211> LENGTH: 104
<212> TYPE: RNA
<213> ORGANISM: Homo sapiens

<400> SEQUENCE: 223
auccuuuugu aguucauaag cuugauguuu gaguuuucac acuuacgugu gaaaugugcc   60
ucccuuaaac cuuguuacua cgucagcaca uuacccauga gaca                   104

<210> SEQ ID NO 224
<211> LENGTH: 82
<212> TYPE: RNA
<213> ORGANISM: Homo sapiens

<400> SEQUENCE: 224
guguugauga ugagaaccuu auauuauccu gaagagaggu gaugacuuaa aaaucaugcu   60
caauaggauu acgcugaggc cc                                            82

<210> SEQ ID NO 225
<211> LENGTH: 65
<212> TYPE: RNA
<213> ORGANISM: Homo sapiens

<400> SEQUENCE: 225
cuaggaggga ugggagagag gacugugagg caugguggc ucuaugguca cgcccaucuu    60
ccuac                                                               65

<210> SEQ ID NO 226
<211> LENGTH: 71
<212> TYPE: RNA
<213> ORGANISM: Homo sapiens

<400> SEQUENCE: 226
cucaccagug augaguugaa uaccgcccca gucugaucaa ugugugacug aaagguauuu   60
ucugagcugu g                                                        71

<210> SEQ ID NO 227
<211> LENGTH: 207
<212> TYPE: RNA
<213> ORGANISM: Homo sapiens

<400> SEQUENCE: 227
uccaacgugg auacacccgg gaggucacuc uccccgggcu cuguccaagu ggcguagggg   60
agcauagggc ucugccccau gauguacaag ucccuuucca caacguugga aauaaagcug  120
```

```
ggccucgugu cugcgccugc auauuccuac agcuucccag aguccugucg acaauuacug    180
gggagacaaa ccaugcagga aacagcc                                       207

<210> SEQ ID NO 228
<211> LENGTH: 80
<212> TYPE: RNA
<213> ORGANISM: Homo sapiens

<400> SEQUENCE: 228
aggcagcaaa uggccagagc ucacacagag ggaugagugc acuucaccug cagugugacu    60
cagcaggcca acagaugcua                                               80

<210> SEQ ID NO 229
<211> LENGTH: 81
<212> TYPE: RNA
<213> ORGANISM: Homo sapiens

<400> SEQUENCE: 229
cuucuggaag cugguuucac augguggcuu agauuuuucc aucuuuguau cuagcaccau    60
uugaaaucag uguuuuagga g                                             81

<210> SEQ ID NO 230
<211> LENGTH: 86
<212> TYPE: RNA
<213> ORGANISM: Homo sapiens

<400> SEQUENCE: 230
uagaauauuu cggcauucua gaugagagau auauauauac cucauaugua uagguauac    60 cucaucuaga augcuguaau auucua                                        86

<210> SEQ ID NO 231
<211> LENGTH: 98
<212> TYPE: RNA
<213> ORGANISM: Homo sapiens

<400> SEQUENCE: 231
cagagaggag cugccacuug ggcacugaaa caauguccau uaggcuuugu uauggaaacu    60
ucuccugauc auuguuugu guccauugag cuuccaau                            98

<210> SEQ ID NO 232
<211> LENGTH: 115
<212> TYPE: RNA
<213> ORGANISM: Homo sapiens

<400> SEQUENCE: 232
ccaccuucag cugaguguag ugcccuacuc cagagggcgu cacucaugua aacuaaaaca    60
ugauuguagc cuuuuggagu agaguaauac acaucacgua acgcauauuu ggugg         115

<210> SEQ ID NO 233
<211> LENGTH: 131
<212> TYPE: RNA
<213> ORGANISM: Homo sapiens

<400> SEQUENCE: 233
cccuccuaca aaggcauguc uauaauuccu ugucuuugga cauguaagaa uuggagggac    60
agaaaugugg acuuggagaa aucggggcc agcuuucuca ucacaggcuc aacaucaacc    120
augccacaua g                                                        131
```

```
<210> SEQ ID NO 234
<211> LENGTH: 22
<212> TYPE: RNA
<213> ORGANISM: Homo sapiens

<400> SEQUENCE: 234
uccuaaaucu gaaaguccaa aa                                              22

<210> SEQ ID NO 235
<211> LENGTH: 73
<212> TYPE: RNA
<213> ORGANISM: Homo sapiens

<400> SEQUENCE: 235
cucugccucc cgugccuacu gagcugaaac acaguugguu uguguacacu ggcucaguuc     60
agcaggaaca ggg                                                        73

<210> SEQ ID NO 236
<211> LENGTH: 22
<212> TYPE: RNA
<213> ORGANISM: Homo sapiens

<400> SEQUENCE: 236
uuagggcccu ggcuccaucu cc                                              22

<210> SEQ ID NO 237
<211> LENGTH: 103
<212> TYPE: RNA
<213> ORGANISM: Homo sapiens

<400> SEQUENCE: 237
auccuuuugu gguucauuag cuugauauug gguuucaca cuauucuaug agaugugccu     60
cccucaaaac uuguuacaac auugacacau uacccuucug aug                      103

<210> SEQ ID NO 238
<211> LENGTH: 22
<212> TYPE: RNA
<213> ORGANISM: Homo sapiens

<400> SEQUENCE: 238
accugagguu gugcauuucu aa                                              22

<210> SEQ ID NO 239
<211> LENGTH: 128
<212> TYPE: RNA
<213> ORGANISM: Homo sapiens

<400> SEQUENCE: 239
ggggugcacu cagggcaggg ggcuugaaga acggcuccuc uguuuacgac acacucaaca     60
ggggugugag gucacaguga ugagaggccc aaacuugugg ccuccccgug aacaaaugcc    120
cuacacau                                                             128

<210> SEQ ID NO 240
<211> LENGTH: 86
<212> TYPE: RNA
<213> ORGANISM: Homo sapiens

<400> SEQUENCE: 240
ugaugacacu cucuggaauu guuacacuac cauaauuaaa gugcacugaa ucuuuuucua     60
ucugaugggg ggggaauaaa auaauu                                         86
```

```
<210> SEQ ID NO 241
<211> LENGTH: 21
<212> TYPE: RNA
<213> ORGANISM: Homo sapiens

<400> SEQUENCE: 241
ugagccucuc cuucccucca g                                                21

<210> SEQ ID NO 242
<211> LENGTH: 20
<212> TYPE: RNA
<213> ORGANISM: Homo sapiens

<400> SEQUENCE: 242
ccugcguguu uucuguccaa                                                  20

<210> SEQ ID NO 243
<211> LENGTH: 107
<212> TYPE: RNA
<213> ORGANISM: Homo sapiens

<400> SEQUENCE: 243
uaccaacccc auggaauuuu uacucaccuu cagucaacug auuugcucuu uggugagau       60 auucagaggc uagguggaga uagagguagc cuugagggug ggugugg                    107

<210> SEQ ID NO 244
<211> LENGTH: 21
<212> TYPE: RNA
<213> ORGANISM: Homo sapiens

<400> SEQUENCE: 244
agcggugcuc cugcgggccg a                                                21

<210> SEQ ID NO 245
<211> LENGTH: 21
<212> TYPE: RNA
<213> ORGANISM: Homo sapiens

<400> SEQUENCE: 245
cagcggagcc uggagagaag g                                                21

<210> SEQ ID NO 246
<211> LENGTH: 22
<212> TYPE: RNA
<213> ORGANISM: Homo sapiens

<400> SEQUENCE: 246
cuuggauuuu ccugggccuc ag                                               22

<210> SEQ ID NO 247
<211> LENGTH: 105
<212> TYPE: RNA
<213> ORGANISM: Homo sapiens

<400> SEQUENCE: 247
auccucuugc aguucauaag caugaugauu ggguuuucac acuccugugu gaaauguacc      60
uuccucaaac cuuuuuauaa caucagcaca uuaccgaaca ugaaa                      105

<210> SEQ ID NO 248
<211> LENGTH: 68
<212> TYPE: RNA
```

<213> ORGANISM: Homo sapiens

<400> SEQUENCE: 248
gacucggcug cgguggacaa guccggcucc agaaccugga caccgcucag ccggccgcgg    60
caggggguc                                                           68

<210> SEQ ID NO 249
<211> LENGTH: 92
<212> TYPE: RNA
<213> ORGANISM: Homo sapiens

<400> SEQUENCE: 249
accuaccuaa cuggguuagg gcccuggcuc caucuccuuu aggaaaaccu ucuggggga    60 guggggcuuc gacccuaacc caggugggcu gu                                 92

<210> SEQ ID NO 250
<211> LENGTH: 63
<212> TYPE: RNA
<213> ORGANISM: Homo sapiens

<400> SEQUENCE: 250
uacggaugag caaagaaagu gguuucuuaa aauggaaucu acucuuugug aagaugcugu    60
gaa                                                                 63

<210> SEQ ID NO 251
<211> LENGTH: 77
<212> TYPE: RNA
<213> ORGANISM: Homo sapiens

<400> SEQUENCE: 251
ggucaaugau gagcugacau guauucugaa ucuaaaguug auuauuagua cuuuaguucu    60
agaauuacug agacaug                                                  77

<210> SEQ ID NO 252
<211> LENGTH: 18
<212> TYPE: RNA
<213> ORGANISM: Homo sapiens

<400> SEQUENCE: 252
cuggagucua ggauucca                                                 18

<210> SEQ ID NO 253
<211> LENGTH: 21
<212> TYPE: RNA
<213> ORGANISM: Homo sapiens

<400> SEQUENCE: 253
cuucuugugc ucuaggauug u                                             21

<210> SEQ ID NO 254
<211> LENGTH: 21
<212> TYPE: RNA
<213> ORGANISM: Homo sapiens

<400> SEQUENCE: 254
uuagugaagg cuauuuuaau u                                             21

<210> SEQ ID NO 255
<211> LENGTH: 22
<212> TYPE: RNA
<213> ORGANISM: Homo sapiens -continued

<400> SEQUENCE: 255
ucggcucucu cccucacccu ag                                      22

<210> SEQ ID NO 256
<211> LENGTH: 22
<212> TYPE: RNA
<213> ORGANISM: Homo sapiens

<400> SEQUENCE: 256
uuuggucccc uucaaccagc ua                                      22

<210> SEQ ID NO 257
<211> LENGTH: 129
<212> TYPE: RNA
<213> ORGANISM: Homo sapiens

<400> SEQUENCE: 257
uuauuuaucu gacagaccug cagcaguuac uggaugcugu uaaaguuucc acuacagaug    60
caagaaaagu gucccacacu uucugucugu cugauguga cagcuaagau uaaaucaggu   120
aggacagua                                                         129

<210> SEQ ID NO 258
<211> LENGTH: 71
<212> TYPE: RNA
<213> ORGANISM: Homo sapiens

<400> SEQUENCE: 258
uauuccaaug augcaagugu gucgugaacu aaggauuaug auuaauccag uuuuguagcu    60
agagggauuu u                                                       71

<210> SEQ ID NO 259
<211> LENGTH: 21
<212> TYPE: RNA
<213> ORGANISM: Homo sapiens

<400> SEQUENCE: 259
aguggcaaag ucuuuccaua u                                        21

<210> SEQ ID NO 260
<211> LENGTH: 86
<212> TYPE: RNA
<213> ORGANISM: Homo sapiens

<400> SEQUENCE: 260
gugacuccca gggacugccu uaggagaaag uuucuggaau gucagaacuu ccagaaacuu    60
ucuccuaagg cagucccugg agucac                                       86

<210> SEQ ID NO 261
<211> LENGTH: 74
<212> TYPE: RNA
<213> ORGANISM: Homo sapiens

<400> SEQUENCE: 261
gguuggugca aaaguaacug cgguuuuugc cuuucaacau aauggcaaaa cccacaauua    60
cuuuugcacc aauc                                                    74

<210> SEQ ID NO 262
<211> LENGTH: 83
<212> TYPE: RNA

```
<213> ORGANISM: Homo sapiens

<400> SEQUENCE: 262
agucugugau gaauugcuuu gacuucugac accucguaug aaaacugcac gugcagucug      60
auuauuuagc aagacugagg cuu                                             83

<210> SEQ ID NO 263
<211> LENGTH: 93
<212> TYPE: RNA
<213> ORGANISM: Homo sapiens

<400> SEQUENCE: 263
ccggggagaa guacggugag ccugucauua uucagagagg cuagauccuc uguuugaga      60 aggaucauga ugggcuccuc gguguucucc agg                                  93

<210> SEQ ID NO 264
<211> LENGTH: 91
<212> TYPE: RNA
<213> ORGANISM: Homo sapiens

<400> SEQUENCE: 264
guucuagagc augguuucuc aucauuugca cuacugauac uggggucag auaauuguuu      60 gugguggggg cuguuguuug cauuguagga u                                    91

<210> SEQ ID NO 265
<211> LENGTH: 22
<212> TYPE: RNA
<213> ORGANISM: Homo sapiens

<400> SEQUENCE: 265
uuggggaaac ggccgcugag ug                                              22

<210> SEQ ID NO 266
<211> LENGTH: 135
<212> TYPE: RNA
<213> ORGANISM: Homo sapiens

<400> SEQUENCE: 266
cugcagccaa uuaagccaac ugaguuccuu uccuugugg ggccagugu gcaauggcug        60 cacacagcag cuuccuuggu aguguacaca gccuguuggu uguaugggu gcucugaggg     120 accuuggaga caggc                                                     135

<210> SEQ ID NO 267
<211> LENGTH: 18
<212> TYPE: RNA
<213> ORGANISM: Homo sapiens

<400> SEQUENCE: 267
ugcuuccuuu cucagcug                                                   18

<210> SEQ ID NO 268
<211> LENGTH: 23
<212> TYPE: RNA
<213> ORGANISM: Homo sapiens

<400> SEQUENCE: 268
ugguucucuu guggcucaag cgu                                             23

<210> SEQ ID NO 269
<211> LENGTH: 80
```

```
<212> TYPE: RNA
<213> ORGANISM: Homo sapiens

<400> SEQUENCE: 269
uauaaaucua guggaaacau uucugcacaa acuagauucu ggacaccagu gugcggaaau     60
gcuucugcua cauuuuuagg                                                 80

<210> SEQ ID NO 270
<211> LENGTH: 66
<212> TYPE: RNA
<213> ORGANISM: Homo sapiens

<400> SEQUENCE: 270
aaagcuggau acucagucau ggcauugua acaugauagu gacagguacu ggguaagacu     60
gcauag                                                                66

<210> SEQ ID NO 271
<211> LENGTH: 22
<212> TYPE: RNA
<213> ORGANISM: Homo sapiens

<400> SEQUENCE: 271
aagugcuguc auagcugagg uc                                              22

<210> SEQ ID NO 272
<211> LENGTH: 212
<212> TYPE: RNA
<213> ORGANISM: Homo sapiens

<400> SEQUENCE: 272
aaugcuauac uuucaugggu cauuucuaua guuuguuauu agagaaguuu cucugaaugu     60
guugagcacc agaaaccacg aggagaugca gcauucucuc cugaacggga agccagcuuu    120
uggcauugcu uugaugcaac uaccauuugc cauugauggc aaugcaucgc uuccucuagg    180
aguguaagag ggaguggaug cagucagagu gg                                  212

<210> SEQ ID NO 273
<211> LENGTH: 76
<212> TYPE: RNA
<213> ORGANISM: Homo sapiens

<400> SEQUENCE: 273
agguuggugc aaaagugauu gcaguguuug ccaauaaaag uaaugacaaa aacugcaguu     60
acuuuugcac cagccc                                                     76

<210> SEQ ID NO 274
<211> LENGTH: 23
<212> TYPE: RNA
<213> ORGANISM: Homo sapiens

<400> SEQUENCE: 274
aggagguggu acuaggggcc agc                                             23

<210> SEQ ID NO 275
<211> LENGTH: 69
<212> TYPE: RNA
<213> ORGANISM: Homo sapiens
```

```
<400> SEQUENCE: 275
ucucagugau gaaaacuuug uccaguucug cuacugacag uaagugaaga uaaagugugu    60
cugaggaga                                                           69

<210> SEQ ID NO 276
<211> LENGTH: 79
<212> TYPE: RNA
<213> ORGANISM: Homo sapiens

<400> SEQUENCE: 276 acugccuuu uucgguuauc auggaccga ugcuguauau cugaaaggua caguacugug      60
auaacugaag aaugguggu                                                79

<210> SEQ ID NO 277
<211> LENGTH: 69
<212> TYPE: RNA
<213> ORGANISM: Homo sapiens

<400> SEQUENCE: 277
ccauuuuaga ggcuggaaua gagauucuug aggcuuggaa gaguaaggau cccuuuaucu    60
guccucuag                                                           69

<210> SEQ ID NO 278
<211> LENGTH: 22
<212> TYPE: RNA
<213> ORGANISM: Homo sapiens

<400> SEQUENCE: 278
uccugcguag gaucugagga gu                                            22

<210> SEQ ID NO 279
<211> LENGTH: 23
<212> TYPE: RNA
<213> ORGANISM: Homo sapiens

<400> SEQUENCE: 279
ucgaggacug guggaagggc cuu                                           23

<210> SEQ ID NO 280
<211> LENGTH: 141
<212> TYPE: RNA
<213> ORGANISM: Homo sapiens

<400> SEQUENCE: 280
ccucauuuuc uuggcaggaa cuuguagucc cacucccugu uauguacaga ggcaaaggga    60
agagcucugg cccccuuggc augucuuugg agccaugcag cuucccgucu gccaguucua   120
uccucaagca ccaggacacc a                                            141

<210> SEQ ID NO 281
<211> LENGTH: 78
<212> TYPE: RNA
<213> ORGANISM: Homo sapiens

<400> SEQUENCE: 281
auacuugagg agaaauuauc cuuggugugu ucgcuuuauu uauGaugaau cauacaagga    60
caauuucuuu uugaguau                                                78

<210> SEQ ID NO 282
```

```
<211> LENGTH: 23
<212> TYPE: RNA
<213> ORGANISM: Homo sapiens

<400> SEQUENCE: 282
ccugcagcga cuugauggcu ucc                                              23

<210> SEQ ID NO 283
<211> LENGTH: 20
<212> TYPE: RNA
<213> ORGANISM: Homo sapiens

<400> SEQUENCE: 283
aaaguagcug uaccauuugc                                                  20

<210> SEQ ID NO 284
<211> LENGTH: 210
<212> TYPE: RNA
<213> ORGANISM: Homo sapiens

<400> SEQUENCE: 284
aagacuauac ucucaggaau cauuucuaua guuuuuuacu agagaaauuu cucugaacgu      60
guagagcacu ggaaaccgug aggagaagcu gccuucucuu cugagcauga agugagcucu     120
caguguugcu ucucugcaac ugccauuugc cauugaugau cguucuucuc uuccucuggg     180
agaguaaaag gguacaggau gcagucugag                                     210

<210> SEQ ID NO 285
<211> LENGTH: 94
<212> TYPE: RNA
<213> ORGANISM: Homo sapiens

<400> SEQUENCE: 285
uggaucgaug augacuuuaa aauggaucuc aucggaaucu gaacaaaaug agugaccaaa      60
ucacuucugu gccacuucug ugagcugagg ucca                                 94

<210> SEQ ID NO 286
<211> LENGTH: 21
<212> TYPE: RNA
<213> ORGANISM: Homo sapiens

<400> SEQUENCE: 286
ggacccaccc ggccgggaau a                                                21

<210> SEQ ID NO 287
<211> LENGTH: 23
<212> TYPE: RNA
<213> ORGANISM: Homo sapiens

<400> SEQUENCE: 287
uugaauucuu ggccuuaagu gau                                              23

<210> SEQ ID NO 288
<211> LENGTH: 18
<212> TYPE: RNA
<213> ORGANISM: Homo sapiens

<400> SEQUENCE: 288
ugagaugaca cuguagcu                                                    18

<210> SEQ ID NO 289
<211> LENGTH: 22
```

```
<212> TYPE: RNA
<213> ORGANISM: Homo sapiens

<400> SEQUENCE: 289
uguaaacauc cccgacugga ag                                        22

<210> SEQ ID NO 290
<211> LENGTH: 101
<212> TYPE: RNA
<213> ORGANISM: Homo sapiens

<400> SEQUENCE: 290
gcgagaagau cucaugcugu gacucucugg agggaagcac uuucuguugu cugaaagaaa    60
acaaagcgcu ucucuuuaga guguuacggu uugagaaaag c                      101

<210> SEQ ID NO 291
<211> LENGTH: 73
<212> TYPE: RNA
<213> ORGANISM: Homo sapiens

<400> SEQUENCE: 291
ugggcuuugc ccgcuuucug agcuggaccc ucucucuacc ucggugcag aacuacagcg    60 gaaggaaucu cug                                                     73

<210> SEQ ID NO 292
<211> LENGTH: 22
<212> TYPE: RNA
<213> ORGANISM: Homo sapiens

<400> SEQUENCE: 292
gagcuuauuc auaaaagugc ag                                        22

<210> SEQ ID NO 293
<211> LENGTH: 23
<212> TYPE: RNA
<213> ORGANISM: Homo sapiens

<400> SEQUENCE: 293
uguaaacauc cuacacucuc agc                                       23

<210> SEQ ID NO 294
<211> LENGTH: 71
<212> TYPE: RNA
<213> ORGANISM: Homo sapiens

<400> SEQUENCE: 294
uggaucaauc augacuacug guauuggaug ggucuucguc agugaaugcc uaucuggaac    60
ucugaggucc a                                                       71

<210> SEQ ID NO 295
<211> LENGTH: 65
<212> TYPE: RNA
<213> ORGANISM: Homo sapiens

<400> SEQUENCE: 295
ugucugggga uuuggagaag uggugagcgc aggucuuugg caccaucucc ccuggucccu    60
uggcu                                                              65

<210> SEQ ID NO 296
<211> LENGTH: 23
<212> TYPE: RNA
```

```
<213> ORGANISM: Homo sapiens

<400> SEQUENCE: 296
ucucugagua ccauaugccu ugu                                          23

<210> SEQ ID NO 297
<211> LENGTH: 22
<212> TYPE: RNA
<213> ORGANISM: Homo sapiens

<400> SEQUENCE: 297
uugagaauga ugaaucauua gg                                           22

<210> SEQ ID NO 298
<211> LENGTH: 22
<212> TYPE: RNA
<213> ORGANISM: Homo sapiens

<400> SEQUENCE: 298
guugggacaa gaggacgguc uu                                           22

<210> SEQ ID NO 299
<211> LENGTH: 20
<212> TYPE: RNA
<213> ORGANISM: Homo sapiens

<400> SEQUENCE: 299
ccugcguguu uucuguccaa                                              20

<210> SEQ ID NO 300
<211> LENGTH: 22
<212> TYPE: RNA
<213> ORGANISM: Homo sapiens

<400> SEQUENCE: 300
aacacaccug guuaaccucu uu                                           22

<210> SEQ ID NO 301
<211> LENGTH: 22
<212> TYPE: RNA
<213> ORGANISM: Homo sapiens

<400> SEQUENCE: 301
ugugacaaua gagaugaaca ug                                           22

<210> SEQ ID NO 302
<211> LENGTH: 82
<212> TYPE: RNA
<213> ORGANISM: Homo sapiens

<400> SEQUENCE: 302
cacaacugca uggcaucguc cccuggguggc uguggccuag ggcaagccac aaagccacuc    60
agugaugaug ccagcaguug ug                                           82

<210> SEQ ID NO 303
<211> LENGTH: 22
<212> TYPE: RNA
<213> ORGANISM: Homo sapiens

<400> SEQUENCE: 303
ugcccugugg acucaguucu gg                                           22
```

```
<210> SEQ ID NO 304
<211> LENGTH: 127
<212> TYPE: RNA
<213> ORGANISM: Homo sapiens

<400> SEQUENCE: 304
uucuaaagug uugaguucag uccagggugg aucccccugcu cuguuaauug aacuggaaca    60
uuuaaacugg cuaggcaaaa ugccuacaua gaaagcauua cucuuuauuc auccccagcc    120
uacaaaa                                                              127

<210> SEQ ID NO 305
<211> LENGTH: 23
<212> TYPE: RNA
<213> ORGANISM: Homo sapiens

<400> SEQUENCE: 305
ggcaggaggg cugugccagg uug                                            23

<210> SEQ ID NO 306
<211> LENGTH: 23
<212> TYPE: RNA
<213> ORGANISM: Homo sapiens

<400> SEQUENCE: 306
uuaaugcuaa ucgugauagg ggu                                            23

<210> SEQ ID NO 307
<211> LENGTH: 21
<212> TYPE: RNA
<213> ORGANISM: Homo sapiens

<400> SEQUENCE: 307
ucccuucuuc cugggcccuc a                                              21

<210> SEQ ID NO 308
<211> LENGTH: 104
<212> TYPE: RNA
<213> ORGANISM: Homo sapiens

<400> SEQUENCE: 308
acucuuuugu aguucauaag ugugaugauu ugguguucau gugaacaugu gaaacgugcc    60
acccucaaac cuuguuacaa uguggcaua uuacccaucu gaca                      104

<210> SEQ ID NO 309
<211> LENGTH: 83
<212> TYPE: RNA
<213> ORGANISM: Homo sapiens

<400> SEQUENCE: 309
ucaggcugug acccucuuga gggaagcacu uucuguuguc ugaaagaaga gaaagugcuu    60
ccuuuuagag gcuuacuguc uga                                            83

<210> SEQ ID NO 310
<211> LENGTH: 22
<212> TYPE: RNA
<213> ORGANISM: Homo sapiens

<400> SEQUENCE: 310
cccugugccc ggcccacuuc ug                                             22

<210> SEQ ID NO 311
```

```
<211> LENGTH: 21
<212> TYPE: RNA
<213> ORGANISM: Homo sapiens

<400> SEQUENCE: 311
uagcagcaca gaaauauugg c                                      21

<210> SEQ ID NO 312
<211> LENGTH: 62
<212> TYPE: RNA
<213> ORGANISM: Homo sapiens

<400> SEQUENCE: 312
gagggagugg ggugggaccc agcuguuggc cauggcgaca acaccugggu ugucccucu    60 ag                                                           62

<210> SEQ ID NO 313
<211> LENGTH: 22
<212> TYPE: RNA
<213> ORGANISM: Homo sapiens

<400> SEQUENCE: 313
cccaauacac ggucgaccuc uu                                     22

<210> SEQ ID NO 314
<211> LENGTH: 21
<212> TYPE: RNA
<213> ORGANISM: Homo sapiens

<400> SEQUENCE: 314
uaacgcauaa uauggacaug u                                      21

<210> SEQ ID NO 315
<211> LENGTH: 110
<212> TYPE: RNA
<213> ORGANISM: Homo sapiens

<400> SEQUENCE: 315
guguugggga cucgcgcgcu ggguccagug guucuuaaca guucaacagu ucuguagcgc   60
aauugugaaa uguuuaggac cacuagaccc ggcgggcgcg gcgacagcga            110

<210> SEQ ID NO 316
<211> LENGTH: 22
<212> TYPE: RNA
<213> ORGANISM: Homo sapiens

<400> SEQUENCE: 316 cuccugggc ccgcacucuc gc                                      22

<210> SEQ ID NO 317
<211> LENGTH: 22
<212> TYPE: RNA
<213> ORGANISM: Homo sapiens

<400> SEQUENCE: 317
uggggaggug uggagucagc au                                     22

<210> SEQ ID NO 318
<211> LENGTH: 21
<212> TYPE: RNA
<213> ORGANISM: Homo sapiens
```

```
<400> SEQUENCE: 318
caucccuugc auggugagg g                                              21

<210> SEQ ID NO 319
<211> LENGTH: 83
<212> TYPE: RNA
<213> ORGANISM: Homo sapiens

<400> SEQUENCE: 319
acaggaacac uggacuuggu gucagauggg augagcccug gcucuguuuc cuagcagcaa   60
ucugaucuug agcuagucac ugg                                          83

<210> SEQ ID NO 320
<211> LENGTH: 134
<212> TYPE: RNA
<213> ORGANISM: Homo sapiens

<400> SEQUENCE: 320
ugccucugac cuggguagag uggcaucugg cugugacauu caucucauau cagccaggga   60
caaagcaacc ccuuguuuau uucagcuugg ccuuugucu gugcccaugc cugguucaug   120
ccuuggacac acua                                                    134

<210> SEQ ID NO 321
<211> LENGTH: 119
<212> TYPE: RNA
<213> ORGANISM: Homo sapiens

<400> SEQUENCE: 321
uucuuauuga gcuccuuucu gucuacuggu ggcagucuau ggauuugcac aagacaaaac   60
uagcgcuauu uuaccuucug ucuuuaaaca gguauauuug acguuuugu gagaaauuc    119

<210> SEQ ID NO 322
<211> LENGTH: 95
<212> TYPE: RNA
<213> ORGANISM: Homo sapiens

<400> SEQUENCE: 322
aaagacaugc uguccacagu guguuugaua agcugacaug ggacagggau ucuuuucacu   60
guugugucag uuuaucaaac ccauacuugg augac                             95

<210> SEQ ID NO 323
<211> LENGTH: 20
<212> TYPE: RNA
<213> ORGANISM: Homo sapiens

<400> SEQUENCE: 323
ucccacuacu ucacuuguga                                              20

<210> SEQ ID NO 324
<211> LENGTH: 18
<212> TYPE: RNA
<213> ORGANISM: Homo sapiens

<400> SEQUENCE: 324
ccgcuuucug agcuggac                                                18

<210> SEQ ID NO 325
<211> LENGTH: 23
<212> TYPE: RNA
```

<213> ORGANISM: Homo sapiens

<400> SEQUENCE: 325
cugauaagaa cagaggccca gau                                              23

<210> SEQ ID NO 326
<211> LENGTH: 81
<212> TYPE: RNA
<213> ORGANISM: Homo sapiens

<400> SEQUENCE: 326
agccuuuagc aaguuguaau cuuuuugcug auggaggguc uugccuccau ggggauggcu      60
gaugaugaug gugcugaagg c                                                81

<210> SEQ ID NO 327
<211> LENGTH: 110
<212> TYPE: RNA
<213> ORGANISM: Homo sapiens

<400> SEQUENCE: 327
ugcccaguga ugacaccauc cuugcucccc gucccccca ggggcuaugg gcgacaccau       60
ggcugcsccu gggcugggcc aguggggcca augcccaggg gcugagggca                 110

<210> SEQ ID NO 328
<211> LENGTH: 53
<212> TYPE: RNA
<213> ORGANISM: Homo sapiens

<400> SEQUENCE: 328
gccuucucuu cccaguucuu ccuggagucg gggaaaagcu ggguugagaa ggu             53

<210> SEQ ID NO 329
<211> LENGTH: 102
<212> TYPE: RNA
<213> ORGANISM: Homo sapiens

<400> SEQUENCE: 329
acccuucuua guucauaagc augaugauug gguuucaua cucaugugug agaugugucu       60
cucucaaacu uugugaaaag ucagcacaug acccaucuga ug                         102

<210> SEQ ID NO 330
<211> LENGTH: 142
<212> TYPE: RNA
<213> ORGANISM: Homo sapiens

<400> SEQUENCE: 330
caccuaaugu gugccaagau cuguucauuu augaucucac cgaguccugu gagguuggca      60
uuguugucug gcauugucug auauacaaca gugccaaccu cacaggacuc agugagguga     120
aacugaggau uaggaaggug ua                                               142

<210> SEQ ID NO 331
<211> LENGTH: 87
<212> TYPE: RNA
<213> ORGANISM: Homo sapiens

<400> SEQUENCE: 331
ucucagccug ugacccucua gagggaagcg cuuucuguug ucugaaagaa aagaaagugc      60 aucuuuuag aggauuacag uuugaga                                           87

```
<210> SEQ ID NO 332
<211> LENGTH: 134
<212> TYPE: RNA
<213> ORGANISM: Homo sapiens

<400> SEQUENCE: 332
uguucugaca ugggaagagu agcuucuggu ugguggagcc caucucacau uagccagaga    60
caaagcaaca ccuuguuuau cccggcuugg cuuuuggccu guguccauga cugguccaua   120
ccuuggacac augg                                                    134

<210> SEQ ID NO 333
<211> LENGTH: 96
<212> TYPE: RNA
<213> ORGANISM: Homo sapiens

<400> SEQUENCE: 333
auccuuuugu gggucauaug caugaugauu ggguguucac gcacaaguau gagaugugcc    60 accuuuuac agcauuggca cauuaccugu cugaug                              96

<210> SEQ ID NO 334
<211> LENGTH: 22
<212> TYPE: RNA
<213> ORGANISM: Homo sapiens

<400> SEQUENCE: 334
gcgacucuga aaacuagaag gu                                            22

<210> SEQ ID NO 335
<211> LENGTH: 104
<212> TYPE: RNA
<213> ORGANISM: Homo sapiens

<400> SEQUENCE: 335 aucuuuugu gguucauaag caugaugauu ggguuuucau accaugugu aagaugugcc      60 uuucucagac cuugccaaaa cacuggcaca uuaccugucu gaua                   104

<210> SEQ ID NO 336
<211> LENGTH: 88
<212> TYPE: RNA
<213> ORGANISM: Homo sapiens

<400> SEQUENCE: 336
ucucaggcug ugacccucua gagggaagcg cuuucuguug gcuaaaagaa aagaaagcgc    60
uucccuucag aguguuaacg cuuugaga                                      88

<210> SEQ ID NO 337
<211> LENGTH: 78
<212> TYPE: RNA
<213> ORGANISM: Homo sapiens

<400> SEQUENCE: 337
uggaccaaug augaugacug guggguaug aguuaaaggu gaugaauagu aagugucuuu     60
guuaguggca aguucaga                                                 78

<210> SEQ ID NO 338
<211> LENGTH: 97
<212> TYPE: RNA
<213> ORGANISM: Homo sapiens
```

```
<400> SEQUENCE: 338
caaguuggca cuguagaaua uugaggaaaa gauggucuua uugcaaagau uuucaauaag    60
accauccuuu ccucaauauu cuguggguguc aucuuug                             97

<210> SEQ ID NO 339
<211> LENGTH: 22
<212> TYPE: RNA
<213> ORGANISM: Homo sapiens

<400> SEQUENCE: 339 cuggguucu gagacagaca gu                                              22

<210> SEQ ID NO 340
<211> LENGTH: 22
<212> TYPE: RNA
<213> ORGANISM: Homo sapiens

<400> SEQUENCE: 340
aacccguaga uccgaucuug ug                                             22

<210> SEQ ID NO 341
<211> LENGTH: 21
<212> TYPE: RNA
<213> ORGANISM: Homo sapiens

<400> SEQUENCE: 341
uaugugaccu cggaugaauc a                                              21

<210> SEQ ID NO 342
<211> LENGTH: 21
<212> TYPE: RNA
<213> ORGANISM: Homo sapiens

<400> SEQUENCE: 342
gaaggcgcuu cccuuuggag u                                              21

<210> SEQ ID NO 343
<211> LENGTH: 22
<212> TYPE: RNA
<213> ORGANISM: Homo sapiens

<400> SEQUENCE: 343
caauguuucc acagugcauc ac                                             22

<210> SEQ ID NO 344
<211> LENGTH: 62
<212> TYPE: RNA
<213> ORGANISM: Homo sapiens

<400> SEQUENCE: 344
gccucccuuc acuuccuggc cauccaggca ucugugucug guccgggaa guggaggagg    60 gc                                                                   62

<210> SEQ ID NO 345
<211> LENGTH: 88
<212> TYPE: RNA
<213> ORGANISM: Homo sapiens
```

<400> SEQUENCE: 345
acuuccuggu auuugaagau gcgguugacc auggugugua cgcuuuauuu gugacguagg    60 acacauggguc uacuucuucu caauauca                                      88

<210> SEQ ID NO 346
<211> LENGTH: 72
<212> TYPE: RNA
<213> ORGANISM: Homo sapiens

<400> SEQUENCE: 346
uggaucaaug augacaaagu aucaugaaug agggauugug aauaaucuau uuuaugaac    60 cuguggucaa au                                                        72

<210> SEQ ID NO 347
<211> LENGTH: 107
<212> TYPE: RNA
<213> ORGANISM: Homo sapiens

<400> SEQUENCE: 347
auccuuuugu gguucauaag caugaugauu agauuuucau gcuauugggu gagauaugcc    60
uuccucagac uuuguuacag cauaggcaca uuacaaccug ucgaua                   107

<210> SEQ ID NO 348
<211> LENGTH: 59
<212> TYPE: RNA
<213> ORGANISM: Homo sapiens

<400> SEQUENCE: 348
guccaggcag gagccggacu ggaccucagg gaagaggcug acccggcccc ucuugcggc     59

<210> SEQ ID NO 349
<211> LENGTH: 76
<212> TYPE: RNA
<213> ORGANISM: Homo sapiens

<400> SEQUENCE: 349
aagccuggca uauuugguau aacuuaagca ccagguaaaa ucggugcuu aaguuguacc     60 aaguauagcc aaguuu                                                    76

<210> SEQ ID NO 350
<211> LENGTH: 219
<212> TYPE: RNA
<213> ORGANISM: Homo sapiens

<400> SEQUENCE: 350
aaggcuauac uuucagggau cauuuuuaua gcuuauuacu agaggaguua augugaaugu    60
guagagcacc agaaaccuug aggaggaggu gcagcguucu cuccgagca uaaagcuggc    120 ccgcaguauu guguugccuc acugcaacug ccauuugcca uugaugauga uuguucucuu   180
ucacugagag aguaagagga caggaugcau ucuaacugg                          219

<210> SEQ ID NO 351
<211> LENGTH: 21
<212> TYPE: RNA
<213> ORGANISM: Homo sapiens

```
<400> SEQUENCE: 351
agguugucug ugaugaguuc g                                              21

<210> SEQ ID NO 352
<211> LENGTH: 23
<212> TYPE: RNA
<213> ORGANISM: Homo sapiens

<400> SEQUENCE: 352
uucaugaacu gggucuagcu ugg                                            23

<210> SEQ ID NO 353
<211> LENGTH: 23
<212> TYPE: RNA
<213> ORGANISM: Homo sapiens

<400> SEQUENCE: 353 uagccccag gcuucacuug gcg                                             23

<210> SEQ ID NO 354
<211> LENGTH: 103
<212> TYPE: RNA
<213> ORGANISM: Homo sapiens

<400> SEQUENCE: 354
auccuuuugu aguucauaag gaugaugacu gaguguucac acucgugugu gagaugugcc    60
acccucagac cuugaaaucu ucagucacuc uuguuaagug aac                     103

<210> SEQ ID NO 355
<211> LENGTH: 20
<212> TYPE: RNA
<213> ORGANISM: Homo sapiens

<400> SEQUENCE: 355
ggcuccuugg ucuaggggua                                                20

<210> SEQ ID NO 356
<211> LENGTH: 18
<212> TYPE: RNA
<213> ORGANISM: Homo sapiens

<400> SEQUENCE: 356
gaaggaccug caccuucg                                                  18

<210> SEQ ID NO 357
<211> LENGTH: 22
<212> TYPE: RNA
<213> ORGANISM: Homo sapiens

<400> SEQUENCE: 357
cuuucagucg gauguuuaca gc                                             22

<210> SEQ ID NO 358
<211> LENGTH: 85
<212> TYPE: RNA
<213> ORGANISM: Homo sapiens

<400> SEQUENCE: 358
cucaagcugu gacucuccag agggaugcac uuucucuuau gugaaaaaaa agaaggcgcu    60
ucccuuuaga gcguuacggu uuggg                                          85
```

```
<210> SEQ ID NO 359
<211> LENGTH: 20
<212> TYPE: RNA
<213> ORGANISM: Homo sapiens

<400> SEQUENCE: 359
gugcaaaagu caucacgguu                                                   20

<210> SEQ ID NO 360
<211> LENGTH: 22
<212> TYPE: RNA
<213> ORGANISM: Homo sapiens

<400> SEQUENCE: 360
acuaaaggau auagaagguu uu                                                22

<210> SEQ ID NO 361
<211> LENGTH: 21
<212> TYPE: RNA
<213> ORGANISM: Homo sapiens

<400> SEQUENCE: 361
aggcccuguc cucugcccca g                                                 21

<210> SEQ ID NO 362
<211> LENGTH: 23
<212> TYPE: RNA
<213> ORGANISM: Homo sapiens

<400> SEQUENCE: 362
uagcagcggg aacaguucug cag                                               23

<210> SEQ ID NO 363
<211> LENGTH: 66
<212> TYPE: RNA
<213> ORGANISM: Homo sapiens

<400> SEQUENCE: 363
cugcgaugau ggcauuucuu aggacaccuu uggauuaaua augaaaacaa cuacucucug       60
agcagc                                                                  66

<210> SEQ ID NO 364
<211> LENGTH: 24
<212> TYPE: RNA
<213> ORGANISM: Homo sapiens

<400> SEQUENCE: 364
uguaggaaca guugaauuuu ggcu                                              24

<210> SEQ ID NO 365
<211> LENGTH: 216
<212> TYPE: RNA
<213> ORGANISM: Homo sapiens

<400> SEQUENCE: 365
aagacugugc uuucagggau caugucuaua guugccacu agagaaguuu uuuugaacau        60
guaguagggc accagaagca caaggaagag gcacagccuu cucuccugag caugaaucug      120
gcucuugguc uugcuuugu ccagcuacca uuugccauug auuaugccu ucucuuccuu        180 ccagaaagua aagggagag aaugcagucu gagugg                                 216
```

```
<210> SEQ ID NO 366
<211> LENGTH: 93
<212> TYPE: RNA
<213> ORGANISM: Homo sapiens

<400> SEQUENCE: 366
auccuuuugu aguucauaag cugaugguug gguuuucacg cucaugugug agauguguuc    60
cuucauaucu gucaacacac uaccgggcug uug                                93

<210> SEQ ID NO 367
<211> LENGTH: 24
<212> TYPE: RNA
<213> ORGANISM: Homo sapiens

<400> SEQUENCE: 367
uugaagggac aagucagaua ugcc                                          24

<210> SEQ ID NO 368
<211> LENGTH: 18
<212> TYPE: RNA
<213> ORGANISM: Homo sapiens

<400> SEQUENCE: 368
auggucaccu ccgggacu                                                 18

<210> SEQ ID NO 369
<211> LENGTH: 22
<212> TYPE: RNA
<213> ORGANISM: Homo sapiens

<400> SEQUENCE: 369
ggaggaaccu uggagcuucg gc                                            22

<210> SEQ ID NO 370
<211> LENGTH: 22
<212> TYPE: RNA
<213> ORGANISM: Homo sapiens

<400> SEQUENCE: 370
agcuguaauu agucaguuuu cu                                            22

<210> SEQ ID NO 371
<211> LENGTH: 110
<212> TYPE: RNA
<213> ORGANISM: Homo sapiens

<400> SEQUENCE: 371
gagcugcuug ccucccccg uuuuuggcaa ugguagaacu cacacuggug agguaacagg     60
auccgguggu ucuagacuug ccaacuaugg ggcgaggacu cagccggcac              110

<210> SEQ ID NO 372
<211> LENGTH: 121
<212> TYPE: RNA
<213> ORGANISM: Homo sapiens

<400> SEQUENCE: 372
caaaguucug gaauuacagg ugugagccac cgugcccagc auuuaaaauu uuaauaugua    60
cuuuuugcaa cccagaacuc auuguucagu augaguuuug auacauauaa gaagggauau   120
u                                                                  121

<210> SEQ ID NO 373
```

```
<211> LENGTH: 22
<212> TYPE: RNA
<213> ORGANISM: Homo sapiens

<400> SEQUENCE: 373
aaaaacugag acuacuuuug ca                                              22

<210> SEQ ID NO 374
<211> LENGTH: 22
<212> TYPE: RNA
<213> ORGANISM: Homo sapiens

<400> SEQUENCE: 374
ugauggagcu gggaauacuc ug                                              22

<210> SEQ ID NO 375
<211> LENGTH: 21
<212> TYPE: RNA
<213> ORGANISM: Homo sapiens

<400> SEQUENCE: 375
acucggcugc gguggacaag u                                               21

<210> SEQ ID NO 376
<211> LENGTH: 82
<212> TYPE: RNA
<213> ORGANISM: Homo sapiens

<400> SEQUENCE: 376
aaggagcacu cacuccaauu cccuggacu gggggcaggc ugccaccucc ugggacagg        60 ggauuggggc aggauguucc ag                                              82

<210> SEQ ID NO 377
<211> LENGTH: 102
<212> TYPE: RNA
<213> ORGANISM: Homo sapiens

<400> SEQUENCE: 377
auccuuuugu aguuuauaag caugaugaug ggugcucaca cucaucugag augugucucc      60
cucuaagccu uguaacaaca ucagcacguu acccuucuga ug                        102

<210> SEQ ID NO 378
<211> LENGTH: 19
<212> TYPE: RNA
<213> ORGANISM: Homo sapiens

<400> SEQUENCE: 378
guggucucuu ggcccccag                                                  19

<210> SEQ ID NO 379
<211> LENGTH: 112
<212> TYPE: RNA
<213> ORGANISM: Homo sapiens

<400> SEQUENCE: 379
aguuuaaaaa auuuguuaag caugaugauu aacuuuucac aauaaugcaa uaauguguga      60
gcuaugccuc ucucaaaccu uauuaugaug uuggcccauu acccaucuga ug             112

<210> SEQ ID NO 380
<211> LENGTH: 23
<212> TYPE: RNA
<213> ORGANISM: Homo sapiens
```

```
<400> SEQUENCE: 380
ggguuuguag cuuugcuggc aug                                           23

<210> SEQ ID NO 381
<211> LENGTH: 59
<212> TYPE: RNA
<213> ORGANISM: Homo sapiens

<400> SEQUENCE: 381
aaacuaauau acccauauuc uggcuaggug aucaucagaa uaugguauua uuaguuugg    59

<210> SEQ ID NO 382
<211> LENGTH: 81
<212> TYPE: RNA
<213> ORGANISM: Homo sapiens

<400> SEQUENCE: 382
gccuguguga ugauggagcu gggaauacuc uggggagaga guccucuuuu cagcuguauu   60
uugcuuccuu cccacacaga c                                             81

<210> SEQ ID NO 383
<211> LENGTH: 22
<212> TYPE: RNA
<213> ORGANISM: Homo sapiens

<400> SEQUENCE: 383
uugcuaagua ggcugagauu ga                                            22

<210> SEQ ID NO 384
<211> LENGTH: 22
<212> TYPE: RNA
<213> ORGANISM: Homo sapiens

<400> SEQUENCE: 384
aaaaguaauu gugguuuuug cc                                            22

<210> SEQ ID NO 385
<211> LENGTH: 85
<212> TYPE: RNA
<213> ORGANISM: Homo sapiens

<400> SEQUENCE: 385
uuaaaugaug auuuuuuuaa acaaauguau cagagugcau ucauucaaag gaauguuguc   60
uucuggcaag uaaaaaucca ugcag                                         85

<210> SEQ ID NO 386
<211> LENGTH: 84
<212> TYPE: RNA
<213> ORGANISM: Homo sapiens

<400> SEQUENCE: 386
uuuugguuga auaugauga guguacaaaa ucuugauuua agugaaugaa aaauuacaag    60
auccaacucu gauuucagcc agag                                          84

<210> SEQ ID NO 387
<211> LENGTH: 104
<212> TYPE: RNA
<213> ORGANISM: Homo sapiens
```

<400> SEQUENCE: 387
auccuuuugu aguucaugag uguaaugauu gaguguucau gcacaugugu gagauaugcc    60
acccuugaac cuuguuacac cguugucaca uugcccguuu gaca                   104

<210> SEQ ID NO 388
<211> LENGTH: 131
<212> TYPE: RNA
<213> ORGANISM: Homo sapiens

<400> SEQUENCE: 388
aggcaggauc uaguuacauu guagcuguga agugcugcau ugucuuugcc cccugcucaa    60
aauaaaacug uuaccuuuca agcccugucu gccaugguge uguagcagca gggauguuug   120
gucucauaca u                                                       131

<210> SEQ ID NO 389
<211> LENGTH: 22
<212> TYPE: RNA
<213> ORGANISM: Homo sapiens

<400> SEQUENCE: 389
cuauacaacu uacuacuuuc cc                                            22

<210> SEQ ID NO 390
<211> LENGTH: 22
<212> TYPE: RNA
<213> ORGANISM: Homo sapiens

<400> SEQUENCE: 390
guagcaccuu gcaggauaag gu                                            22

<210> SEQ ID NO 391
<211> LENGTH: 61
<212> TYPE: RNA
<213> ORGANISM: Homo sapiens

<400> SEQUENCE: 391
uccgcucugu ggaguggggu gccuguccce ugccacuggg ugacccaccc cucuccacca    60
g                                                                   61

<210> SEQ ID NO 392
<211> LENGTH: 134
<212> TYPE: RNA
<213> ORGANISM: Homo sapiens

<400> SEQUENCE: 392
uuggcccuua ucgaagcugc agcugcuucc gcauagcugc uguggucaaa aaggagccca    60
gagugacagu uuccuugac ggucgccguu cuguuguug uaacugaucu gcaacauuuu   120
gggaaaauac aguu                                                    134

<210> SEQ ID NO 393
<211> LENGTH: 22
<212> TYPE: RNA
<213> ORGANISM: Homo sapiens

<400> SEQUENCE: 393
ugugacuggu ugaccagagg gg                                            22

<210> SEQ ID NO 394

```
<211> LENGTH: 22
<212> TYPE: RNA
<213> ORGANISM: Homo sapiens

<400> SEQUENCE: 394
caagggacca agcauucauu au                                                  22

<210> SEQ ID NO 395
<211> LENGTH: 22
<212> TYPE: RNA
<213> ORGANISM: Homo sapiens

<400> SEQUENCE: 395
ucccaagggu gagaugcugc ca                                                  22

<210> SEQ ID NO 396
<211> LENGTH: 82
<212> TYPE: RNA
<213> ORGANISM: Homo sapiens

<400> SEQUENCE: 396
ugguacucgg agggagguug uccgugguga guucgcauua uuuaaugaug cccaauacac         60
ggucgaccuc uuuucgguau ca                                                  82

<210> SEQ ID NO 397
<211> LENGTH: 55
<212> TYPE: RNA
<213> ORGANISM: Homo sapiens

<400> SEQUENCE: 397
ccacugcugg ccggggcccc uacucaaggc uaggaggccu uggccaagga caguc              55

<210> SEQ ID NO 398
<211> LENGTH: 22
<212> TYPE: RNA
<213> ORGANISM: Homo sapiens

<400> SEQUENCE: 398
cuucugauca agauuugugg ug                                                  22

<210> SEQ ID NO 399
<211> LENGTH: 111
<212> TYPE: RNA
<213> ORGANISM: Homo sapiens

<400> SEQUENCE: 399
aagcuuauga ugacguaagu gugacgacau uggguuuuca cguucaugug ugagaugugc         60
cucccucaag ccuuauuaca augccaguac auuuuuuuc cacaucugau g                  111

<210> SEQ ID NO 400
<211> LENGTH: 85
<212> TYPE: RNA
<213> ORGANISM: Homo sapiens

<400> SEQUENCE: 400
ucaggcaaag ggauauuuac agauacuuuu uaaaauuugu uugaguugag gcagauuaaa         60
uaucuguauu cuccuuugcc ugcag                                               85

<210> SEQ ID NO 401
<211> LENGTH: 21
<212> TYPE: RNA
<213> ORGANISM: Homo sapiens
```

```
<400> SEQUENCE: 401
cggcgcccgu gucuccucca g                                            21

<210> SEQ ID NO 402
<211> LENGTH: 22
<212> TYPE: RNA
<213> ORGANISM: Homo sapiens

<400> SEQUENCE: 402
augaagccuu cucugccuua cg                                           22

<210> SEQ ID NO 403
<211> LENGTH: 21
<212> TYPE: RNA
<213> ORGANISM: Homo sapiens

<400> SEQUENCE: 403
aaaaguaauu gcaguuuuug c                                            21

<210> SEQ ID NO 404
<211> LENGTH: 104
<212> TYPE: RNA
<213> ORGANISM: Homo sapiens

<400> SEQUENCE: 404 aucuuucgu aguucauaag ugugaugacu ggguauucau gcauguaugu gggauaugcc    60
acccuugacc cuuguuacaa cauuagcaca uuaaccaucu gaca                   104

<210> SEQ ID NO 405
<211> LENGTH: 69
<212> TYPE: RNA
<213> ORGANISM: Homo sapiens

<400> SEQUENCE: 405
uggagggcug cgggacugua gagggcauga gcucaggagc ucaggccagc ucauggugca   60
aggccucug                                                          69

<210> SEQ ID NO 406
<211> LENGTH: 74
<212> TYPE: RNA
<213> ORGANISM: Homo sapiens

<400> SEQUENCE: 406
uggaccagug auggugacug guggugugug agucaugcac agugaauauc augucugg    60 aacucugagg ucca                                                    74

<210> SEQ ID NO 407
<211> LENGTH: 22
<212> TYPE: RNA
<213> ORGANISM: Homo sapiens

<400> SEQUENCE: 407
auagcagcau gaaccugucu ca                                           22

<210> SEQ ID NO 408
<211> LENGTH: 21
<212> TYPE: RNA
<213> ORGANISM: Homo sapiens
```

```
<400> SEQUENCE: 408
aaaauuucuu ucacuacuua g                                           21

<210> SEQ ID NO 409
<211> LENGTH: 63
<212> TYPE: RNA
<213> ORGANISM: Homo sapiens

<400> SEQUENCE: 409
uggcgaugag gagguaccua uuguguugag uaacggugau aauuuuauac gcuauucuga   60
gcc                                                               63

<210> SEQ ID NO 410
<211> LENGTH: 77
<212> TYPE: RNA
<213> ORGANISM: Homo sapiens

<400> SEQUENCE: 410
gucagugaug agcaacauuc accaucuuuc guuugagucu cacggccaug agaucaaccc   60
caugcaccgc ucugaga                                                77

<210> SEQ ID NO 411
<211> LENGTH: 78
<212> TYPE: RNA
<213> ORGANISM: Homo sapiens

<400> SEQUENCE: 411
ggcaccauua gguagacugg gauuuguugu ugagcgcagu aagacaacaa caaaaucacu   60
agucuuccag auggggcc                                               78

<210> SEQ ID NO 412
<211> LENGTH: 90
<212> TYPE: RNA
<213> ORGANISM: Homo sapiens

<400> SEQUENCE: 412
ucccaugcug ugacccucua gaggaagcac uuucuguuug uugucugaga aaaacaaag    60 ugcuucccuu uagaguguua ccguuuggga                                  90

<210> SEQ ID NO 413
<211> LENGTH: 105
<212> TYPE: RNA
<213> ORGANISM: Homo sapiens

<400> SEQUENCE: 413
aauugucagc aggcaauuau cugaggaugc aggagaggaa gggggcuucu uuugacgcc    60 uacuucauca gcugcuccuc agaucagagc cuugcagguc aggcc                 105

<210> SEQ ID NO 414
<211> LENGTH: 142
<212> TYPE: RNA
<213> ORGANISM: Homo sapiens

<400> SEQUENCE: 414
uugcccgaug auuauaaaaa gacgcguuau uaagaggacu uuaugcugga guucuugacg   60
uuuuucucuc uuuucuauac uucuuuuucu ucuuugaau guccagcguc cugugagcga   120
agauuaugag auaugagggc aa                                          142
```

```
<210> SEQ ID NO 415
<211> LENGTH: 96
<212> TYPE: RNA
<213> ORGANISM: Homo sapiens

<400> SEQUENCE: 415
gugacccugg gcaaguuccu gaagaucaga cacaucagau cccuuaucug uaaaaugggc    60
augauccagg aaccugccuc uacgguugcc uugggg                              96

<210> SEQ ID NO 416
<211> LENGTH: 22
<212> TYPE: RNA
<213> ORGANISM: Homo sapiens

<400> SEQUENCE: 416
uagcaccauc ugaaaucggu ua                                             22

<210> SEQ ID NO 417
<211> LENGTH: 80
<212> TYPE: RNA
<213> ORGANISM: Homo sapiens

<400> SEQUENCE: 417
gguuggcuau aacuaucauu uccaagguug ugcuuuuagg aaauguuggc uguccugcgg    60
agagagaaug gggagccagg                                                80

<210> SEQ ID NO 418
<211> LENGTH: 73
<212> TYPE: RNA
<213> ORGANISM: Homo sapiens

<400> SEQUENCE: 418
cucugccucc cgugccuacu gagcugaaac acaguugguu uguguacacu ggcucaguuc    60
agcaggaaca ggg                                                       73

<210> SEQ ID NO 419
<211> LENGTH: 21
<212> TYPE: RNA
<213> ORGANISM: Homo sapiens

<400> SEQUENCE: 419
ucgugucccu cuuguccaca g                                              21

<210> SEQ ID NO 420
<211> LENGTH: 85
<212> TYPE: RNA
<213> ORGANISM: Homo sapiens

<400> SEQUENCE: 420
gugaggacuc gggaggugga ggguggugcc gccggggccg ggcgcuguuu cagcucgcuu    60 cucccccac cuccucucuc cucag                                           85

<210> SEQ ID NO 421
<211> LENGTH: 22
<212> TYPE: RNA
<213> ORGANISM: Homo sapiens

<400> SEQUENCE: 421
ucucagcugc ugcccucucc ag                                             22
```

```
<210> SEQ ID NO 422
<211> LENGTH: 23
<212> TYPE: RNA
<213> ORGANISM: Homo sapiens

<400> SEQUENCE: 422
acuucaccug guccacuagc cgu                                            23

<210> SEQ ID NO 423
<211> LENGTH: 17
<212> TYPE: RNA
<213> ORGANISM: Homo sapiens

<400> SEQUENCE: 423
cagccugaca ggaacag                                                   17

<210> SEQ ID NO 424
<211> LENGTH: 96
<212> TYPE: RNA
<213> ORGANISM: Homo sapiens

<400> SEQUENCE: 424 uggggagug aagaguagau aaaauauugg uaccugauga aucugaggcc agguuucaau     60
acuuuaucug cucuucauuu ccccauaucu acuuac                              96

<210> SEQ ID NO 425
<211> LENGTH: 103
<212> TYPE: RNA
<213> ORGANISM: Homo sapiens

<400> SEQUENCE: 425
auucuuuagu aguucauaau gcuaugauug gguuccaug ugcacaugua agaugugccu      60 cucuaagcc uuguugugac aucagcacau uacccaucug aug                      103

<210> SEQ ID NO 426
<211> LENGTH: 129
<212> TYPE: RNA
<213> ORGANISM: Homo sapiens

<400> SEQUENCE: 426
cucauaccua aacccaagaa ucacuuucuu auagugauga uuuaaacaga ugcaaacagc    60
gagcacaucu ugucaccuuu gcgggacugu ggcugugccc cucgcaguaa auuggaggu    120 ucuacaucc                                                          129

<210> SEQ ID NO 427
<211> LENGTH: 74
<212> TYPE: RNA
<213> ORGANISM: Homo sapiens

<400> SEQUENCE: 427
uauauauaga gauguaugga aucuguauau aucuauauau auguguauau auagauucca    60
uaaaucuaua uaug                                                     74

<210> SEQ ID NO 428
<211> LENGTH: 71
<212> TYPE: RNA
<213> ORGANISM: Homo sapiens
```

```
<400> SEQUENCE: 428
uggaacaaug augagagugu gucaugaacc aagguuauga uuaaucuagu ucugugcauc    60
ugaaauccgu u                                                        71

<210> SEQ ID NO 429
<211> LENGTH: 17
<212> TYPE: RNA
<213> ORGANISM: Homo sapiens

<400> SEQUENCE: 429
ggugaggcua gcuggug                                                  17

<210> SEQ ID NO 430
<211> LENGTH: 67
<212> TYPE: RNA
<213> ORGANISM: Homo sapiens

<400> SEQUENCE: 430
agagauggua gacuauggaa cguaggcguu augauuucug accauguaa cauguccac     60 uaacucu                                                             67

<210> SEQ ID NO 431
<211> LENGTH: 101
<212> TYPE: RNA
<213> ORGANISM: Homo sapiens

<400> SEQUENCE: 431
auccuuuagu ucuuaaacau gacaauugga uguuuaugca uaugugugag augugucacc   60
cuugaaccuu guuaccaugu cugcacauua ccuaucugac a                      101

<210> SEQ ID NO 432
<211> LENGTH: 77
<212> TYPE: RNA
<213> ORGANISM: Homo sapiens

<400> SEQUENCE: 432
ugauagggaa accaggcaag aaauauuguc uccucaaguu gcgacgagac aguaguucuu   60
gccugguuuc ucuauca                                                  77

<210> SEQ ID NO 433
<211> LENGTH: 23
<212> TYPE: RNA
<213> ORGANISM: Homo sapiens

<400> SEQUENCE: 433
acaaaguaca gcauuagccu uag                                           23

<210> SEQ ID NO 434
<211> LENGTH: 84
<212> TYPE: RNA
<213> ORGANISM: Homo sapiens

<400> SEQUENCE: 434
ccagucacgu ccccuuauca cuuuccagc ccagcuuugu gacuguaagu guuggacgga    60
gaacugauaa ggguagguga uuga                                          84

<210> SEQ ID NO 435
<211> LENGTH: 125
<212> TYPE: RNA
```

<213> ORGANISM: Homo sapiens

<400> SEQUENCE: 435

| acagacucac uuugcaccug gcugcagccu caugggggug cuuuuuccau gugccaggga | 60 |
| aacauucugg ggguguugugg cugccugacc uaucaagggu gaugcagcug ucuggggaua | 120 |
| cagga | 125 |

<210> SEQ ID NO 436
<211> LENGTH: 131
<212> TYPE: RNA
<213> ORGANISM: Homo sapiens

<400> SEQUENCE: 436

| ggcuugcugg ugcuuaccac aggcugaauu cuuacacuga cuauauagaa aaggagguag | 60 |
| aguaaaccua cccaauauac cccucagccc aggcucugug ccugaucuau auugugaaug | 120 |
| ugggaacaua g | 131 |

<210> SEQ ID NO 437
<211> LENGTH: 132
<212> TYPE: RNA
<213> ORGANISM: Homo sapiens

<400> SEQUENCE: 437

| cuucccauuu auuugcugcu uguagucuca cagugauacg agcaguuaua cgcaugggau | 60 |
| aaaauaacau ugggccacug uaaauugaga ugaaguaacc auuuucaucu cuucugcagg | 120 |
| gacuagacau ug | 132 |

<210> SEQ ID NO 438
<211> LENGTH: 97
<212> TYPE: RNA
<213> ORGANISM: Homo sapiens

<400> SEQUENCE: 438

| ucuuccucuc uguccucugg aauuugguuu cugaggcacu aguagguga uagcaugacu | 60 |
| gacugccuca cugaccacuu ccagaugagg guuacuc | 97 |

<210> SEQ ID NO 439
<211> LENGTH: 97
<212> TYPE: RNA
<213> ORGANISM: Homo sapiens

<400> SEQUENCE: 439

| ggccuagcca aauacuguau uuugaucga cauuugguug aaaaauaucu auguauagu | 60 |
| aaaccugugu uguucaagag uccacugugu uuugcug | 97 |

<210> SEQ ID NO 440
<211> LENGTH: 69
<212> TYPE: RNA
<213> ORGANISM: Homo sapiens

<400> SEQUENCE: 440

| ccaccacuua aacguggaug uacuugcuuu gaaacuaaag aaguaagugc uuccauguuu | 60 |
| uggugaugg | 69 |

<210> SEQ ID NO 441
<211> LENGTH: 201
<212> TYPE: RNA
<213> ORGANISM: Homo sapiens

<400> SEQUENCE: 441
uccagcagua gucagcuguc uggacagaac cauuccuggg aucauguuac acugcuggga    60
gaagaauguc uucucuucau ccaguugcgu ccaucacugu ucggguggug ucuggcacug   120
gugcaaggca gaacugugcu uccuugagag gugcugagc auucaccuug gcugcuuggu    180
ucuagucuag gagcagacac a                                             201

<210> SEQ ID NO 442
<211> LENGTH: 22
<212> TYPE: RNA
<213> ORGANISM: Homo sapiens

<400> SEQUENCE: 442
uuuguucguu cggcucgcgu ga                                             22

<210> SEQ ID NO 443
<211> LENGTH: 94
<212> TYPE: RNA
<213> ORGANISM: Homo sapiens

<400> SEQUENCE: 443
gaauccgguc cguacaaacu cugcuguguu gaaugauugg ugaguuuguu ugcucauuga    60
uugaaucacu gcagaguuug uacggaccgg auuc                                94

<210> SEQ ID NO 444
<211> LENGTH: 82
<212> TYPE: RNA
<213> ORGANISM: Homo sapiens

<400> SEQUENCE: 444
guguugauga ugagaaccuu auauuauccu gaagagaggu gaugacuuaa aaaucaugcu    60
caauaggauu acgcugaggc cc                                             82

<210> SEQ ID NO 445
<211> LENGTH: 22
<212> TYPE: RNA
<213> ORGANISM: Homo sapiens

<400> SEQUENCE: 445
cucuagaggg aagcacuuuc uc                                             22

<210> SEQ ID NO 446
<211> LENGTH: 81
<212> TYPE: RNA
<213> ORGANISM: Homo sapiens

<400> SEQUENCE: 446
guuccacucu agcagcacgu aaauauuggc guagugaaau auauauuaaa caccaauauu    60
acugugcugc uuuaguguga c                                              81

<210> SEQ ID NO 447
<211> LENGTH: 90
<212> TYPE: RNA
<213> ORGANISM: Homo sapiens

<400> SEQUENCE: 447
uugaggcacu ggguagugga ugauggagac ucgguaccca cugcugaggg uggggaccaa    60
gucugcguca uccucuccuc agugccucaa                                     90

```
<210> SEQ ID NO 448
<211> LENGTH: 20
<212> TYPE: RNA
<213> ORGANISM: Homo sapiens

<400> SEQUENCE: 448
aggcauggga ggucagguga                                                      20

<210> SEQ ID NO 449
<211> LENGTH: 100
<212> TYPE: RNA
<213> ORGANISM: Homo sapiens

<400> SEQUENCE: 449
cagagucucc uucguguaca gggaggagac uguacgugag agauagucag auccgcaugu          60
uagagcagag ucuccuucgu guacagggag gagauuguac                               100

<210> SEQ ID NO 450
<211> LENGTH: 21
<212> TYPE: RNA
<213> ORGANISM: Homo sapiens

<400> SEQUENCE: 450
auugaaaccu cuaagagugg a                                                    21

<210> SEQ ID NO 451
<211> LENGTH: 115
<212> TYPE: RNA
<213> ORGANISM: Homo sapiens

<400> SEQUENCE: 451
ucuguuuauc accagauccu agaacccuau caauauuguc ucugcugugu aaauaguucu          60
gaguagugca auauugcuua uaggguuuug guguuuggaa agaacaaugg gcagg             115

<210> SEQ ID NO 452
<211> LENGTH: 22
<212> TYPE: RNA
<213> ORGANISM: Homo sapiens

<400> SEQUENCE: 452
cuuggcaccu agcaagcacu ca                                                   22

<210> SEQ ID NO 453
<211> LENGTH: 129
<212> TYPE: RNA
<213> ORGANISM: Homo sapiens

<400> SEQUENCE: 453
acuggaggac uaagaaggcu gagucugaug aaguaagacu uugcugauac auuccuccua          60 gaaaaaggg uuggagagag cagccuucac ugaagaguau cacagggcug acuguacuac          120
ccaacacuc                                                                129

<210> SEQ ID NO 454
<211> LENGTH: 72
<212> TYPE: RNA
<213> ORGANISM: Homo sapiens

<400> SEQUENCE: 454 uugguaagu gcuuccaugc uucaguuucc uuacugguaa gauggaugua guaauagcac          60
cuaccuuaua ga                                                             72
```

```
<210> SEQ ID NO 455
<211> LENGTH: 21
<212> TYPE: RNA
<213> ORGANISM: Homo sapiens

<400> SEQUENCE: 455
cgaccucggc gaccccucac u                                            21

<210> SEQ ID NO 456
<211> LENGTH: 87
<212> TYPE: RNA
<213> ORGANISM: Homo sapiens

<400> SEQUENCE: 456
ugguuggguu uggauuguug uacuuuuuuu uuuguucguu gcauuuuag gaacaaaaaa   60 aaaagcccaa cccuucacac cacuuca                                      87

<210> SEQ ID NO 457
<211> LENGTH: 72
<212> TYPE: RNA
<213> ORGANISM: Homo sapiens

<400> SEQUENCE: 457
uggaggugau gaacugucug agccugaccu uguagaaugg aggcaaaaaa acugauuuaa  60
ugagccugau cc                                                      72

<210> SEQ ID NO 458
<211> LENGTH: 22
<212> TYPE: RNA
<213> ORGANISM: Homo sapiens

<400> SEQUENCE: 458
caugcuagga uagaaagaau gg                                           22

<210> SEQ ID NO 459
<211> LENGTH: 22
<212> TYPE: RNA
<213> ORGANISM: Homo sapiens

<400> SEQUENCE: 459
cucaguagcc aguguagauc cu                                           22

<210> SEQ ID NO 460
<211> LENGTH: 150
<212> TYPE: RNA
<213> ORGANISM: Homo sapiens

<400> SEQUENCE: 460
ugcccggccu cccauuaaau ugguuuuuca gacaaaucac aaauuuguuu agguauaagu  60 auacccaug uaaucuuugg gacauacuua ugcuaaaaua auuguccuu guugauugga   120 aauuuuaauu uuaauuaggu guccuguauu                                  150

<210> SEQ ID NO 461
<211> LENGTH: 21
<212> TYPE: RNA
<213> ORGANISM: Homo sapiens

<400> SEQUENCE: 461
ugcguuucuc cucuugagca g                                            21
```

```
<210> SEQ ID NO 462
<211> LENGTH: 133
<212> TYPE: RNA
<213> ORGANISM: Homo sapiens

<400> SEQUENCE: 462
gcauggccga auacuguguu uuuaucagua guuuacacag ccagacacca ugcaaaagca      60
gucuucccuu uagaaugacu gaugguaugc uaagguuuuu cauagcauau cauuauuaaa    120
ggugaauaca aau                                                        133

<210> SEQ ID NO 463
<211> LENGTH: 24
<212> TYPE: RNA
<213> ORGANISM: Homo sapiens

<400> SEQUENCE: 463
aacaacaaaa ucacuagucu ucca                                            24

<210> SEQ ID NO 464
<211> LENGTH: 82
<212> TYPE: RNA
<213> ORGANISM: Homo sapiens

<400> SEQUENCE: 464
ccugccgggg cuaaagugcu gacagugcag auaguggucc ucccgugcu accgcacugu      60 ggguacuugc ugcuccagca gg                                              82

<210> SEQ ID NO 465
<211> LENGTH: 82
<212> TYPE: RNA
<213> ORGANISM: Homo sapiens

<400> SEQUENCE: 465
gggucaauga ugagaaucuu auauuguccu gaagagaggu gaugacuuaa aaaucaugcu     60
caauaggauu acgcugaggc cc                                              82

<210> SEQ ID NO 466
<211> LENGTH: 21
<212> TYPE: RNA
<213> ORGANISM: Homo sapiens

<400> SEQUENCE: 466
uaauuuuaug uauaagcuag u                                               21

<210> SEQ ID NO 467
<211> LENGTH: 135
<212> TYPE: RNA
<213> ORGANISM: Homo sapiens

<400> SEQUENCE: 467
gcauggguuu ggauuuauga ugggcuggau ucccuaggcc ucucauagua ccccaugcca     60
gagcaaacug uagccccaac cauugccggg ccucuaugcc uguaggcugc uggcacugaa    120 gugguugca cagua                                                       135

<210> SEQ ID NO 468
<211> LENGTH: 22
<212> TYPE: RNA
<213> ORGANISM: Homo sapiens
```

```
<400> SEQUENCE: 468
accuuccucu ccauggqucu uu                                              22

<210> SEQ ID NO 469
<211> LENGTH: 148
<212> TYPE: RNA
<213> ORGANISM: Homo sapiens

<400> SEQUENCE: 469
cuucgaugaa gagaugauga cgagucugac uuggggaugu ucucuuugcc cagguggccu     60
acucugugcu gcguucugug gcacaguuua aagagcccug guugaaguaa uuuccuaaag    120
augacuuaga ggcauuuguc ugagaagg                                       148

<210> SEQ ID NO 470
<211> LENGTH: 21
<212> TYPE: RNA
<213> ORGANISM: Homo sapiens

<400> SEQUENCE: 470
uguguCccau uauuguqaqu u                                               21

<210> SEQ ID NO 471
<211> LENGTH: 90
<212> TYPE: RNA
<213> ORGANISM: Homo sapiens

<400> SEQUENCE: 471
ugcccuucgc gaaucuuuuu gcggucuggg cuugcuguac auaacucaau agccggaagc     60
ccuuacccca aaaagcauuu gcggagggcg                                      90

<210> SEQ ID NO 472
<211> LENGTH: 22
<212> TYPE: RNA
<213> ORGANISM: Homo sapiens

<400> SEQUENCE: 472
aggacuggac ucccggcagc cc                                              22

<210> SEQ ID NO 473
<211> LENGTH: 23
<212> TYPE: RNA
<213> ORGANISM: Homo sapiens

<400> SEQUENCE: 473
uguaguguuu ccuacuuuau gga                                             23

<210> SEQ ID NO 474
<211> LENGTH: 65
<212> TYPE: RNA
<213> ORGANISM: Homo sapiens

<400> SEQUENCE: 474
gagggcuagg uggggggcuu gaagccccga gaugccucac gucuucaccc cucucaccua     60
agcag                                                                 65

<210> SEQ ID NO 475
<211> LENGTH: 23
<212> TYPE: RNA
<213> ORGANISM: Homo sapiens
```

```
<400> SEQUENCE: 475
acuugggcac ugaaacaaug ucc                                       23

<210> SEQ ID NO 476
<211> LENGTH: 22
<212> TYPE: RNA
<213> ORGANISM: Homo sapiens

<400> SEQUENCE: 476
aucauaugaa ccaaacucua au                                        22

<210> SEQ ID NO 477
<211> LENGTH: 64
<212> TYPE: RNA
<213> ORGANISM: Homo sapiens

<400> SEQUENCE: 477
ugaugagggg guagaaagug gcugaagcga gauguuuguc uaaaagcacu uuucugucuc 60
ccag                                                             64

<210> SEQ ID NO 478
<211> LENGTH: 72
<212> TYPE: RNA
<213> ORGANISM: Homo sapiens

<400> SEQUENCE: 478
ccuggugaug acagacgaca uugucagcca aucccaugu gguagugagg acauguccug  60
caguucugaa gg                                                    72

<210> SEQ ID NO 479
<211> LENGTH: 72
<212> TYPE: RNA
<213> ORGANISM: Homo sapiens

<400> SEQUENCE: 479
agauucagcu uucccuucag agccuggcuu uggcaucuau gaaagccagg cucugaaggg 60
aaaguugaau cu                                                    72

<210> SEQ ID NO 480
<211> LENGTH: 104
<212> TYPE: RNA
<213> ORGANISM: Homo sapiens

<400> SEQUENCE: 480
aucauuuugc agcuuauaca ugugaugacu ggguuuuuua acucauaagu gagaugugcc 60
uuucuuacau cuuauuauga cauuaguaca uuacccauuu gaua                 104

<210> SEQ ID NO 481
<211> LENGTH: 91
<212> TYPE: RNA
<213> ORGANISM: Homo sapiens

<400> SEQUENCE: 481
auccuucugu aguuuaugag ugugaugauu ggcuguucau gugcauguau gagaugugcc 60
acccuugaac cuugucaugu cugaugugaa a                               91

<210> SEQ ID NO 482
<211> LENGTH: 19
<212> TYPE: RNA
<213> ORGANISM: Homo sapiens
```

```
<400> SEQUENCE: 482
ucucccuuga gggcacuuu                                              19

<210> SEQ ID NO 483
<211> LENGTH: 74
<212> TYPE: RNA
<213> ORGANISM: Homo sapiens

<400> SEQUENCE: 483
uagaccagug augagaaucu gucaugaacc aaggaguauu auuaaucuaa uucuguuuac  60
cugagaguuu uaaa                                                   74

<210> SEQ ID NO 484
<211> LENGTH: 86
<212> TYPE: RNA
<213> ORGANISM: Homo sapiens

<400> SEQUENCE: 484
aagagccaau gauguuuuua uucaaaaugu cugaaccugu cugaagcauc ccagugaugc  60
aacuucugug ugauacugag gcuuuu                                      86

<210> SEQ ID NO 485
<211> LENGTH: 100
<212> TYPE: RNA
<213> ORGANISM: Homo sapiens

<400> SEQUENCE: 485
auccuuuugu gguucauaag caugaugauu ggguuuccac auucuuguga gaugggccuc  60
ccuccaaccu uguuaugaug ucagcacauu acccuugacg                       100

<210> SEQ ID NO 486
<211> LENGTH: 74
<212> TYPE: RNA
<213> ORGANISM: Homo sapiens

<400> SEQUENCE: 486
augauuauau gagggacaga ugccagaagc acugguuaug auuugcaucu ggcauccguc  60
acacagauaa uuau                                                   74

<210> SEQ ID NO 487
<211> LENGTH: 22
<212> TYPE: RNA
<213> ORGANISM: Homo sapiens

<400> SEQUENCE: 487
aggugcucca ggcuggcuca ca                                          22

<210> SEQ ID NO 488
<211> LENGTH: 22
<212> TYPE: RNA
<213> ORGANISM: Homo sapiens

<400> SEQUENCE: 488
ucacaaaucu auaauaugca gg                                          22

<210> SEQ ID NO 489
<211> LENGTH: 100
<212> TYPE: RNA
<213> ORGANISM: Homo sapiens
```

<400> SEQUENCE: 489
ucccaucugg acccugcugg gcagggcuuc ugagcuccuu agcacuagca ggaggggcuc    60
caggggcccu cccuccaugg cagccaggac aggacucuca    100

<210> SEQ ID NO 490
<211> LENGTH: 74
<212> TYPE: RNA
<213> ORGANISM: Homo sapiens

<400> SEQUENCE: 490
uggaccaaug augacaacug ccggcguaug aguguuggu gaugaauaau acgugucuag    60
aacucugagg ucca    74

<210> SEQ ID NO 491
<211> LENGTH: 77
<212> TYPE: RNA
<213> ORGANISM: Homo sapiens

<400> SEQUENCE: 491
uuccagcccg aggccucugu gacgucacgg ugucugcggg aggagaccau gacgucacag    60
aggcuucgcg cucugag    77

<210> SEQ ID NO 492
<211> LENGTH: 87
<212> TYPE: RNA
<213> ORGANISM: Homo sapiens

<400> SEQUENCE: 492
ggucgcauuu cuccuucuua ccagcgcguu uucaguuuca uagggaagcc uuccaugaa    60 acuggagcgc cuggaggaga aggggcc    87

<210> SEQ ID NO 493
<211> LENGTH: 23
<212> TYPE: RNA
<213> ORGANISM: Homo sapiens

<400> SEQUENCE: 493 ugaccccau gucgccucug uag    23

<210> SEQ ID NO 494
<211> LENGTH: 62
<212> TYPE: RNA
<213> ORGANISM: Homo sapiens

<400> SEQUENCE: 494
aaaaguacuu gcggauuugc caucaccuuu accuuuaaug gcaaaacugc aguuacuuuu    60
gc    62

<210> SEQ ID NO 495
<211> LENGTH: 76
<212> TYPE: RNA
<213> ORGANISM: Homo sapiens

<400> SEQUENCE: 495
ggucgcuuaa aucccaaugc uagacccggu ggcaaucaag gucuagccac caggucuagc    60
auugggauuu aagccc    76

<210> SEQ ID NO 496
<211> LENGTH: 79

```
<212> TYPE: RNA
<213> ORGANISM: Homo sapiens

<400> SEQUENCE: 496
auuaauaugg aagggagaag agcuuuaaug cucugaaaau gacuccaauc auuaaagcuc      60
uucucccuuc cauauuaau                                                  79

<210> SEQ ID NO 497
<211> LENGTH: 69
<212> TYPE: RNA
<213> ORGANISM: Homo sapiens

<400> SEQUENCE: 497
ugcacugaug acagugaacc auaaaccaag aauuaugauu uauccaguuc uaugaaucuu      60
aaguccauu                                                             69

<210> SEQ ID NO 498
<211> LENGTH: 110
<212> TYPE: RNA
<213> ORGANISM: Homo sapiens

<400> SEQUENCE: 498
auccuuuugu aguucauaag cgugaugacu gugguuucau gcuugugugu gagagaugggg     60 ugggccuccc ucaaaccuug uuacgacgua ggcccauuac ccaucugaca                110

<210> SEQ ID NO 499
<211> LENGTH: 205
<212> TYPE: RNA
<213> ORGANISM: Homo sapiens

<400> SEQUENCE: 499
ccaaugugua auauccuggg auaucauuuu uucuaggcuu ugccacaug gcuuagggga       60 gcaugggcu cugccccaug auguacaguc ccuuuccuca guguuggaga ugaagcuggg      120 ucgguguuu gcacuuucau auccuguag cuucucagaa uccuguggac agugacuggg      180
gagacaaacc augcaggaaa uaugu                                          205

<210> SEQ ID NO 500
<211> LENGTH: 103
<212> TYPE: RNA
<213> ORGANISM: Homo sapiens

<400> SEQUENCE: 500
auccuucuau auaguucaua agcuugauga ucgguguuca cacacaugug agauacgcca      60
ccugugaacc uuguuaggac aucagcacau uacccaucug aca                      103

<210> SEQ ID NO 501
<211> LENGTH: 104
<212> TYPE: RNA
<213> ORGANISM: Homo sapiens

<400> SEQUENCE: 501
auccuuuugu aguucauaag cacaaugauu gaauuuucau gcucaugugu gagauaugcc      60
ucacuccagu cuuguuacag uguuagcaca uuaccuaucu gaua                     104

<210> SEQ ID NO 502
<211> LENGTH: 77
<212> TYPE: RNA
<213> ORGANISM: Homo sapiens
```

-continued

<400> SEQUENCE: 502
uggacaaaug auuagauuag auugucuuau aaaccaaaga uuauaguuau uccaauuaug    60
ugcauuugag auccacu    77

<210> SEQ ID NO 503
<211> LENGTH: 82
<212> TYPE: RNA
<213> ORGANISM: Homo sapiens

<400> SEQUENCE: 503
cagucagugu cgagaaccuu auauuguucu gaagagaggu ggugacuuaa aaaucaugcu    60
caauaggauu acgcugaggc cc    82

<210> SEQ ID NO 504
<211> LENGTH: 94
<212> TYPE: RNA
<213> ORGANISM: Homo sapiens

<400> SEQUENCE: 504
uggaucgaug augacuuuca uacaugcauu ccuuggaaag cugaacaaaa ugagugaaaa    60
cucuauaccg ucauccucgu cgaacugagg ucca    94

<210> SEQ ID NO 505
<211> LENGTH: 135
<212> TYPE: RNA
<213> ORGANISM: Homo sapiens

<400> SEQUENCE: 505
uguccuugac uuggguagag ugaugucugg uuggugcugc cuaucucaua uaagccaggg    60
acaaaucaau gccuuauuua uuccagcuug gcuuuggguc ugugcccaua ccugguuuau    120
gccuuggaca caugg    135

<210> SEQ ID NO 506
<211> LENGTH: 149
<212> TYPE: RNA
<213> ORGANISM: Homo sapiens

<400> SEQUENCE: 506
cagauggcuc cgaaguuuac auccuauuag guuugugcaa aaguaauugc ggauuuugcc    60
auuaaaagua auggcaaaaa uagcaauuau uuuuguacca gccaguauc uuuucuccuu    120 cuaccaaacu uugucccuga gccaucuca    149

<210> SEQ ID NO 507
<211> LENGTH: 208
<212> TYPE: RNA
<213> ORGANISM: Homo sapiens

<400> SEQUENCE: 507
aagacuauac uuucagggau cauuucuaca uuuccgggua auuucuuuga acauguggag    60
caccggaaac caccaggagg aggcacagca uuuucucugg agcgugaagc caguucuugg    120
uguugcugca uagcaacugc cauuugccuu ugaugaucau ucuucuuuc cuuuaggaga    180 auaagagggg gagaacccag ucugaggg    208

<210> SEQ ID NO 508
<211> LENGTH: 59
<212> TYPE: RNA
<213> ORGANISM: Homo sapiens

```
<400> SEQUENCE: 508
cgggcucugg gugcagugg ggucccacg ccgcggcaac caccacuguc ucucccag        59

<210> SEQ ID NO 509
<211> LENGTH: 23
<212> TYPE: RNA
<213> ORGANISM: Homo sapiens

<400> SEQUENCE: 509
uuuguaugga uaugugugug uau                                            23

<210> SEQ ID NO 510
<211> LENGTH: 128
<212> TYPE: RNA
<213> ORGANISM: Homo sapiens

<400> SEQUENCE: 510
aggucauuuc aaagaggucu ugugaggcug ugaaaccaag agcucuuaac acugcgacca    60
aagauggaag uucucuauag gaugccaugg cauugauggu ugcuauguuu ucuugaggag   120
auauaaga                                                            128

<210> SEQ ID NO 511
<211> LENGTH: 23
<212> TYPE: RNA
<213> ORGANISM: Homo sapiens

<400> SEQUENCE: 511
ccagccacgg acugagagug cau                                            23

<210> SEQ ID NO 512
<211> LENGTH: 103
<212> TYPE: RNA
<213> ORGANISM: Homo sapiens

<400> SEQUENCE: 512
aucccuuuau aguucccgag caugacgauu ggguguucac augcaugugu gagauguacc    60
acccucgcau cuuguuagac guuggcacau uacccgucug acc                     103

<210> SEQ ID NO 513
<211> LENGTH: 24
<212> TYPE: RNA
<213> ORGANISM: Homo sapiens

<400> SEQUENCE: 513
guuccacacu gacacugcag aagu                                           24

<210> SEQ ID NO 514
<211> LENGTH: 22
<212> TYPE: RNA
<213> ORGANISM: Homo sapiens

<400> SEQUENCE: 514
aguauucugu accagggaag gu                                             22

<210> SEQ ID NO 515
<211> LENGTH: 106
<212> TYPE: RNA
<213> ORGANISM: Homo sapiens
```

<400> SEQUENCE: 515
gcgcagcgcc cugucuccca gccugaggug cagugcugca ucucggguca guugggaguc   60
ugagaugaag cacuguagcu caggaagaga gaaguuguuc ugcagc   106

<210> SEQ ID NO 516
<211> LENGTH: 75
<212> TYPE: RNA
<213> ORGANISM: Homo sapiens

<400> SEQUENCE: 516
uaucugugau gaucuuaucc cgaaccugaa cuucuguuga aaaaaaaaaa cuuuuacgga   60
ucuggcuucu gagau   75

<210> SEQ ID NO 517
<211> LENGTH: 102
<212> TYPE: RNA
<213> ORGANISM: Homo sapiens

<400> SEQUENCE: 517
auaaucuugu aguucauaag caugaugauu gccuuuucac acucguauga gaugugccuc   60
ccuugaaccu uguuaugaug uuggcacauu acccaucuga ug   102

<210> SEQ ID NO 518
<211> LENGTH: 131
<212> TYPE: RNA
<213> ORGANISM: Homo sapiens

<400> SEQUENCE: 518
ugggaggcug auacacaaau ugggcugaaa uacugcucua cuugucacca ugccucccua   60
gaauaaacug ccuuuugaug accgggacga auugagugaa aucguaacgg acagauacgg   120
ggcagacaga u   131

<210> SEQ ID NO 519
<211> LENGTH: 22
<212> TYPE: RNA
<213> ORGANISM: Homo sapiens

<400> SEQUENCE: 519
ccagagaugg uugccuuccu au   22

<210> SEQ ID NO 520
<211> LENGTH: 23
<212> TYPE: RNA
<213> ORGANISM: Homo sapiens

<400> SEQUENCE: 520
cggggccaug gagcagccug ugu   23

<210> SEQ ID NO 521
<211> LENGTH: 109
<212> TYPE: RNA
<213> ORGANISM: Homo sapiens

<400> SEQUENCE: 521 auucuuugc uguucguaag cauaaggauc agguauucau ggucaugugu aagacgugcc   60
ucccuccaac cuuguuacga uguggacguc agcacauacc cauuugaug   109

<210> SEQ ID NO 522

```
<211> LENGTH: 110
<212> TYPE: RNA
<213> ORGANISM: Homo sapiens

<400> SEQUENCE: 522
gcugcuggaa gguguaggua cccucaaugg cucaguagcc agaguagauc cugucuuucg    60
uaaucagcag cuacaucugg cuacuggguc ucgauggca ucuucuagcu              110

<210> SEQ ID NO 523
<211> LENGTH: 75
<212> TYPE: RNA
<213> ORGANISM: Homo sapiens

<400> SEQUENCE: 523
uggaccaaug augugaaugg aaugcaucug aauaaaaauu augaucaauc aguuuuugga    60
acaacugagg uccac                                                    75

<210> SEQ ID NO 524
<211> LENGTH: 108
<212> TYPE: RNA
<213> ORGANISM: Homo sapiens

<400> SEQUENCE: 524
aggccccugu aguccccgag cacgaugacu gggguguucac gugcacgugu gggaugugcc   60
acccucugaa ccuuguuacg auguuggcac auuacccugg accugacc              108

<210> SEQ ID NO 525
<211> LENGTH: 97
<212> TYPE: RNA
<213> ORGANISM: Homo sapiens

<400> SEQUENCE: 525
uauuaugcca ugacauugug ucaauaugcg augaugüguu gugauggcac agcgucauca   60
cguggugacg caaucaucaug acguaagacg ucacaac                           97

<210> SEQ ID NO 526
<211> LENGTH: 96
<212> TYPE: RNA
<213> ORGANISM: Homo sapiens

<400> SEQUENCE: 526
uucaaaaaag accauauauc cuugaagagu aacugcugaa cuuauucacu ggcaguggc    60 cuuauagcac agugaaugac cagguuagag acaugc                             96

<210> SEQ ID NO 527
<211> LENGTH: 215
<212> TYPE: RNA
<213> ORGANISM: Homo sapiens

<400> SEQUENCE: 527
aagacuauac uuucagggau cauuucuaua guuaguugcu agagaaguuu cucuggacau    60
guggagcacc agaaaccaug agaaggagau guaguguucu cuccggagca ugaagcuggc   120 ucuuggguguu gcuucgcugc accugccauu ugccauugac aaucauucuu cucuuccucu  180
gggagaguaa ggaggagagg acacagucug agugg                              215

<210> SEQ ID NO 528
<211> LENGTH: 23
<212> TYPE: RNA
<213> ORGANISM: Homo sapiens
```

```
<400> SEQUENCE: 528
cugcagccac uuggggaacu ggu                                         23

<210> SEQ ID NO 529
<211> LENGTH: 58
<212> TYPE: RNA
<213> ORGANISM: Homo sapiens

<400> SEQUENCE: 529
ugcuggcuca uuucauaugu gugcugagaa aauucacaca uaugaaguga gccagcac   58

<210> SEQ ID NO 530
<211> LENGTH: 22
<212> TYPE: RNA
<213> ORGANISM: Homo sapiens

<400> SEQUENCE: 530
ccugacaccc caucugcccu ca                                          22

<210> SEQ ID NO 531
<211> LENGTH: 21
<212> TYPE: RNA
<213> ORGANISM: Homo sapiens

<400> SEQUENCE: 531
uuacacagcu ggacagaggc a                                           21

<210> SEQ ID NO 532
<211> LENGTH: 110
<212> TYPE: RNA
<213> ORGANISM: Homo sapiens

<400> SEQUENCE: 532
aguauaauua uuacauaguu uuugaugucg cagauacugc aucaggaacu gauuggauaa 60
gaaucaguca ccaucaguuc cuaaugcauu gccuucagca ucuaaacaag            110

<210> SEQ ID NO 533
<211> LENGTH: 18
<212> TYPE: RNA
<213> ORGANISM: Homo sapiens

<400> SEQUENCE: 533 ggugggggu guuguuuu                                                18

<210> SEQ ID NO 534
<211> LENGTH: 98
<212> TYPE: RNA
<213> ORGANISM: Homo sapiens

<400> SEQUENCE: 534
aggagccacc uuccgagccu ccaguaccac gugucagggc cacaugagcu gggccucgug 60
ggccugaugu ggugcugggg ccucaggggu cugcucuu                         98

<210> SEQ ID NO 535
<211> LENGTH: 22
<212> TYPE: RNA
<213> ORGANISM: Homo sapiens

<400> SEQUENCE: 535
uagcaccauu ugaaaucggu ua                                          22
```

```
<210> SEQ ID NO 536
<211> LENGTH: 104
<212> TYPE: RNA
<213> ORGANISM: Homo sapiens

<400> SEQUENCE: 536 auccuuugu aguucaugag caugaugauu gguuguucac guacaugugu gagauguguc      60
acccucgaac cuuguggcaa uguuggaaua uuaccugucu gaca                    104

<210> SEQ ID NO 537
<211> LENGTH: 120
<212> TYPE: RNA
<213> ORGANISM: Homo sapiens

<400> SEQUENCE: 537
gauucacagc agaaagacag cuaaucuagu gugcuagcug uagagcaagu uugcugcaaa     60
cacccuaagg agggucucug gccaaaugag uagaaucuga caguaauccu ugcuaaaagu    120

<210> SEQ ID NO 538
<211> LENGTH: 71
<212> TYPE: RNA
<213> ORGANISM: Homo sapiens

<400> SEQUENCE: 538
cuacaaugau ggcauaugu uucaucgaca gcaguucacc cauugagugu ugauaccgug      60
ggucugagug a                                                         71

<210> SEQ ID NO 539
<211> LENGTH: 81
<212> TYPE: RNA
<213> ORGANISM: Homo sapiens

<400> SEQUENCE: 539
auucaggccg guccugcaga gaggaagccc uuccaauacc uguaagcaga agggcuuccu     60
cucugcagga ccggccugaa u                                              81

<210> SEQ ID NO 540
<211> LENGTH: 74
<212> TYPE: RNA
<213> ORGANISM: Homo sapiens

<400> SEQUENCE: 540
uggaccaaug augacaaaua ccggcguaug agucuuggau gaugaauaau acgucugg       60 aacucugagg ucca                                                      74

<210> SEQ ID NO 541
<211> LENGTH: 47
<212> TYPE: RNA
<213> ORGANISM: Homo sapiens

<400> SEQUENCE: 541
gccuaggagu ccuuggucag uggggacaug gagaaggcuu cugagga                  47

<210> SEQ ID NO 542
<211> LENGTH: 81
<212> TYPE: RNA
<213> ORGANISM: Homo sapiens
```

<400> SEQUENCE: 542
gugagggacu gggauuugug gggcgaggag ggaccuguac uagccauggu ucugaucaca    60 uauguccau cccuccauca g    81

<210> SEQ ID NO 543
<211> LENGTH: 73
<212> TYPE: RNA
<213> ORGANISM: Homo sapiens

<400> SEQUENCE: 543
guuucugaug aagccuaugu ugguagggac aacuaagguu guugaugaau gcuaacagcu    60
cuaacacaca cac    73

<210> SEQ ID NO 544
<211> LENGTH: 72
<212> TYPE: RNA
<213> ORGANISM: Homo sapiens

<400> SEQUENCE: 544
cuugggaaug gcaaggaaac cguuaccauu acugaguuua guaaugguaa ugguucucuu    60
gcuauaccca ga    72

<210> SEQ ID NO 545
<211> LENGTH: 22
<212> TYPE: RNA
<213> ORGANISM: Homo sapiens

<400> SEQUENCE: 545
gugagccagu ggaauggaga gg    22

<210> SEQ ID NO 546
<211> LENGTH: 81
<212> TYPE: RNA
<213> ORGANISM: Homo sapiens

<400> SEQUENCE: 546
accuccuccc gugaaucaca auguccuua auagcaaucc uuaaaugcca uuaaggacau    60
uugugauuga ugggaggagg a    81

<210> SEQ ID NO 547
<211> LENGTH: 96
<212> TYPE: RNA
<213> ORGANISM: Homo sapiens

<400> SEQUENCE: 547
aacuauucuu agguugaugc agaaguaacu acgguuuuug caguugaaag uaauggcaaa    60
gaccgugacu acuuuugcaa cagccuaaua guuucu    96

<210> SEQ ID NO 548
<211> LENGTH: 149
<212> TYPE: RNA
<213> ORGANISM: Homo sapiens

<400> SEQUENCE: 548
auccaagggg auucccucuc caagggaaca ugcagugccc cucucaggaa aguaacaacc    60
uggaauagaa ucuggcaugc cuaaggucuu ugaggaauag aggaauagag gaugcuuguu    120
uccucugccu uccuuggcug ccuacaugg    149

```
<210> SEQ ID NO 549
<211> LENGTH: 72
<212> TYPE: RNA
<213> ORGANISM: Homo sapiens

<400> SEQUENCE: 549
acaacauguu uuuaggacau guaugucugg ugcaauaauu gggacauacu uaugcuaaaa        60
aaauuagugu uc                                                           72

<210> SEQ ID NO 550
<211> LENGTH: 100
<212> TYPE: RNA
<213> ORGANISM: Homo sapiens

<400> SEQUENCE: 550
acuuuauacg uguaauugug augaggaugg auagcaagga agccgcuccc accugacccu        60
cacggccucc guguuaccug uccucuaggu gggacgcucg                            100

<210> SEQ ID NO 551
<211> LENGTH: 83
<212> TYPE: RNA
<213> ORGANISM: Homo sapiens

<400> SEQUENCE: 551
agcuuaggua ccaauuuggc cacaaugggu uagaacacua uuccauugug uucuuaccca        60
ccauggccaa aauugggccu aag                                               83

<210> SEQ ID NO 552
<211> LENGTH: 76
<212> TYPE: RNA
<213> ORGANISM: Homo sapiens

<400> SEQUENCE: 552
guccucugau gacuucaugu uagugccacc ugucugggcc acggagaacc caugauggaa        60
cugagaaucu gaggaa                                                       76

<210> SEQ ID NO 553
<211> LENGTH: 22
<212> TYPE: RNA
<213> ORGANISM: Homo sapiens

<400> SEQUENCE: 553
uugcucugag cuccgagaaa gc                                                22

<210> SEQ ID NO 554
<211> LENGTH: 92
<212> TYPE: RNA
<213> ORGANISM: Homo sapiens

<400> SEQUENCE: 554
acccuuuugu aguucauaag caggaugacu gaguuuucau gcacuugugu gagaugcgcc        60
ucccucaaug uuggcacauu accaucuga ug                                       92

<210> SEQ ID NO 555
<211> LENGTH: 68
<212> TYPE: RNA
<213> ORGANISM: Homo sapiens
```

```
<400> SEQUENCE: 555
cuucaauuuu auuuuaaaac ggugagauuu uguuuugucu gagaaaaucu cgcuguuuua    60
gacugagg                                                             68

<210> SEQ ID NO 556
<211> LENGTH: 217
<212> TYPE: RNA
<213> ORGANISM: Homo sapiens

<400> SEQUENCE: 556
aagacuauac uuucagggau cauuucuaua gugguuacu agagaaguuu cucugaacgu     60
guagagcacc gaaaccacg aggaagagag guagcguuuu cuccugagcg ugaagccggc    120
uuucuggcgu ugcuuggcug caacugccgu cagccauuga ugaucguucu ucucuccgua   180 uugggggagug agagggagag aacgcggucu gaguggu                            217

<210> SEQ ID NO 557
<211> LENGTH: 22
<212> TYPE: RNA
<213> ORGANISM: Homo sapiens

<400> SEQUENCE: 557
aauguggacu ggugugacca aa                                             22

<210> SEQ ID NO 558
<211> LENGTH: 22
<212> TYPE: RNA
<213> ORGANISM: Homo sapiens

<400> SEQUENCE: 558
ugggaacuua guagagguuu aa                                             22

<210> SEQ ID NO 559
<211> LENGTH: 67
<212> TYPE: RNA
<213> ORGANISM: Homo sapiens

<400> SEQUENCE: 559
auggaggugg agagucauca gcagcacuga gcaggcagug uugucugcug aguuccacg     60 ucauuug                                                              67

<210> SEQ ID NO 560
<211> LENGTH: 133
<212> TYPE: RNA
<213> ORGANISM: Homo sapiens

<400> SEQUENCE: 560
aagccagcca augaaucugc uuaccugauu guguuugugc agacauacuu uaaaaacugg    60
caauaguaaa gccauguuac gagccuuaag gacauugaag ucguuaaggu cccugagaau   120
ggcuauaaca aau                                                      133

<210> SEQ ID NO 561
<211> LENGTH: 22
<212> TYPE: RNA
<213> ORGANISM: Homo sapiens

<400> SEQUENCE: 561
ucugcaagug ucagaggcga gg                                             22
```

<210> SEQ ID NO 562
<211> LENGTH: 23
<212> TYPE: RNA
<213> ORGANISM: Homo sapiens

<400> SEQUENCE: 562
ugugcaaauc uaugcaaaac uga					23

<210> SEQ ID NO 563
<211> LENGTH: 22
<212> TYPE: RNA
<213> ORGANISM: Homo sapiens

<400> SEQUENCE: 563
caaucagcaa guauacugcc cu					22

<210> SEQ ID NO 564
<211> LENGTH: 81
<212> TYPE: RNA
<213> ORGANISM: Homo sapiens

<400> SEQUENCE: 564
uaaaugaaaa aguaguaguc aaauaugcag aucuauguca uauauacaga uauguauaug		60 ugacugcuac uuuuuuguuu a						81

<210> SEQ ID NO 565
<211> LENGTH: 17
<212> TYPE: RNA
<213> ORGANISM: Homo sapiens

<400> SEQUENCE: 565
cagccugaca ggaacag						17

<210> SEQ ID NO 566
<211> LENGTH: 127
<212> TYPE: RNA
<213> ORGANISM: Homo sapiens

<400> SEQUENCE: 566
uucuaaagug uugaguucag uccagggugg auccccugcu cuguuaauug aacuggaaca		60 uuuaaacugg cuaggcaaaa ugccuacaua gaaagcauua cucuuuauuc auccccagcc		120 uacaaaa								127

<210> SEQ ID NO 567
<211> LENGTH: 22
<212> TYPE: RNA
<213> ORGANISM: Homo sapiens

<400> SEQUENCE: 567
caaaguuuaa gauccuugaa gu					22

<210> SEQ ID NO 568
<211> LENGTH: 22
<212> TYPE: RNA
<213> ORGANISM: Homo sapiens

<400> SEQUENCE: 568
cuucugauca agauuugugg ug					22

<210> SEQ ID NO 569
<211> LENGTH: 22

```
<212> TYPE: RNA
<213> ORGANISM: Homo sapiens

<400> SEQUENCE: 569
gaauguugcu cggugaaccc cu                                              22

<210> SEQ ID NO 570
<211> LENGTH: 22
<212> TYPE: RNA
<213> ORGANISM: Homo sapiens

<400> SEQUENCE: 570
gugcauggcu guauauauaa ca                                              22

<210> SEQ ID NO 571
<211> LENGTH: 73
<212> TYPE: RNA
<213> ORGANISM: Homo sapiens

<400> SEQUENCE: 571
ugggcuuugc ccgcuuucug agcuggaccc ucucucuacc ucuggugcag aacuacagcg      60
gaaggaaucu cug                                                        73

<210> SEQ ID NO 572
<211> LENGTH: 71
<212> TYPE: RNA
<213> ORGANISM: Homo sapiens

<400> SEQUENCE: 572
gcauuggaau aggggauauc ucagcauguu gagcccuguc ucugggagc ugacuucuac       60 cucuuccaaa g                                                          71

<210> SEQ ID NO 573
<211> LENGTH: 107
<212> TYPE: RNA
<213> ORGANISM: Homo sapiens

<400> SEQUENCE: 573
auccaaggug auuccuucuc caaggggac auccagugac ccucucagga aguagcaacu       60
uggaauagaa uaguccagga guuccaggac cagccuggcc aauaugg                  107

<210> SEQ ID NO 574
<211> LENGTH: 22
<212> TYPE: RNA
<213> ORGANISM: Homo sapiens

<400> SEQUENCE: 574
gcccucuguc accuugcaga cg                                              22

<210> SEQ ID NO 575
<211> LENGTH: 21
<212> TYPE: RNA
<213> ORGANISM: Homo sapiens

<400> SEQUENCE: 575
aagccucugu ccccaccccca g                                              21

<210> SEQ ID NO 576
<211> LENGTH: 22
<212> TYPE: RNA
<213> ORGANISM: Homo sapiens
```

<400> SEQUENCE: 576
uuagccaauu guccaucuuu ag 22

<210> SEQ ID NO 577
<211> LENGTH: 104
<212> TYPE: RNA
<213> ORGANISM: Homo sapiens

<400> SEQUENCE: 577
aucuuuuugu aguucaugag cgugaugacu gaguguucau gugcaugugu gaggcgugcc 60
acccuuaaac cuuguuauaa caucagcaca uuacccacau gaca 104

<210> SEQ ID NO 578
<211> LENGTH: 21
<212> TYPE: RNA
<213> ORGANISM: Homo sapiens

<400> SEQUENCE: 578
caucccuugc augguggagg g 21

<210> SEQ ID NO 579
<211> LENGTH: 125
<212> TYPE: RNA
<213> ORGANISM: Homo sapiens

<400> SEQUENCE: 579
cuggagacua agaaaccagu ccuugaaguc aagcugacuc ugcuuuuagc cuccuaaauu 60
aaaagauaga uagaauaggu cuuguuugca aaauaaauuc aagaucuacu caucuaucaa 120
uagca 125

<210> SEQ ID NO 580
<211> LENGTH: 22
<212> TYPE: RNA
<213> ORGANISM: Homo sapiens

<400> SEQUENCE: 580
cagugcaaug uuaaaagggc au 22

<210> SEQ ID NO 581
<211> LENGTH: 21
<212> TYPE: RNA
<213> ORGANISM: Homo sapiens

<400> SEQUENCE: 581
cuacaggcug gaaugggcuc a 21

<210> SEQ ID NO 582
<211> LENGTH: 115
<212> TYPE: RNA
<213> ORGANISM: Homo sapiens

<400> SEQUENCE: 582
agcacuugug uuugcuuuug uuugacugu ggacaaagac uuauaguaga caggcacgaa 60
aaaauaaauc cucuuuugca acccaugagu uguuauacau gcaagaagga auauu 115

<210> SEQ ID NO 583
<211> LENGTH: 22
<212> TYPE: RNA
<213> ORGANISM: Homo sapiens

<400> SEQUENCE: 583
ugcccugugg acucaguucu gg                                              22

<210> SEQ ID NO 584
<211> LENGTH: 24
<212> TYPE: RNA
<213> ORGANISM: Homo sapiens

<400> SEQUENCE: 584
cuucugccug cauucuacuc ccag                                            24

<210> SEQ ID NO 585
<211> LENGTH: 22
<212> TYPE: RNA
<213> ORGANISM: Homo sapiens

<400> SEQUENCE: 585
cuauacaacu uacuacuuuc cc                                              22

<210> SEQ ID NO 586
<211> LENGTH: 96
<212> TYPE: RNA
<213> ORGANISM: Homo sapiens

<400> SEQUENCE: 586
cuucugcuaa gguuuacacu auagaugcag gaaaaaaaau guccucacac ugucugucug     60
auuguggcag cugagauuga auagagaaau auggg                               96

<210> SEQ ID NO 587
<211> LENGTH: 23
<212> TYPE: RNA
<213> ORGANISM: Homo sapiens

<400> SEQUENCE: 587
ccggggcaga uugguguagg gug                                             23

<210> SEQ ID NO 588
<211> LENGTH: 82
<212> TYPE: RNA
<213> ORGANISM: Homo sapiens

<400> SEQUENCE: 588
gggucaauga ugagaaccuu auaauguucu gaagagaggu gaugacuuaa aaaucaugcu     60
caauaggauu acgcugaggc cc                                              82

<210> SEQ ID NO 589
<211> LENGTH: 76
<212> TYPE: RNA
<213> ORGANISM: Homo sapiens

<400> SEQUENCE: 589
uacuugaaga gaaguuguuc gugguggauu cgcuuuacuu augacgaauc auucacggac     60
aacacuuuuu ucagua                                                    76

<210> SEQ ID NO 590
<211> LENGTH: 23
<212> TYPE: RNA
<213> ORGANISM: Homo sapiens

```
<400> SEQUENCE: 590 ugaccccau gucgccucug uag                                              23

<210> SEQ ID NO 591
<211> LENGTH: 23
<212> TYPE: RNA
<213> ORGANISM: Homo sapiens

<400> SEQUENCE: 591
ccugcagcga cuugauggcu ucc                                             23

<210> SEQ ID NO 592
<211> LENGTH: 22
<212> TYPE: RNA
<213> ORGANISM: Homo sapiens

<400> SEQUENCE: 592
augcaggccu guguacagca cu                                              22

<210> SEQ ID NO 593
<211> LENGTH: 101
<212> TYPE: RNA
<213> ORGANISM: Homo sapiens

<400> SEQUENCE: 593
gcgagaagau cucaugcugu gacucucugg agggaagcac uuucguugu cugaaagaaa      60 acaaagcgcu ucucuuuaga guguuacggu uugagaaaag c                        101

<210> SEQ ID NO 594
<211> LENGTH: 22
<212> TYPE: RNA
<213> ORGANISM: Homo sapiens

<400> SEQUENCE: 594
ugugacaaua gagaugaaca ug                                              22

<210> SEQ ID NO 595
<211> LENGTH: 82
<212> TYPE: RNA
<213> ORGANISM: Homo sapiens

<400> SEQUENCE: 595
uugcugcaaa aauaauugca guuuuugcca uuauuuuuaa uaauuauaau aauggccaaa     60
acugcaguua uuuuugcacc aa                                              82

<210> SEQ ID NO 596
<211> LENGTH: 72
<212> TYPE: RNA
<213> ORGANISM: Homo sapiens

<400> SEQUENCE: 596
ucugcucuga gagagcucga uggcaggugc cuccguguug ccgaacccuc cuacgcugcu     60
cucucacucc ag                                                         72

<210> SEQ ID NO 597
<211> LENGTH: 20
<212> TYPE: RNA
<213> ORGANISM: Homo sapiens
```

<400> SEQUENCE: 597
ucguuugccu uuuucugcuu                                           20

<210> SEQ ID NO 598
<211> LENGTH: 22
<212> TYPE: RNA
<213> ORGANISM: Homo sapiens

<400> SEQUENCE: 598
gugacugaua ccuuggaggc au                                        22

<210> SEQ ID NO 599
<211> LENGTH: 85
<212> TYPE: RNA
<213> ORGANISM: Homo sapiens

<400> SEQUENCE: 599
cgcuggcgac gggacauuau uacuuuuggu acgcgcugug acacuucaaa cucguaccgu  60
gaguaauaau gcgccgucca cggca                                      85

<210> SEQ ID NO 600
<211> LENGTH: 211
<212> TYPE: RNA
<213> ORGANISM: Homo sapiens

<400> SEQUENCE: 600
aagaugacac uuugaggcau cgugucuaug guucauuacu acagaagcuu cucuggaugu  60
guaaagcaca ggaaaccagg cagaggaggc acagggugcu cuccagaacg agaagccagc 120
uccuggaguu guuugcugca acugccauuc cccguugaug accaugcucu ccuucagaa  180 gagggagagu gagaggacca aguccaagug g                               211

<210> SEQ ID NO 601
<211> LENGTH: 22
<212> TYPE: RNA
<213> ORGANISM: Homo sapiens

<400> SEQUENCE: 601
ucccaagggu gagaugcugc ca                                         22

<210> SEQ ID NO 602
<211> LENGTH: 23
<212> TYPE: RNA
<213> ORGANISM: Homo sapiens

<400> SEQUENCE: 602
aauguggaag uggucugagg cau                                        23

<210> SEQ ID NO 603
<211> LENGTH: 71
<212> TYPE: RNA
<213> ORGANISM: Homo sapiens

<400> SEQUENCE: 603
ggagaggagg caagaugcug gcauagcugu ugaacuggga accugcuaug ccaacauauu  60
gccaucuuuc c                                                     71

<210> SEQ ID NO 604
<211> LENGTH: 66
<212> TYPE: RNA

```
<213> ORGANISM: Homo sapiens

<400> SEQUENCE: 604
ggcugccagg gaggcugguu uggaggaguc ugguggccug uucucuucac cugccucugc      60
cugcag                                                                66

<210> SEQ ID NO 605
<211> LENGTH: 80
<212> TYPE: RNA
<213> ORGANISM: Homo sapiens

<400> SEQUENCE: 605
gguauuuaaa agguagauuu uccuucuaug guuacguguu ugaugguuaa ucauagagga      60
aaauccacgu uuucaguauc                                                 80

<210> SEQ ID NO 606
<211> LENGTH: 22
<212> TYPE: RNA
<213> ORGANISM: Homo sapiens

<400> SEQUENCE: 606
uaacacuguc ugguaacgau gu                                              22

<210> SEQ ID NO 607
<211> LENGTH: 22
<212> TYPE: RNA
<213> ORGANISM: Homo sapiens

<400> SEQUENCE: 607
aucaaauaag gacuagucug ca                                              22

<210> SEQ ID NO 608
<211> LENGTH: 21
<212> TYPE: RNA
<213> ORGANISM: Homo sapiens

<400> SEQUENCE: 608
aggcccuguc cucugcccca g                                               21

<210> SEQ ID NO 609
<211> LENGTH: 24
<212> TYPE: RNA
<213> ORGANISM: Homo sapiens

<400> SEQUENCE: 609
ccucacccag cucucuggcc cucu                                            24

<210> SEQ ID NO 610
<211> LENGTH: 107
<212> TYPE: RNA
<213> ORGANISM: Homo sapiens

<400> SEQUENCE: 610
auccuuuugu gguucauaag caugaugauu agauuuucau gcuauggguu gagauaugcc      60
uuccucagac uuuguuacag cauaggcaca uuacaaccug ucugaua                  107

<210> SEQ ID NO 611
<211> LENGTH: 110
<212> TYPE: RNA
<213> ORGANISM: Homo sapiens
```

<400> SEQUENCE: 611
ccgcagagug ugacuccugu ucuguguaug gcacugguag aauucacugu gaacagucuc    60
agucagugaa uuaccgaagg gccauaaaca gagcagagac agauccacga              110

<210> SEQ ID NO 612
<211> LENGTH: 23
<212> TYPE: RNA
<213> ORGANISM: Homo sapiens

<400> SEQUENCE: 612
agcucggucu gaggccccuc agu                                           23

<210> SEQ ID NO 613
<211> LENGTH: 17
<212> TYPE: RNA
<213> ORGANISM: Homo sapiens

<400> SEQUENCE: 613
uggagagaaa ggcagua                                                  17

<210> SEQ ID NO 614
<211> LENGTH: 72
<212> TYPE: RNA
<213> ORGANISM: Homo sapiens

<400> SEQUENCE: 614
acuccaugau gaacccaaaa ugccaaguau augacugaac uuacaaguga uaccaucuua    60
cgacugaaga gu                                                       72

<210> SEQ ID NO 615
<211> LENGTH: 105
<212> TYPE: RNA
<213> ORGANISM: Homo sapiens

<400> SEQUENCE: 615
auccuuuugu aguucaugag gaugauggu gggguguuuca cacaugugug ugaaauguac    60
cacccucaaa ccuuguuaca augucagcac auuaccugcc ugacc                  105

<210> SEQ ID NO 616
<211> LENGTH: 78
<212> TYPE: RNA
<213> ORGANISM: Homo sapiens

<400> SEQUENCE: 616
uggccgauuu uggcacuagc acauuuuugc uugugucucu ccgcucugag caaucaugug    60
cagugccaau augggaaa                                                 78

<210> SEQ ID NO 617
<211> LENGTH: 21
<212> TYPE: RNA
<213> ORGANISM: Homo sapiens

<400> SEQUENCE: 617
acuccaguuu uaguucucuu g                                             21

<210> SEQ ID NO 618
<211> LENGTH: 23
<212> TYPE: RNA
<213> ORGANISM: Homo sapiens

```
<400> SEQUENCE: 618
ucagcaccag gauauuguug gag                                             23

<210> SEQ ID NO 619
<211> LENGTH: 134
<212> TYPE: RNA
<213> ORGANISM: Homo sapiens

<400> SEQUENCE: 619
ucgaugggug ggauaauccu uaccuguucc ucguuuugga gggcagauag aacaugauga     60
uuggagaugc augaaaugug auuaaugccu cugccuaauc aggacuugca acacccugag    120
uacuccucuc ugau                                                     134

<210> SEQ ID NO 620
<211> LENGTH: 103
<212> TYPE: RNA
<213> ORGANISM: Homo sapiens

<400> SEQUENCE: 620
auccuuuugu aguucauaag ugugaugauu agguuuucac auuugugugu gagauguauc     60
ucccucaaac auuuuaugac aucggcauau uauccuucug aug                     103

<210> SEQ ID NO 621
<211> LENGTH: 22
<212> TYPE: RNA
<213> ORGANISM: Homo sapiens

<400> SEQUENCE: 621
cuccuauaug augccuuucu uc                                              22

<210> SEQ ID NO 622
<211> LENGTH: 21
<212> TYPE: RNA
<213> ORGANISM: Homo sapiens

<400> SEQUENCE: 622
uaaaguaaau augcaccaaa a                                               21

<210> SEQ ID NO 623
<211> LENGTH: 22
<212> TYPE: RNA
<213> ORGANISM: Homo sapiens

<400> SEQUENCE: 623
uugagaauga ugaaucauua gg                                              22

<210> SEQ ID NO 624
<211> LENGTH: 215
<212> TYPE: RNA
<213> ORGANISM: Homo sapiens

<400> SEQUENCE: 624
aagacuauac uuucagggau cauuuguaua guucguuacu agagaauuuu cucugaaugu     60
guagaacacc agaaaccaca aggaggaggc gcagcguucu cuccgagcg ugaagccggg    120 uccuggguguu gcuucacugc aacugccauu ugccauugau gauuguucuu cucuuccuuu  180
gggagaguaa gaggcaaagg augcagucug aaugg                              215

<210> SEQ ID NO 625
<211> LENGTH: 22
```

```
<212> TYPE: RNA
<213> ORGANISM: Homo sapiens

<400> SEQUENCE: 625
aaccaucgac cguugagugg ac                                              22

<210> SEQ ID NO 626
<211> LENGTH: 59
<212> TYPE: RNA
<213> ORGANISM: Homo sapiens

<400> SEQUENCE: 626
ggggccaggc agggaggugg gaccauggggg gccuugcugu gugaccaccg uuccugcag     59

<210> SEQ ID NO 627
<211> LENGTH: 104
<212> TYPE: RNA
<213> ORGANISM: Homo sapiens

<400> SEQUENCE: 627 aucuuuugu aguucauaag caugaugauu auguuuuac auucaugugu aagaugugcc       60
ucccucaaac cuuguuauga ugucagcaua uuaccugucu gaug                      104

<210> SEQ ID NO 628
<211> LENGTH: 21
<212> TYPE: RNA
<213> ORGANISM: Homo sapiens

<400> SEQUENCE: 628
acugacagga gagcauuuug a                                               21

<210> SEQ ID NO 629
<211> LENGTH: 133
<212> TYPE: RNA
<213> ORGANISM: Homo sapiens

<400> SEQUENCE: 629
aagccagcca augaaucugc uuaccugauu guguuugugc agacauacuu uaaaaacugg     60
caauaguaaa gccauguuac gagccuuaag gacaugaag ucguuaaggu cccugagaau      120
ggcuauaaca aau                                                        133

<210> SEQ ID NO 630
<211> LENGTH: 22
<212> TYPE: RNA
<213> ORGANISM: Homo sapiens

<400> SEQUENCE: 630
aguauucugu accagggaag gu                                              22

<210> SEQ ID NO 631
<211> LENGTH: 133
<212> TYPE: RNA
<213> ORGANISM: Homo sapiens

<400> SEQUENCE: 631
uccaucuguu uggcagaccu ggagcaguua gugucugcug cuaagguuuc cauuacagau     60
gugagaaaaa aaaguguucu ucugcuuucu gucugucuca guggcaacca agauugaaug    120
ggggauauga gag                                                        133

<210> SEQ ID NO 632
```

```
<211> LENGTH: 104
<212> TYPE: RNA
<213> ORGANISM: Homo sapiens

<400> SEQUENCE: 632
auucuuuugu aauucauaag caugaugacu cgguauucac gugcaugugu gagaugugcc    60
acccuggaac cuuguugcaa cgucagcaca uuaugggucu gaca                    104

<210> SEQ ID NO 633
<211> LENGTH: 72
<212> TYPE: RNA
<213> ORGANISM: Homo sapiens

<400> SEQUENCE: 633
augaccaaug gugagagugu aucaugaagc aaggaaugug auuaauccag uucuguaaac    60
ccaaguucca gu                                                       72

<210> SEQ ID NO 634
<211> LENGTH: 24
<212> TYPE: RNA
<213> ORGANISM: Homo sapiens

<400> SEQUENCE: 634
uuggaagcuu ggaccaacua gcug                                          24

<210> SEQ ID NO 635
<211> LENGTH: 105
<212> TYPE: RNA
<213> ORGANISM: Homo sapiens

<400> SEQUENCE: 635
auccuuuugu aguucaugag caugaccauc gaguguuuac augcaugugu gagauaugac    60
accuucugaa ccuuguuacg gaguuggcau guuacccauc uaacc                   105

<210> SEQ ID NO 636
<211> LENGTH: 202
<212> TYPE: RNA
<213> ORGANISM: Homo sapiens

<400> SEQUENCE: 636
aagauuauau uuucagggau cauuucuaua guuugcacu agggaaguuc cucugaaugu     60
guagagcacc agaaacauga ggaagaggca cagguucuc uccgagugu gaagcuggcu    120 cuuggcgcug cuuuccugca acugcuauuu gccaucgug auugggaga gucagaggga    180 gaggaugaug cagucugagu gg                                           202

<210> SEQ ID NO 637
<211> LENGTH: 85
<212> TYPE: RNA
<213> ORGANISM: Homo sapiens

<400> SEQUENCE: 637
auccuuuugu aguucaugag caugaugauu ggguguucac gugcaugugu gagaugugac    60
acccuugcac auuacucgcc ugacc                                         85

<210> SEQ ID NO 638
<211> LENGTH: 22
<212> TYPE: RNA
<213> ORGANISM: Homo sapiens
```

<400> SEQUENCE: 638
agacccuggu cugcacucua uc                                      22

<210> SEQ ID NO 639
<211> LENGTH: 22
<212> TYPE: RNA
<213> ORGANISM: Homo sapiens

<400> SEQUENCE: 639
uaacaaacac cuguaaaaca gc                                      22

<210> SEQ ID NO 640
<211> LENGTH: 110
<212> TYPE: RNA
<213> ORGANISM: Homo sapiens

<400> SEQUENCE: 640
ugcccaguga ugacaccauc cuugcucccc gugcccccca ggggcuaugg gcgacaccau    60
ggcugccccu gggcugggcc aguggggcca augcccaggg gcugagggca               110

<210> SEQ ID NO 641
<211> LENGTH: 72
<212> TYPE: RNA
<213> ORGANISM: Homo sapiens

<400> SEQUENCE: 641
cagccaggag ggaaggggcu gagaacagga ccugugcuca cuggggccug caugacccuu    60 cccucccccac ag                                                72

<210> SEQ ID NO 642
<211> LENGTH: 68
<212> TYPE: RNA
<213> ORGANISM: Homo sapiens

<400> SEQUENCE: 642
acucacugau gaguagcuuc ugacuuucau ucgaguuug cugaacccag augccauucc     60
ugggaagg                                                      68

<210> SEQ ID NO 643
<211> LENGTH: 103
<212> TYPE: RNA
<213> ORGANISM: Homo sapiens

<400> SEQUENCE: 643
auccuuuugu gguucauuag cuugauauug gguuuucaca cuauucuaug agaugugccu    60
cccucaaaac uuguuacaac auugacacau uacccuucug aug                103

<210> SEQ ID NO 644
<211> LENGTH: 81
<212> TYPE: RNA
<213> ORGANISM: Homo sapiens

<400> SEQUENCE: 644
uauuaauaug gaagggagaa gagcuuuaau gauuggaguc auuuucagag cauuaaagcu    60
cuucucccuu ccauauuaau g                                       81

<210> SEQ ID NO 645
<211> LENGTH: 87
<212> TYPE: RNA

```
<213> ORGANISM: Homo sapiens

<400> SEQUENCE: 645
ucucaggcug ugacccucua aagggaagcg cuuucugugg ucagaaagaa aagcaagugc      60
uuccuuuuag aggguuaccg uuuggga                                         87

<210> SEQ ID NO 646
<211> LENGTH: 21
<212> TYPE: RNA
<213> ORGANISM: Homo sapiens

<400> SEQUENCE: 646
uucuuuguuu uuaauucaca g                                               21

<210> SEQ ID NO 647
<211> LENGTH: 21
<212> TYPE: RNA
<213> ORGANISM: Homo sapiens

<400> SEQUENCE: 647
uuuuaaggac acugagggau c                                               21

<210> SEQ ID NO 648
<211> LENGTH: 75
<212> TYPE: RNA
<213> ORGANISM: Homo sapiens

<400> SEQUENCE: 648
gaauguggga aagagaaaga acaaguaaaa ggaauuuuca uuuccagcc ccuaauuguu      60 cugucuuucu cccag                                                      75

<210> SEQ ID NO 649
<211> LENGTH: 60
<212> TYPE: RNA
<213> ORGANISM: Homo sapiens

<400> SEQUENCE: 649
ucggcuaagg aaguccugug cucaguuuug uagcaucaaa acuaggauuu cucuuguuac      60

<210> SEQ ID NO 650
<211> LENGTH: 71
<212> TYPE: RNA
<213> ORGANISM: Homo sapiens

<400> SEQUENCE: 650
uggaucgaug augacugcug guggcguaug agucauaugc gaugaauacg ugucuagaac      60
ucugaggucc a                                                          71

<210> SEQ ID NO 651
<211> LENGTH: 67
<212> TYPE: RNA
<213> ORGANISM: Homo sapiens

<400> SEQUENCE: 651
cccggugugu guguagagga agaagggaag cugggaaccu gacugccucu cccucuuuac      60
ccacuag                                                               67

<210> SEQ ID NO 652
<211> LENGTH: 26
<212> TYPE: RNA
<213> ORGANISM: Homo sapiens
```

```
<400> SEQUENCE: 652
aaguaguugg uuuguaugag augguu                                     26

<210> SEQ ID NO 653
<211> LENGTH: 21
<212> TYPE: RNA
<213> ORGANISM: Homo sapiens

<400> SEQUENCE: 653
aucacauugc cagggauuuc c                                          21

<210> SEQ ID NO 654
<211> LENGTH: 104
<212> TYPE: RNA
<213> ORGANISM: Homo sapiens

<400> SEQUENCE: 654
auucuuuugu aguucuuagg cacgaugauu ggguguucau gugcauguuu gagaugugcc 60
ucccucaaac cuuguucuua caucagcacc uuacacgucu aaca                 104

<210> SEQ ID NO 655
<211> LENGTH: 18
<212> TYPE: RNA
<213> ORGANISM: Homo sapiens

<400> SEQUENCE: 655
cauucaacua gugauugu                                              18

<210> SEQ ID NO 656
<211> LENGTH: 53
<212> TYPE: RNA
<213> ORGANISM: Homo sapiens

<400> SEQUENCE: 656
gccuucucuu cccaguucuu ccuggagucg gggaaaagcu ggguugagaa ggu        53

<210> SEQ ID NO 657
<211> LENGTH: 104
<212> TYPE: RNA
<213> ORGANISM: Homo sapiens

<400> SEQUENCE: 657
aguuuuucau aguucauaag caugaugagu ggguuuucau guucaugugu gaggugugcc 60
ucccucaaac cuuguuauga ugucaacaca uugcccaucu gaug                 104

<210> SEQ ID NO 658
<211> LENGTH: 75
<212> TYPE: RNA
<213> ORGANISM: Homo sapiens

<400> SEQUENCE: 658
ugcagaugau guaaaagaau auuugcuauc ugagagaugg ugaugacauu uuaaaccacc 60
aagaucgcug augca                                                 75

<210> SEQ ID NO 659
<211> LENGTH: 21
<212> TYPE: RNA
<213> ORGANISM: Homo sapiens
```

```
<400> SEQUENCE: 659
gcugcaccgg agacugggua a                                               21

<210> SEQ ID NO 660
<211> LENGTH: 23
<212> TYPE: RNA
<213> ORGANISM: Homo sapiens

<400> SEQUENCE: 660
cuacccucgg ucugcuuacc aca                                             23

<210> SEQ ID NO 661
<211> LENGTH: 74
<212> TYPE: RNA
<213> ORGANISM: Homo sapiens

<400> SEQUENCE: 661
agcaauugga aagauugca gaguaaguuc cugauuaaga aauggaauuu acucugcaau      60
cuucuccaau ugcu                                                       74

<210> SEQ ID NO 662
<211> LENGTH: 98
<212> TYPE: RNA
<213> ORGANISM: Homo sapiens

<400> SEQUENCE: 662
aggagccacc uuccgagccu ccaguaccac gugucagggc cacaugagcu gggccucgug     60
ggccugaugu ggugcugggg ccucaggggu cugcucuu                             98

<210> SEQ ID NO 663
<211> LENGTH: 86
<212> TYPE: RNA
<213> ORGANISM: Homo sapiens

<400> SEQUENCE: 663
cucaccucau ucauuuaccu ucucuuacag aucacuuuuc ugcacuggac agugaucugu     60
aagagaaagu aaaugaaaga ggugag                                          86

<210> SEQ ID NO 664
<211> LENGTH: 21
<212> TYPE: RNA
<213> ORGANISM: Homo sapiens

<400> SEQUENCE: 664
aaaaguaauu gcaguuuuug c                                               21

<210> SEQ ID NO 665
<211> LENGTH: 85
<212> TYPE: RNA
<213> ORGANISM: Homo sapiens

<400> SEQUENCE: 665
uccuccccgg agccaggaug cagcucaagc cacagcaggg uguuuagcgc ucuucagugg     60
cuccagauug uggcgcuggu gcagg                                           85

<210> SEQ ID NO 666
<211> LENGTH: 82
<212> TYPE: RNA
<213> ORGANISM: Homo sapiens
```

```
<400> SEQUENCE: 666
gggucaauga ugagaaccgu auauuguccu gaagagcggu gaugacuuaa aaauaaugcu    60
caauaggauu acgcugaggc cc                                            82

<210> SEQ ID NO 667
<211> LENGTH: 19
<212> TYPE: RNA
<213> ORGANISM: Homo sapiens

<400> SEQUENCE: 667 ugaggugggua ggauguaga                                               19

<210> SEQ ID NO 668
<211> LENGTH: 90
<212> TYPE: RNA
<213> ORGANISM: Homo sapiens

<400> SEQUENCE: 668
aagacccuuc agcugcaaac aacagcuucc uugguaguuu augcagccug uuucuuguau    60
gggcugcucu aagggaccau ggagacaggc                                    90

<210> SEQ ID NO 669
<211> LENGTH: 22
<212> TYPE: RNA
<213> ORGANISM: Homo sapiens

<400> SEQUENCE: 669
agcuguaauu agucaguuuu cu                                            22

<210> SEQ ID NO 670
<211> LENGTH: 49
<212> TYPE: RNA
<213> ORGANISM: Homo sapiens

<400> SEQUENCE: 670
uucccagcca acgcaccaaa aaugauaugg gucuguuguc uggagaaac               49

<210> SEQ ID NO 671
<211> LENGTH: 100
<212> TYPE: RNA
<213> ORGANISM: Homo sapiens

<400> SEQUENCE: 671
auacuuuugu aggucauaag cugaggauug gguuucaug cucuugugug agauaugcuu    60
cucucaaacc uucugaccug ggcacauuac ccagcuaaug                        100

<210> SEQ ID NO 672
<211> LENGTH: 20
<212> TYPE: RNA
<213> ORGANISM: Homo sapiens

<400> SEQUENCE: 672
ccugcguguu uucuguccaa                                               20

<210> SEQ ID NO 673
<211> LENGTH: 102
<212> TYPE: RNA
<213> ORGANISM: Homo sapiens
```

<400> SEQUENCE: 673
uuccuguugg uuccuaagug ugaugauugg guuuucacau ucaugugug a caugugccuc    60 ccucaaaucu ugugaugaug ucggcacgug acccaucuga cg    102

<210> SEQ ID NO 674
<211> LENGTH: 100
<212> TYPE: RNA
<213> ORGANISM: Homo sapiens

<400> SEQUENCE: 674
cccccagaau cugucaggca ccagccaggc auugcucagc ccguucccu cuggggagc    60 aaggaguggu gcuggguuug ucucugcugg gguuucccu    100

<210> SEQ ID NO 675
<211> LENGTH: 21
<212> TYPE: RNA
<213> ORGANISM: Homo sapiens

<400> SEQUENCE: 675
gcuaguccug acucagccag u    21

<210> SEQ ID NO 676
<211> LENGTH: 76
<212> TYPE: RNA
<213> ORGANISM: Homo sapiens

<400> SEQUENCE: 676
acaaugauga cuuaaauuac uuuuugccgu uacccagcu gagguugucu uugaagaaau    60
aauuuuaaga cugaga    76

<210> SEQ ID NO 677
<211> LENGTH: 21
<212> TYPE: RNA
<213> ORGANISM: Homo sapiens

<400> SEQUENCE: 677
cacaagguau ugguauuacc u    21

<210> SEQ ID NO 678
<211> LENGTH: 130
<212> TYPE: RNA
<213> ORGANISM: Homo sapiens

<400> SEQUENCE: 678
uggacauuua uuuuuauuca guuuuuucuc aaggugaagg uaacguuug uagauguccu    60 agagaaauau uguagcuuuc uguucacccu uugcaacuaa aaagcaugga cguuccacu    120 acugagauuu    130

<210> SEQ ID NO 679
<211> LENGTH: 131
<212> TYPE: RNA
<213> ORGANISM: Homo sapiens

<400> SEQUENCE: 679
cuucccauuu auuugcugcu auagcucau aaugauacaa gcaguuauau gcaugggaua    60
aaauaauauu gggacauugu aaauugaaau gaaguaacca uuucaucuu uucugcaugg    120 acaagacauu g    131

```
<210> SEQ ID NO 680
<211> LENGTH: 60
<212> TYPE: RNA
<213> ORGANISM: Homo sapiens

<400> SEQUENCE: 680
ugugaaugac ccccuuccag agccaaaauc accagggaug gaggaggggu cuugggurcu      60

<210> SEQ ID NO 681
<211> LENGTH: 23
<212> TYPE: RNA
<213> ORGANISM: Homo sapiens

<400> SEQUENCE: 681
uugaagagga ggugcucugu agc                                             23

<210> SEQ ID NO 682
<211> LENGTH: 105
<212> TYPE: RNA
<213> ORGANISM: Homo sapiens

<400> SEQUENCE: 682
gaguucuaac guauuagguu ggugcaaaag uaauaguggu uuugccauu aaaaguaaug       60 acaaaaacug uaauuacuuu uggaacaaua uuaauagaau uucag                    105

<210> SEQ ID NO 683
<211> LENGTH: 72
<212> TYPE: RNA
<213> ORGANISM: Homo sapiens

<400> SEQUENCE: 683
ggucaaugau guaauggcau guauuagcug aauccaaagu ugaagugaau ucuaaaauua     60
caccaagacc uu                                                         72

<210> SEQ ID NO 684
<211> LENGTH: 89
<212> TYPE: RNA
<213> ORGANISM: Homo sapiens

<400> SEQUENCE: 684
gucagcagug ccuuagcagc acguaaauau uggcguuaag auucuaaaau uaucccagu       60 auuaacugug cugcugaagu aagguugac                                       89

<210> SEQ ID NO 685
<211> LENGTH: 134
<212> TYPE: RNA
<213> ORGANISM: Homo sapiens

<400> SEQUENCE: 685
uguucugaca ugggaagagu agcuucuggu uggugagcc caucucacau uagccagaga       60
caaagcaaca ccuuguuuau cccggcuugg cuuuuggccu guguccauga cugguccaua    120
ccuuggacac augg                                                      134

<210> SEQ ID NO 686
<211> LENGTH: 104
<212> TYPE: RNA
<213> ORGANISM: Homo sapiens
```

```
<400> SEQUENCE: 686
aucccuuugu aguucauaag cgugaugauu ggguguucau gcucauacau gagcugugcc      60
ucccucaagc uuuguuguga caucaucaua uuaccugucc gaug                     104

<210> SEQ ID NO 687
<211> LENGTH: 22
<212> TYPE: RNA
<213> ORGANISM: Homo sapiens

<400> SEQUENCE: 687
accugccagc accucccugc ag                                              22

<210> SEQ ID NO 688
<211> LENGTH: 65
<212> TYPE: RNA
<213> ORGANISM: Homo sapiens

<400> SEQUENCE: 688
gagggcuagg uggggggcuu gaagccccga gaugccucac gcuucacccc cucucaccua      60
agcag                                                                 65

<210> SEQ ID NO 689
<211> LENGTH: 22
<212> TYPE: RNA
<213> ORGANISM: Homo sapiens

<400> SEQUENCE: 689
caucuuccag uacaguguug ga                                              22

<210> SEQ ID NO 690
<211> LENGTH: 67
<212> TYPE: RNA
<213> ORGANISM: Homo sapiens

<400> SEQUENCE: 690
gcgggcuucg cgggcgaagg caaagucgau uuccaaaagu gacuuccuc acucccguga       60 agucggc                                                               67

<210> SEQ ID NO 691
<211> LENGTH: 21
<212> TYPE: RNA
<213> ORGANISM: Homo sapiens

<400> SEQUENCE: 691
aguuaaugaa uccuggaaag u                                               21

<210> SEQ ID NO 692
<211> LENGTH: 135
<212> TYPE: RNA
<213> ORGANISM: Homo sapiens

<400> SEQUENCE: 692
ugccccugac cugggaagag aggggccugg cuggugguau ccaucucaua ccagcuaggg      60
augaagaaac cgcuugcuca ucccagccug gcuccgguc uaugcccaug ccugguucgu     120
gccuuggaca uauca                                                     135

<210> SEQ ID NO 693
<211> LENGTH: 19
<212> TYPE: RNA
```

<213> ORGANISM: Homo sapiens

<400> SEQUENCE: 693
agagcuggcu gaagggcag                                            19

<210> SEQ ID NO 694
<211> LENGTH: 75
<212> TYPE: RNA
<213> ORGANISM: Homo sapiens

<400> SEQUENCE: 694
cagggguuug gggaaacggc cgcugaguga ggcgucggcu guguucuca ccgcggucuu    60 uuccucccac ucuug                                                75

<210> SEQ ID NO 695
<211> LENGTH: 120
<212> TYPE: RNA
<213> ORGANISM: Homo sapiens

<400> SEQUENCE: 695
gauccaggga acccuagagc aggggggaugg cagagcaaaa ucauggccu acagcugccu   60 cuugccaaac ugcacuggau uuugugucuc ccauucccca gagcugucug aggugcuuug  120

<210> SEQ ID NO 696
<211> LENGTH: 83
<212> TYPE: RNA
<213> ORGANISM: Homo sapiens

<400> SEQUENCE: 696
uucacaaugu cuauugaagg aucucaucac cuuuagagag cuguggucau gccccuuaaa   60
gugaauuugg agguuuuaua ccc                                        83

<210> SEQ ID NO 697
<211> LENGTH: 96
<212> TYPE: RNA
<213> ORGANISM: Homo sapiens

<400> SEQUENCE: 697
gugacccugg gcaaguuccu gaagaucaga cacaucagau cccuuaucug uaaaaugggc   60
augauccagg aaccugccuc uacgguugcc uugggg                          96

<210> SEQ ID NO 698
<211> LENGTH: 86
<212> TYPE: RNA
<213> ORGANISM: Homo sapiens

<400> SEQUENCE: 698
cuuacaucac acacagaguu aacucaaaau ggacuaauuu uuccacuagu uaguccauuu   60
caaguuaacu cuguguguga uguagu                                     86

<210> SEQ ID NO 699
<211> LENGTH: 127
<212> TYPE: RNA
<213> ORGANISM: Homo sapiens

<400> SEQUENCE: 699
auuacuugaa aaucacuccc aggcuuuggc cauggcagca ggugagauuc aaggcccaga   60
gccuccaggg ccucagcuca ccgcacacug ccccgugugu ggugggggaaa cccagaccccc 120 aacaggu                                                         127

```
<210> SEQ ID NO 700
<211> LENGTH: 22
<212> TYPE: RNA
<213> ORGANISM: Homo sapiens

<400> SEQUENCE: 700
caggucacgu cucugcaguu ac                                              22

<210> SEQ ID NO 701
<211> LENGTH: 149
<212> TYPE: RNA
<213> ORGANISM: Homo sapiens

<400> SEQUENCE: 701
caucaagacc cagcugaguc acugucacug ccuaccaauc ucgaccggac cucgaccggc     60
ucgucugugu ugccaaucga cucggcgugg cgucggucgu gguagauagg cggucaugca    120
uacgaauuuu cagcucuugu ucuggugac                                     149

<210> SEQ ID NO 702
<211> LENGTH: 136
<212> TYPE: RNA
<213> ORGANISM: Homo sapiens

<400> SEQUENCE: 702
ccucuucuca gaacacuucc ugggucugau ugguggccca gggagcuguc agagaagagc     60
agagcaaaug gccuucacuu uguagaugag auggcaggag gguggauugu uggucucagu    120 caguggugggg acagac                                                   136

<210> SEQ ID NO 703
<211> LENGTH: 22
<212> TYPE: RNA
<213> ORGANISM: Homo sapiens

<400> SEQUENCE: 703
aucaugaugg gcuccucggu gu                                              22

<210> SEQ ID NO 704
<211> LENGTH: 129
<212> TYPE: RNA
<213> ORGANISM: Homo sapiens

<400> SEQUENCE: 704
aagcaggauu cagacuacaa uauagcuguu aagugcugua uugucauucc cccugcucaa     60
auuaaaguug uuucuuaacu auacccaucu gcuauucugu agcagccagg gaugcuuggu    120
cacauacau                                                            129

<210> SEQ ID NO 705
<211> LENGTH: 136
<212> TYPE: RNA
<213> ORGANISM: Homo sapiens

<400> SEQUENCE: 705
gcuguccugg accuguuggc accacagaca guugcucugc ugugccugug gccucggggc     60
aaagagaaag uggcgauuuc uacacucagu gcucgggaac caguggggcac ugagaauggu   120 uuauggccug acauua                                                    136

<210> SEQ ID NO 706
```

```
<211> LENGTH: 136
<212> TYPE: RNA
<213> ORGANISM: Homo sapiens

<400> SEQUENCE: 706
ucgucaggug ggagaauucu uacauguucc uccuuuugca aggcagauua gaacaugaug      60 auuggguuc gcauaauaug ugauuaacgu uucuguguaa ucaggacuug caacaucccg      120
aaugcccuua ccugac                                                    136

<210> SEQ ID NO 707
<211> LENGTH: 72
<212> TYPE: RNA
<213> ORGANISM: Homo sapiens

<400> SEQUENCE: 707
uggaucaaug augacaaagu aucaugaaug agggauugug aauaaucuau uuuaugaac      60 cuguggucaa au                                                         72

<210> SEQ ID NO 708
<211> LENGTH: 22
<212> TYPE: RNA
<213> ORGANISM: Homo sapiens

<400> SEQUENCE: 708
uaugucugcu gaccaucacc uu                                              22

<210> SEQ ID NO 709
<211> LENGTH: 74
<212> TYPE: RNA
<213> ORGANISM: Homo sapiens

<400> SEQUENCE: 709
ugaggaugaa agacccauug aggagaaggu ucugcuggcu gagaaccuuc cucuccaugg      60
gucuuucauc cuca                                                       74

<210> SEQ ID NO 710
<211> LENGTH: 101
<212> TYPE: RNA
<213> ORGANISM: Homo sapiens

<400> SEQUENCE: 710
auccuuuugu gguucauaag aauagggauu gggauuucac acucaugugu gagaugugcc      60
ucccuuaaac cuuaagaugu uggcacauua ccuauuugau g                        101

<210> SEQ ID NO 711
<211> LENGTH: 104
<212> TYPE: RNA
<213> ORGANISM: Homo sapiens

<400> SEQUENCE: 711
auccuuuugu aguucauuag cauaaugauu ggguuucac acucaggcgu gagaugugcc      60
ucucucaaac cuugcuacga uguuggcaca uugccuaucu ggca                     104

<210> SEQ ID NO 712
<211> LENGTH: 21
<212> TYPE: RNA
<213> ORGANISM: Homo sapiens

<400> SEQUENCE: 712
aaaauuucuu ucacuacuua g                                               21
```

```
<210> SEQ ID NO 713
<211> LENGTH: 22
<212> TYPE: RNA
<213> ORGANISM: Homo sapiens

<400> SEQUENCE: 713
uuuuucauua uugcuccuga cc                                              22

<210> SEQ ID NO 714
<211> LENGTH: 129
<212> TYPE: RNA
<213> ORGANISM: Homo sapiens

<400> SEQUENCE: 714
cucauaccua aacccaagaa ucacuuucuu auagugauga uuuaaacaga ugcaaacagc     60
gagcacaucu ugucaccuuu gcgggacugu ggcugugccc cucgcaguaa auuuggaggu    120
ucuacaucc                                                           129

<210> SEQ ID NO 715
<211> LENGTH: 77
<212> TYPE: RNA
<213> ORGANISM: Homo sapiens

<400> SEQUENCE: 715
uguuuaucuc uagggugau cuauuagaau uacuuaucug agccaaagua auucaaguaa      60
uucaggugua gugaaac                                                   77

<210> SEQ ID NO 716
<211> LENGTH: 212
<212> TYPE: RNA
<213> ORGANISM: Homo sapiens

<400> SEQUENCE: 716
aaugcuauac uuucaugggu cauuucuaua guuuguuauu agagaaguuu cucugaaugu     60
guugagcacc agaaaccacg aggagaugca gcauucucuc cugaacggga agccagcuuu    120
uggcauugcu uugaugcaac uaccauuugc cauugauggc aaugcaucgc uuccucuagg    180
aguguaagag ggaguggaug cagucagagu gg                                  212

<210> SEQ ID NO 717
<211> LENGTH: 88
<212> TYPE: RNA
<213> ORGANISM: Homo sapiens

<400> SEQUENCE: 717
accaaguuuc aguucaugua aacauccuac acucagcugu aauacaugga uuggcuggga     60
gguggauguu uacuucagcu gacuugga                                       88

<210> SEQ ID NO 718
<211> LENGTH: 96
<212> TYPE: RNA
<213> ORGANISM: Homo sapiens

<400> SEQUENCE: 718
uucaaaaaag accauauauc cuugaagagu aacugcugaa cuuauucacu ggcagugggc     60
cuuauagcac agugaaugac cagguuagag acaugc                              96

<210> SEQ ID NO 719
```

```
<211> LENGTH: 22
<212> TYPE: RNA
<213> ORGANISM: Homo sapiens

<400> SEQUENCE: 719
auucugcauu uuuagcaagu uc                                              22

<210> SEQ ID NO 720
<211> LENGTH: 133
<212> TYPE: RNA
<213> ORGANISM: Homo sapiens

<400> SEQUENCE: 720
uucucaccua aacccaagaa ucacuguuuc uuauagcggu gguuuaaaca gaggugcaaa     60
cagcaaguga aucucgucgc cuuugcgggg cuguggccau gccccucaaa ggaaauuugg    120
aggcucuaca gcc                                                      133

<210> SEQ ID NO 721
<211> LENGTH: 109
<212> TYPE: RNA
<213> ORGANISM: Homo sapiens

<400> SEQUENCE: 721 gcuuuauau uguagguuuu ugcucaugca ccaugguugu cugagcaugc agcaugcuug      60
ucugcucaua ccccaugguu ucugagcagg aaccuucauu gucuacugc                109

<210> SEQ ID NO 722
<211> LENGTH: 97
<212> TYPE: RNA
<213> ORGANISM: Homo sapiens

<400> SEQUENCE: 722
aucugaguug ggagggucccc ucccaaaug ugucuugggg uggggauca agacacauuu      60 ggagagggaa ccucccaacu cggccucugc caucauu                             97

<210> SEQ ID NO 723
<211> LENGTH: 115
<212> TYPE: RNA
<213> ORGANISM: Homo sapiens

<400> SEQUENCE: 723
ucuguuuauc accagauccu agaacccuau caauauugc ucugcugugu aaauaguucu      60
gaguagugca auauugcuua uagguuuug guguuuggaa agaacaaugg gcagg          115

<210> SEQ ID NO 724
<211> LENGTH: 140
<212> TYPE: RNA
<213> ORGANISM: Homo sapiens

<400> SEQUENCE: 724
auccaaggcg auucccucuc caaggggaca ucuagugccc cucucaggaa aguagcaacu     60
uggaauagaa ucuggcaugc cuaaggucuu ugaggaacag ggaugcuuau uuccucugcc    120
uuccuuggcu gccuacauag                                                140

<210> SEQ ID NO 725
<211> LENGTH: 77
<212> TYPE: RNA
<213> ORGANISM: Homo sapiens
```

<400> SEQUENCE: 725
ugauagggaa accaggcaag aaauauuguc uccucaaguu gcgacgagac aguaguucuu     60
gccugguuuc ucuauca                                                    77

<210> SEQ ID NO 726
<211> LENGTH: 56
<212> TYPE: RNA
<213> ORGANISM: Homo sapiens

<400> SEQUENCE: 726
ccacugcaga gccugggaag ggagcugucc ggcucceccag gcucugcagu gggagg         56

<210> SEQ ID NO 727
<211> LENGTH: 72
<212> TYPE: RNA
<213> ORGANISM: Homo sapiens

<400> SEQUENCE: 727
ccuggugaug acagacgaca uugucagcca aucccccaugu gguagugagg acaugccug      60 caguucugaa gg                                                         72

<210> SEQ ID NO 728
<211> LENGTH: 128
<212> TYPE: RNA
<213> ORGANISM: Homo sapiens

<400> SEQUENCE: 728
ugcacuuaug uauguuuuug uuuaacuugu ggacaaagac uuuaggaaag gugcaaaaaa     60
uaaaucuucu uuugcaaccc agaacucauu guucaguaug aguuuugaua cauaucagaa    120
uggauacu                                                             128

<210> SEQ ID NO 729
<211> LENGTH: 21
<212> TYPE: RNA
<213> ORGANISM: Homo sapiens

<400> SEQUENCE: 729
ucacgcggag agauggcuuu g                                               21

<210> SEQ ID NO 730
<211> LENGTH: 123
<212> TYPE: RNA
<213> ORGANISM: Homo sapiens

<400> SEQUENCE: 730
ugccccuuuu aagguugaca cagugcauua agcagaaggg uuaaguaagu cuccauaaaa     60
cccagagaag agaauguaaa gcuccucuuu ggaggagcua gacuccuguc uggagucaca    120
gcu                                                                  123

<210> SEQ ID NO 731
<211> LENGTH: 95
<212> TYPE: RNA
<213> ORGANISM: Homo sapiens

<400> SEQUENCE: 731
agugauauaa uagagggugc acaggcaugg gaggucaggu gagcucagcu cccugccuca     60
ccugagcucc cgugccugug cacccucuau uggcu                                95

```
<210> SEQ ID NO 732
<211> LENGTH: 23
<212> TYPE: RNA
<213> ORGANISM: Homo sapiens

<400> SEQUENCE: 732
cggggccaug gagcagccug ugu                                              23

<210> SEQ ID NO 733
<211> LENGTH: 103
<212> TYPE: RNA
<213> ORGANISM: Homo sapiens

<400> SEQUENCE: 733
aggaauuuuu aacccgauca cuagauuauc uacaagggaa uuuuuuuua auuuaaaaaa        60 uucccuugua gauaacccgg uggucagguu ggauggcucc aug                       103

<210> SEQ ID NO 734
<211> LENGTH: 139
<212> TYPE: RNA
<213> ORGANISM: Homo sapiens

<400> SEQUENCE: 734
ugcacugcgu gguaucugca cucagcaguu uacuccugcu aggguguuca aaggucagug       60
ccauagaaau ccaguaucug guuucauugg uuuucuuggc uuugugcuug uuaaaccugg      120
uauuucuauu gauacagca                                                  139

<210> SEQ ID NO 735
<211> LENGTH: 22
<212> TYPE: RNA
<213> ORGANISM: Homo sapiens

<400> SEQUENCE: 735
guugggacaa gaggacgguc uu                                               22

<210> SEQ ID NO 736
<211> LENGTH: 21
<212> TYPE: RNA
<213> ORGANISM: Homo sapiens

<400> SEQUENCE: 736
aaaaacugca aucacuuuug c                                                21

<210> SEQ ID NO 737
<211> LENGTH: 22
<212> TYPE: RNA
<213> ORGANISM: Homo sapiens

<400> SEQUENCE: 737
agguggaugc aaugugaccu ca                                               22

<210> SEQ ID NO 738
<211> LENGTH: 93
<212> TYPE: RNA
<213> ORGANISM: Homo sapiens

<400> SEQUENCE: 738
gugcuuccug cgggcugagc gcgggcugag cgcugccagu cagcgcucac auuaaggcug       60
acagcgcccu gccuggcucg gccggcgaag cuc                                   93
```

-continued

```
<210> SEQ ID NO 739
<211> LENGTH: 87
<212> TYPE: RNA
<213> ORGANISM: Homo sapiens

<400> SEQUENCE: 739
ucucagccug ugacccucua gagggaagcg cuuucuguug ucugaaagaa aagaaagugc    60
aucuuuuuag aggauuacag uuugaga                                       87

<210> SEQ ID NO 740
<211> LENGTH: 22
<212> TYPE: RNA
<213> ORGANISM: Homo sapiens

<400> SEQUENCE: 740
ugcaacuuac cugagucauu ga                                            22

<210> SEQ ID NO 741
<211> LENGTH: 22
<212> TYPE: RNA
<213> ORGANISM: Homo sapiens

<400> SEQUENCE: 741
cacuguuuca ccacuggcuc uu                                            22

<210> SEQ ID NO 742
<211> LENGTH: 91
<212> TYPE: RNA
<213> ORGANISM: Homo sapiens

<400> SEQUENCE: 742
uauaacauug uauauaccca cugugauauu aagaguaaua gcucucuagg uuauuaugaa    60
uaauaucaca guagguguac acaauguugu a                                  91

<210> SEQ ID NO 743
<211> LENGTH: 127
<212> TYPE: RNA
<213> ORGANISM: Homo sapiens

<400> SEQUENCE: 743
cuggagacua agaaaauaga guccuugaaa ucaagcugac ucugcuuuua gccuccuaaa    60 ugaaaggua gauagaacag gucuuguuug caaaauaaau ucaagaccua cuuaucuacc   120
aacagca                                                            127

<210> SEQ ID NO 744
<211> LENGTH: 87
<212> TYPE: RNA
<213> ORGANISM: Homo sapiens

<400> SEQUENCE: 744
gcccauuugc cuuggcuugg gguggcaguc cugugggaau gagagaugcc aaacuggacc    60
ugccagcccc guuccagggc acagcau                                       87

<210> SEQ ID NO 745
<211> LENGTH: 208
<212> TYPE: RNA
<213> ORGANISM: Homo sapiens
```

<400> SEQUENCE: 745
ccaaugugga uacacccagg aggucacucu cuccccaggc uguguccaag uagcauaggg    60
gagcacaggg cucugucccc augauguacu guccuuuucc augacauugg agaugaagcu   120
ggaccucaac ucugcacaug cauauuccua caacuuucuca gaguccugug gauaaugacg  180
gaggagagaa accaugcagg aaacagcc                                      208

<210> SEQ ID NO 746
<211> LENGTH: 132
<212> TYPE: RNA
<213> ORGANISM: Homo sapiens

<400> SEQUENCE: 746
ugagaugaga ucaugccauu gcacuccagc cuggacgaca gagcgagacu ucaucucaaa    60
aaaaaaaaag gauccucagg gcugccaacc uuauaguaga aguugaggug guaguggauu   120
ucuccuacac aa                                                       132

<210> SEQ ID NO 747
<211> LENGTH: 81
<212> TYPE: RNA
<213> ORGANISM: Homo sapiens

<400> SEQUENCE: 747 ccaguccug aguuuaugca agaugcccau gggagcccag agacguccua uggcgagacu     60
ggcauguacu cacacaacug a                                             81

<210> SEQ ID NO 748
<211> LENGTH: 22
<212> TYPE: RNA
<213> ORGANISM: Homo sapiens

<400> SEQUENCE: 748
auugccucug uucuaaacaca ag                                           22

<210> SEQ ID NO 749
<211> LENGTH: 99
<212> TYPE: RNA
<213> ORGANISM: Homo sapiens

<400> SEQUENCE: 749
cgcccaccuc agcucccccaa aaugcuggga uuacaggcau gagccacugc ggucgaccau    60
gaccuggaca uguuugugcc caguacuguc aguuugcag                          99

<210> SEQ ID NO 750
<211> LENGTH: 77
<212> TYPE: RNA
<213> ORGANISM: Homo sapiens

<400> SEQUENCE: 750
auuguuacau ugauaaaauc aaaucaccau cuuuuagcua agcuugugcu ggauuugcuu    60
uuuuucugau aaagaug                                                  77

<210> SEQ ID NO 751
<211> LENGTH: 22
<212> TYPE: RNA
<213> ORGANISM: Homo sapiens

```
<400> SEQUENCE: 751
gcagagugca aacaauuuug ac                                             22

<210> SEQ ID NO 752
<211> LENGTH: 98
<212> TYPE: RNA
<213> ORGANISM: Homo sapiens

<400> SEQUENCE: 752
aacauguugu cuggguacc cuacucugga gagugacaau cauguauaau uaaauuugau     60
ugacacuucu gugaguagag uaacgcauga cacguacg                            98

<210> SEQ ID NO 753
<211> LENGTH: 74
<212> TYPE: RNA
<213> ORGANISM: Homo sapiens

<400> SEQUENCE: 753
gggugaggua guagguugua uaguuuqggg cucugcccug cuaugggaua acauacaau     60 cuacugucuu uccu                                                      74

<210> SEQ ID NO 754
<211> LENGTH: 22
<212> TYPE: RNA
<213> ORGANISM: Homo sapiens

<400> SEQUENCE: 754
aaagugcauc cuuuuagagu gu                                             22

<210> SEQ ID NO 755
<211> LENGTH: 22
<212> TYPE: RNA
<213> ORGANISM: Homo sapiens

<400> SEQUENCE: 755
ccgcacugug gguacuugcu gc                                             22

<210> SEQ ID NO 756
<211> LENGTH: 94
<212> TYPE: RNA
<213> ORGANISM: Homo sapiens

<400> SEQUENCE: 756
uggaucgaug augacuucca uauauacauu ccuuggaaag cugaacaaaa ugagugaaaa     60
cucuauacug ucauccucgu cgaacugagg ucca                                94

<210> SEQ ID NO 757
<211> LENGTH: 22
<212> TYPE: RNA
<213> ORGANISM: Homo sapiens

<400> SEQUENCE: 757
ucugugagac caaagaacua cu                                             22

<210> SEQ ID NO 758
<211> LENGTH: 77
<212> TYPE: RNA
<213> ORGANISM: Homo sapiens
```

```
<400> SEQUENCE: 758
uggacaaaug auuagauuag auuguguuau aaaccaaaga uuauaguuau uccaauuaug    60
ugcauuugag auccacu                                                  77

<210> SEQ ID NO 759
<211> LENGTH: 89
<212> TYPE: RNA
<213> ORGANISM: Homo sapiens

<400> SEQUENCE: 759
cuggccucca gggcuuugua caugguaggc uuucauucau ucguuugcac auucggugaa    60
ggucuacugu gugccaggcc cugugccag                                     89

<210> SEQ ID NO 760
<211> LENGTH: 22
<212> TYPE: RNA
<213> ORGANISM: Homo sapiens

<400> SEQUENCE: 760
gagcuuggau gagcugggcu ga                                            22

<210> SEQ ID NO 761
<211> LENGTH: 71
<212> TYPE: RNA
<213> ORGANISM: Homo sapiens

<400> SEQUENCE: 761
ucaauaauga aaucuucuga uuuggugaga aauaaugccu uaaaauuaca cucaauagga    60
uuaugcugag g                                                        71

<210> SEQ ID NO 762
<211> LENGTH: 22
<212> TYPE: RNA
<213> ORGANISM: Homo sapiens

<400> SEQUENCE: 762
agacaucaag aucagucccca aa                                           22

<210> SEQ ID NO 763
<211> LENGTH: 77
<212> TYPE: RNA
<213> ORGANISM: Homo sapiens

<400> SEQUENCE: 763
auuuuggcca acucugaccc cuuagguuga ugucagaaug agguguacca accuaggugg    60
ucagaguugg ccaaaau                                                  77

<210> SEQ ID NO 764
<211> LENGTH: 20
<212> TYPE: RNA
<213> ORGANISM: Homo sapiens

<400> SEQUENCE: 764
aaguccugcu ucuguugcag                                               20

<210> SEQ ID NO 765
<211> LENGTH: 17
<212> TYPE: RNA
<213> ORGANISM: Homo sapiens
```

```
<400> SEQUENCE: 765
auggagaagg cuucuga                                              17

<210> SEQ ID NO 766
<211> LENGTH: 22
<212> TYPE: RNA
<213> ORGANISM: Homo sapiens

<400> SEQUENCE: 766
aaaaguauuu gcggguuuug uc                                        22

<210> SEQ ID NO 767
<211> LENGTH: 20
<212> TYPE: RNA
<213> ORGANISM: Homo sapiens

<400> SEQUENCE: 767
ccucugggcc cuuccuccag                                           20

<210> SEQ ID NO 768
<211> LENGTH: 22
<212> TYPE: RNA
<213> ORGANISM: Homo sapiens

<400> SEQUENCE: 768
ccaaggaagg aggcuggaca uc                                        22

<210> SEQ ID NO 769
<211> LENGTH: 68
<212> TYPE: RNA
<213> ORGANISM: Homo sapiens

<400> SEQUENCE: 769
gacacuuggg agggaagaca gcuggagagu auggucacag cagcauccuc cucuguuuuc   60
uuuccuag                                                        68

<210> SEQ ID NO 770
<211> LENGTH: 22
<212> TYPE: RNA
<213> ORGANISM: Homo sapiens

<400> SEQUENCE: 770
agggaaggag gcuuggucuu ag                                        22

<210> SEQ ID NO 771
<211> LENGTH: 22
<212> TYPE: RNA
<213> ORGANISM: Homo sapiens

<400> SEQUENCE: 771
ccagagaugg uugccuuccu au                                        22

<210> SEQ ID NO 772
<211> LENGTH: 22
<212> TYPE: RNA
<213> ORGANISM: Homo sapiens

<400> SEQUENCE: 772
aucgugcauc ccuuuagagu gu                                        22

<210> SEQ ID NO 773
<211> LENGTH: 81
```

-continued

```
<212> TYPE: RNA
<213> ORGANISM: Homo sapiens

<400> SEQUENCE: 773
accugcccug ggcuuucuag ucucagcucu ccugaccagc ugagcuggag gagagcugag    60
acuagaaagc ccagggcagg u                                             81

<210> SEQ ID NO 774
<211> LENGTH: 23
<212> TYPE: RNA
<213> ORGANISM: Homo sapiens

<400> SEQUENCE: 774
agcagcauug uacagggcua uga                                           23

<210> SEQ ID NO 775
<211> LENGTH: 21
<212> TYPE: RNA
<213> ORGANISM: Homo sapiens

<400> SEQUENCE: 775
uuggccacaa uggguuagaa c                                             21

<210> SEQ ID NO 776
<211> LENGTH: 69
<212> TYPE: RNA
<213> ORGANISM: Homo sapiens

<400> SEQUENCE: 776
auguaauaau guucaucaaa ugucugaccu gaaaugagca uguagacaag uuaauuuaac    60
acugaagaa                                                           69

<210> SEQ ID NO 777
<211> LENGTH: 56
<212> TYPE: RNA
<213> ORGANISM: Homo sapiens

<400> SEQUENCE: 777
aaagguaacu gugauuuuug cuauuagaaa guaauggcaa aaacugcaau uacuuu        56

<210> SEQ ID NO 778
<211> LENGTH: 21
<212> TYPE: RNA
<213> ORGANISM: Homo sapiens

<400> SEQUENCE: 778
cgcuuugcuc agccagugua g                                             21

<210> SEQ ID NO 779
<211> LENGTH: 101
<212> TYPE: RNA
<213> ORGANISM: Homo sapiens

<400> SEQUENCE: 779
aaccaugaau gcaagaagcg uaugauuggg uuuucaugcu cacgugugaa auggaccacc    60
cucaaaccug guuaugcuau cagcacauua ccugucugau g                       101

<210> SEQ ID NO 780
<211> LENGTH: 134
<212> TYPE: RNA
<213> ORGANISM: Homo sapiens
```

```
<400> SEQUENCE: 780
acucucucgg cucugcauag uugcacuugg cuucacccgu gugacuuucg uaacggggag     60
agagagaaaa gaucccuca ggaccucgga ugggccuuac uguggccucu cuuccuuga     120 ggggugcaac aggc                                                    134

<210> SEQ ID NO 781
<211> LENGTH: 22
<212> TYPE: RNA
<213> ORGANISM: Homo sapiens

<400> SEQUENCE: 781
uggaauguaa ggaagugugu gg                                             22

<210> SEQ ID NO 782
<211> LENGTH: 85
<212> TYPE: RNA
<213> ORGANISM: Homo sapiens

<400> SEQUENCE: 782
auuacagaca ugagcgacug ugccugacca aaagucaaca uuaaacaaca aaucuuggcc    60
aggcacagug gcucaugccu guaau                                          85

<210> SEQ ID NO 783
<211> LENGTH: 22
<212> TYPE: RNA
<213> ORGANISM: Homo sapiens

<400> SEQUENCE: 783
ccucugaaau ucaguucuuc ag                                             22

<210> SEQ ID NO 784
<211> LENGTH: 104
<212> TYPE: RNA
<213> ORGANISM: Homo sapiens

<400> SEQUENCE: 784
aucauuuugc agcuuauaca ugugaugacu ggguuuuuua acucauaagu gagaugugcc    60
uuucuuacau cuuauuauga cauuaguaca uuacccauuu gaua                    104

<210> SEQ ID NO 785
<211> LENGTH: 88
<212> TYPE: RNA
<213> ORGANISM: Homo sapiens

<400> SEQUENCE: 785
ucccaugcug ugaccuucca aagggaagcg cuuucuguuu guuuucucuu aaacaaagug    60
ccucccuuua gaguguuacc guuuggga                                       88

<210> SEQ ID NO 786
<211> LENGTH: 92
<212> TYPE: RNA
<213> ORGANISM: Homo sapiens

<400> SEQUENCE: 786
agaucauuga ugacuuccau auaccauuc cuuggaaagc ugaacaacau gagugaaaac     60
ucuacugaaa aagaaaaga aaugggaggc cg                                   92

<210> SEQ ID NO 787
<211> LENGTH: 22
```

```
<212> TYPE: RNA
<213> ORGANISM: Homo sapiens

<400> SEQUENCE: 787
uaauacuguc ugguaaaacc gu                                             22

<210> SEQ ID NO 788
<211> LENGTH: 77
<212> TYPE: RNA
<213> ORGANISM: Homo sapiens

<400> SEQUENCE: 788
ccucacuuau cugacucuga aaucuucuaa augguaccca cuuuauuuag aacguuuuag    60
ggucaaauaa guacagg                                                  77

<210> SEQ ID NO 789
<211> LENGTH: 23
<212> TYPE: RNA
<213> ORGANISM: Homo sapiens

<400> SEQUENCE: 789
ucaaggccag agucccaca gca                                             23

<210> SEQ ID NO 790
<211> LENGTH: 22
<212> TYPE: RNA
<213> ORGANISM: Homo sapiens

<400> SEQUENCE: 790
ucgggcgcaa gagcacugca gu                                             22

<210> SEQ ID NO 791
<211> LENGTH: 82
<212> TYPE: RNA
<213> ORGANISM: Homo sapiens

<400> SEQUENCE: 791
ggguguacac ccccugcgac auuggaagua guacaucuc ucccuuggau gcuacgaaca     60
auaucacaga agguguacac cc                                             82

<210> SEQ ID NO 792
<211> LENGTH: 22
<212> TYPE: RNA
<213> ORGANISM: Homo sapiens

<400> SEQUENCE: 792
aggacuggac ucccggcagc cc                                             22

<210> SEQ ID NO 793
<211> LENGTH: 22
<212> TYPE: RNA
<213> ORGANISM: Homo sapiens

<400> SEQUENCE: 793
agaggcugag aaggugaugu ug                                             22

<210> SEQ ID NO 794
<211> LENGTH: 76
<212> TYPE: RNA
<213> ORGANISM: Homo sapiens
```

-continued

<400> SEQUENCE: 794
caaauacaug augaucucac cucaguuuga acucucucac ugaucacuug augacaauaa    60
aagaucugau auugug                                                   76

<210> SEQ ID NO 795
<211> LENGTH: 133
<212> TYPE: RNA
<213> ORGANISM: Homo sapiens

<400> SEQUENCE: 795
acugccccua gaggcguugc agcuguggcu gccgugucac aucugguca uuagguggca    60 gagauuagag aggcuauguc uacgcucagc guucugcccc gugaacguuu gaauguuuga   120
uagucucaca cuc                                                     133

<210> SEQ ID NO 796
<211> LENGTH: 134
<212> TYPE: RNA
<213> ORGANISM: Homo sapiens

<400> SEQUENCE: 796
gucugcauuu gaaagugauc aucagcuagc cugugucuuc gcaucgaua guacaggccg    60 gugaacugcg caaagcauuu ucugcauuug gaggguccau cucuauccuu ggaaaugcua   120
gugcuuuucu caca                                                    134

<210> SEQ ID NO 797
<211> LENGTH: 73
<212> TYPE: RNA
<213> ORGANISM: Homo sapiens

<400> SEQUENCE: 797
aaaauggagc uggccaaaaa gcaggcagag acuuuaaaag cgucucugcc ugcuuuuugg    60
ccagcuccgu uuu                                                      73

<210> SEQ ID NO 798
<211> LENGTH: 82
<212> TYPE: RNA
<213> ORGANISM: Homo sapiens

<400> SEQUENCE: 798
cagucagugu cgagaaccuu auauuguucu gaagagaggu ggugacuuaa aaaucaugcu    60
caauaggauu acgcugaggc cc                                            82

<210> SEQ ID NO 799
<211> LENGTH: 112
<212> TYPE: RNA
<213> ORGANISM: Homo sapiens

<400> SEQUENCE: 799
agacgaggag uuaagaguuc auucggcugu ccagauguau ccaaguaccc uguguuauuu    60
ggcaauaaau acaucugggc aacugacuga acuuucacu uuucaugacu ca           112

<210> SEQ ID NO 800
<211> LENGTH: 19
<212> TYPE: RNA
<213> ORGANISM: Homo sapiens -continued

```
<400> SEQUENCE: 800
accgugcaaa gguagcaua                                                  19

<210> SEQ ID NO 801
<211> LENGTH: 101
<212> TYPE: RNA
<213> ORGANISM: Homo sapiens

<400> SEQUENCE: 801 auccuuugu aagucauaag ugugauuggg uuucaugcu cuugugucaa augugccucc       60
cucaaaccuu guuacgaagu gggcacacua cccaccugau g                        101

<210> SEQ ID NO 802
<211> LENGTH: 71
<212> TYPE: RNA
<213> ORGANISM: Homo sapiens

<400> SEQUENCE: 802
aagaucaaug augacuacug uuaguguaug aguuacacau gaugaauaca ugucugaaac    60
ucugaggucc a                                                         71

<210> SEQ ID NO 803
<211> LENGTH: 67
<212> TYPE: RNA
<213> ORGANISM: Homo sapiens

<400> SEQUENCE: 803
uggaaaagag aggagcagug gugcuguggc aguggcagag gucgcuacag cccugugauc    60
uuuccag                                                              67

<210> SEQ ID NO 804
<211> LENGTH: 105
<212> TYPE: RNA
<213> ORGANISM: Homo sapiens

<400> SEQUENCE: 804
aacauuuaaa aaauguauc aaggcguggu gauuagguuu ucacacucau gugugagaug     60
ugccucccuu gaacuuuguu acauggcac uuuacccauu ugaca                    105

<210> SEQ ID NO 805
<211> LENGTH: 22
<212> TYPE: RNA
<213> ORGANISM: Homo sapiens

<400> SEQUENCE: 805
ugagguagua aguuguauug uu                                             22

<210> SEQ ID NO 806
<211> LENGTH: 93
<212> TYPE: RNA
<213> ORGANISM: Homo sapiens

<400> SEQUENCE: 806
aucuacaaug gugaugggug aauuuguaga aggaugaaag ucaagaauc cuucugggaa     60 cuaauuuuug gccuucaaca agaauuguga uau                                 93

<210> SEQ ID NO 807
<211> LENGTH: 63
<212> TYPE: RNA
```

<213> ORGANISM: Homo sapiens

<400> SEQUENCE: 807
gugcauguga ugaagcaaau caguaugaau gaauucauga uacuguaaac gcuuucugau    60
gua                                                                 63

<210> SEQ ID NO 808
<211> LENGTH: 107
<212> TYPE: RNA
<213> ORGANISM: Homo sapiens

<400> SEQUENCE: 808
agaagaugcu acuacuagg uuggugcaaa aguaauugug guuuuugcau uuaaaguaau    60
ggccaaaacc gcgauuacuc uugcacgaac cuaacgguaa cacuucu                107

<210> SEQ ID NO 809
<211> LENGTH: 89
<212> TYPE: RNA
<213> ORGANISM: Homo sapiens

<400> SEQUENCE: 809
acgcgccuga ugcggaccug gguuagcgga gugaggccca guggucaccg ccgcccuccg    60
cagguccagg uugccgugcg caugugccu                                      89

<210> SEQ ID NO 810
<211> LENGTH: 91
<212> TYPE: RNA
<213> ORGANISM: Homo sapiens

<400> SEQUENCE: 810
uuuucaaagc aaugugugac agguacaggg acaaaucccg uuaauaagua agaggauuug    60
ugcuuggcuc ugucacaugc cacuuugaaa a                                   91

<210> SEQ ID NO 811
<211> LENGTH: 86
<212> TYPE: RNA
<213> ORGANISM: Homo sapiens

<400> SEQUENCE: 811
uggggcccug gcugggauau caucauauac uguaaguuug cgaugagaca cuacaguaua    60
gaugauguac uagccgggc accccc                                          86

<210> SEQ ID NO 812
<211> LENGTH: 216
<212> TYPE: RNA
<213> ORGANISM: Homo sapiens

<400> SEQUENCE: 812
aagauuauau uuccaggggu cauuucugug guucauuacu uaaaggaguu uccccaagug    60
uguagagcac uggaaaccac aggaagauau gcaauguucu cucccgagca cgaagcucgu   120 ucuuggguguu gcuucauugc aacugccauu ugccauugau cauuguuuuu uucuuccuuu   180
ggggagauua agaggaagag gacacagucu gaguga                            216

<210> SEQ ID NO 813
<211> LENGTH: 77
<212> TYPE: RNA
<213> ORGANISM: Homo sapiens

<400> SEQUENCE: 813
ucacuuuggu gccuaggcug agacugcagu ggugcaaucu caguucacug cagccuugac    60
cuccugggcu cagguga                                                   77

<210> SEQ ID NO 814
<211> LENGTH: 135
<212> TYPE: RNA
<213> ORGANISM: Homo sapiens

<400> SEQUENCE: 814
cuccaugugu cuuuggaacc ugucagcugu ggcaguugcc cuuccuagcc auggaagagu    60
aaguauauuc uuguuuauug gcaaagcugu caccauuuca uugguaucag auucugacuu   120
gcacaaguaa cauuc                                                   135

<210> SEQ ID NO 815
<211> LENGTH: 104
<212> TYPE: RNA
<213> ORGANISM: Homo sapiens

<400> SEQUENCE: 815
auccuuuuga aguucauaag cauggugauu ggguuuucac acucaugugu gagauguacc    60
acccuuaaag cuuguuauga uguaggcaca uuacccaucu gaca                   104

<210> SEQ ID NO 816
<211> LENGTH: 82
<212> TYPE: RNA
<213> ORGANISM: Homo sapiens

<400> SEQUENCE: 816
ugagcuguug gauucggggc cguagcacug ucugagaggu uuacauuucu cacagugaac    60
cggucucuuu uucagcugcu uc                                            82

<210> SEQ ID NO 817
<211> LENGTH: 278
<212> TYPE: RNA
<213> ORGANISM: Homo sapiens

<400> SEQUENCE: 817
aggucgauga ugauugguaa aaggucugau ugcacugaau gucacggucc cuuuguugcc    60
cucaacuccc agcagcccau uuuuuccuc ccgucacauu uaagcaugu guaugggauc   120 auggagcagc ugauaauuug gGauucuguc agugugugu ucugagagug aucggcucac   180
agcugacgag uauccaacaa aaccaguuac acaggagacu gacgaguggc agucaugggu   240
gugauggugc augaucucaa guuuucaauc ugagaccu                         278

<210> SEQ ID NO 818
<211> LENGTH: 84
<212> TYPE: RNA
<213> ORGANISM: Homo sapiens

<400> SEQUENCE: 818
gcaucuugca gagccguucc aaugcgacac cucuagagug ucaucccua gaaugucacc    60 uuggaaagac ucugcaagau gccu                                          84

<210> SEQ ID NO 819
<211> LENGTH: 96
<212> TYPE: RNA

-continued

<213> ORGANISM: Homo sapiens

<400> SEQUENCE: 819
gguauuguua gauuaauuuu gugggacauu aacaacagca ucagaagcaa caucagcuuu    60
aguuaaugaa uccuggaaag uuaagugacu uuauuu    96

<210> SEQ ID NO 820
<211> LENGTH: 22
<212> TYPE: RNA
<213> ORGANISM: Homo sapiens

<400> SEQUENCE: 820
uaugcauugu auuuuaggu cc    22

<210> SEQ ID NO 821
<211> LENGTH: 22
<212> TYPE: RNA
<213> ORGANISM: Homo sapiens

<400> SEQUENCE: 821
ugaaguuaca ucauggucgc uu    22

<210> SEQ ID NO 822
<211> LENGTH: 127
<212> TYPE: RNA
<213> ORGANISM: Homo sapiens

<400> SEQUENCE: 822
gacuucucac ugagcuucuu ucugucuguu gcuggcagcu uauggauuca uaugagcaga    60
gagaaucaca gaacuagcau acuuuuguc uuuacaggag uauauuuggc ugucuuguga    120
gauauua    127

<210> SEQ ID NO 823
<211> LENGTH: 69
<212> TYPE: RNA
<213> ORGANISM: Homo sapiens

<400> SEQUENCE: 823
ugguucagug uugacuacug gugucgugug agucauacaa ugaauacaug ucuggaacuc    60
ugaggccca    69

<210> SEQ ID NO 824
<211> LENGTH: 114
<212> TYPE: RNA
<213> ORGANISM: Homo sapiens

<400> SEQUENCE: 824
auccuuuugc gguucauaaa gaaccaagau gacuggguuu caugcuaaug caugacaugu    60
gccucccuca aaucauguug ccucauggc uuauuggcac auuaccgucu gagg    114

<210> SEQ ID NO 825
<211> LENGTH: 18
<212> TYPE: RNA
<213> ORGANISM: Homo sapiens

<400> SEQUENCE: 825 ggugggggu uuguuuu    18

<210> SEQ ID NO 826
<211> LENGTH: 22

```
<212> TYPE: RNA
<213> ORGANISM: Homo sapiens

<400> SEQUENCE: 826
ugcuggcuca uuucauaugu gu                                              22

<210> SEQ ID NO 827
<211> LENGTH: 22
<212> TYPE: RNA
<213> ORGANISM: Homo sapiens

<400> SEQUENCE: 827
caaaaguaau uguggauuuu gu                                              22

<210> SEQ ID NO 828
<211> LENGTH: 72
<212> TYPE: RNA
<213> ORGANISM: Homo sapiens

<400> SEQUENCE: 828
guguuuaggg uacucagagc aaguugugaa acacaggugu uuuuuaaccu caccuugcau     60
cugcaucccc ag                                                         72

<210> SEQ ID NO 829
<211> LENGTH: 53
<212> TYPE: RNA
<213> ORGANISM: Homo sapiens

<400> SEQUENCE: 829
ucacuuuagg agaaguaaag uagaacuuug guuucaacu uuccuacag ugu              53

<210> SEQ ID NO 830
<211> LENGTH: 115
<212> TYPE: RNA
<213> ORGANISM: Homo sapiens

<400> SEQUENCE: 830
gugccuaagg uuaacacagc gccuuaagag gcuaacacag aagggcaaag uaagucucca     60
uaaaacccag agaagacugu gaaccccucu cuggauccug ucuggaguca cagcu         115

<210> SEQ ID NO 831
<211> LENGTH: 68
<212> TYPE: RNA
<213> ORGANISM: Homo sapiens

<400> SEQUENCE: 831
ccucauugau uaguagcuuc ugacuuuugu ucugaguuug cugaagcuag augccauucc     60
agauaaga                                                              68

<210> SEQ ID NO 832
<211> LENGTH: 22
<212> TYPE: RNA
<213> ORGANISM: Homo sapiens

<400> SEQUENCE: 832
ugggagagca ggguauugug ga                                              22

<210> SEQ ID NO 833
<211> LENGTH: 65
<212> TYPE: RNA
<213> ORGANISM: Homo sapiens
```

-continued

```
<400> SEQUENCE: 833
guucaugaua aguaacauuu cuucaauuug accugaugug uauugaagaa aaccagcauc    60
ugagg                                                                65

<210> SEQ ID NO 834
<211> LENGTH: 22
<212> TYPE: RNA
<213> ORGANISM: Homo sapiens

<400> SEQUENCE: 834
cgucuuaccc agcaguguuu gg                                             22

<210> SEQ ID NO 835
<211> LENGTH: 23
<212> TYPE: RNA
<213> ORGANISM: Homo sapiens

<400> SEQUENCE: 835
uauggagugg acuuucagcu ggc                                            23

<210> SEQ ID NO 836
<211> LENGTH: 76
<212> TYPE: RNA
<213> ORGANISM: Homo sapiens

<400> SEQUENCE: 836
gggucaauga ugagauguua ccuugaagag aaaugaugac guaaaaauua aguucaguug    60
gauuacgcug aggccc                                                    76

<210> SEQ ID NO 837
<211> LENGTH: 64
<212> TYPE: RNA
<213> ORGANISM: Homo sapiens

<400> SEQUENCE: 837
gagcucuggg aggggcuggg uuuggcagga caguuuccaa gcccugucuc cucccaucuu    60
ccag                                                                 64

<210> SEQ ID NO 838
<211> LENGTH: 19
<212> TYPE: RNA
<213> ORGANISM: Homo sapiens

<400> SEQUENCE: 838
uugccauguc uaagaagaa                                                 19

<210> SEQ ID NO 839
<211> LENGTH: 80
<212> TYPE: RNA
<213> ORGANISM: Homo sapiens

<400> SEQUENCE: 839
ugagaggccg caccuugccu ugcugcccgg gccgugcacc cgugggcccc agggcgacgc    60
ggcgggggcg gcccuagcga                                                80

<210> SEQ ID NO 840
<211> LENGTH: 99
<212> TYPE: RNA
<213> ORGANISM: Homo sapiens
```

```
<400> SEQUENCE: 840
uuuagcgguu ucucccugaa gugaugugua acugaucagg aucuacucau gucgucuuug      60
guaaaguuau gucgcuuguc agggugagga gaguuuuug                             99
```

METHODS FOR PREDICTING PROSTATE CANCER AND USES THEREOF

CROSS-REFERENCE TO RELATED APPLICATIONS

This application claims the benefit of U.S. Provisional Application No. 62/978,184, filed Feb. 18, 2020, and U.S. Provisional Application No. 62/819,325, filed Mar. 15, 2019, which are incorporated by reference herein in their entirety.

FIELD OF THE INVENTION

The present invention relates to compositions and methods for diagnosing, prognosing, monitoring, and treating a patient with prostate cancer. In particular, the invention relates to the use of small non-coding RNAs (sncRNAs) such as miRNA and snoRNA as expression signatures for identifying a clinically significant prostate cancer.

BACKGROUND

The current method of screening for prostate cancer includes a digital rectal examination followed by a prostate-specific antigen (PSA) test. The former is invasive and the latter requires drawing of a blood sample from the subject.

Patients with a suspicious DRE and/or an elevated PSA level are subjected to a systematic 12-needle core biopsy or Magnetic Resonance Imaging (MRI)-guided targeted needle biopsy. This standard diagnosis strategy is invasive, imprecise and associated with significant costly morbidities, most notably bacterial infections.

The PSA test has significant drawbacks. In addition to indicating prostate cancer, elevated PSA levels may also indicate urinary tract infection or prostatitis (an inflammation or the prostate or benign prostatic hyperplasia or BPH). The test overdiagnoses prostate cancer, and many men are unnecessarily subjected to core needle biopsies. The prostate tissue collected during the biopsy is then examined by a pathologist and assigned a Gleason score that assesses the grade of the disease. The Gleason score is the sum of two numbers: (1) a primary grade assigned by the pathologist based on the pathologist's determination of the grade of the tumor in the most common pathology (2) a secondary grade based on the determination of the grade of the tumor in the next most prominent pathology. For each area, a score of one to five is assigned based on how aggressive the tumor appears and the two numbers are added together to provide the final Gleason Score. A tumor with cells that appear close to normal is assigned a low Gleason score (six or below, reported as Gleason 3+3) whereas a tumor with cells that appear clearly different from those of a normal prostate is assigned a higher Gleason score (seven or above). Low-grade tumors based on low Gleason scores are less likely to be aggressive; whereas tumors with high Gleason score are more likely to be aggressive and metastasize. There are aspects of the Gleason Scoring System that have been problematic since they were implemented—most noteably the fact that tumors that are Gleason 3+4 and Gleason 4+3 are both reported as Gleason 7, even though the clinical outcomes of these groups are clearly different. A recent refinement of the Gleason Score, referred to as Grade Grouping, has been adopted to eliminate this issue (Grade Group 1 (GG1) encompasses Gleason 3+3; GG2—Gleason 3+4; GG3—Gleason 4+3; GG4—Gleason 4+4 and GG5—Gleason 5+4 or higher. This change to the scoring system has simplified the reporting of the histopathology of prostate cancer and has eliminated the ambiguity associated with "Gleason 7" tumors, making classifying outcome more straight forward.

Approximately 50-70% of patients recommended for core needle biopsy on the basis of "elevated" PSA (>3 ng/mL) have negative biopsies, while 14% of men with PSA<3 ng/mL have prostate cancer but are not routinely biopsied because of their low PSA levels. The combination of PSA screening and core needle biopsy is both invasive and has poor performance characteristics, which leaves physicians and patients with no reliable measures on which to base their choices of treatment options. The result is that many men needlessly opt for clinical intervention, very often prostatectomy. It also hinders the development of new prognostic tools since the Gleason Score "gold standard" is not itself a reliable indicator of prostate tumor progression.

This problem has been recognized for at least 30 years. It remains a major issue today. The intervening years have seen many attempts to develop prognostic markers for aggressive disease, including ploidy, nuclear morphology and nuclear matrix architecture, microarray-based transcriptome analyses, DNA methylation status, and detection of gene fusions such as the TMPRSS2:ETS family fusions. None of these methodologies have proved to be significantly better than Gleason Scores as indicators of prostate tumor progression. Furthermore, they do not identify the cancer stage or grade adequately.

Tests have been developed that are designed to distinguish cancer states using mRNA expression profiles. However, each demonstrates significant shortcomings. First, with only a few exceptions, these assays used tumor material derived from radical prostatectomy specimens, and therefore are at best predictive of early tumor recurrence. While potentially useful for making post-surgical clinical decisions related to continuing clinical decisions, they do not help distinguish prostate cancer grades prior to surgery. Secondly, a number of these genomic approaches have focused on specific pathways that have been implicated in prostate cancer progression, including the androgen receptor (AR) modulated gene expression, epithelial-stromal interactions, and cell cycle. These assays assume that all prostate tumors progress along a common pathway. Other commercially available biomarker assays use mRNA expression profiles generated by real-time PCR of a small subset of genes.

To date there has been very few genome wide transcriptome studies of sncRNAs in prostate cancer. One study compared the miRNA and snoRNA signatures in (i) freshly frozen radical prostatectomy samples and (ii) adjacent normal tissue from the same patient using Illumina/Solexa deep sequencing and microarray analysis on the Affymetrix miRNA® v.2 microarrays that contains 723 human miRNAs catalogued in Sanger miRBase v.10.1. (Wellcome Sanger Institute). This study provides a valuable data set for comparing the complement of sncRNAs expressed in prostate cancer and peritumoral benign tissue but is not useful for the rational design of a panel of sncRNAs that is prognostic and/or predictive for tumor progression prior to clinical intervention. It is also handicapped as a general screening technology, since the technique requires micro-dissected flash frozen material that is only available after surgery, and therefore cannot be used for diagnosis.

Accordingly, an improved method of predicting screening and classifying prostate cancer is needed. The present disclosure relates to a non-invasive (by eliminating or reducing the unnecessary core needle biopsy) method for screening the presence or absence of prostate cancer that is highly sensitive and specific.

The method also provides a platform for disease management that is useful for the diagnosis, classification, prognosis, and monitoring of the progression and treatment of the disease. The disclosed method is based on the interrogation of a large set of at least 200 small non-coding RNAs (sncRNAs) isolated from urinary exosomes in combination with the Sentinel™ PCa, Sentinel™ CS and Sentinel™ HG tests. The Sentinel™ PCa, Sentinel™ CS and Sentinel™ HG tests are based on algorithmic analyses and comparisons of snRNA sequences catalogued from a large target population having no evidence of prostate cancer (NEPC) or having prostate cancer (GG1-GG5) for the Sentinel™ PCa Test; having low grade cancer (GG1) versus intermediate and high grade cancer (GG2-GG5) for the Sentinel™ CS Test; and having low and favorable intermediate grade cancer (GG1+GG2) versus unfavorable intermediate and high grade (GG3-GG5) cancer for the Sentinel™ HG Test. The three Sentinel™ Tests, that can be performed on a single urine sample, are used to sequentially determine whether a patient has prostate cancer or not, and whether patients with prostate cancer have low- or favorable intermediate-grade disease that can be monitored on active surveillance protocols or high-grade disease that needs immediate treatment.

SUMMARY OF THE DISCLOSURE

In one aspect, the disclosure provides a method of screening a subject for prostate cancer comprising: (i) obtaining a biological sample from the subject, (ii) detecting the aggregate expression profile of a signature collection of small non-coding RNAs (sncRNAs) from the biological sample wherein the collection of sncRNAs comprises SEQ ID NOs: 1-280, (iii) correlating the aggregate expression profile of SEQ ID NOs: 1-280 from the subject by comparing the aggregate expression level of SEQ ID NOs: 1-280 in a training data set from a target population having no evidence of prostate cancer (NEPC) or having prostate cancer; and (iv) classifying the subject as NEPC or has prostate cancer based on the results in (iii). This procedure is embodied in the Sentinel™ PCa test.

In yet another aspect, the disclosure provides a method of determining whether a patient diagnosed as having cancer has low-grade (GG1) or intermediate or high grade disease (GG2-GG5) or not, comprising: (i) obtaining a biological sample from a subject, (ii) detecting the aggregate expression profile of a signature collection of small non-coding RNAs (sncRNAs) from the biological sample wherein the collection of sncRNAs comprises SEQ ID NOs: 281-560, (iii) correlating the aggregate expression profile of SEQ ID NOs: 281-560 from the subject by comparing the aggregate expression profile of SEQ ID NOs: 281-560 in a training data set from a target population known to have low risk, low grade (GG1) or intermediate and high grade, intermediate and high risk prostate cancer (GG2-GG5) and (iv) classifying the subject as GG1 or GG2-GG5 based on the results obtained from (iii). This procedure is embodied in the Sentinel™ CS test.

In yet another aspect, the disclosure provides a method of determining whether a patient diagnosed as having cancer has high-grade (GG3-GG5) or not (low or intermediate grade disease (GG1+GG2), comprising: (i) obtaining a biological sample from a subject, (ii) detecting the aggregate expression profile of a signature collection of small non-coding RNAs (sncRNAs) from the biological sample wherein the collection of sncRNAs comprises SEQ ID NOs: 561-840, (iii) correlating the aggregate expression profile of SEQ ID NOs: 561-840 from the subject by comparing the aggregate expression profile of SEQ ID NOs: 561-840 in a training data set from a target population known to have high grade, high risk prostate cancer (GG3-GG5) or low- or intermediate-risk cancer (GG1+GG2) and (iv) classifying the subject as GG3-GG5 or GG1+GG2 based on the results obtained from (iii). This procedure is embodied in the Sentinel™ HG test.

In yet another aspect, the disclosure provides a method for treating a prostate cancer comprising: (i) obtaining a biological sample from a subject, (ii) detecting the aggregate expression profile of a signature collection of small non-coding RNAs (sncRNAs) from the biological sample wherein the collection of sncRNAs comprises SEQ ID NOs: 281-840, (iii) correlating the aggregate expression profile of SEQ ID NOs: 1-840 from the subject by comparing the aggregate expression profile of SEQ ID NOs: 281-840 in a training data set from a target populations having NEPC, GG1, GG2, GG3, GG4 or GG5 prostate cancer, (iv) classifying the subject as having low-intermediate-grade, prostate cancer (GG1-GG2) or high-grade prostate cancer (GG3-GG5) based on the results obtained from (iii), and (v) treating the subject classified as having high-risk prostate cancer by administering one or more chemotherapeutic agents, hormones, immunotherapeutic, radiation, cryotherapy, surgery or a combination thereof.

In a further aspect, the disclosure provides a method for determining the likelihood of survival, disease recurrence or response to treatment for a subject with prostate cancer comprising: (i) obtaining a biological sample from a patient, (ii) detecting the aggregate expression profile of a signature collection of small non-coding RNAs (sncRNAs) from the biological sample wherein the collection of sncRNAs comprises SEQ ID NOs: 1-840, (iii) comparing the aggregate expression profile of SEQ ID NOs: 1-840 after treatment with that prior to treatment, (iv) correlating the aggregate expression profile of SEQ ID Nos: 1-840 from the subject by comparing the aggregate expression profile of SEQ ID Nos: 1-840 in a training data set from a target populations having no evidence of prostate cancer (NEPC) or having prostate cancer and the aggregate expression profile of SEQ ID Nos: 1-840 in a training data set from a target populations having Grade Group 1, 2, 3 or 4-5; and (v) determining the likelihood of survival, disease recurrence or response to treatment in a subject treated for prostate cancer.

In one aspect, the disclosure provides a method for predicting future prostate cancer in a subject comprising: (i) obtaining a biological sample from a patient, (ii) detecting the aggregate expression profile of a signature collection of small non-coding RNAs (sncRNAs) from the biological sample wherein the collection of sncRNAs comprises SEQ ID NOs: 1-280, (iii) correlating the aggregate expression profile of SEQ ID Nos: 1-280 from the subject by comparing the aggregate expression profile of SEQ ID Nos: 1-280 in a training data set from a target population from a target populations having Grade Group 1, 2, 3 or 4-5; (iv) determining the likelihood of a subject at risk of having Grade Group 2-5 prostate cancer based on the results obtained from (iii), and (iv) treating the subject predicted with a high risk of developing aggressive prostate cancer by administering one or more chemotherapeutic agents, hormones, immunotherapeutic, radiation, cryotherapy, surgery or a combination thereof.

In another aspect, the disclosure provides a system for determining whether a patient has no cancer or has cancer and classifying the subject with cancer as (i) indolent (low grade, GG1), (ii) intermediate or high grade (GG2-GG5), (iii) low/intermediate risk (GG1-GG2) or (iv) aggressive (high grade, GG3-GG5) prostate cancer comprising at least three processors configured to (a) interrogate sncRNA sequences for informative sequences, (b) determine and compare a Sentinel Score to determine if the subject has prostate cancer or no prostate cancer and to classify the prostate cancer stage group.

BRIEF DESCRIPTION OF THE DRAWINGS

The patent or application file contains at least one drawing executed in color. Copies of this patent or patent application publication with color drawing(s) will be provided by the Office upon request and payment of the necessary fees.

The patient first provides a urine sample for a three-layered Sentinel™ Analysis. Total urinary exosomal RNA is extracted and interrogated for expression of sncRNAs (SEQ ID NOs: 1-280) specific for the Sentinel™ PCa Test; sncRNAs (SEQ ID NOs: 281-560) specific for the Sentinel™ CS Test; and sncRNAs (SEQ ID NOs: 561-840) specific for the Sentinel™ HG Test. The expression signature will be used to classify patients into those with prostate cancer, and those without prostate cancer (Sentinel™ PCa Test, 1st layer). Patients with negative score will return every 12 months for monitoring.

In the second layer, patients with positive Sentinel™ PCa Score (those with prostate cancer) will be subjected to a secondary analysis that classifies them into having clinically insignificant (GG1) tumors or clinically significant tumors (GG2-GG5) using the Sentinel™ CS Test. Patients with clinically insignificant (GG1) tumors will be recommended for active surveillance (AS) and monitored continuously with quarterly Sentinel™ CS tests, to establish that the tumor has not progressed to GG2 or higher. Patients with clinically significant tumors (GG2-GG5) will be referred for immediate therapy.

For some patients, a third classification layer, the Sentinel™ HG Test, will further classify patients as having GG1-GG2 tumors or GG3-GG5 tumors. This test is designed to identify patients with GG3-GG5 cancers that need immediate intervention. Patients with GG1 or GG2 can be monitored by quarterly Sentinel™ HG Test to identify patients that progress to GG3 and therefore need therapeutic intervention. The availability of the Sentinel™ CS and Sentinel™ HG provides both patients and health care providers with the individualized information for treatment decision-making.

Figures 5A, 5B:
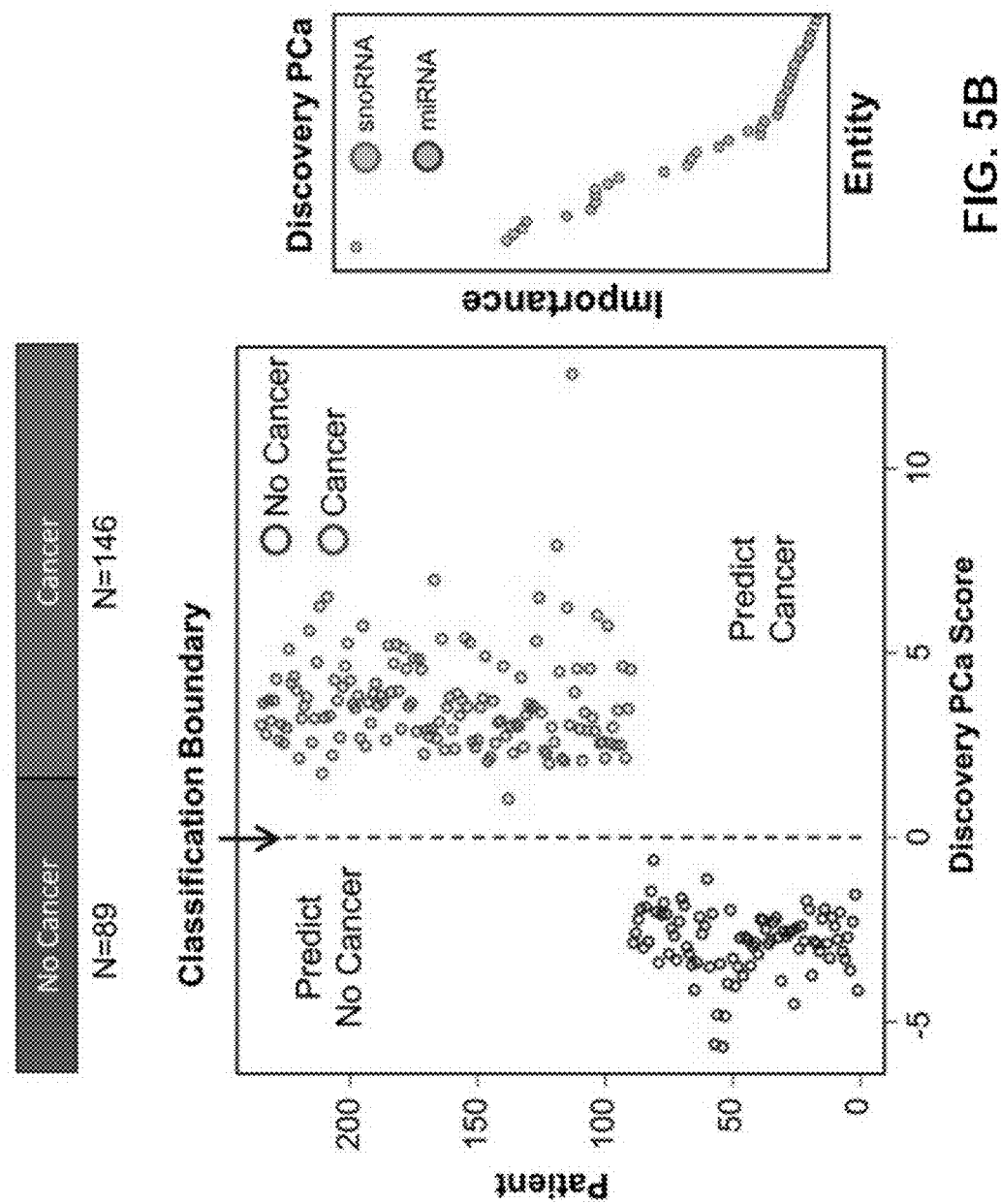

FIGS. 5A-5B show[[s]] the output of the Discovery PCa Experiments. The PCa Discovery Studies use very carefully defined patient cohort [NEPC=89; Cancer (GG1-GG5) =146] with well characterized histopathology to identify the most informative sequences among the 6,599 sncRNAs interrogated on the miR4.0 microarrays.

FIG. 5A: Scatter plot of no cancer (NEPC) and cancer (GG1-GG5) status in the training data set. Positive Discovery PCa Score is indicative of having prostate cancer and a negative Discovery PCa Score is indicative of no cancer. The cancer status as determined by histopathology of core biopsies is shown in blue (no cancer) and red (cancer) circles.

FIG. 5B: Identification of informative sncRNAs for the Sentinel™ PCa Test Identification of the most informative sncRNA entities (top 35 are shown, each circle represents a single entity) for discriminating between no cancer and cancer status using the proprietary Selection Algorithm. The resultant Sentinel™ PCa Test interrogates 280 sncRNA including the 145 most informative sncRNA sequences, which comprises of 60 snoRNA and 85 miRNA entities as shown in the bar graph. Green: miRNA entities; Yellow: snoRNA entities.

Figures 6A, 6B:
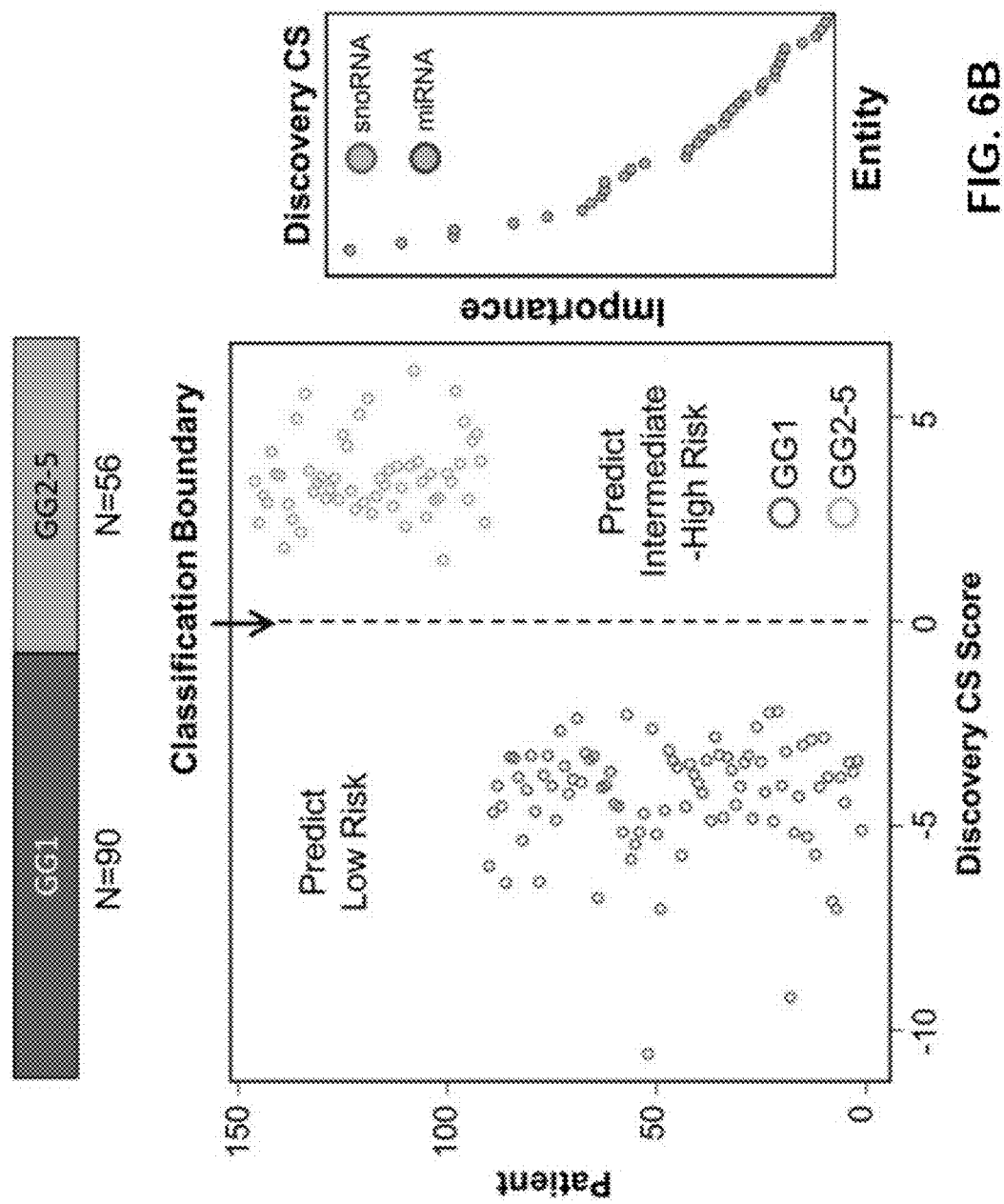

FIG. 6A shows the output of the Discovery CS Experiments. The CS Discovery Studies use very carefully defined patient cohorts [GG1=90; GG2-GG5=56] with well characterized histopathology to identify the most informative sequences among the 6,599 sncRNAs interrogated on the miR4.0 microarrays. Positive Discovery CS Score is indicative of having GG2-GG5 cancer (yellow circles) and a negative Discovery CS Score is indicative of having GG1 cancer. (green circles)

FIG. 6B: Identification of informative sncRNAs for the Sentinel™ CS Test Identification of the most informative sncRNA entities (top 35 are shown, each circle represents a single entity) for discriminating between GG1 and GG2-GG5 cancer status using the proprietary Selection Algorithm. The resultant Sentinel™ CS Test interrogates 280 sncRNA including the 145 most informative sncRNA sequences, which comprises of 66 snoRNA and 130 miRNA entities as shown in the bar graph. Green: miRNA entities; Yellow: snoRNA entities.

Figures 7A, 7B:
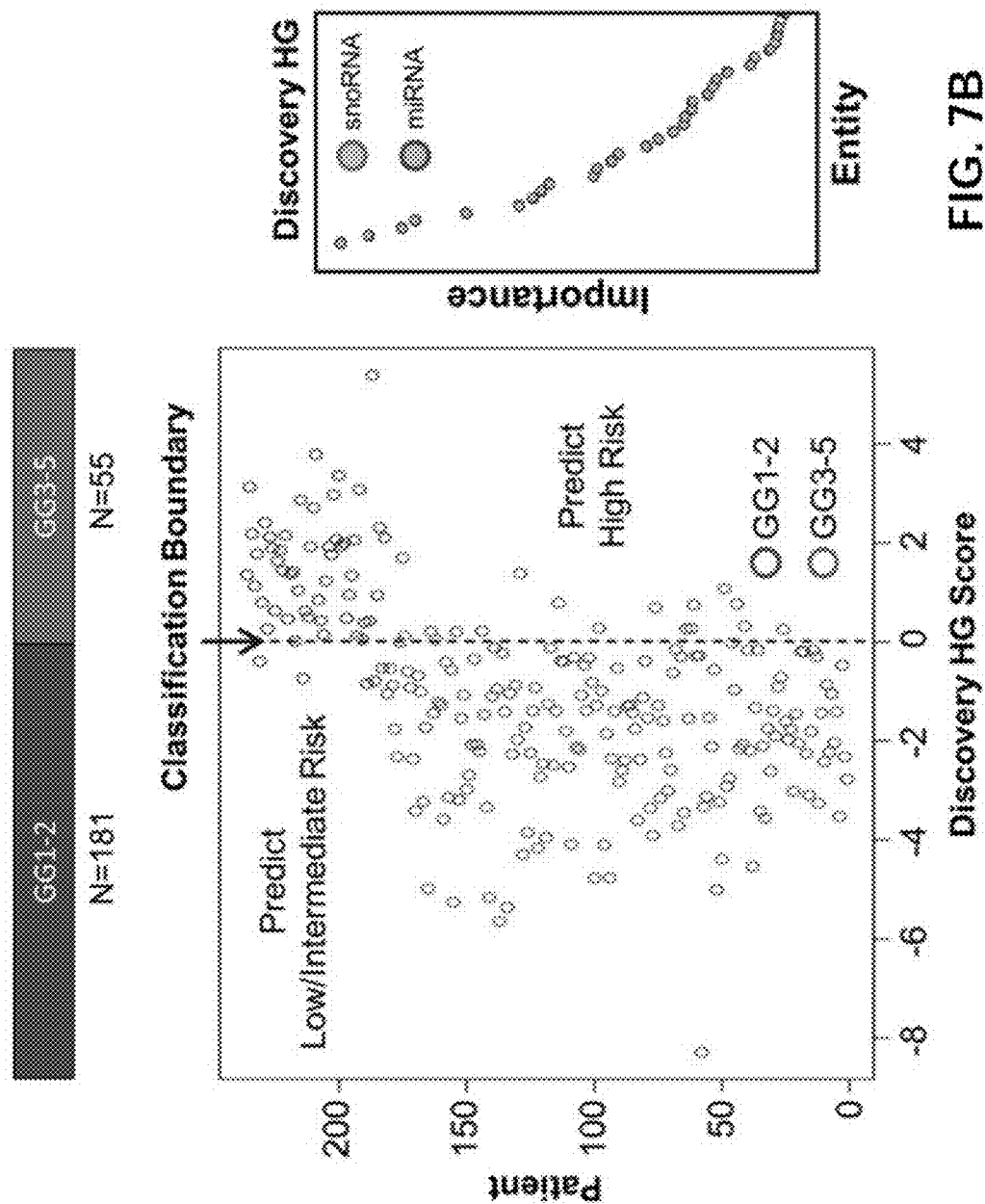

FIG. 7A shows the output of the Discovery HG Experiments. The HG Discovery Studies use very carefully defined patient cohorts [GG1+GG2=181; GG3-GG5=55] with well characterized histopathology to identify the most informative sequences among the 6,599 sncRNAs interrogated on the miR4.0 microarrays. Positive Discovery HG Score is indicative of having GG3-GG5 cancer (purple circles) and a negative Discovery HG Score is indicative of having GG1+ GG2 cancer (brown circles).

FIG. 7B: Identification of informative sncRNAs for the Sentinel™ HG Test. Identification of the most informative sncRNA entities (top 35 are shown, each circle represents a single entity) for discriminating between GG1 and GG2-GG5 cancer status using the proprietary Selection Algorithm. The resultant Sentinel™ CS Test interrogates 280 sncRNA including the 196 most informative sncRNA sequences, which comprises of 66 snoRNA and 130 miRNA entities as shown in the bar graph. Green: miRNA entities; Yellow: snoRNA entities.

Figure 8B:
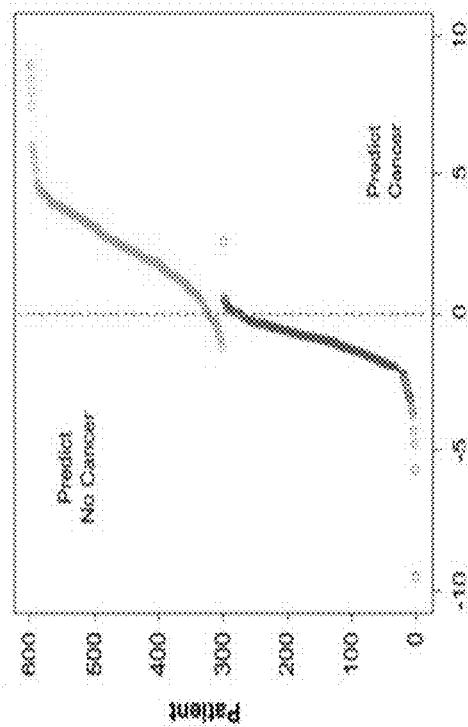
Figure 8C:
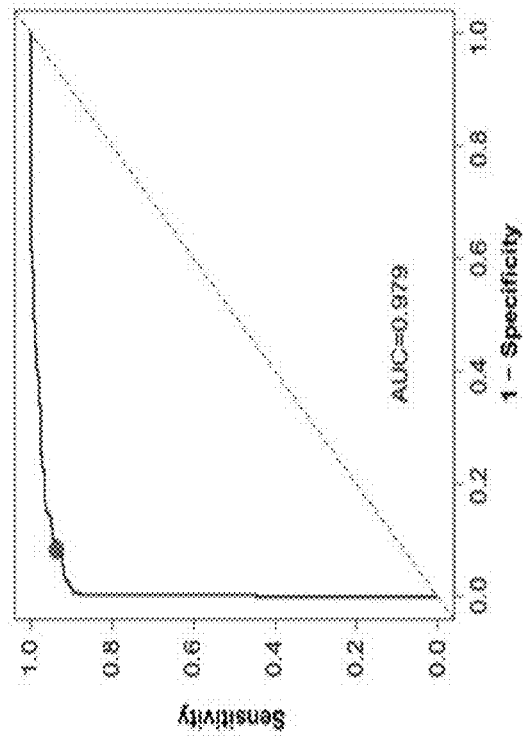
Figure 8A:
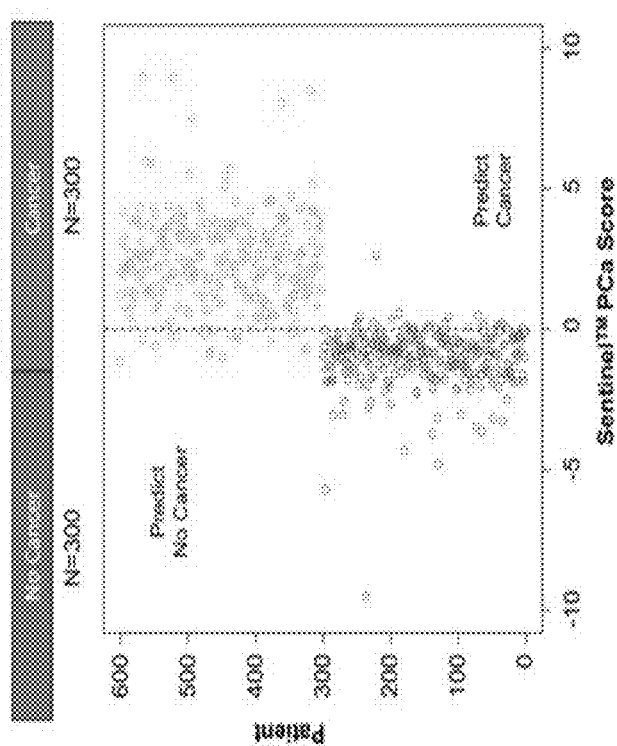

FIGS. 8A-8C show the clinical validation of high throughput OpenArray™ interrogation of urinary exosomal sncRNA using the Sentinel™ PCa Test. The data from a case-control study of 1436 men (836 subjects in the training group used to cross-validate the interrogation of sncRNAs identified in the Discovery PCa phase and 600 independent subjects used in the validation study) are shown.

FIG. 8A: Scatter plot of cancer status in the validation group set that examines 600 patients (300 no cancer; 300 cancer). Classification of no cancer (black circle) and cancer (green circle) patients where a positive Sentinel™ PCa Score is indicative of having prostate cancer and a negative Sentinel™ PCa Score is indicative of no cancer.

FIG. 8B: Sorted plot of cancer status in the validation group set that examines 600 patients. Classification of no cancer (black circle) and cancer (green circle) patients where a positive Sentinel™ PCa Score is indicative of having prostate cancer and a negative Sentinel™ PCa Score is indicative of no cancer.

FIG. 8C: Receiver Operator Curve (ROC) for Sentinel™ PCa Test. The ROC curve for the analysis of 600 patients in testing group shown in FIGS. 8A and 8B was calculated by successively calculating (1-specificity) for different user-defined false negative rates. Performance characteristics reported in Table 6 (see, [000112]) were from the user defined false negative rate of 0.05.

FIGS. 9A-9C show the clinical validation of high throughput OpenArray™ interrogation of urinary exosomal sncRNA using the Sentinel™ CS Test. The data from a case-control study of 1436 men (836 subjects in the training group used to cross-validate the interrogation of sncRNAs identified in the Discovery CS phase and 600 independent subjects used in the validation study) are shown.

FIG. 9A: Scatter plot of cancer status in the validation group set that examines 300 prostate cancer patients (146 GG1-low grade and 154 GG2-GG5 intermediate and high grade). Classification of low grade (teal circle) and intermediate and high-grade cancer (orange circle) patients where a positive Sentinel™ CS Score is indicative of having high-grade prostate cancer and a negative Sentinel™ CS Score is indicative of low-grade cancer.

FIG. 9B: Sorted plot of cancer status in the validation group set as shown in FIG. 9A that examines 300 prostate cancer patients. Classification of low grade (teal circle) and high-grade cancer (orange circle) patients where a positive Sentinel™ CS Score is indicative of having high-grade prostate cancer and a negative Sentinel™ CS Score is indicative of low-grade cancer.

FIG. 9C: Receiver Operator Curve (ROC) for Sentinel™ CS Test. The ROC curve for the analysis of 300 prostate cancer patients, as shown in FIGS. 9A and 9B was calculated by successively calculating (1-specificity) for different user-defined false negative rates. Performance characteristics reported in Table 6 (see, [000112]) were from the user defined false negative rate of 0.05 (shown in red).

FIGS. 10A-10C show the clinical validation of high throughput OpenArray™ interrogation of urinary exosomal sncRNA using the Sentinel™ HG Test. The data from a case-control study of 1436 men (836 subjects in the training group used to cross-validate the interrogation of the same sncRNAs identified in the Discovery HG phase and 600 independent subjects used in the validation study) are shown.

FIG. 10A: Scatter plot of cancer status in the validation group set that examines 300 prostate cancer patients (200 GG1+GG2 low grade and 100 GG3-GG5 intermediate and high grade). Classification of low grade (teal circle) and intermediate and high-grade cancer (orange circle) patients where a positive Sentinel™ CS Score is indicative of having high-grade prostate cancer and a negative Sentinel™ CS Score is indicative of low-grade cancer.

FIG. 10B: Sorted plot of cancer status in the validation group set as shown in FIG. 10A that examines 300 prostate cancer patients. Classification of low grade (blue circle) and high-grade cancer (red circle) patients where a positive Sentinel™ HG Score is indicative of having high grade prostate cancer and a negative Sentinel™ HG Score is indicative of low-grade cancer.

FIG. 10C: Receiver Operator Curve (ROC) for Sentinel™ HG Test. The ROC curve for the analysis of 300 prostate cancer patients, as shown in FIGS. 10A and 10B was calculated by successively calculating (1-specificity) for different user-defined false negative rates. Performance characteristics reported in Table 6 (see, [000112]) were from the user defined false negative rate of 0.05 (shown in red).

DETAILED DESCRIPTION

The present subject matter may be understood more readily by reference to the following detailed description that forms a part of this disclosure. It is to be understood that this invention is not limited to the specific products, methods, conditions or parameters described and/or shown herein, and that the terminology used is for the purpose of describing particular aspect and embodiments by way of example only and is not intended to be limiting of the claimed invention.

The disclosure relates to a method for screening, diagnosing and treating prostate cancer in a subject. The method provides robust tests for (1) classifying a male patient with unknown prostate cancer status and (2) accurately distinguishing between prostate cancer grades in biological samples from patients. The method is based on the detection and correlation of the aggregate expression profiles of a collection of sncRNAs from the patient's biological sample to determine if a patient has prostate cancer or not using Sentinel™ PCa Test. For the patient identified as having prostate cancer, the exosomal sncRNA is further interrogated using the Sentinel™ Clinical Significant (CS) Test to distinguish patients with clinically significant or aggressive (GG2-GG5) from those with clinically insignificant or indolent (GG1) prostate cancer, and the Sentinel™ High Grade (HG) Test to identify patients with high grade, high risk (GG3-GG5) prostate cancer.

The disclosed method is based on an unbiased statistical approach developed to identify important interactions of individual sequences and combinations of sequences that correlate best to a phenotype of interest. The approach is based on (i) the modulating effects of miRNA on mRNA and (ii) the influence of snoRNAs on mRNA translatability through post-transcriptional modification of ribosomal RNAs, tRNAs and other nuclear RNAs, which lead to new protein products that alters protein function and phenotype.

The disclosed computational/statistical approach analyses urinary exosomal sncRNAs to provide a very granular analysis of the critical associations between sncRNAs that leads to the identification of Sentinel sequences that accurately predict the prostate cancer phenotype. This is illustrated in the accompanying FIG. 3. For example, in the single entity analysis, the expression level of individual sncRNAs is correlated to the Grade Group of the prostate cancer (the phenotype). For each sncRNA entity there are two informative outcomes: either an increase in the expression level of the entity relative to the control pathology (e.g., no cancer) or a decreased expression level. No change of expression between the two phenotypes indicates that there is no association (1) with either phenotypes, and (2) the entity is not useful as a marker of either phenotype. Thus, when single entity is used in the analysis, there are only two informative outcomes, leaving all of the possible sncRNA interactions unexplored.

Figure 1:
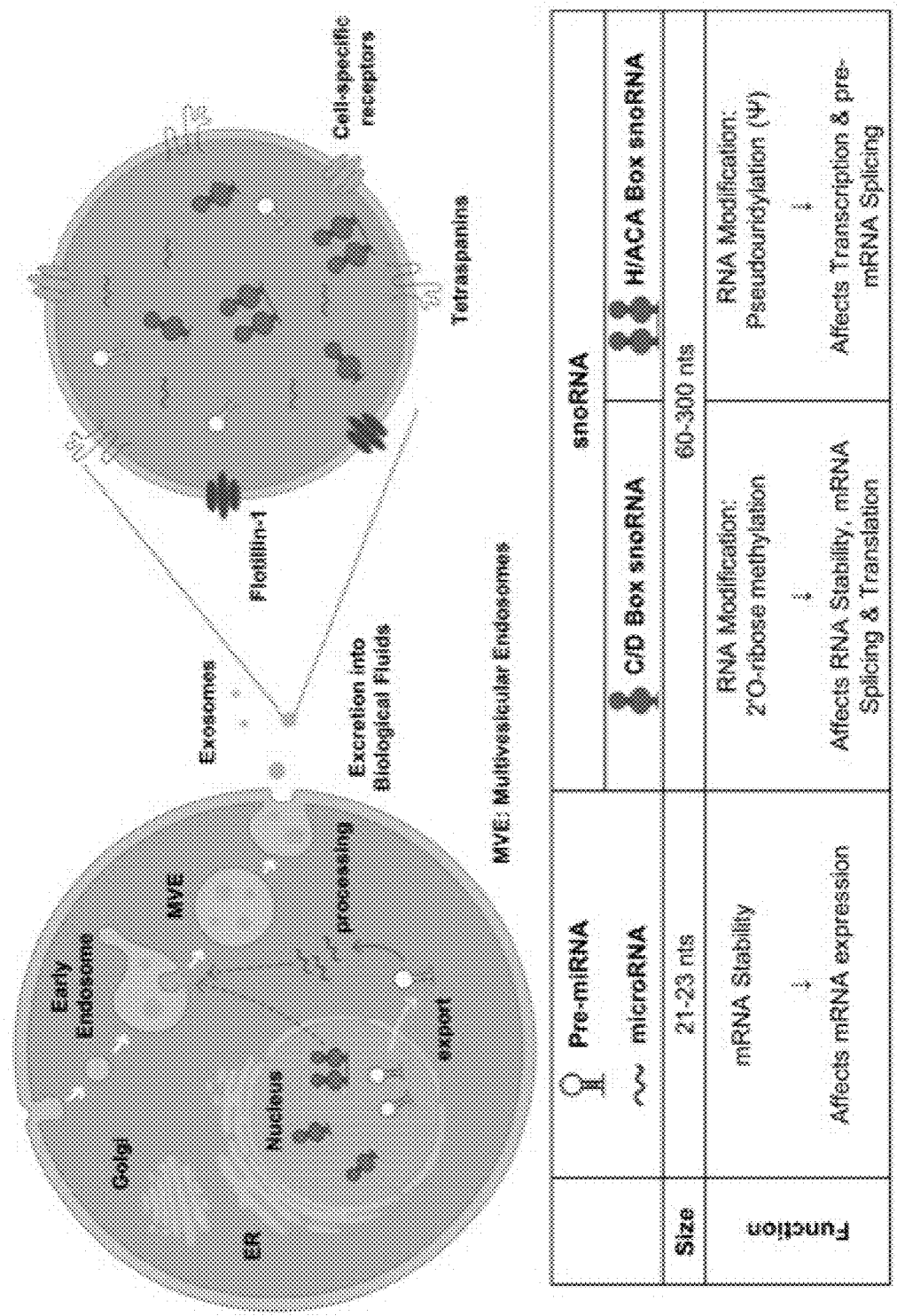
FIG. 1: Exosomes are small extracellular, membrane bound vesicles that are formed in the early endosomes and released from cells. Exosomes contain proteins, mRNAs and an array of sncRNAs [miRNAs and C/D box and H/ACA Box small nucleolar RNA (snoRNAs)] that reflect the biology of the cell.
Figure 2:
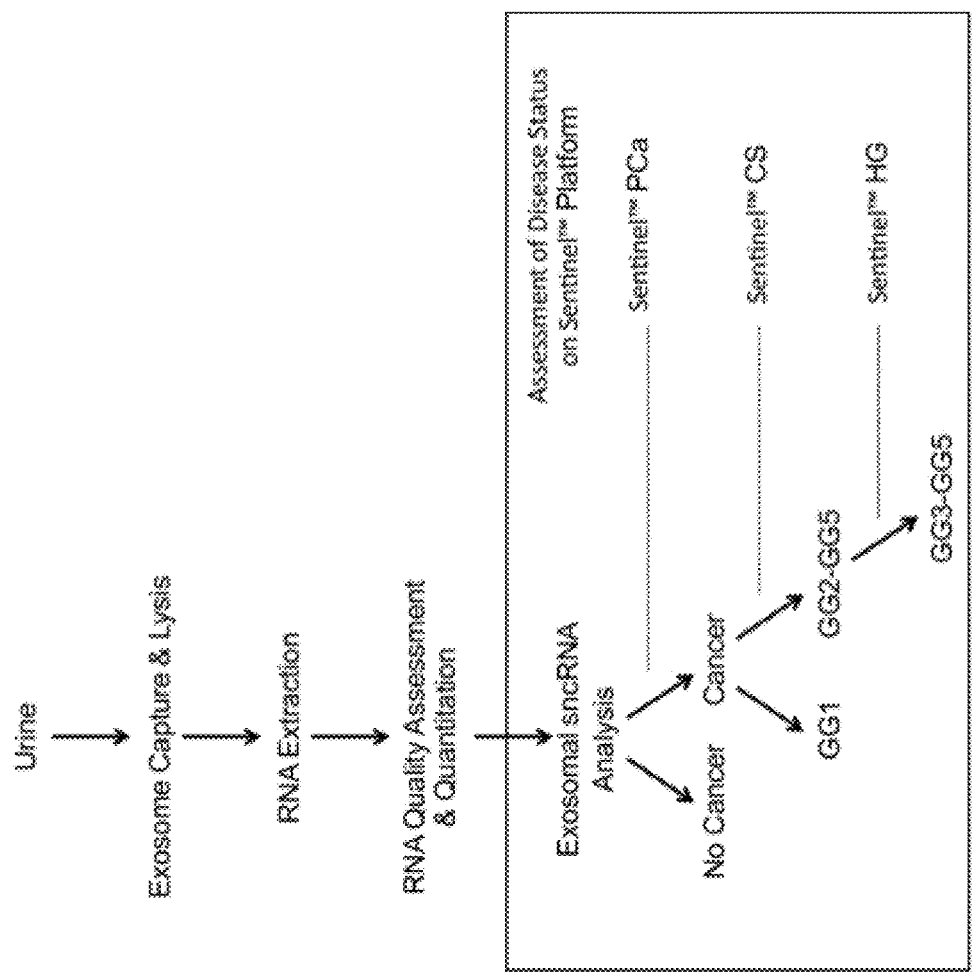
FIG. 2: Using a commercial kit, cell-free urine is collected from the patient. The exosomes in the urine are captured, and the RNA is extracted from the exosomes. The RNA yield is measured using the Qubit assay (ThermoFisher) and the sample quality is assessed using the Agilent 2100 bioanalyzer. The resultant sncRNA levels are interrogated using custom made OpenArray™ (Thermo Fisher) plates that are specifically designed for the miR Scientific Sentinel™ PCa, Sentinel™ CS or Sentinel™ HG Tests. Interrogate is a common term of art for the simultaneous analysis of a large number of sequences in a biological sample. The resultant readout for amplification curves for snoRNA and microRNA (collectively called sncRNAs), are then analyzed and used to diagnose the patient, and when cancer is present to classify the disease, and monitor treatment accordingly.
Figure 3:
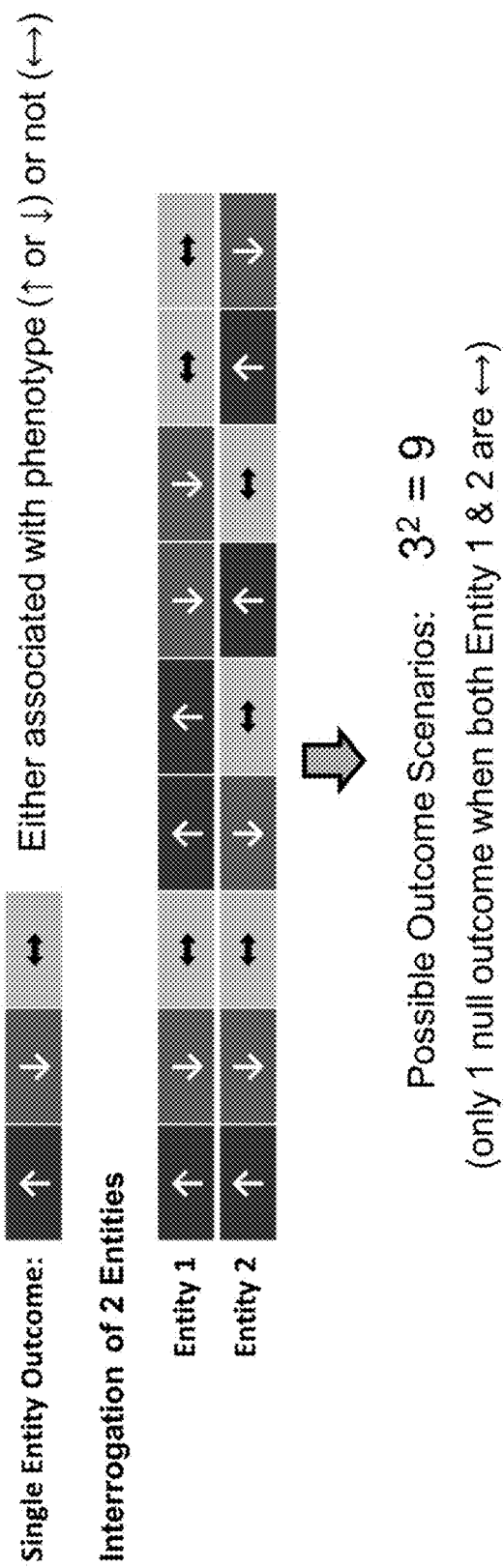
FIG. 3 illustrates the complexity of using more than a single entity to establish an unbiased statistical approach to identify important interactions to identify individual and combinations of sncRNAs and to correlate the grade grouping or prostate cancer phenotype. (See, [00048]-[00051]).

In the two entities analysis, examining the association of the expression changes for all possible interactions between two entities results in 8 different informative outcomes and 1 non-informative outcome (when neither entity is differentially expressed in their phenotype) (see, FIG. 3 "Interrogation of 2 Entities). Thus, in the context of the Sentinel™ Tests, when the association of all possible combinations of two sncRNA entities with a specific grade group are compared, there are 8 different ways that will lead to a meaningful association between pairs of sncRNAs and grade groups. This provides a more detailed analysis that uncovers hidden associations between expression levels of sncRNAs and Grade Grouping.

Using the same approach of three or four or more sncRNA entities provides a very granular analysis of the association between sncRNA expression and phenotype (grade grouping), making it possible to assess a patient of unknown disease status and predict the individual disease status using the expression levels of urinary exosomal sncRNA selected by the algorithm.

Development of Sentinel™ PCa, and Sentinel™ HG Test Sentinel™ CS Platforms

The Sentinel™ PCa Test is a classification platform or algorithm based on the analysis of a collection of signature sncRNA (i.e., miRNAs and snoRNAs sequences) levels. The predictive value of each sequence is defined via a data-driven Selection Algorithm that is independent of the a priori determined biological role of the sequences in prostate biology. The Selection Algorithm is trained on a dataset consisting of: (1) control subjects who presented in urology for conditions unrelated to prostate cancer; (2) subjects with suspicion of prostate cancer known to not have prostate cancer based on the biopsy results; and (3) patients diagnosed with prostate cancer and whose core needle biopsy histopathology was reported as Grade Groups 1 through 5 (GG1-GG5).

To establish robust datasets for the Sentinel™ Tests, exosomal sncRNAs obtained from the urinary exosomes of these training set of patients were interrogated using the Affymetrix miR 4.0 microarrays to define expression signatures. These studies using selected subjects with well characterized histopathology are referred to as the Discovery PCa, Discovery CS, and Discovery HG Tests. The patients included in the "no cancer" group were carefully selected from age-matched men who were seen at urology clinics for issues unrelated to urological oncology, and from men who had one or more 12-needle diagnostic core needle biopsy that showed no evidence of prostate cancer (NEPC). For patients in the "cancer" cohort, the pathological grade group classification of the core needle biopsies each tumor was thoroughly assessed. These carefully select groups of patients (no cancer and cancer group in different stages of cancer) form the training set in the development of the Discovery PCa, CS and HG Tests. The demographics of the 235 patients used for the Discovery experiments are shown in Table 4 (see, [000103]-[000104])

The Selection Algorithm

The most informative sncRNA sequences that discriminate between cancer and no cancer were identified using Selection algorithm which determines which sncRNA sequences are differentially represented between patients that do not have prostate cancer (NEPC) and those with prostate cancer (GG1-GG5). This is exemplified below for the Discovery PCa Test. The Selection algorithm tests how well the levels of the urinary exosomal sncRNAs correlate with pathological stage of the disease (cancer/no cancer) in a large population of participants [89 subjects with NEPC and 146 patients with cancer (GG1-GG5)] with carefully defined pathology. The Selection algorithm individually assesses how well each of the 6,599 sncRNAs interrogated on the miR4.0 arrays correlates the known pathology of the tumor. Since many sncRNA are coordinately modulated, the algorithm then assesses all combinations of 2 sncRNAs, 3 sncRNAs or 4 sncRNAs, followed by examination of each individual sncRNA using a leave-one-out strategy to assess the importance of each individual sncRNA in the pathology of the disease. As would be expected leaving out most of the 6,599 sncRNA sequences from the Selection algorithm has no impact on the distinction between having prostate cancer and no prostate cancer because they are not differentially associated with either pathology. The impact of the sncRNAs assessment can be visualized using the importance plot shown in FIG. 5B. The importance plots show the following: (1) some exosomal sncRNAs are present in different levels in different pathologies, (2) the sncRNAs are snoRNAs and miRNAs indicating that one type of sncRNA is insufficient for the disclosed analysis and (3) the diagnosis using the algorithm does not change with more than 280 sncRNA sequences in the classification assessment.

The informative sequences for the Discovery CS Test (which differentiates between low-risk (GG1) and intermediate- and high-risk prostate cancer (GG2-GG5), were identified using the appropriate Grade Groups and the same Selection strategy (FIG. 6A-6B). The patient population for this analysis included 89 subjects with NEPC and 146 patients with cancer (GG1-GG5)]

The informative sequences for the Discovery HG Test (which differentiates between low- and intermediate-risk (GG1+GG2) and high-grade, high-risk (GG3-GG5) prostate cancers were similarly determined (FIGS. 7A-7B). The patient population for this analysis included 181 patients with GG1+GG2 cancer and 55 patients with GG3-GG5 cancer. (FIGS. 7A-7B).

It is important to note that while some of the sncRNAs are common between the tests, their relative importance in the Classification of disease status varies from test to test (i.e., Discovery PCa Test, CS Test, and HG Test).

For each Test the most informative 280 sncRNAs SEQ. ID NOs: 1-840) were used to design customized OpenArray™ platforms. The OpenArray™ platform for each Sentinel™ Test was further validated in a large case-control study of 1436 patients. The demographics of the subjects used to train and validate the Sentinel™ PCa, Sentinel™ CS and Sentinel™ HG Tests are shown in Table 5 (see [000109]-[000110]). A stratified random sample of 600 subjects was selected to identify the validation dataset; the remaining 836 subjects served as the training dataset. The validation sample of 600 patients was stratified so that an equal number of subjects were biopsy negative versus biopsy positive (300 each), and of the biopsy positive cases, 200 were GG1+GG2 (146 GG1 and 54 GG2) and 100 GG3-GG5.

The Sentinel™ PCa Test to Identify Prostate Cancer

The Sentinel™ PCa, Sentinel™ CS and Sentinel™ HG Tests are based on a Classification Algorithm that takes as input the sncRNA expression signature for each patient with unknown disease status and produces a Sentinel™ Score; the participant is classified by comparing this Score to the pre-determined cutoff value (obtained from cross-validation in the training dataset) that controls sensitivity for classifying a future patient with unknown disease status (but known expression signature), at a user-defined level (typically 95% or greater).

The Sentinel PCa Score is compared to a calculated cutoff that controls sensitivity for a future patient at a desired level of, for example, 95% to distinguish between having prostate cancer and no prostate cancer for the PCa Test (FIG. 5A-5B). The Sentinel™ PCa Test utilizes 280 sncRNA (identified by the Discovery PCa Test), of which 145 unique sncRNAs: 60 miRNAs and 85 snoRNAs are highly informative. This defines the classification boundary used to dichotomize patients into prostate cancer or not. The cutoff is determined by the algorithm such that the Sentinel™ PCa score, which dichotomizes the patients into cancer/no cancer, correctly classify the patient as having cancer 19 times out of 20 (i.e., with 95% sensitivity).

TABLE 1

SEQ ID NOs: 1-280 Used in the PCa Test Analysis

| SEQ ID NO: | Sequence Name | Sequence |
|---|---|---|
| 1 | hsa-miR-548ac | CAAAAACCGGCAAUUACUUUUG |
| 2 | MIR6687 | GAGAAUGGGGGGACAGAUGGAGAGGACACAGGCUGGCACUGAGGUCCCCUCC ACUUUCCUCCUAG |
| 3 | MIR3150B | GAGGGAAAGCAGGCCAACCUCGAGGAUCUCCCCAGCCUUGGCGUUCAGGUGC UGAGGAGAUCGUCGAGGUUGGCCUGCUUCCCCUC |
| 4 | MIR1301 | GGAUUGUGGGGGGUCGCUCUAGGCACCGCAGCACUGUGCUGGGGAUGUUGCA GCUGCCUGGGAGUGACUUCACACAGUCCUC |
| 5 | MIR548P | AUUAGGUUGGUAUAAAAUUAAUUGCAGUUUUUGUCAUUACUUUCAAUAGCA AAAACUGCAGUUACUUUUGCACCAAUGUAAUAC |
| 6 | hsa-let-7b-5p | UGAGGUAGUAGGUUGUGUGGUU |
| 7 | ENSG00000222185 | UGGACCAAUGAUGUGAAUGGAAUGCAUCUGAAUAAAAAUUAUGAUCAAUCA GUUUUUGGAACAACUGAGGUCCAC |
| 8 | MIR578 | AGAUAAAUCUAUAGACAAAAUACAAUCCCGGACAACAAGAAGCUCCUAUAGC UCCUGUAGCUUCUUGUGCUCUAGGAUUGUAUUUUGUUUAUAUAU |
| 9 | hsa-miR-323a-3p | CACAUUACACGGUCGACCUCU |
| 10 | hsa-miR-4283 | UGGGGCUCAGCGAGUUU |
| 11 | MIR4438 | UAAGUGUAAACUUAAGGACUGUCUUUUCUAAGCCUGUGCCUUGCCUUUCCUU UGGCACAGGCUUAGAAAAGACAGUCUUUAAGUUUACAUUC |
| 12 | MIR1205 | GAAGGCCUCUGCAGGGUUUGCUUUGAGGUACUUCCUUCCUGUCAACCCUGUU CUGGAGUCUGU |
| 13 | hsa-miR-6866-3p | GAUCCCUUUAUCUGUCCUCUAG |
| 14 | hsa-miR-6839-3p | UUGGGUUUUCUCUUCAAUCCAG |
| 15 | hsa-miR-8061 | CUUAGAUUAGAGGAUAUUGUU |
| 16 | hsa-miR-4323 | CAGCCCCACAGCCUCAGA |
| 17 | MIR6784 | UACAGGCCGGGGCUUUGGGUGAGGGACCCCCGGAGUCUGUCACGGUCUCACC CCAACUCUGCCCCAG |
| 18 | SNORA22 | UUGCACAGUGAACACCCAAGUGUGCUUUAUAGUUCCCUUGGCUUUGACCCUG UGCUAGAGCAUUGCCUGCUCUUCUCCUCUGCAUUAAAAGGAAUAUUUAUCCU UUUAAAUGUAUUCAGAAAGCCAGCACAUUA |

TABLE 1-continued

SEQ ID NOs: 1-280 Used in the PCa Test Analysis

| SEQ ID NO: | Sequence Name | Sequence |
|---|---|---|
| 19 | MIR6803 | CUCCUCUGGGGGUGGGGGCUGGGCGUGGUGGACAGCGAUGCAUCCCUCGCCUUCUCACCCUCAG |
| 20 | MIR371A | GUGGCACUCAAACUGUGGGGGCACUUUCUGCUCUCUGGUGAAAGUGCCGCCAUCUUUUGAGUGUUAC |
| 21 | MIR378E | CUGACUCCAGUGUCCAGGCCAGGGGCAGACAGUGGACAGAGAACAGUGCCCAAGACCACUGGACUUGGAGUCAGGACAU |
| 22 | hsa-miR-6825-5p | UGGGGAGGUGUGGAGUCAGCAU |
| 23 | ENSG00000252204 | AUGACCUGUGAAACCAAGGGCUCCUAAUGCUAUGACCAAAGACUGAAGCUCUCUAUGAGAUGCCAGCCACUCAAUAGUGCACUUUUCUGAGAAGAUAUAAGA |
| 24 | MIR7847 | GUGUCGGCUGUGGCGUGACUGUCCCUCUGUGUCCCCACUAGGCCCACUGCUCAGUGGAGCGUGGAGGACGAGGAGGAGGCCGUCCACGAGCAAUGCCAGCAU |
| 25 | hsa-miR-147b-3p | GUGUGCGGAAAUGCUUCUGCUA |
| 26 | MIR181A1 | UGAGUUUUGAGGUUGCUUCAGUGAACAUUCAACGCUGUCGGUGAGUUUGGAAUUAAAAUCAAAACCAUCGACCGUUGAUUGUACCCUAUGGCUAACCAUCAUUACUCCA |
| 27 | hsa-miR-424-5p | CAGCAGCAAUUCAUGUUUUGAA |
| 28 | MIR4712 | GACAGGAUUCCAGUACAGGUCUCUCAUUUCCUUCAUGAUUAGGAAUACUACUUUGAAAUGAGAGACCUGUACUGUAUCUGUU |
| 29 | hsa-miR-4487 | AGAGCUGGCUGAAGGGCAG |
| 30 | hsa-miR-18b-3p | UGCCCUAAAUGCCCCUUCUGGC |
| 31 | ENSG00000238298 | UUAUUUUUGUAGUUGAUGAAUGUGCUGAUUGGGUAUUCUCGUGUGUGUGAGGUGCCACCCUCAAACUUUGUUAUGAUGUUGGCACAUUACCCAUCUGAUA |
| 32 | hsa-miR-4435 | AUGGCCAGAGCUCACACAGAGG |
| 33 | hsa-miR-2114-3p | CGAGCCUCAAGCAAGGGACUU |
| 34 | hsa-miR-4758-3p | UGCCCCACCUGCUGACCACCCUC |
| 35 | SNORD113-1 | AAAGUGAGUGAUGAAUAGUUCUGUGGCAUAUGAAUCAUUAAUUUUGAUUAAACCCUAAACUCUGAAGUCC |
| 36 | hsa-miR-21-3p | CAACACCAGUCGAUGGGCUGU |
| 37 | ENSG00000239123 | AUCCUUUUGUGGGUUCAUAAGCAUGAUGAUCAGGUUUUCAGGCAUAUGUGUACGAUGUGCCUCCUUCAAACUUUGUUAGGAUGCUACCACGCUACCCAUCUGACU |
| 38 | hsa-miR-4680-5p | AGAACUCUUGCAGUCUUAGAUGU |
| 39 | MIR5580 | UGCUGGCUCAUUUCAUAUGUGUGCUGAGAAAAUUCACACAUAUGAAGUGAGCCAGCAC |
| 40 | SNORD42B | GUGCAUAUGAUGGAAAAGUUUUAAUCUCCUGACACUUGUGAUGUCUUCAAAGGAACCACUGAUGCAC |
| 41 | MIR365A | ACCGCAGGGAAAUGAGGGACUUUUGGGGGCAGAUGUGUUUCCAUUCCACUAUCAUAAUGCCCCUAAAAAUCCUUAUUGCUCUUGCA |
| 42 | SNORD114-21 | UGGAUCAAUGAUGACCACUGGUGGCGUAUGAGUCAUAUGUGAUGAAUACGUGUCUGGAACUCUGAGGUCCA |

TABLE 1-continued

SEQ ID NOs: 1-280 Used in the PCa Test Analysis

| SEQ ID NO: | Sequence Name | Sequence |
|---|---|---|
| 43 | ENSG00000252945 | UGAGUUUUGGGAUGAGACCCUGGAAUAAGUGCUGGACACAGUGCCUGAAUCAGACUGUGGAAAUAUUAAUGUAUUUUAUUUUUACUUA |
| 44 | MIR4757 | UUCCAGCCCGAGGCCUCUGUGACGUCACGGUGUCUGCGGGAGGAGACCAUGACGUCACAGAGGCUUCGCGCUCUGAG |
| 45 | hsa-miR-1267 | CCUGUUGAAGUGUAAUCCCCA |
| 46 | SNORD114-24 | UGGAUCGAUGGUGACUGUUGAUGGCAUAUGACUCACAUAUGAUGAGUACGUAUCUGGAACUCUGAGGUCUG |
| 47 | ENSG00000238676 | AUCCUUUUGUACUUGGUAAGCAUGAUGAUUGGGUUUUUAUGCUUAUAUGAGACAUGCUUGUCUCAAAUCUUGUUACAGCACAUUACCCUUCCUACU |
| 48 | hsa-miR-628-3p | UCUAGUAAGAGUGGCAGUCGA |
| 49 | MIR7158 | GGCUCAAUCUCUGGUCCUGCAGCCUUCUGCCUUUGGCUUUCUGAAGCGAGCUGAACUAGAGAUUGGGCCCA |
| 50 | ENSG00000238605 | GUCCUUUUGUAGUCCAUAAGCAUGGUGAUUUGGUUUCAUGCUCAUGUGUCAGAUAUGCUUCCCUCAAACCUUGUUACAGCAUCAUCACAUUACCUGUUUGAUG |
| 51 | ENSG00000212618 | UUCUUACAAAUCUAAAUGUGCUUUGAUGCAAGUAUAUUUGAAUCCCUUUCCAUCUGAUAACUGAGCAAAAUAAUA |
| 52 | hsa-miR-429 | UAAUACUGUCUGGUAAAACCGU |
| 53 | hsa-miR-338-5p | AACAAUAUCCUGGUGCUGAGUG |
| 54 | hsa-miR-3650 | AGGUGUGUCUGUAGAGUCC |
| 55 | hsa-miR-520d-5p | CUACAAAGGGAAGCCCUUUC |
| 56 | SNORD28 | GUCAGAUGAUUUGAAUUGAUAAGCUGAUGUUCUGUGAGGUACAAAAGUUAAUAGCAUGUUAGAGUUCUGAUGGCA |
| 57 | hsa-miR-34b-3p | CAAUCACUAACUCCACUGCCAU |
| 58 | hsa-miR-548av-3p | AAAACUGCAGUUACUUUUGC |
| 59 | ENSG00000200042 | AAAAUUAUACUUUCAGCAAUCAUCUCUAUAGUUUGUUACUAGAGAAGCUUCUGUGAAUGUGUAGAGCACCGGAAACCACAAGGCAAAGGCUCAGCAUUCUCUCCUAAGCGCGAAGCUGGCUCCUGGUGUUGGUUGGCCGCAACUGCCAUUUGCCAUUGAUGAUCAUUCUUCUCUUCCUGUGGUAGAGGAAGAGGGAGAGAAUGCAGUUUGAGUGG |
| 60 | ENSG00000238596 | AUCCUUCUGUAGUUCGUGAGCAUGAUGAUUGGGUGCUCACACACAUAUGUGAGAUGUACCACCCUCAAACCUUGUUACAAUGUCAGCACAUUACCCAUCUGACC |
| 61 | hsa-miR-1253 | AGAGAAGAAGAUCAGCCUGCA |
| 62 | MIR3910-2 | UUUUUUUGUUGCUUGUCUUGGUUUUAUGCCUUUUAUGUGCCUUGAUAUAAAAGGCAUAAAACCAAGACAAGCAACAGAAAAA |
| 63 | MIR4690 | GAGCAGGCGAGGCUGGGCUGAACCCGUGGGUGAGGAGUGCAGCCCAGCUGAGGCCUCUGC |
| 64 | hsa-miR-192-5p | CUGACCUAUGAAUUGACAGCC |
| 65 | hsa-miR-302b-5p | ACUUUAACAUGGAAGUGCUUUC |
| 66 | hsa-miR-668-3p | UGUCACUCGGCUCGGCCCACUAC |

TABLE 1-continued

SEQ ID NOs: 1-280 Used in the PCa Test Analysis

| SEQ ID NO: | Sequence Name | Sequence |
|---|---|---|
| 67 | hsa-miR-4720-5p | CCUGGCAUAUUUGGUAUAACUU |
| 68 | hsa-miR-223-3p | UGUCAGUUUGUCAAAUACCCCA |
| 69 | ENSG00000239018 | AUCCUGUUAUGAUUCAUAAGCAUGAUGACUGAGUUUUCACACUCCUGUGUGAGAUGUGCCUCCCUCUAACCUUAUUACAACAUUGACAUCUUACUCAUUUGACA |
| 70 | hsa-miR-100-5p | AACCCGUAGAUCCGAACUUGUG |
| 71 | hsa-miR-124-5p | CGUGUUCACAGCGGACCUUGAU |
| 72 | ENSG00000201151 | CUAAAACAAUGUCAAUAGUUUUCAUCAACAGCAGUUGAACCUAGUAAGUGUCGAUACUUUGGGUCUGAGUGG |
| 73 | hsa-miR-550a-5p | AGUGCCUGAGGGAGUAAGAGCCC |
| 74 | SNORA38B | CCCUCCUACAAAGGCAUGUCUAUAGUUCCUUGUCUUUGGACAUGUAAGAAUUGGAGGCAAAGAAAUGUGGACUUGGAGAAAUCUGGGGCCAGCUUGCUCUCCGCAGGCUCAAGAUCAACCAUCCCACAUAG |
| 75 | hsa-miR-636 | UGUGCUUGCUCGUCCCGCCCGCA |
| 76 | hsa-miR-6739-5p | UGGGAAAGAGAAAGAACAAGUA |
| 77 | hsa-miR-4764-3p | UUAACUCCUUUCACACCCAUGG |
| 78 | hsa-miR-7851-3p | UACCUGGGAGACUGAGGUUGGA |
| 79 | ENSG00000212168 | CUGUAAUGAUGUUGCUCAAAUAUCUGACCUGAAAUGAUUAUAUAGACCAAUUUAAUACUGAAGAA |
| 80 | SNORA9 | UAGCAAGCCUCCAGCGUGCUUGGGUCUGCGGUGACCCUAUGCAUUCCUUCAGUGCUUGCUAGAACAGUUUUGAAACGGUUUGAGGCCUUGCCCUGCUCCAUCCAGAGCAAGGUUAUAGAAAUUUCAGACAAUG |
| 81 | hsa-miR-3115 | AUAUGGGUUUACUAGUUGGU |
| 82 | ENSG00000252071 | AACCUAUGUAUCAUAUCACAUUGGGUUUUCAUGCUCAUGUGUGAGAAGUGCCUCUUUCAAACCUUGUUCUGACACAUUAUCUUACA |
| 83 | hsa-miR-6829-5p | UGGGCUGCUGAGAAGGGGCA |
| 84 | MIR4693 | GUUUAAAGAAUACUGUGAAUUUCACUGUCACAAAUUCAAAUAAAGUGAGAGUGGAAUUCACAGUAUUUAAGGAAU |
| 85 | MIR3162 | CUGACUUUUUUAGGGAGUAGAAGGGUGGGGAGCAUGAACAAUGUUUCUCACUCCCUACCCCUCCACUCCCCAAAAAAGUCAG |
| 86 | hsa-miR-7152-3p | UCUGGUCCUGGACAGGAGGC |
| 87 | ENSG00000252236 | GGUCUCUUGUGUCGGCACCUGGGUGGCUUGCCGCCCACACAACCAAAUUAAAAAAUAACACAGAAGGGUAAGGUAAGUCUCCAUUAAACCCAGGAAAGAGACUGGAAAACUCCCUCUUUUGGAGCCUGUCUAUAGUCACAGGU |
| 88 | MIR153-2 | AGCGGUGGCCAGUGUCAUUUUUGUGAUGUUGCAGCUAGUAAUAUGAGCCCAGUUGCAUAGUCACAAAAGUGAUCAUUGGAAACUGUG |
| 89 | hsa-miR-7154-3p | AGGAGGACAAGUUGUGGGAU |

TABLE 1-continued

SEQ ID NOs: 1-280 Used in the PCa Test Analysis

| SEQ ID NO: | Sequence Name | Sequence |
|---|---|---|
| 90 | hsa-miR-1468-3p | AGCAAAAUAAGCAAAUGGAAAA |
| 91 | MIR4446 | CUGGUCCAUUUCCCUGCCAUUCCCUUGGCUUCAAUUUACUCCCAGGGCUGGCAGUGACAUGGGUCAA |
| 92 | hsa-miR-5681a | AGAAAGGGUGGCAAUACCUCUU |
| 93 | MIR592 | UAUUAUGCCAUGACAUUGUGUCAAUAUGCGAUGAUGUGUUGUGAUGGCACAGCGUCAUCACGUGGUGACGCAACAUCAUGACGUAAGACGUCACAAC |
| 94 | MIR4521 | UCGGCUAAGGAAGUCCUGUGCUCAGUUUUGUAGCAUCAAAACUAGGAUUUCUCUUGUUAC |
| 95 | MIR636 | UGGCGGCCUGGGCGGGAGCGCGCGGGCGGGGCCGGCCCCGCUGCCUGGAAUUAACCCCGCUGUGCUUGCUCGUCCCGCCCGCAGCCCUAGGCGGCGUCG |
| 96 | ENSG00000238734 | AUCCUUUUGUAAUACAUAAGCAUAAUGAUUGGGUUUUUAUGUUCACAUGUUUGAUAUGCCUCCCUCAAAUCCUCUUAUGAUGUCGGCACAUUACCCAUCUGAGG |
| 97 | hsa-miR-6087 | UGAGGCGGGGGGGCGAGC |
| 98 | MIR4498 | AGGGCUGGGCUGGCAGGGCAAGUGCUGCAGAUCUUUGUCUAAGCAGCCCCUGCCUUGGAUCUCCCA |
| 99 | hsa-miR-6740-5p | AGUUUGGGAUGGAGAGAGGAGA |
| 100 | hsa-miR-381-5p | AGCGAGGUUGCCCUUUGUAUAU |
| 101 | hsa-miR-302e | UAAGUGCUUCCAUGCUU |
| 102 | hsa-miR-4688 | UAGGGGCAGCAGAGGACCUGGG |
| 103 | hsa-miR-1976 | CCUCCUGCCCUCCUUGCUGU |
| 104 | ENSG00000252128 | ACUCCAUGAUGAACCCAAAAUGCCAAGUAUAUGACUGAACUUACAAGUGAUACCAUCUUACGACUGAAGAGU |
| 105 | ENSG00000238922 | AUGCUUUUGUAGUUCGUAAGCAUGAUGAUUGGGUUUUCUUGCUCUUGUAUGAGAUGUGCCUCCGUCAUACCUUGGAAACCUGACUUGAAA |
| 106 | hsa-miR-6515-5p | UUGGAGGGUGUGGAAGACAUC |
| 107 | hsa-miR-6838-3p | AAGUCCUGCUUCUGUUGCAG |
| 108 | MIR892A | GCAGUGCCUUACUCAGAAAGGUGCCAGUCACUUACACUACAUGUCACUGUGUCCUUUCUGCGUAGAGUAAGGCUC |
| 109 | ENSG00000251959 | ACAAGGGUUCUAAUUUCACUACAUCCCCUCCAAUAUUUGGUAUCUUUCCUUUCUUAAAAAAUAGCCAGCCUAGUGAGUGUGAAGUGGCAUCUCAAUGUGGUUUUGAUUU |
| 110 | ENSG00000207100 | UGCACUGCGUGGUAUCUGCACUCAGCAGUUUACUCCUGCUAGGGUGUUCAAAGGUCAGUGCCAUAGAAAAUCCAGUAUCUGGUUUCAUUGGUUUUCUUGGCUUUGUGCUUGUUAAACCUGGUAUUUCUAUUGAUACAGCA |
| 111 | ENSG00000238843 | AUACUUUUGUAGGUCAUAAGCUGAGGAUUGGGUUUUCAUGCUCUUGUGUGAGAUAUGCUUCUCUCAAACCUUCUGACCUGGGCACAUUACCCAGCUAAUG |
| 112 | ENSG00000221496 | UUUCUAUAGUUUAUUACCAGAAAAGUUUCUCAGAAUGUGUAGAGCACUGGAAACCAUGAGGAAGAGGCAUAGCGUUCUCUCUUGAGCAUCAAGUUGGCUGUUGGUGUUUGCUUUGCUGCAAACGCCAUUUGUAUUGUCUUCCUUGUCUUCCUUUAGGAGAGUAAGAGGGAGAGGACACAGUCUGGGUAG |

TABLE 1-continued

SEQ ID NOs: 1-280 Used in the PCa Test Analysis

| SEQ ID NO: | Sequence Name | Sequence |
|---|---|---|
| 113 | hsa-miR-4640-3p | CACCCCCUGUUUCCUGGCCCAC |
| 114 | MIR2117 | GCUCUGAUUUACUUCUGUCCGGCAUGGUGAACAGCAGGAUUGGCUGUAGCUG UUCUCUUUGCCAAGGACAGAUCUGAUCU |
| 115 | hsa-miR-642b-5p | GGUUCCCUCUCCAAAUGUGUCU |
| 116 | MIR25 | GGCCAGUGUUGAGAGGCGGAGACUUGGGCAAUUGCUGGACGCUGCCCUGGGC AUUGCACUUGUCUCGGUCUGACAGUGCCGGCC |
| 117 | ENSG00000238748 | AUCCUUUUGUAGUUCAUAAAUGUGAUAAUUGGGUGUUCACGUGCAUGUAUG AGAUGUCUGAGUCCCUCAAACCUUGUUACAACAUUGGUACAUUACCCAUUUU ACC |
| 118 | hsa-miR-6074 | GAUAUUCAGAGGCUAGGUGG |
| 119 | MIRLET7F2 | CUAUACAGUCUACUGUCUUUCC |
| 120 | hsa-miR-6868-3p | UUCCUUCUGUUGUCUGUGCAG |
| 121 | MIR4320 | GACAUGUGGGGUUUGCUGUAGACAUUUCAGAUAACUCGGGAUUCUGUAGCUU CCUGGCAACUUUG |
| 122 | ENSG00000238651 | AUCCUUUUGUAGUUUAUAAGCGUGAUGACUGGGGUUUCACGUGCAUGUGUG AAAUGUGCCUUCCCCAAGCCUUGUUAUGACCCAUUGGAACAUUACCCCUUU GACA |
| 123 | hsa-miR-6510-3p | CACCGACUCUGUCUCCUGCAG |
| 124 | hsa-miR-4312 | GGCCUUGUUCCUGUCCCCA |
| 125 | hsa-miR-4769-3p | UCUGCCAUCCUCCCUCCCCUAC |
| 126 | hsa-miR-6728-5p | UUGGGAUGGUAGGACCAGAGGGG |
| 127 | MIR5192 | UUAGUUCCAGCCUCCUGGCUCACCUGGAACCAUUUCUCCUGGGAAGCAUGGU AGCCAGGAGAGUGGAUUCCAGGUGGUGAGGGCUUGGUACU |
| 128 | hsa-miR-191-5p | CAACGGAAUCCCAAAAGCAGCUG |
| 129 | hsa-miR-658 | GGCGGAGGGAAGUAGGUCCGUUGGU |
| 130 | hsa-miR-5584-3p | UAGUUCUUCCCUUUGCCCAAUU |
| 131 | MIR155 | CUGUUAAUGCUAAUCGUGAUAGGGGUUUUUGCCUCCAACUGACUCCUACAUA UUAGCAUUAACAG |
| 132 | hsa-miR-3687 | CCCGGACAGGCGUUCGUGCGACGU |
| 133 | ENSG00000238807 | AUCCUUUUGUAGUUCAUCAGUGUCAUGAGUGGGUUUUCACGCACAUGUGUCA AAUAUGCCUCCCCUCAAACUGUUACGUCAUUGGCAUAUUACCUGACGUGAAG |
| 134 | hsa-miR-5090 | CCGGGGCAGAUUGGUGUAGGGUG |
| 135 | hsa-miR-3065-3p | UCAGCACCAGGAUAUUGUUGGAG |
| 136 | hsa-miR-5697 | UCAAGUAGUUUCAUGAUAAAGG |

TABLE 1-continued

SEQ ID NOs: 1-280 Used in the PCa Test Analysis

| SEQ ID NO: | Sequence Name | Sequence |
|---|---|---|
| 137 | hsa-miR-3934-3p | UGCUCAGGUUGCACAGCUGGGA |
| 138 | ENSG00000200150 | UGAAUCAAUGGUGACCACUGGUGGCAUAUAAGUCAUGGAUGAUGAAUAUGAGAAGAAAAGAAUCUAGGUUUUU |
| 139 | ENSG00000238947 | AUCCUUUUGUGGUUCAUCCGCCUGAUGAUUGGGUUUUCAUGCAGACGUGUGAGCUGUGCCUCCCUCAAGCCUUGUUACAACAUCCGACAUCCGCACAUUACCUGUCUGAUG |
| 140 | MIR1289-2 | CCACGGUCCUAGUUAAAAAGGCACAUUCCUAGACCCUGCCUCAGAACUACUGAACAGAGUCACUGGGUGUGGAGUCCAGGAAUCUGCAUUUUUACCCCUAUCGCCCCCGCC |
| 141 | hsa-miR-6862-3p | CCUCACCCAGCUCUCUGGCCCUCU |
| 142 | hsa-miR-487a-3p | AAUCAUACAGGGACAUCCAGUU |
| 143 | MIR590 | UAGCCAGUCAGAAAUGAGCUUAUUCAUAAAAGUGCAGUAUGGUGAAGUCAAUCUGUAAUUUUAUGUAUAAGCUAGUCUCUGAUUGAAACAUGCAGCA |
| 144 | hsa-miR-4646-5p | ACUGGGAAGAGGAGCUGAGGGA |
| 145 | MIR4635 | CCGGGACUUUGUGGGUUCUGACCCCACUUGGAUCACGCCGACAACACUGGUCUUGAAGUCAGAACCCGCAAAGUCCUGG |
| 146 | SNORD74 | CUGCCUCUGAUGAAGCCUGUGUUGGUAGGGACAUCUGAGAGUAAUGAUGAAUGCCAACCGCUCUGAUGGUGG |
| 147 | hsa-miR-190b-5p | UGAUAUGUUUGAUAUUGGGUU |
| 148 | MIR4723 | AGUUGGUGGGGGAGCCAUGAGAUAAGAGCACCUCCUAGAGAAUGUUGAACUAAAGGUGCCCUCUCUGGCUCCUCCCCAAAG |
| 149 | ENSG00000212397 | AUUCUUAAAUGAAUGAUGAAAUACCAAAAAGAAAAAUAAGCAAAGAACAGAUAACAGAAAGAAGCACAGCAAAUACAACAUAAUACUGACAGUAAAAAU |
| 150 | MIR3123 | AUGGAUUUGAUUGAAUGAUUCUCCCAUUUCCACAUGGAGAGUGGAGCCCAGAGAAUUGUUUAAUCAUGUAUCCAU |
| 151 | hsa-miR-29b-1-5p | GCUGGUUUCAUAUGGUGGUUUAGA |
| 152 | MIR4489 | GGGGGUGGGGCUAGUGAUGCAGGACGCUGGGGACUGGAGAAGUCCUGCCUGACCCUGUCCCA |
| 153 | ENSG00000239197 | AAGCAUGGCACACUGGAUGGGCGUUCUGCUUCUCUUUAAAGAGCAUGGAUUUAUCCAUACCAUGUGACAUGAAUGAAAUGAGGAGUUUUCAGGGCUGCCAACCUCUUGGUUAAGGUUCUGUGUAGUAUAUUUCUCCUACAAUA |
| 154 | ENSG00000252380 | UGGACCAAUGAUGAGAAUAUGUCAUGAACCAAGGAAUAUGAUUAAUCCAAUUCUGUGUACUGGAGGGUCAAA |
| 155 | hsa-miR-4795-5p | AGAAGUGGCUAAUAAUAUUGA |
| 156 | MIR4685 | UAGCCCAGGGCUGGAGUGGGGCAAGGUUGUUGGUGAUAUGGCUUCCUCUCCCUUCCUGCCCUGGCUAG |
| 157 | hsa-miR-3669 | ACGGAAUAUGUAUACGGAAUAUA |
| 158 | MIR3202-2 | AUUAAUAUGGAAGGGAGAAGAGCUUUAAUGCUCUGAAAAUGACUCCAAUCAUUAAAGCUCUUCUCCCUUCCAUAUUAAU |
| 159 | MIR5694 | GCCAACUGCAGAUCAUGGGACUGUCUCAGCCCCAUAUGUAUCUGAAGGCUGAGAAGUCCCAUGAUCCGCACUUGGC |
| 160 | hsa-miR-6742-5p | AGUGGGGUGGGACCCAGCUGUU |

TABLE 1-continued

SEQ ID NOs: 1-280 Used in the PCa Test Analysis

| SEQ ID NO: | Sequence Name | Sequence |
|---|---|---|
| 161 | hsa-miR-22-3p | AAGCUGCCAGUUGAAGAACUGU |
| 162 | hsa-miR-6734-3p | CCCUUCCCUCACUCUUCUCUCAG |
| 163 | ENSG00000252258 | UCCCAUCUCUUAAAUAAAAAGAUUUUUUUUUUAAGAAGUUGUACAUGUGCAAUGGCUGCAAACAGCAGCUUCCUUGGCAGUGUGUGCAGCCUGUUUCUUGUAUGGGUUGCUCUAAGGGACCUUGGAGACAGGC |
| 164 | hsa-miR-5787 | GGGCUGGGGCGCGGGGAGGU |
| 165 | hsa-miR-4442 | GCCGGACAAGAGGGAGG |
| 166 | ENSG00000199713 | UCAUCAGGUGGGAUAAUCCUUACCUGUUCCUCGUUUUGGAGGGCAGAUAGAACAGGAUAAUUGGAGUUUGCAUGAUCCAUGAUUAAUGUCUCUGUGUAAUCAGGACUUGCAAACUCUGAUUGUUCAUAUCUGAU |
| 167 | hsa-miR-27a-3p | UUCACAGUGGCUAAGUUCCGC |
| 168 | hsa-miR-4667-5p | ACUGGGGAGCAGAAGGAGAACC |
| 169 | hsa-miR-7641 | UUGAUCUCGGAAGCUAAGC |
| 170 | MIR320C2 | CUUCUCUUUCCAGUUCUUCCCAGAAUUGGGAAAAGCUGGGUUGAGAGGGU |
| 171 | MIR6759 | UAUUGUUGUGGGUGGGCAGAAGUCUGUUUUCUUCAUGGUUUUCUGACCUUUGCCUCUCCCCUCAG |
| 172 | hsa-miR-4428 | CAAGGAGACGGGAACAUGGAGC |
| 173 | MIR3158-2 | AUUCAGGCCGGUCCUGCAGAGAGGAAGCCCUUCCAAUACCUGUAAGCAGAAGGGCUUCCUCUCUGCAGGACCGGCCUGAAU |
| 174 | ENSG00000238306 | AUCUUUUGUGGGUUCACAAGUGUGAUGAUUAGGUUUUCAGACUCAUGUGUGAGACAUGCCUUCCUCAAACCUUCUUAUGCUAUCAGCACAUAAUCGGCUGACA |
| 175 | hsa-miR-513a-3p | UAAAUUUCACCUUUCUGAGAAGG |
| 176 | ENSG00000206913 | GAGCUUCCAGGAUCACCCCUGCAGAGUGGCUAAUAUUCUGCCAGCUUCGGAAAGGGAGGGGAAGCAAGCCUGGCAGAGGCACCCAUUCCAUUCCCAGCUUGCUUAGUAGCUGGCCAUGGGAAGACACUGUGCAACACUG |
| 177 | ENSG00000207199 | UCUUAGUGAUGAAAACUUUGUCCAGUUCUGCUAAUGACUUUAAGUGAUGAUAAACUAUGUCUGAGGGGA |
| 178 | ENSG00000207094 | AUCCAAGGCGAUUCCCUCUCCAAGGGGACAUCUAGUGCCCCUCUCAGGAAAGUAGCAACUUGGAAUAGAAUCUGGCAUGCCUAAGGUCUUUGAGGAACAGGGAUGCUUAUUUCCUCUGCCUUCCUUGGCUGCCUACAUAG |
| 179 | hsa-miR-3194-3p | AGCUCUGCUGCUCACUGGCAGU |
| 180 | ENSG00000206897 | UAGCAAGCCUCCAGCGUGCUUGGGUCUGCAGUGACCCCGUGGAUUCCUACAGGGCUUGCCAGAACAGUUUUGAAAUGGUUUGAGGCCUUGCCGUGCUCCAUGUAGAGCAAGGUUAUAGAAAUUUCAGACAAUG |
| 181 | hsa-miR-4639-3p | UCACUCUCACCUUGCUUUGC |
| 182 | SNORD116-16 | UGGAUCGAUGAUGACUUUCAUACAUGCAUUCCUUGGAAAGCUGAACAAAAUGAGUGAAAACUCUAUACCGUCAUCCUCGUCGAACUGAGGUCCA |
| 183 | MIR1324 | CCUGAAGAGGUGCAUGAAGCCUGGUCCUGCCCUCACUGGGAACCCCCUUCCCUCUGGGUACCAGACAGAAUUCUAUGCACUUUCCUGGAGGUCCA |

TABLE 1-continued

SEQ ID NOs: 1-280 Used in the PCa Test Analysis

| SEQ ID NO: | Sequence Name | Sequence |
|---|---|---|
| 184 | hsa-miR-611 | GCGAGGACCCCUCGGGGUCUGAC |
| 185 | ENSG00000221043 | AAGACUCUACUCUCAGGGCUCAUUUCUGUCAUUCAAUACUAGAGAAGUUUCUCUGAAUGUUUAGAGCACUGGAAACCAAACGGAGGAGGCGGGCAUUCUUUCCUGAGCAUGCAGCCAGCUCAUAGUGUUGUUUUGUUGCAGCUGCCGCUUGCCAUUGAUGAUCCUUCUUCUCUUCCUUCAGGGGAGUAAGGAGACGACGCGGUCUUAGUGG |
| 186 | hsa-miR-4744 | UCUAAAGACUAGACUUCGCUAUG |
| 187 | ENSG00000252805 | AAGACUACACUUUCAGGGAUAAUUUCUAUAGUUCAUUACUAGAGAAGUUUCUCUGAAUGUGUAGAGCACCAUAAAAUACAUUUUAUUUUUUAUUUGAGACAGGGUCUCACUCUGUCACCCAAGCUGGAGUGCAGUGG |
| 188 | MIR6500 | CCUGCCUGCAGAAAGGAGCUAUCCACUCCAGGUGUCCUUUCUUCUGAGAGCUGGACACUUGUUGGGAUGACCUGCCUGCAGGUAGG |
| 189 | hsa-miR-4768-5p | AUUCUCUCUGGAUCCCAUGGAU |
| 190 | MIR4419B | CUCAGGCUCAGUGGUGCAUGCUUAUAGUCCCAGCCACUCUGGAGGCUGAAGGAAGAUGGCUUGAGCCU |
| 191 | hsa-miR-7107-3p | UGGUCUGUUCAUUCUCUCUUUUUGGCC |
| 192 | ENSG00000239083 | AUCCUUCUGUGGCUGAUAUGUGUGAUGAGGGGUUUUCACACUCUUGCGUGGGACGUGCAACCUCUUUAGAACAGUGGCACAUUACCUGUCCUACA |
| 193 | MIR513C | GCGUACAGUGCCUUUCUCAAGGAGGUGUCGUUUAUGUGAACUAAAAUAUAAAUUUCACCUUUCUGAGAAGAGUAAUGUACAGCA |
| 194 | hsa-miR-627-3p | UCUUUUCUUUGAGACUCACU |
| 195 | hsa-miR-6780a-5p | UUGGGAGGGAAGACAGCUGGAGA |
| 196 | ENSG00000212378 | AUGUAAUAAUGUUCAUCAAAUGUCUGACCUGAAAUGAGCAUGUAGACAAGUUAAUUUAACACUGAAGAA |
| 197 | MIR559 | GCUCCAGUAACAUCUUUAAAGUAAAUAUGCACCAAAAUUACUUUUGGUAAAUACAGUUUUGGUGCAUAUUUACUUUAGGAUGUUACUGGAGCUCCCA |
| 198 | SNORA70G | CUGCAGCCUAUUAAGCCAACUGAGUUCCUUUCCUCAUGGGGGGCCCAGUGUGCAAUGGCUGCAAACAGCAGCUUCCUUGGUAGUGUAUGCAGCCUGUGUGUUGUAUUGUAUGGGUUGCUCUAAGGGACCCUGGAGACAGUC |
| 199 | hsa-miR-548v | AGCUACAGUUACUUUUGCACCA |
| 200 | hsa-miR-4645-3p | AGACAGUAGUUCUUGCCUGGUU |
| 201 | hsa-miR-3689d | GGGAGGUGUGAUCUCACACUCG |
| 202 | hsa-miR-4798-3p | AACUCACGAAGUAUACCGAAGU |
| 203 | hsa-miR-7162-3p | UCUGAGGUGGAACAGCAGC |
| 204 | hsa-miR-145-3p | GGAUUCCUGGAAAUACUGUUCU |
| 205 | ENSG00000202268 | AAUUGUAUACUUUCAGGGAUCAUUCCAUAGGUUGUUACUAGAGAAGUUUUUUUAGAUGUGUAGAACACUGGAAACCACGAGGAGGAGGCGCAGCAUUCUCUCUGACCAUGAAGCCGGCUCUUGGUGUUGUUUCAUUGCAACUGUCAUUGCCAUUGAUGAUCGUUCUCUUCCUCUGGAGAGUAAGAGGGAGAGGACACAGUUUGAGUGG |

TABLE 1-continued

SEQ ID NOs: 1-280 Used in the PCa Test Analysis

| SEQ ID NO: | Sequence Name | Sequence |
|---|---|---|
| 206 | ENSG00000238455 | AUCCAUUUGUAGUUCAGAAACAUGACUAUUGUCUUUUCAAGCUUAUAUGAGAUCUGGCUCCCUCAAUCCUUGCUAUGAUAUCAGUACAUUACCUGUCUGAUG |
| 207 | MIR4420 | CUCUUGGUAUGAACAUCUGUGUGUUCAUGUCUCUCUGUGCACAGGGGACGAGAGUCACUGAUGUCUGUAGCUGAGAC |
| 208 | SNORD115-6 | GGGUCAAUGAUGAGAACCUUAUAUUGUUCUGAAGAGAGGUGAUGACUUAAAAAUCAUGCUCAAUAGGAUUACGCUGAGGCCC |
| 209 | hsa-miR-4460 | AUAGUGGUUGUGAAUUUACCUU |
| 210 | hsa-miR-136-5p | ACUCCAUUUGUUUUGAUGAUGGA |
| 211 | hsa-miR-466 | AUACACAUACACGCAACACACAU |
| 212 | ENSG00000201847 | ACCACCAGUGAUGAGUUGAAUACUGCCCCAGUCUGAUCAACAUGCGUGAAAGAUAUUUUCUGAGCUGUG |
| 213 | hsa-miR-579-5p | UCGCGGUUUGUGCCAGAUGACG |
| 214 | hsa-miR-550a-3p | UGUCUUACUCCCUCAGGCACAU |
| 215 | MIR3167 | GGCUGUGGAGGCACCAGUAUUUCUGAAAUUCUUUUUCUGAAAUUCUUCAGGAAGGAUUUCAGAAAUACUGGUGUCCCGACAGCC |
| 216 | MIR676 | GCAUGACUCUUCAACCUCAGGACUUGCAGAAUUAAUGGAAUGCUGUCCUAAGGUUGUUGAGUUGUGC |
| 217 | hsa-miR-2113 | AUUUGUGCUUGGCUCUGUCAC |
| 218 | ENSG00000212611 | AUACAUGAUGACUUACAUGGACUCUCAUUCAGCUAAUGACUUGCUGCUGAAACAUGGAAAUCUGAUUUUU |
| 219 | hsa-miR-6783-3p | UUCCUGGGCUUCUCCUCUGUAG |
| 220 | hsa-miR-1265 | CAGGAUGUGGUCAAGUGUUGUU |
| 221 | MIR4493 | CCAGAGAUGGGAAGGCCUUCCGGUGAUUAUCACAGCCAUGCCUUUACCUCCAGAAGGCCUUUCCAUCUCUGUC |
| 222 | hsa-miR-4524b-3p | GAGACAGGUUCAUGCUGCUA |
| 223 | ENSG00000238475 | AUCCUUUUGUAGUUCAUAAGCUUGAUGUUUGAGUUUUCACACUUACGUGUGAAAUGUGCCUCCCUUAAACCUUGUUACUACGUCAGCACAUUACCCAUGAGACA |
| 224 | SNORD115-1 | GUGUUGAUGAUGAGAACCUUAUAUUAUCCUGAAGAGAGGUGAUGACUUAAAAAUCAUGCUCAAUAGGAUUACGCUGAGGCCC |
| 225 | MIR8085 | CUAGGAGGGAUGGGAGAGAGGACUGUGAGGCAUGGGUGGCUCUAUGGUCACGCCCAUCUUCCUAC |
| 226 | SNORD31 | CUCACCAGUGAUGAGUUGAAUACCGCCCCAGUCUGAUCAAUGUGUGACUGAAAGGUAUUUUCUGAGCUGUG |
| 227 | SNORA73A | UCCAACGUGGAUACACCCGGGAGGUCACUCUCCCCGGGCUCUGUCCAAGUGGCGUAGGGGAGCAUAGGGCUCUGCCCCAUGAUGUACAAGUCCCUUUCCACAACGUUGGAAAUAAAGCUGGGCCUCGUGUCUGCGCCUGCAUAUUCCUACAGCUUCCCAGAGUCCUGUCGACAAUUACUGGGGAGACAAACCAUGCAGGAAACAGCC |
| 228 | MIR4435-1 | AGGCAGCAAAUGGCCAGAGCUCACACAGAGGGAUGAGUGCACUUCACCUGCAGUGUGACUCAGCAGGCCAACAGAUGCUA |
| 229 | MIR29B2 | CUUCUGGAAGCUGGUUUCACAUGGUGGCUUAGAUUUUUCCAUCUUUGUAUCUAGCACCAUUUGAAAUCAGUGUUUUAGGAG |

TABLE 1-continued

SEQ ID NOs: 1-280 Used in the PCa Test Analysis

| SEQ ID NO: | Sequence Name | Sequence |
|---|---|---|
| 230 | MIR4777 | UAGAAUAUUUCGGCAUUCUAGAUGAGAGAUAUAUAUAUACCUCAUAUGUAU AUGGUAUACCUCAUCUAGAAUGCUGUAAUAUUCUA |
| 231 | MIR635 | CAGAGAGGAGCUGCCACUUGGGCACUGAAACAAUGUCCAUUAGGCUUUGUUA UGGAAACUUCUCCUGAUCAUUGUUUUGUGUCCAUUGAGCUUCCAAU |
| 232 | MIR508 | CCACCUUCAGCUGAGUGUAGUGCCCUACUCCAGAGGGCGUCACUCAUGUAAA CUAAAACAUGAUUGUAGCCUUUUGGAGUAGAGUAAUACACAUCACGUAACGC AUAUUUGGUGG |
| 233 | ENSG000 00201042 | CCCUCCUACAAAGGCAUGUCUAUAAUUCCUUGUCUUUGGACAUGUAAGAAUU GGAGGGACAGAAAUGUGGACUUGGAGAAAUCUGGGGCCAGCUUUCUCAUCAC AGGCUCAACAUCAACCAUGCCACAUAG |
| 234 | hsa-miR-5009-3p | UCCUAAAUCUGAAAGUCCAAAA |
| 235 | MIR24-2 | CUCUGCCUCCCGUGCCUACUGAGCUGAAACACAGUUGGUUUGUGUACACUGG CUCAGUUCAGCAGGAACAGGG |
| 236 | hsa-miR-1296-5p | UUAGGGCCCUGGCUCCAUCUCC |
| 237 | ENSG000 00238914 | AUCCUUUGUGGGUUCAUUAGCUUGAUAUUGGGUUUUCACACUAUUCUAUGAG AUGUGCCUCCCUCAAAACUUGUUACAACAUUGACACAUUACCCUUCUGAUG |
| 238 | hsa-miR-544b | ACCUGAGGUUGUGCAUUUCUAA |
| 239 | ENSG000 00221398 | GGGGUGCACUCAGGGCAGGGGGCUUGAAGAACGGCUCCUCUGUUUACGACAC ACUCAACAGGGGUGUGAGGUCACAGUGAUGAGAGGCCCAAACUUGUGGCCUC CCCGUGAACAAAUGCCCUACACAU |
| 240 | ENSG000 00253072 | UGAUGACACUCUCUGGAAUUGUUACACUACCAUAAUUAAAGUGCACUGAAUC UUUUUCUAUCUGAUGGGGGGGAAUAAAAUAAUU |
| 241 | hsa-miR-6823-3p | UGAGCCUCUCCUUCCCUCCAG |
| 242 | hsa-miR-4520a-5p | CCUGCGUGUUUUCUGUCCAA |
| 243 | MIR6074 | UACCAACCCCAUGGAAUUUUUACUCACCUUCAGUCAACUGAUUUGCUCUUUG GUGGAGAUAUUCAGAGGCUAGGUGGAGAUAGAGGUAGCCUUGAGGGUGGGU GUGG |
| 244 | hsa-miR-4746-3p | AGCGGUGCUCCUGCGGGCCGA |
| 245 | hsa-miR-7846-3p | CAGCGGAGCCUGGAGAGAAGG |
| 246 | hsa-miR-5004-3p | CUUGGAUUUUCCUGGGCCUCAG |
| 247 | ENSG000 00238595 | AUCCUCUUGCAGUUCAUAAGCAUGAUGAUUGGGUUUUCACACUCCUGUGUGA AAUGUACCUUCCUCAAACCUUUUUAUAACAUCAGCACAUUACCGAACAUGAA A |
| 248 | MIR4638 | GACUCGGCUGCGGUGGACAAGUCCGGCUCCAGAACCUGGACACCGCUCAGCC GGCCGCGGCAGGGGUC |
| 249 | MIR1296 | ACCUACCUAACUGGGUUAGGGCCCUGGCUCCAUCUCCUUUAGGAAAACCUUC UGUGGGGAGUGGGCUUCGACCCUAACCCAGGUGGGCUGU |
| 250 | MIR1255B1 | UACGGAUGAGCAAAGAAAGUGGUUUCUUAAAAUGGAAUCUACUCUUUGUGA AGAUGCUGUGAA |
| 251 | ENSG000 00200051 | GGUCAAUGAUGAGCUGACAUGUAUUCUGAAUCUAAAGUUGAUUAUUAGUAC UUUAGUUCUAGAAUUACUGAGACAUG |
| 252 | hsa-miR-4309 | CUGGAGUCUAGGAUUCCA |

TABLE 1-continued

SEQ ID NOs: 1-280 Used in the PCa Test Analysis

| SEQ ID NO: | Sequence Name | Sequence |
|---|---|---|
| 253 | hsa-miR-578 | CUUCUUGUGCUCUAGGAUUGU |
| 254 | hsa-miR-3606-5p | UUAGUGAAGGCUAUUUUAAUU |
| 255 | hsa-miR-6741-3p | UCGGCUCUCUCCCUCACCCUAG |
| 256 | hsa-miR-133b | UUUGGUCCCCUUCAACCAGCUA |
| 257 | ENSG00000251858 | UUAUUUAUCUGACAGACCUGCAGCAGUUACUGGAUGCUGUUAAAGUUUCCACUACAGAUGCAAGAAAAGUGUCCCACACUUUCUGUCUGUCUGAUUGUGACAGCUAAGAUUAAAUCAGGUAGGACAGUA |
| 258 | ENSG00000252256 | UAUUCCAAUGAUGCAAGUGUGUCGUGAACUAAGGAUUAUGAUUAAUCCAGUUUUGUAGCUAGAGGGAUUUU |
| 259 | hsa-miR-3688-5p | AGUGGCAAAGUCUUUCCAUAU |
| 260 | MIR3199-2 | GUGACUCCCAGGGACUGCCUUAGGAGAAAGUUUCGGAAUGUCAGAACUUCCAGAAACUUUCUCCUAAGGCAGUCCCUGGAGUCAC |
| 261 | MIR548W | GGUUGGUGCAAAAGUAACUGCGGUUUUUGCCUUUCAACAUAAUGGCAAAACCCACAAUUACUUUUGCACCAAUC |
| 262 | SNORD60 | AGUCUGUGAUGAAUUGCUUUGACUUCUGACACCUCGUAUGAAAACUGCACGUGCAGUCUGAUUAUUUAGCAAGACUGAGGCUU |
| 263 | MIR433 | CCGGGGAGAAGUACGGUGAGCCUGUCAUUAUUCAGAGAGGCUAGAUCCUCUGUGUUGAGAAGGAUCAUGAUGGGCUCCUCGGUGUUCUCCAGG |
| 264 | MIR4447 | GUUCUAGAGCAUGGUUUCUCAUCAUUUGCACUACUGAUACUUGGGGUCAGAUAAUUGUUUGUGGUGGGGCUGUUGUUUGCAUUGUAGGAU |
| 265 | hsa-miR-2110 | UUGGGGAAACGGCCGCUGAGUG |
| 266 | ENSG00000207274 | CUGCAGCCAAUUAAGCCAACUGAGUUCCUUUCCUUGUGGGGGCCCAGUGUGCAAUGGCUGCACACAGCAGCUUCCUUGGUAGUGUACACAGCCUGUUGGUUGUAUGGGUUGCUCUGAGGGACCUUGGAGACAGGC |
| 267 | hsa-miR-7162-5p | UGCUUCCUUUCUCAGCUG |
| 268 | hsa-miR-597-3p | UGGUUCUCUUGUGGGCUCAAGCGU |
| 269 | MIR147B | UAUAAAUCUAGUGGAAACAUUUCUGCACAAACUAGAUUCUGGACACCAGUGUGCGGAAAUGCUUCUGCUACAUUUUUAGG |
| 270 | MIR4264 | AAAGCUGGAUACUCAGUCAUGGUCAUUGUAACAUGAUAGUGACAGGUACUGGGUAAGACUGCAUAG |
| 271 | hsa-miR-512-3p | AAGUGCUGUCAUAGCUGAGGUC |
| 272 | ENSG00000201329 | AAUGCUAUACUUUCAUGGGUCAUUUCUAUAGUUUGUUAUUAGAGAAGUUUCUCUGAAUGUGUUGAGCACCAGAAACCACGAGGAGAUGCAGCAUUCUCUCCUGAACGGGAAGCCAGCUUUUGGACAUUGCUUUGAUGCAACUACCAUUUGCCAUUGAUGGCAAUGCAUCGCUUCCCUCUAGGAGUGUAAGAGGGAGUGGAUGCAGUCAGAGUGG |
| 273 | MIR548AH | AGGUUGGUGCAAAAGUGAUUGCAGUGUUUGCCAAUAAAAGUAAUGACAAAAACUGCAGUUACUUUUGCACCAGCCC |
| 274 | hsa-miR-6851-5p | AGGAGGUGGUACUAGGGGCCAGC |
| 275 | SNORD38B | UCUCAGUGAUGAAAACUUUGUCCAGUUCUGCUACUGACAGUAAGUGAAGAUAAAGUGUGUCUGAGGAGA |

TABLE 1-continued

SEQ ID NOs: 1-280 Used in the PCa Test Analysis

| SEQ ID NO: | Sequence Name | Sequence |
|---|---|---|
| 276 | MIR101-2 | ACUGUCCUUUUUCGGUUAUCAUGGUACCGAUGCUGUAUAUCUGAAAGGUACA GUACUGUGAUAACUGAAGAAUGGUGGU |
| 277 | MIR6866 | CCAUUUUAGAGGCUGGAAUAGAGAUUCUUGAGGCUUGGAAGAGUAAGGAUC CCUUUAUCUGUCCUCUAG |
| 278 | hsa-miR-3193 | UCCUGCGUAGGAUCUGAGGAGU |
| 279 | hsa-miR-3131 | UCGAGGACUGGUGGAAGGGCCUU |
| 280 | ENSG00000223027 | CCUCAUUUUCUUGGCAGGAACUUGUAGUCCCACUCCCUGUUAUGUACAGAGG CAAAGGGAAGAGCUCUGGCCCCCUUGGCAUGUCUUUGGAGCCAUGCAGCUUC CCGUCUGCCAGUUCUAUCCUCAAGCACCAGGACACCA |

The Sentinel™ CS Test to Identify Low Grade (Indolent) Prostate Cancer

The Sentinel™ Clinically Significant (CS) Test uses a similar classification algorithm to produce a Sentinel™ CS Score that is compared to a calculated cutoff. The cutoff controls sensitivity for a future patient at a desired level (95%), to distinguish between Clinically Significant cancer (GG2-GG5) (if the Sentinel™ CS Score is greater than or equal to the cutoff) and Clinically Insignificant cancer (GG1) (if the Sentinel™ CS Score is less than the cutoff). The algorithm is trained using only the subset of patients known to have prostate cancer in the dataset used to train the Sentinel™ PCa Test. Similarly, using the Classification Algorithm, 280 sncRNAs were used as a basis to define an expression signature for the Sentinel™ CS Test. The Sentinel™ CS Test utilizes 280 sncRNA (identified by the Discovery CS Test, of which 135 unique sncRNAs: 130 miRNA and 66 snoRNAs are highly informative.

TABLE 2

SEQ ID NOs: 281-560 Used in the CS Test Analysis

| SEQ ID NO: | Sequence Name | Sequence |
|---|---|---|
| 281 | MIR539 | AUACUUGAGGAGAAAUUAUCCUUGGUGUGUUCGCUUUAUUUAUGAUG AAUCAUACAAGGACAAUUUCUUUUUGAGUAU |
| 282 | hsa-miR-1184 | CCUGCAGCGACUUGAUGGCUUCC |
| 283 | hsa-miR-562 | AAAGUAGCUGUACCAUUUGC |
| 284 | ENSG00000207215 | AAGACUAUACUCUCAGGAAUCAUUUCUAUAGUUUUUUACUAGAGAAA UUUCUCUGAACGUGUAGAGCACUGGAAACCGUGAGGAGAAGCUGCCU UCUCUUCUGAGCAUGAAGUGAGCUCUCAGUGUUGCUUCUCUGCAACUG CCAUUUGCCAUUGAUGAUCGUUCUUCUCUUCCUCUGGGAGAGUAAAA GGGUACAGGAUGCAGUCUGAG |
| 285 | SNORD116-25 | UGGAUCGAUGAUGACUUUAAAAUGGAUCUCAUCGGAAUCUGAACAAA AUGAGUGACCAAAUCACUUCUGUGCCACUUCGUGAGCUGAGGUCCA |
| 286 | hsa-miR-1180-5p | GGACCCACCCGGCCGGGAAUA |
| 287 | hsa-miR-4452 | UUGAAUUCUUGGCCUUAAGUGAU |
| 288 | hsa-miR-4770 | UGAGAUGACACUGUAGCU |
| 289 | hsa-miR-30d-5p | UGUAAACAUCCCCGACUGGAAG |
| 290 | MIR518C | GCGAGAAGAUCUCAUGCUGUGACUCUCUGGAGGGAAGCACUUUCUGU UGUCUGAAAGAAAACAAAGCGCUUCUCUUUAGAGUGUUACGGUUUGA GAAAAGC |

TABLE 2-continued

SEQ ID NOs: 281-560 Used in the CS Test Analysis

| SEQ ID NO: | Sequence Name | Sequence |
|---|---|---|
| 291 | MIR4315-1 | UGGGCUUUGCCCGCUUUCUGAGCUGGACCCUCUCUCUACCUCUGGUGC AGAACUACAGCGGAAGGAAUCUCUG |
| 292 | hsa-miR-590-5p | GAGCUUAUUCAUAAAAGUGCAG |
| 293 | hsa-miR-30c-5p | UGUAAACAUCCUACACUCUCAGC |
| 294 | SNORD114-30 | UGGAUCAAUCAUGACUACUGGUAUUGGAUGGGUCUUCGUCAGUGAAU GCCUAUCUGGAACUCUGAGGUCCA |
| 295 | MIR4450 | UGUCUGGGGAUUUGGAGAAGUGGUGAGCGCAGGUCUUUGGCACCAUC UCCCCUGGUCCCUUGGCU |
| 296 | hsa-miR-3921 | UCUCUGAGUACCAUAUGCCUUGU |
| 297 | hsa-miR-580-3p | UUGAGAAUGAUGAAUCAUUAGG |
| 298 | hsa-miR-3122 | GUUGGGACAAGAGGACGGUCUU |
| 299 | hsa-miR-4520a-5p | CCUGCGUGUUUUCUGUCCAA |
| 300 | hsa-miR-329-3p | AACACACCUGGUUAACCUCUUU |
| 301 | hsa-miR-4504 | UGUGACAAUAGAGAUGAACAUG |
| 302 | MIR4642 | CACAACUGCAUGGCAUCGUCCCCUGGUGGCUGUGGCCUAGGGCAAGCC ACAAAGCCACUCAGUGAUGAUGCCAGCAGUUGUG |
| 303 | hsa-miR-146b-3p | UGCCCUGUGGACUCAGUUCUGG |
| 304 | ENSG00000206731 | UUCUAAAGUGUUGAGUUCAGUCCAGGGUGGAUCCCCUGCUCUGUUAA UUGAACUGGAACAUUUAAACUGGCUAGGCAAAAUGCCUACAUAGAAA GCAUUACUCUUUAUUCAUCCCCAGCCUACAAAA |
| 305 | hsa-miR-4722-5p | GGCAGGAGGGCUGUGCCAGGUUG |
| 306 | hsa-miR-155-5p | UUAAUGCUAAUCGUGAUAGGGGU |
| 307 | hsa-miR-5088-3p | UCCCUUCUUCCUGGGCCCUCA |
| 308 | ENSG00000238334 | ACUCUUUUGUAGUUCAUAAGUGUGAUGAUUUGGUGUUCAUGUGAACA UGUGAAACGUGCCACCCUCAAACCUUGUUACAAUGUGGGCAUAUUACC CAUCUGACA |
| 309 | MIR526B | UCAGGCUGUGACCCUCUUGAGGGAAGCACUUUCUGUUGUCUGAAAGA AGAGAAAGUGCUUCCUUUUAGAGGCUUACUGUCUGA |
| 310 | hsa-miR-1914-5p | CCCUGUGCCCGGCCCACUUCUG |
| 311 | hsa-miR-195-5p | UAGCAGCACAGAAAUAUUGGC |
| 312 | MIR6742 | GAGGGAGUGGGGUGGGACCCAGCUGUUGGCCAUGGCGACAACACCUG GGUUGUCCCCUCUAG |
| 313 | hsa-miR-323b-3p | CCCAAUACACGGUCGACCUCUU |
| 314 | hsa-miR-3912-3p | UAACGCAUAAUAUGGACAUGU |

TABLE 2-continued

SEQ ID NOs: 281-560 Used in the CS Test Analysis

| SEQ ID NO: | Sequence Name | Sequence |
|---|---|---|
| 315 | MIR203A | GUGUUGGGGACUCGCGCGCUGGGUCCAGUGGUUCUUAACAGUUCAAC AGUUCUGUAGCGCAAUUGUGAAAUGUUUAGGACCACUAGACCCGGCG GGCGCGGCGACAGCGA |
| 316 | hsa-miR-1343-3p | CUCCUGGGGCCCGCACUCUCGC |
| 317 | hsa-miR-6825-5p | UGGGGAGGUGUGGAGUCAGCAU |
| 318 | hsa-miR-188-5p | CAUCCCUUGCAUGGUGGAGGG |
| 319 | MIR378H | ACAGGAACACUGGACUUGGUGUCAGAUGGGAUGAGCCCUGGCUCUGU UUCCUAGCAGCAAUCUGAUCUUGAGCUAGUCACUGG |
| 320 | ENSG00000212626 | UGCCUCUGACCUGGGUAGAGUGGCAUCUGGCUGUGACAUUCAUCUCAU AUCAGCCAGGGACAAAGCAACCCCUUGUUUAUUUCAGCUUGGCCUUUU GUCUGUGCCCAUGCCUGGUUCAUGCCUUGGACACACUA |
| 321 | ENSG00000212580 | UUCUUAUUGAGCUCCUUUCUGUCUACUGGUGGCAGUCUAUGGAUUUG CACAAGACAAAACUAGCGCUAUUUUACCUUCUGUCUUUAAACAGGUA UAUUUGACUGUUUUGUGAGAAAUUC |
| 322 | MIR599 | AAAGACAUGCUGUCCACAGUGUGUUUGAUAAGCUGACAUGGGACAGG GAUUCUUUUCACUGUUGUGUCAGUUUAUCAAACCCAUACUUGGAUGA C |
| 323 | hsa-miR-4301 | UCCCACUACUUCACUUGUGA |
| 324 | hsa-miR-4315 | CCGCUUUCUGAGCUGGAC |
| 325 | hsa-miR-3161 | CUGAUAAGAACAGAGGCCCAGAU |
| 326 | MIR4502 | AGCCUUUAGCAAGUUGUAAUCUUUUUGCUGAUGGAGGGUCUUGCCUC CAUGGGGAUGGCUGAUGAUGAUGGUGCUGAAGGC |
| 327 | SNORD23 | UGCCCAGUGAUGACACCAUCCUUGCUCCCCGUGCCCCCCAGGGGCUAU GGGCGACACCAUGGCUGCCCCUGGGCUGGGCCAGUGGGGCCAAUGCCC AGGGGCUGAGGGCA |
| 328 | MIR320E | GCCUUCUCUUCCCAGUUCUUCCUGGAGUCGGGGAAAAGCUGGGUUGAG AAGGU |
| 329 | ENSG00000238545 | ACCCUUCUUAGUUCAUAAGCAUGAUGAUUGGGUUUUCAUACUCAUGU GUGAGAUGUGUCUCUCUCAAACUUUGUGAAAAGUCAGCACAUGACCC AUCUGAUG |
| 330 | MIR1294 | CACCUAAUGUGUGCCAAGAUCUGUUCAUUUAUGAUCUCACCGAGUCCU GUGAGGUUGGCAUUGUUGUCUGGCAUUGUCUGAUAUACAACAGUGCC AACCUCACAGGACUCAGUGAGGUGAAACUGAGGAUUAGGAAGGUGUA |
| 331 | MIR519C | UCUCAGCCUGUGACCCUCUAGAGGGAAGCGCUUUCUGUUGUCUGAAAG AAAAGAAAGUGCAUCUUUUUAGAGGAUUACAGUUUGAGA |
| 332 | ENSG00000212391 | UGUUCUGACAUGGGAAGAGUAGCUUCUGGUUGGUGGAGCCCAUCUCA CAUUAGCCAGAGACAAAGCAACACCUUGUUUAUCCCGGCUUGGCUUUU GGCCUGUGUCCAUGACUGGUCCAUACCUUGGACACAUGG |
| 333 | ENSG00000238436 | AUCCUUUUGUGGGUCAUAUGCAUGAUGAUUGGGUGUUCACGCACAAG UAUGAGAUGUGCCACCUUUUUACAGCAUUGGCACAUUACCUGUCUGA UG |
| 334 | hsa-miR-4431 | GCGACUCUGAAAACUAGAAGGU |
| 335 | ENSG00000238948 | AUCUUUUUGUGGUUCAUAAGCAUGAUGAUUGGGUUUUCAUACCAUUG UGUAAGAUGUGCCUUUCUCAGACCUUGCCAAAACACUGGCACAUUACC UGUCUGAUA |

TABLE 2-continued

SEQ ID NOs: 281-560 Used in the CS Test Analysis

| SEQ ID NO: | Sequence Name | Sequence |
|---|---|---|
| 336 | MIR518E | UCUCAGGCUGUGACCCUCUAGAGGGAAGCGCUUUCUGUUGGCUAAAA GAAAAGAAAGCGCUUCCCUUCAGAGUGUUAACGCUUUGAGA |
| 337 | ENSG000 00201500 | UGGACCAAUGAUGAUGACUGGUGGUGUAUGAGUUAAAGGUGAUGAAU AGUAAGUGUCUUUGUUAGUGGCAAGUUCAGA |
| 338 | MIR3915 | CAAGUUGGCACUGUAGAAUAUUGAGGAAAAGAUGGUCUUAUUGCAAA GAUUUUCAAUAAGACCAUCCUUUCCUCAAUAUUCUGUGGUGUCAUCU UUG |
| 339 | hsa-miR-3170 | CUGGGGUUCUGAGACAGACAGU |
| 340 | hsa-miR-99a-5p | AACCCGUAGAUCCGAUCUUGUG |
| 341 | hsa-miR-4501 | UAUGUGACCUCGGAUGAAUCA |
| 342 | hsa-miR-524-3p | GAAGGCGCUUCCCUUUGGAGU |
| 343 | hsa-miR-33a-3p | CAAUGUUUCCACAGUGCAUCAC |
| 344 | MIR4669 | GCCUCCCUUCACUUCCUGGCCAUCCAGGCAUCUGUGUCUGUGUCCGGG AAGUGGAGGAGGGC |
| 345 | MIR1197 | ACUUCCUGGUAUUUGAAGAUGCGGUUGACCAUGGUGUGUACGCUUUA UUUGUGACUAGGACACAUGGUCUACUUCUUCUCAAUAUCA |
| 346 | ENSG000 00252740 | UGGAUCAAUGAUGACAAAGUAUCAUGAAUGAGGGAUUGUGAAUAAUC UAUUUUUAUGAACCUGUGGUCAAAU |
| 347 | ENSG000 00238368 | AUCCUUUUGUGGUUCAUAAGCAUGAUGAUUAGAUUUUCAUGCUAUUG GGUGAGAUAUGCCUUCCUCAGACUUUGUUACAGCAUAGGCACAUUAC AACCUGUCUGAUA |
| 348 | MIR4673 | GUCCAGGCAGGAGCCGGACUGGACCUCAGGGAAGAGGCUGACCCGGCC CCUCUUGCGGC |
| 349 | MIR4720 | AAGCCUGGCAUAUUUGGUAUAACUUAAGCACCAGGUAAAAUCUGGUG CUUAAGUUGUACCAAGUAUAGCCAAGUUU |
| 350 | ENSG000 00212321 | AAGGCUAUACUUUCAGGGAUCAUUUUUAUAGCUUAUUACUAGAGGAG UUAAUGUGAAUGUGUAGAGCACCAGAAACCUUGAGGAGGAGGUGCAG CGUUCUCUCCUGAGCAUAAAGCUGGCCCGCAGUAUUGUGUUGCCUCAC UGCAACUGCCAUUUGCCAUUGAUGAUGAUUGUUCUCUUUCACUGAGA GAGUAAGAGGACAGGAUGCAUUCUAACUGG |
| 351 | hsa-miR-410-5p | AGGUUGUCUGUGAUGAGUUCG |
| 352 | hsa-miR-7154-5p | UUCAUGAACUGGGUCUAGCUUGG |
| 353 | hsa-miR-3943 | UAGCCCCCAGGCUUCACUUGGCG |
| 354 | ENSG000 00238530 | AUCCUUUUGUAGUUCAUAAGGAUGAUGACUGAGUGUUCACACUCGUG UGUGAGAUGUGCCACCCUCAGACCUUGAAAUCUUCAGUCACUCUUGUU AAGUGAAC |
| 355 | hsa-miR-4448 | GGCUCCUUGGUCUAGGGGUA |
| 356 | hsa-miR-6816-3p | GAAGGACCUGCACCUUCG |
| 357 | hsa-miR-30e-3p | CUUUCAGUCGGAUGUUUACAGC |
| 358 | MIR525 | UCAAGCUGUGACUCUCCAGAGGGAUGCACUUUCUCUUAUGUGAAAA AAAAGAAGGCGCUUCCCUUUAGAGCGUUACGGUUUGGG |

TABLE 2-continued

SEQ ID NOs: 281-560 Used in the CS Test Analysis

| SEQ ID NO: | Sequence Name | Sequence |
|---|---|---|
| 359 | hsa-miR-548aw | GUGCAAAAGUCAUCACGGUU |
| 360 | hsa-miR-4509 | ACUAAAGGAUAUAGAAGGUUUU |
| 361 | hsa-miR-6775-3p | AGGCCCUGUCCUCUGCCCCAG |
| 362 | hsa-miR-503-5p | UAGCAGCGGGAACAGUUCUGCAG |
| 363 | SNORD58B | CUGCGAUGAUGGCAUUUCUUAGGACACCUUUGGAUUAAUAAUGAAAA CAACUACUCUCUGAGCAGC |
| 364 | hsa-miR-8065 | UGUAGGAACAGUUGAAUUUUGGCU |
| 365 | ENSG00000200545 | AAGACUGUGCUUUCAGGGAUCAUGUCUAUAGUUUGCCACUAGAGAAG UUUUUUUGAACAUGUAGUAGGGCACCAGAAGCACAAGGAAGAGGCAC AGCCUUCUCUCCUGAGCAUGAAUCUGGCUCUUGGUCUUGCUUUGUUCC AGCUACCAUUUGCCAUUGAUUAUGUCCUUCUCUUCCUUCCAGAAAGUA AAAGGGAGAGAAUGCAGUCUGAGUGG |
| 366 | ENSG00000238801 | AUCCUUUUGUAGUUCAUAAGCUGAUGGUUGGGUUUUCACGCUCAUGU GUGAGAUGUGUUCCUUCAUAUCUGUCAACACACUACCGGGCUGUUG |
| 367 | hsa-miR-6864-5p | UUGAAGGGACAAGUCAGAUAUGCC |
| 368 | hsa-miR-5587-5p | AUGGUCACCUCCGGGACU |
| 369 | hsa-miR-3928-3p | GGAGGAACCUUGGAGCUUCGGC |
| 370 | hsa-miR-1537-5p | AGCUGUAAUUAGUCAGUUUUCU |
| 371 | MIR182 | GAGCUGCUUGCCUCCCCCGUUUUUGGCAAUGGUAGAACUCACACUGG UGAGGUAACAGGAUCCGGUGGUUCUAGACUUGCCAACUAUGGGGCGA GGACUCAGCCGGCAC |
| 372 | ENSG00000253047 | CAAAGUUCUGGAAUUACAGGUGUGAGCCACCGUGCCCAGCAUUUAAA AUUUUAAUAUGUACUUUUUGCAACCCAGAACUCAUUGUUCAGUAUGA GUUUUGAUACAUAUAAGAAGGGAUAUU |
| 373 | hsa-miR-548e-3p | AAAAACUGAGACUACUUUUGCA |
| 374 | hsa-miR-8082 | UGAUGGAGCUGGGAAUACUCUG |
| 375 | hsa-miR-4638-5p | ACUCGGCUGCGGUGGACAAGU |
| 376 | MIR8089 | AAGGAGCACUCACUCCAAUUUCCCUGGACUGGGGGCAGGCUGCCACCU CCUGGGGACAGGGGAUUGGGGCAGGAUGUUCCAG |
| 377 | ENG00000238339 | AUCCUUUUGUAGUUUAUAAGCAUGAUGAUGGGUGCUCACACUCAUCU GAGAUGUGUCUCCCUCUAAGCCUUGUAACAACAUCAGCACGUUACCCU UCUGAUG |
| 378 | hsa-miR-6848-3p | GUGGUCUCUUGGCCCCCAG |
| 379 | ENSG00000239144 | AGUUUAAAAAAUUUGUUAAGCAUGAUGAUUAACUUUCACAAUAAUG CAAUAAUGUGUGAGCUAUGCCUCUCUCAAACCUUAUUAUGAUGUUGG CCCAUUACCCAUCUGAUG |
| 380 | hsa-miR-5087 | GGGUUUGUAGCUUUGCUGGCAUG |

TABLE 2-continued

SEQ ID NOs: 281-560 Used in the CS Test Analysis

| SEQ ID NO: | Sequence Name | Sequence |
|---|---|---|
| 381 | MIR5583-1 | AAACUAAUAUACCCAUAUUCUGGCUAGGUGAUCAUCAGAAUAUGGGU AUAUUAGUUUGG |
| 382 | MIR8082 | GCCUGUGUGAUGAUGGAGCUGGGAAUACUCUGGGGAGAGAGUCCUCU UUUCAGCUGUAUUUUGCUUCCUUCCCACACAGAC |
| 383 | hsa-miR-4639-5p | UUGCUAAGUAGGCUGAGAUUGA |
| 384 | hsa-miR-548d-5p | AAAAGUAAUUGUGGUUUUUGCC |
| 385 | ENSG00000252576 | UUAAAUGAUGAUUUUUUUAAACAAAUGUAUCAGAGUGCAUUCAUUCA AAGGAAUGUUGUCUUCUGGCAAGUAAAAAUCCAUGCAG |
| 386 | SNORD19B | UUUUGGUUGAAAUAUGAUGAGUGUACAAAAUCUUGAUUUAAGUGAAU GAAAAAUUACAAGAUCCAACUCUGAUUUCAGCCAGAG |
| 387 | ENSG00000238666 | AUCCUUUUGUAGUUCAUGAGUGUAAUGAUUGAGUGUUCAUGCACAUG UGAGAUAUGCCACCCUUGAACCUUGUUACACCGUUGUCACAUUGCC CGUUUGACA |
| 388 | ENSG00000199363 | AGGCAGGAUCUAGUUACAUUGUAGCUGUGAAGUGCUGCAUUGUCUUU GCCCCUGCUCAAAAUAAAACUGUUACCUUUCAAGCCCUGUCUGCCAU GGUGCUGUAGCAGCAGGGAUGUUUGGUCUCAUACAU |
| 389 | hsa-miR-98-3p | CUAUACAACUUACUACUUUCCC |
| 390 | hsa-miR-5682 | GUAGCACCUUGCAGGAUAAGGU |
| 391 | MIR7114 | UCCGCUCUGUGGAGUGGGGUGCCUGUCCCCUGCCACUGGGUGACCCAC CCCUCUCCACCAG |
| 392 | SNORA16A | UUGGCCCUUAUCGAAGCUGCAGCUGCUUCCGCAUAGCUGCUGUGGUCA AAAGGAGCCCAGAGUGACAGUUUUCCUUGACGGUCGCCGUUCUGUU UGUUGUAACUGAUCUGCAACAUUUUGGGAAAAUACAGUU |
| 393 | hsa-miR-134-5p | UGUGACUGGUUGACCAGAGGGG |
| 394 | hsa-miR-4475 | CAAGGGACCAAGCAUUCAUUAU |
| 395 | hsa-miR-6814-5p | UCCCAAGGGUGAGAUGCUGCCA |
| 396 | MIR323B | UGGUACUCGGAGGGAGGUUGUCCGUGGUGAGUUCGCAUUAUUUAAUG AUGCCCAAUACACGGUCGACCUCUUUUCGGUAUCA |
| 397 | MIR4266 | CCACUGCUGGCCGGGGCCCCUACUCAAGGCUAGGAGGCCUUGGCCAAG GACAGUC |
| 398 | hsa-miR-4762-3p | CUUCUGAUCAAGAUUUGUGGUG |
| 399 | ENSG00000252525 | AAGCUUAUGAUGACGUAAGUGUGACGACAUUGGGUUUUCACGUUCAU GUGUGAGAUGUGCCUCCCUCAAGCCUUAUUACAAUGCCAGUACAUUUU UUUUCCACAUCUGAUG |
| 400 | MIR4742 | UCAGGCAAAGGGAUAUUUACAGAUACUUUUUAAAAUUUGUUUGAGUU GAGGCAGAUUAAAUAUCUGUAUUCUCCUUUGCCUGCAG |
| 401 | hsa-miR-6789-3p | CGGCGCCCGUGUCUCCUCCAG |
| 402 | hsa-miR-7843-3p | AUGAAGCCUUCUCUGCCUUACG |
| 403 | hsa-miR-548ar-5p | AAAAGUAAUUGCAGUUUUUGC |

TABLE 2-continued

SEQ ID NOs: 281-560 Used in the CS Test Analysis

| SEQ ID NO: | Sequence Name | Sequence |
|---|---|---|
| 404 | ENSG00000238732 | AUCUUUUCGUAGUUCAUAAGUGUGAUGACUGGGUAUUCAUGCAUGUA UGUGGGAUAUGCCACCCUUGACCCUUGUUACAACAUUAGCACAUUAAC CAUCUGACA |
| 405 | MIR8052 | UGGAGGGCUGCGGGACUGUAGAGGGCAUGAGCUCAGGAGCUCAGGCC AGCUCAUGGUGCAAGGCCUCUG |
| 406 | SNORD114-11 | UGGACCAGUGAUGGUGACUGGUGGUGUGUGAGUCAUGCACAGUGAAU AUCAUGUGUCUGGAACUCUGAGGUCCA |
| 407 | hsa-miR-4524a-5p | AUAGCAGCAUGAACCUGUCUCA |
| 408 | hsa-miR-3606-3p | AAAAUUUCUUUCACUACUUAG |
| 409 | SNORD54 | UGGCGAUGAGGAGGUACCUAUUGUGUUGAGUAACGGUGAUAAUUUUA UACGCUAUUCUGAGCC |
| 410 | SNORD32A | GUCAGUGAUGAGCAACAUUCACCAUCUUUCGUUUGAGUCUCACGGCCA UGAGAUCAACCCCAUGCACCGCUCUGAGA |
| 411 | MIR3529 | GGCACCAUUAGGUAGACUGGGAUUUGUUGUUGAGCGCAGUAAGACAA CAACAAAAUCACUAGUCUUCCAGAUGGGGCC |
| 412 | MIR520G | UCCCAUGCUGUGACCCUCUAGAGGAAGCACUUUCUGUUUGUUGUCUGA GAAAAAACAAAGUGCUUCCCUUUAGAGUGUUACCGUUUGGGA |
| 413 | MIR4330 | AAUUGUCAGCAGGCAAUUAUCUGAGGAUGCAGGAGAGGAAGGGGGCU UCUUUUUGACGCCUACUUCAUCAGCUGCUCCUCAGAUCAGAGCCUUGC AGGUCAGGCC |
| 414 | SNORD97 | UUGCCCGAUGAUUAUAAAAAGACGCGUUAUUAAGAGGACUUUAUGCU GGAGUUCUUGACGUUUUUCUCUCUUUUCUAUACUUCUUUUUCUUUCU UUGAAUGUCCAGCGUCCUGUGAGCGAAGAUUAUGAGAUAUGAGGGCA A |
| 415 | MIR640 | GUGACCCUGGGCAAGUUCCUGAAGAUCAGACACAUCAGAUCCCUUAUC UGUAAAAUGGGCAUGAUCCAGGAACCUGCCUCUACGGUUGCCUUGGG G |
| 416 | hsa-miR-29a-3p | UAGCACCAUCUGAAAUCGGUUA |
| 417 | MIR5739 | GGUUGGCUAUAACUAUCAUUUCCAAGGUUGUGCUUUUAGGAAAUGUU GGCUGUCCUGCGGAGAGAGAAUGGGGAGCCAGG |
| 418 | MIR24-2 | CUCUGCCUCCCGUGCCUACUGAGCUGAAACACAGUUGGUUUGUGUACA CUGGCUCAGUUCAGCAGGAACAGGG |
| 419 | hsa-miR-6774-3p | UCGUGUCCCUCUUUGUCCACAG |
| 420 | MIR1224 | GUGAGGACUCGGGAGGUGGAGGGUGGUGCCGCCGGGGCCGGGCGCUG UUUCAGCUCGCUUCUCCCCCCACCUCCCUCUCUCCUCAG |
| 421 | hsa-miR-6787-3p | UCUCAGCUGCUGCCCUCUCCAG |
| 422 | hsa-miR-412-3p | ACUUCACCUGGUCCACUAGCCGU |
| 423 | hsa-miR-4293 | CAGCCUGACAGGAACAG |
| 424 | MIR577 | UGGGGGAGUGAAGAGUAGAUAAAAUAUUGGUACCUGAUGAAUCUGAG GCCAGGUUUCAAUACUUUAUCUGCUCUUCAUUUCCCCAUAUCUACUUA C |
| 425 | ENSG00000238294 | AUUCUUUAGUAGUUCAUAAUGCUAUGAUUGGGUUUCCAUGUGCACAU GUAAGAUGUGCCUCUCUCAAGCCUUGUUGUGACAUCAGCACAUUACCC AUCUGAUG |

TABLE 2-continued

SEQ ID NOs: 281-560 Used in the CS Test Analysis

| SEQ ID NO: | Sequence Name | Sequence |
|---|---|---|
| 426 | ENSG00000252458 | CUCAUACCUAAACCCAAGAAUCACUUUCUUAUAGUGAUGAUUUAAAC AGAUGCAAACAGCGAGCACAUCUUGUCACCUUUGCGGGACUGUGGCUG UGCCCCUCGCAGUAAAUUUGGAGGUUCUACAUCC |
| 427 | MIR3171 | UAUAUAUAGAGAUGUAUGGAAUCUGUAUAUAUCUAUAUAUAUGUGUA UAUAUAGAUUCCAUAAAUCUAUAUAUG |
| 428 | ENSG00000253068 | UGGAACAAUGAUGAGAGUGUGUCAUGAACCAAGGUUAUGAUUAAUCU AGUUCUGUGCAUCUGAAAUCCGUU |
| 429 | hsa-miR-4316 | GGUGAGGCUAGCUGGUG |
| 430 | MIR379 | AGAGAUGGUAGACUAUGGAACGUAGGCGUUAUGAUUUCUGACCUAUG UAACAUGGUCCACUAACUCU |
| 431 | ENSG00000239015 | AUCCUUUAGUUCUUAAACAUGACAAUUGGAUGUUUAUGCAUAUGUGU GAGAUGUGUCACCCUUGAACCUUGUUACCAUGUCUGCACAUUACCUAU CUGACA |
| 432 | MIR4645 | UGAUAGGGAAACCAGGCAAGAAAUAUUGUCUCCUCAAGUUGCGACGA GACAGUAGUUCUUGCCUGGUUUCUCUAUCA |
| 433 | hsa-miR-3973 | ACAAAGUACAGCAUUAGCCUUAG |
| 434 | MIR184 | CCAGUCACGUCCCCUUAUCACUUUUCCAGCCCAGCUUUGUGACUGUAA GUGUUGGACGGAGAACUGAUAAGGGUAGGUGAUUGA |
| 435 | ENSG00000221083 | CAGACUCACUUUGCACCUGGCUGCAGCCUCAUGGGGGUGCUUUUUCC AUGUGCCAGGGAAACAUUCUGGGGUGUUUGUGGCUGCCUGACCUAUCA AGGGUGAUGCAGCUGUCUGGGGAUACAGGA |
| 436 | ENSG00000207171 | GGCUUGCUGGUGCUUACCACAGGCUGAAUUCUUACACUGACUAUAUA GAAAAGGAGGUAGAGUAAACCUACCCAAUAUACCCCUCAGCCCAGGCU CUGUGCCUGAUCUAUAUUGUGAAUGUGGGAACAUAG |
| 437 | SNORA20 | CUUCCCAUUUAUUUGCUGCUUGUAGUCUCACAGUGAUACGAGCAGUU AUACGCAUGGGAUAAAAUAACAUUGGGCCACUGUAAAUUGAGAUGAA GUAACCAUUUCAUCUCUUCUGCAGGGACUAGACAUUG |
| 438 | MIR5002 | UCUUCCUCUCUGUCCUCUGGAAUUUGGUUUCUGAGGCACUUAGUAGG UGAUAGCAUGACUGACUGCCUCACUGACCACUUCCAGAUGAGGGUUAC UC |
| 439 | MIR649 | GGCCUAGCCAAAUACUGUAUUUUUGAUCGACAUUUGGUUGAAAAAUA UCUAUGUAUUAGUAAACCUGUGUUGUUCAAGAGUCCACUGUGUUUUG CUG |
| 440 | MIR302A | CCACCACUUAAACGUGGAUGUACUUGCUUUGAAACUAAAGAAGUAAG UGCUUCCAUGUUUUGGUGAUGG |
| 441 | ENSG00000223111 | UCCAGCAGUAGUCAGCUGUCUGGACAGAACCAUUCCUGGGAUCAUGUU ACACUGCUGGGAGAAGAAUGUCUUCUUCAUCCAGUUGCGUCCAUCA CUGUUCUGGUGGUGUCUGGCACUGGUGCAAGGCAGAACUGUGCUUCC UUGAGAGUGCUGAGCAUUCACCUUGGCUGCUUGGUUCUAGUCUAG GAGCAGACACA |
| 442 | hsa-miR-375-3p | UUUGUUCGUUCGGCUCGCGUGA |
| 443 | MIR3678 | GAAUCCGGUCCGUACAAACUCUGCUGUGUUGAAUGAUUUGGUGAGUUU GUUUGCUCAUUGAUUGAAUCACUGCAGAGUUUGUACGGACCGGAUUC |
| 444 | SNORD115-1 | GUGUUGAUGAUGAGAACCUUAUAUUUAUCCUGAAGAGAGGUGAUGACU UAAAAAUCAUGCUCAAUAGGAUUACGCUGAGGCCC |
| 445 | hsa-miR-518f-5p | CUCUAGAGGGAAGCACUUUCUC |
| 446 | MIR16-2 | GUUCCACUCUAGCAGCACGUAAAUAUUGGCGUAGUGAAAUAUAUAUU AAACACCAAUAUUACUGUGCUGCUUUAGUGUGAC |

TABLE 2-continued

SEQ ID NOs: 281-560 Used in the CS Test Analysis

| SEQ ID NO: | Sequence Name | Sequence |
|---|---|---|
| 447 | MIR3691 | UUGAGGCACUGGGUAGUGGAUGAUGGAGACUCGGUACCCACUGCUGAGGGUGGGGACCAAGUCUGCGUCAUCCUCUCCUCAGUGCCUCAA |
| 448 | hsa-miR-3622b-5p | AGGCAUGGGAGGUCAGGUGA |
| 449 | MIR4441 | CAGAGUCUCCUUCGUGUACAGGGAGGAGACUGUACGUGAGAGAUAGUCAGAUCCGCAUGUUAGAGCAGAGUCUCCUUCGUGUACAGGGAGGAGAUUGUAC |
| 450 | hsa-miR-510-3p | AUUGAAACCUCUAAGAGUGGA |
| 451 | MIR454 | UCUGUUUAUCACCAGAUCCUAGAACCCUAUCAAUAUUGUCUCUGCUGUGUAAAUAGUUCUGAGUAGUGCAAUAUUGCUUAUAGGGUUUUGGUGUUUGGAAAGAACAAUGGGCAGG |
| 452 | hsa-miR-1271-5p | CUUGGCACCUAGCAAGCACUCA |
| 453 | SCARNA4 | ACUGGAGGACUAAGAAGGCUGAGUCUGAUGAAGUAAGACUUUGCUGAUACAUUCCUCUAGAAAAAAGGGUUGGAGAGAGCAGCCUUCACUGAAGAGUAUCACAGGGCUGACUGUACUACCCAACACUC |
| 454 | MIR302E | UUGGGUAAGUGCUUCCAUGCUUCAGUUUCCUUACUGGUAAGAUGGAUGUAGUAAUAGCACCUACCUUAUAGA |
| 455 | hsa-miR-6790-3p | CGACCUCGGCGACCCCUCACU |
| 456 | MIR3613 | UGGUUGGGUUUGGAUUGUUGUACUUUUUUUUUGUUCGUUGCAUUUUUAGGAACAAAAAAAAAAGCCCAACCCUUCACACCACUUCA |
| 457 | SNORD57 | UGGAGGUGAUGAACUGUCUGAGCCUGACCUUGUAGAAUGGAGGCAAAAAAACUGAUUUAAUGAGCCUGAUCC |
| 458 | hsa-miR-3146 | CAUGCUAGGAUAGAAAGAAUGG |
| 459 | hsa-miR-222-5p | CUCAGUAGCCAGUGUAGAUCCU |
| 460 | MIR1302-5 | UGCCCGGCCUCCCAUUAAAUUGGUUUUUCAGACAAAUCACAAAUUUGUUUAGGUAUAAGUAUAUCCCAUGUAAUCUUUGGGACAUACUUAUGCUAAAAUAAUUGUUCCUUGUUGAUUGGAAAUUUUAAUUUUAAUUAGGUGUCCUGUAUU |
| 461 | hsa-miR-6854-3p | UGCGUUUCUCCUCUUGAGCAG |
| 462 | SNORA15 | GCAUGGCCGAAUACUGUGUUUUUAUCAGUAGUUUACACAGCCAGACACCAUGCAAAAGCAGUCUUCCCUUUAGAAUGACUGAUGGUAUGCUAAGGUUUUUCAUAGCAUAUCAUUAUUAAAGGUGAAUACAAAU |
| 463 | hsa-miR-3529-3p | AACAACAAAAUCACUAGUCUUCCA |
| 464 | MIR106B | CCUGCCGGGGCUAAAGUGCUGACAGUGCAGAUAGUGGUCCUCUCCGUGCUACCGCACUGUGGGUACUUGCUGCUCCAGCAGG |
| 465 | SNORD115-39 | GGGUCAAUGAUGAGAAUCUUAUAUUGUCCUGAAGAGAGGUGAUGACUUAAAAAUCAUGCUCAAUAGGAUUACGCUGAGGCCC |
| 466 | hsa-miR-590-3p | UAAUUUUAUGUAUAAGCUAGU |
| 467 | ENSG00000199787 | GCAUGGGUUUGGAUUUAUGAUGGGCUGGAUUCCCUAGGCCUCUCAUAGUACCCCAUGCCAGAGCAAACUGUAGCCCCAACCAUUGCCGGGCCUCUAUGCCUGUAGGCUGCUGGCACUGAAGUGGGUUGCACAGUA |
| 468 | hsa-miR-3667-3p | ACCUUCCUCUCCAUGGGUCUUU |

TABLE 2-continued

SEQ ID NOs: 281-560 Used in the CS Test Analysis

| SEQ ID NO: | Sequence Name | Sequence |
|---|---|---|
| 469 | SNORD15A | CUUCGAUGAAGAGAUGAUGACGAGUCUGACUUGGGGAUGUUCUCUUU GCCCAGGUGGCCUACUCUGUGCUGCGUUCUGUGGCACAGUUUAAAGAG CCCUGGUUGAAGUAAUUUCCUAAAGAUGACUUAGAGGCAUUUGUCUG AGAAGG |
| 470 | hsa-miR-3657 | UGUGUCCCAUUAUUGGUGAUU |
| 471 | MIR129-2 | UGCCCUUCGCGAAUCUUUUGCGGUCUGGGCUUGCUGUACAUAACUCA AUAGCCGGAAGCCCUUACCCCAAAAAGCAUUUGCGGAGGGCG |
| 472 | hsa-miR-4515 | AGGACUGGACUCCCGGCAGCCC |
| 473 | hsa-miR-142-3p | UGUAGUGUUUCCUACUUUAUGGA |
| 474 | MIR6802 | GAGGGCUAGGUGGGGGCUUGAAGCCCCGAGAUGCCUCACGUCUUCAC CCCUCUCACCUAAGCAG |
| 475 | hsa-miR-635 | ACUUGGGCACUGAAACAAUGUCC |
| 476 | hsa-miR-5007-3p | AUCAUAUGAACCAAACUCUAAU |
| 477 | MIR6835 | UGAUGAGGGGUAGAAAGUGGCUGAAGCGAGAUGUUUGUCUAAAAGC ACUUUUCUGUCUCCCAG |
| 478 | SNORD96B | CCUGGUGAUGACAGACGACAUUGUCAGCCAAUCCCCAUGUGGUAGUGA GGACAUGUCCUGCAGUUCUGAAGG |
| 479 | MIR4755 | AGAUUCAGCUUUCCCUUCAGAGCCUGGCUUUGGCAUCUAUGAAAGCCA GGCUCUGAAGGGAAAGUUGAAUCU |
| 480 | ENSG00000238488 | AUCAUUUUGCAGCUUAUACAUGUGAUGACUGGGUUUUUAACUCAUA AGUGAGAUGUGCCUUUCUUACAUCUUAUUAUGACAUUAGUACAUUAC CCAUUUGAUA |
| 481 | ENSG00000238624 | AUCCUUCUGUAGUUUAUGAGUGUGAUGAUUGGCUGUUCAUGUGCAUG UAUGAGAUGUGCCACCCUUGAACCUUGUCAUGUCUGAUGUGAAA |
| 482 | hsa-miR-4287 | UCUCCCUUGAGGGCACUUU |
| 483 | ENSG00000252154 | UAGACCAGUGAUGAGAAUCUGUCAUGAACCAAGGAGUAUUAUUAAUC UAAUUCUGUUUACCUGAGAGUUUUAAA |
| 484 | SNORD91B | AAGAGCCAAUGAUGUUUUUAUUCAAAAUGUCUGAACCUGUCUGAAGC AUCCCAGUGAUGCAACUUCUGUGUGAUACUGAGGCUUUU |
| 485 | ENSG00000238769 | AUCCUUUUGUGGUUCAUAAGCAUGAUGAUUGGGUUUCCACAUUCUUG UGAGAUGGGCCUCCCUCCAACCUUGUUAUGAUGUCAGCACAUUACCCU UGACG |
| 486 | MIR3126 | AUGAUUAUAUGAGGGACAGAUGCCAGAAGCACUGGUUAUGAUUUGCA UCUGGCAUCCGUCACACAGAUAAUUAU |
| 487 | hsa-miR-3907 | AGGUGCUCCAGGCUGGCUCACA |
| 488 | hsa-miR-4719 | UCACAAAUCUAUAAUAUGCAGG |
| 489 | MIR612 | UCCCAUCUGGACCCUGCUGGGCAGGGCUUCUGAGCUCCUUAGCACUAG CAGGAGGGGCUCCAGGGGCCCUCCCUCCAUGGCAGCCAGGACAGGACU CUCA |
| 490 | SNORD114-14 | UGGACCAAUGAUGACAACUGCCGGCGUAUGAGUGUUGGGUGAUGAAU AAUACGUGUCUAGAACUCUGAGGUCCA |
| 491 | MIR4757 | UUCCAGCCCGAGGCCUCUGUGACGUCACGGUGUCUGCGGGAGGAGACC AUGACGUCACAGAGGCUUCGCGCUCUGAG |

TABLE 2-continued

SEQ ID NOs: 281-560 Used in the CS Test Analysis

| SEQ ID NO: | Sequence Name | Sequence |
|---|---|---|
| 492 | MIR4738 | GGUCGCAUUUCUCCUUCUUACCAGCGCGUUUUCAGUUUCAUAGGGAAGCCUUUCCAUGAAACUGGAGCGCCUGGAGGAGAAGGGGCC |
| 493 | hsa-miR-6859-3p | UGACCCCCAUGUCGCCUCUGUAG |
| 494 | MIR548AV | AAAAGUACUUGCGGAUUUGCCAUCACCUUUACCUUUAAUGGCAAAACUGCAGUUACUUUUGC |
| 495 | MIR4733 | GGUCGCUUAAAUCCCAAUGCUAGACCCGGUGGCAAUCAAGGUCUAGCCACCAGGUCUAGCAUUGGGAUUUAAGCCC |
| 496 | MIR3202-2 | AUUAAUAUGGAAGGGAGAAGAGCUUUAAUGCUCUGAAAAUGACUCCAAUCAUUAAAGCUCUUCUCCCUUCCAUAUUAAU |
| 497 | ENSG00000252728 | UGCACUGAUGACAGUGAACCAUAAACCAAGAAUUAUGAUUUAUCCAGUUCUAUGAAUCUUAAGUCCAUU |
| 498 | ENSG00000238767 | AUCCUUUGUAGUUCAUAAGCGUGAUGACGUGGUUUCAUGCUUGUGUGUGAGAUGGGUGGGCCUCCCUCAAACCUUGUUACGACGUAGGCCCAUUACCCAUCUGACA |
| 499 | ENSG00000199977 | CCAAUGUGUAAUAUCCUGGGAUAUCAUUUUUUCUAGGCUUUGUCCACAUGGCUUAGGGGAGCAUAGGGCUCUGCCCCAUGAUGUACAGUCCCUUUCCUCAGUGUUGGAGAUGAAGCUGGGUCUGGUGUUUGCACUUUCAUAUUCCUGUAGCUUCUCAGAAUCCUGUGGACAGUGACUGGGGAGACAAACCAUGCAGGAAAUAUGU |
| 500 | ENSG00000238564 | AUCCUUCUAUAUAGUUCAUAAGCUUGAUGAUCGGUGUUCACACACAUGUGAGAUACGCCACCUGUGAACCUUGUUAGGACAUCAGCACAUUACCCAUCUGACA |
| 501 | ENSG00000238970 | AUCCUUUUGUAGUUCAUAAGCACAAUGAUUGAAUUUUCAUGCUCAUGUGUGAGAUAUGCCUCACUCCAGUCUUGUUACAGUGUUAGCACAUUACCUAUCUGAUA |
| 502 | ENSG00000252298 | UGGACAAAUGAUUAGAUUAGAUUGUGUUAUAAACCAAAGAUUAUAGUUAUUCCAAUUAUGUGCAUUUGAGAUCCACU |
| 503 | ENSG00000200398 | CAGUCAGUGUCGAGAACCUUAUAUUGUUCUGAAGAGAGGUGGUGACUUAAAAAUCAUGCUCAAUAGGAUUACGCUGAGGCCC |
| 504 | SNORD116-16 | UGGAUCGAUGAUGACUUUCAUACAUGCAUUCCUUGGAAAGCUGAACAAAAUGAGUGAAAACUCUAUACCGUCAUCCUCGUCGAACUGAGGUCCA |
| 505 | ENSG00000212445 | UGUCCUUGACUUGGGUAGAGUGAUGUCUGGUUGGUGCUGCCUAUCUCAUAUAAGCCAGGGACAAAUCAAUGCCUUAUUUAUUCCAGCUUGGCUUUUGGUCUGUGCCCAUACCUGGUUUAUGCCUUGGACACAUGG |
| 506 | MIR548I3 | CAGAUGGCUCCGAAGUUUACAUCCUAUUAGGUUUGUGCAAAAGUAAUUGCGGAUUUUGCCAUUAAAAGUAAUGCAAAAAUAGCAAUUAUUUUUGUACCAGCCUAGUAUCUUUUCUCCUUCUACCAAACUUUGUCCCUGAGCCAUCUCA |
| 507 | ENSG00000199851 | AAGACUAUACUUUCAGGGAUCAUUUCUACAUUUCCGGGUAAUUUCUUUGAACAUGUGGAGCACCGGAAACCACCAGGAGGAGGCACAGCAUUUUCUCUGGAGCUGAAGCCAGUUCUUGGUGUUGCUGCAUAGCAACUGCCAUUUGCCUUUGAUGAUCAUUCUUCUUUUCCUUUAGGAGAAUAAGAGGGGGAGAACCCAGUCUGAGGG |
| 508 | MIR6776 | CGGGCUCUGGGUGCAGUGGGGGUUCCCACGCCGCGGCAACCACCACUGUCUCUCCCCAG |
| 509 | hsa-miR-3149 | UUUGUAUGGAUAUGUGUGUGUAU |
| 510 | ENSG00000201701 | AGGUCAUUUCAAAGAGGCUUGUGAGGCUGUGAAACCAAGAGCUCUUAACACUGCGACCAAAGAUGGAAGUUCUCUAUAGGAUGCCAUGGCAUUUGAUGGUGCUAUGUUUUCUUGAGGAGAUAUAAGA |
| 511 | hsa-miR-4691-3p | CCAGCCACGGACUGAGAGUGCAU |

TABLE 2-continued

SEQ ID NOs: 281-560 Used in the CS Test Analysis

| SEQ ID NO: | Sequence Name | Sequence |
|---|---|---|
| 512 | ENSG00000238327 | AUCCCUUUAUAGUUCCCGAGCAUGACGAUUGGGUGUUCACAUGCAUG UGUGAGAUGUACCACCCUCGCAUCUUGUUAGACGUUGGCACAUUACCC GUCUGACC |
| 513 | hsa-miR-3692-3p | GUUCCACACUGACACUGCAGAAGU |
| 514 | hsa-miR-630 | AGUAUUCUGUACCAGGGAAGGU |
| 515 | MIR143 | GCGCAGCGCCCUGUCUCCCAGCCUGAGGUGCAGUGCUGCAUCUCUGGU CAGUUGGGAGUCUGAGAUGAAGCACUGUAGCUCAGGAAGAGAGAAGU UGUUCUGCAGC |
| 516 | SNORD50A | UAUCUGUGAUGAUCUUAUCCCGAACCUGAACUUCUGUUGAAAAAAAA AAACUUUUACGGAUCUGGCUUCUGAGAU |
| 517 | ENSG00000238625 | AUAAUCUUGUAGUUCAUAAGCAUGAUGAUUGCCUUUUCACACUCGUA UGAGAUGUGCCUCCCUUGAACCUUGUUAUGAUGUUGGCACAUUACCCA UCUGAUG |
| 518 | SCARNA8 | UGGGAGGCUGAUACACAAAUUGGGCUGAAAUACUGCUCUACUUGUCA CCAUGCCUCCCUAGAAUAAACUGCCUUUUGAUGACCGGGACGAAUUGA GUGAAAUCGUAACGGACAGAUACGGGGCAGACAGAU |
| 519 | hsa-miR-4756-3p | CCAGAGAUGGUUGCCUUCCUAU |
| 520 | hsa-miR-6762-5p | CGGGGCCAUGGAGCAGCCUGUGU |
| 521 | ENSG00000239135 | AUUCUUUUGCUGUUCGUAAGCAUAAGGAUCAGGUAUUCAUGGUCAUG UGUAAGACGUGCCUCCCUCCAACCUUGUUACGAUGUGGACGUCAGCAC AUACCCAUUUGAUG |
| 522 | MIR222 | GCUGCUGGAAGGUGUAGGUACCCUCAAUGGCUCAGUAGCCAGUGUAG AUCCUGUCUUUCGUAAUCAGCAGCUACAUCUGGCUACUGGGUCUCUGA UGGCAUCUUCUAGCU |
| 523 | ENSG00000222185 | UGGACCAAUGAUGUGAAUGGAAUGCAUCUGAAUAAAAAAUUAUGAUCA AUCAGUUUUUGGAACAACUGAGGUCCAC |
| 524 | ENSG00000238557 | AGGCCCCUGUAGUUCCCGAGCACGAUGACUGGGUGUUCACGUGCACGU GUGGGAUGUGCCACCCUCUGAACCUUGUUACGAUGUUGGCACAUUACC CUGGACCUGACC |
| 525 | MIR592 | UAUUAUGCCAUGACAUUGUGUCAAUAUGCGAUGAUGUGUUGUGAUGG CACAGCGUCAUCACGUGGUGACGCAACAUCAUGACGUAAGACGUCACA AC |
| 526 | ENSG00000251778 | UUCAAAAAGACCAUAUAUCCUUGAAGAGUAACUGCUGAACUUAUUC ACUGGCAGUGGGCCUUAUAGCACAGUGAAUGACCAGGUUAGAGACAU GC |
| 527 | ENSG00000200538 | AAGACUAUACUUUCAGGGAUCAUUUCUAUAGUUAGUUGCUAGAGAAG UUUCUCUGGACAUGUGGAGCACCAGAAACCAUGAGAAGGAGAUGUAG UGUUCUCUCCGGAGCAUGAAGCUGGCUCUUGGUGUUGCUUCGCUGCAC CUGCCAUUUGCCAUUGACAAUCAUUCUUCUCUUCCUCUGGGAGAGUAA GGAGGAGAGGACACAGUCUGAGUGG |
| 528 | hsa-miR-7156-3p | CUGCAGCCACUUGGGGAACUGGU |
| 529 | MIR5580 | UGCUGGCUCAUUUCAUAUGUGUGCUGAGAAAAUUCACACAUAUGAAG UGAGCCAGCAC |
| 530 | hsa-miR-6730-3p | CCUGACACCCCAUCUGCCCUCA |
| 531 | hsa-miR-4672 | UUACACAGCUGGACAGAGGCA |

TABLE 2-continued

SEQ ID NOs: 281-560 Used in the CS Test Analysis

| SEQ ID NO: | Sequence Name | Sequence |
|---|---|---|
| 532 | MIR217 | AGUAUAAUUAUUACAUAGUUUUUGAUGUCGCAGAUACUGCAUCAGGA ACUGAUUGGAUAAGAAUCAGUCACCAUCAGUUCCUAAUGCAUUGCCU UCAGCAUCUAAACAAG |
| 533 | hsa-miR-4472 | GGUGGGGGUGUUUGUUUU |
| 534 | MIR770 | AGGAGCCACCUUCCGAGCCUCCAGUACCACGUGUCAGGGCCACAUGAG CUGGGCCUCGUGGGCCUGAUGUGGUGCUGGGGCCUCAGGGGUCUGCUC UU |
| 535 | hsa-miR-29c-3p | UAGCACCAUUUGAAAUCGGUUA |
| 536 | ENSG00000239068 | AUCCUUUUGUAGUUCAUGAGCAUGAUGAUUGGUUGUUCACGUACAUG UGUGAGAUGUGUCACCCUCGAACCUUGUGGCAAUGUUGGAAUAUUAC CUGUCUGACA |
| 537 | ENSG00000252443 | GAUUCACAGCAGAAAGACAGCUAAUCUAGUGUGCUAGCUGUAGAGCA AGUUUGCUGCAAACACCUCAAGGAGGGUCUCUGGCCAAAUGAGUAGA AUCUGACAGUAAUCCUUGCUAAAAGU |
| 538 | ENSG00000207299 | CUACAAUGAUGGCAAUAUGUUUCAUCGACAGCAGUUCACCCAUUGAG UGUUGAUACCGUGGGUCUGAGUGA |
| 539 | MIR3158-2 | AUUCAGGCCGGUCCUGCAGAGAGGAAGCCCUUCCAAUACCUGUAAGCA GAAGGGCUUCCUCUCUGCAGGACCGGCCUGAAU |
| 540 | SNORD114-12 | UGGACCAAUGAUGACAAAUACCGGCGUAUGAGUCUUGGAUGAUGAAU AAUACGUGUCUGGAACUCUGAGGUCCA |
| 541 | MIR4531 | GCCUAGGAGUCCUUGGUCAGUGGGGACAUGGAGAAGGCUUCUGAGGA |
| 542 | MIR6834 | GUGAGGGACUGGGAUUUGUGGGGCGAGGAGGGACCUGUACUAGCCAU GGUUCUGAUCACAUAUGUCCCAUCCCUCCAUCAG |
| 543 | ENSG00000201025 | GUUUCUGAUGAAGCCUAUGUUGGUAGGGACAACUAAGGUUGUUGAUG AAUGCUAACAGCUCUAACACACACAC |
| 544 | MIR451A | CUUGGGAAUGGCAAGGAAACCGUUACCAUUACUGAGUUUAGUAAUGG UAAUGGUUCUCUUGCUAUACCCAGA |
| 545 | hsa-miR-6807-5p | GUGAGCCAGUGGAAUGGAGAGG |
| 546 | MIR4477B | ACCUCCUCCCGUGAAUCACAAAUGUCCUUAAUAGCAAUCCUUAAAUGC CAUUAAGGACAUUUGUGAUUGAUGGGAGGAGGA |
| 547 | MIR548AO | AACUAUUCUUAGGUUGAUGCAGAAGUAACUACGGUUUUUGCAGUUGA AAGUAAUGGCAAAGACCGUGACUACUUUUGCAACAGCCUAAUAGUUU CU |
| 548 | ENSG00000207027 | AUCCAAGGGGAUUCCCUCUCCAAGGGAACAUGCAGUGCCCCUCUCAGG AAAGUAACAACCUGGAAUAGAAUCUGGCAUGCCUAAGGUCUUUGAGG AAUAGAGGAAUAGAGGAUGCUUGUUUCCUCUGCCUUCCUUGGCUGCC UACAUGG |
| 549 | MIR1302-7 | ACAACAUGUUUUUAGGACAUGUAUGUCUGGUGCAAUAAUUGGGACAU ACUUAUGCUAAAAAAAUUAGUGUUC |
| 550 | MIR3605 | ACUUUAUACGUGUAAUUGUGAUGAGGAUGGAUAGCAAGGAAGCCGCU CCCACCUGACCCCUCACGGCCUCCGUGUUACCUGUCCUCUAGGUGGGAC GCUCG |
| 551 | MIR588 | AGCUUAGGUACCAAUUUGGCCACAAUGGGUUAGAACACUAUUCCAUUG UGUUCUUACCCACCAUGGCCAAAAUUGGGCCUAAG |
| 552 | ENSG00000212532 | GUCCUCUGAUGACUUCAUGUUUAGUGCCACCUGUCUGGGCCACGGAGAA CCCAUGAUGGAACUGAGAAUCUGAGGAA |
| 553 | hsa-miR-5691 | UUGCUCUGAGCUCCGAGAAAGC |

TABLE 2-continued

SEQ ID NOs: 281-560 Used in the CS Test Analysis

| SEQ ID NO: | Sequence Name | Sequence |
|---|---|---|
| 554 | ENSG00000238506 | ACCCUUUUGUAGUUCAUAAGCAGGAUGACUGAGUUUUCAUGCACUUG UGUGAGAUGCGCCUCCCUCAAUGUUGGCACAUUACCUAUCUGAUG |
| 555 | MIR553 | CUUCAAUUUUAUUUUAAAACGGUGAGAUUUUGUUUUGUCUGAGAAAA UCUCGCUGUUUUAGACUGAGG |
| 556 | SNORD3A | AAGACUAUACUUUCAGGGAUCAUUUCUAUAGUGUGUUACUAGAGAAG UUUCUCUGAACGUGUAGAGCACCGAAAACCACGAGGAAGAGAGGUAG CGUUUUCUCCUGACGUGAAGCCGGCUUUCUGGCGUUGCUUGGCUGCAA CUGCCGUCAGCCAUUGAUGAUCGUUCUUCUCUCCGUAUUGGGGAGUGA GAGGGAGAGAACGCGGUCUGAGUGGU |
| 557 | hsa-miR-4491 | AAUGUGGACUGGUGUGACCAAA |
| 558 | hsa-miR-4471 | UGGGAACUUAGUAGAGGUUUAA |
| 559 | MIR4288 | AUGGAGGUGGAGAGUCAUCAGCAGCACUGAGCAGGCAGUGUUGUCUG CUGAGUUUCCACGUCAUUUG |
| 560 | SNORA33 | AAGCCAGCCAAUGAAUCUGCUUACCUGAUUGUGUUUGUGCAGACAUA CUUUAAAAACUGGCAAUAGUAAAGCCAUGUUACGAGCCUUAAGGACA UUGAAGUCGUUAAGGUCCCUGAGAAUGGCUAUAACAAAU |

The Sentinel™ HG Test to Identify Patients with High Grade Prostate Cancer

For individuals classified as having prostate cancer, a similar approach was used to train and validate the Sentinel™ High Grade (HG) which discriminates between GG1+GG2 (low- and favorable-intermediate risk cancer) and unfavorable-intermediate and high-risk prostate cancer (GG3-GG5). These informative sequences identified form the basis of the Sentinel™ HG Test. Additional analyses demonstrated that the same cohort of sncRNAs can be used to dichotomize the patients with cancer into GG1+GG2 (low and intermediate risk cancer) from GG3-5 (high risk cancers). This biostatistical analysis forms the basis for the Sentinel™ HG Test, which utilizes 280 sncRNAs, identified by the Discovery HG Test, of which 280 unique sncRNAs: 191 miRNA and 89 snoRNAs are highly informative

TABLE 3

SEQ ID NOs: 561-840 Used in the HG Test Analysis

| SEQ ID NO: | Sequence Name | Sequence |
|---|---|---|
| 561 | hsa-miR-2276-3p | UCUGCAAGUGUCAGAGGCGAGG |
| 562 | hsa-miR-19a-3p | UGUGCAAAUCUAUGCAAAACUGA |
| 563 | hsa-miR-34a-3p | CAAUCAGCAAGUAUACUGCCCU |
| 564 | MIR3924 | UAAAUGAAAAAGUAGUAGUCAAAUAUGCAGAUCUAUGUCAUAUA UACAGAUAUGUAUAUGUGACUGCUACUUUUUUGUUUA |
| 565 | hsa-miR-4293 | CAGCCUGACAGGAACAG |
| 566 | ENSG00000206731 | UUCUAAAGUGUUGAGUUCAGUCCAGGGUGGAUCCCCUGCUCUGU UAAUUGAACUGGAACAUUUAAACUGGCUAGGCAAAAUGCCUACA UAGAAAGCAUUACUCUUUAUUCAUCCCCAGCCUACAAAA |
| 567 | hsa-miR-561-3p | CAAAGUUUAAGAUCCUUGAAGU |
| 568 | hsa-miR-4762-3p | CUUCUGAUCAAGAUUUGUGGUG |
| 569 | hsa-miR-409-3p | GAAUGUUGCUCGGUGAACCCCU |

TABLE 3-continued

SEQ ID NOs: 561-840 Used in the HG Test Analysis

| SEQ ID NO: | Sequence Name | Sequence |
|---|---|---|
| 570 | hsa-miR-5011-3p | GUGCAUGGCUGUAUAUAUAACA |
| 571 | MIR4315-1 | UGGGCUUUGCCCGCUUUCUGAGCUGGACCCUCUCUCUACCUCUGG UGCAGAACUACAGCGGAAGGAAUCUCUG |
| 572 | MIR6505 | GCAUUGGAAUAGGGGAUAUCUCAGCAUGUUGAGCCCUGUCUCUG GGGAGCUGACUUCUACCUCUUCCAAAG |
| 573 | ENSG00000212338 | AUCCAAGGUGAUUCCUUCUCCAAGGGGACAUCCAGUGACCCUCU CAGGAAGUAGCAACUUGGAAUAGAAUAGUCCAGGAGUUCCAGGA CCAGCCUGGCCAAUAUGG |
| 574 | hsa-miR-2276-5p | GCCCUCUGUCACCUUGCAGACG |
| 575 | hsa-miR-6819-3p | AAGCCUCUGUCCCCACCCCAG |
| 576 | hsa-miR-4662a-5p | UUAGCCAAUUGUCCAUCUUUAG |
| 577 | ENSG00000239145 | AUCUUUUGUAGUUCAUGAGCGUGAUGACUGAGUGUUCAUGUGC AUGUGUGAGGCGUGCCACCCUUAAACCUUGUUAUAACAUCAGCA CAUUACCCACAUGACA |
| 578 | hsa-miR-188-5p | CAUCCCUUGCAUGGUGGAGGG |
| 579 | ENSG00000252193 | CUGGAGACUAAGAAACCAGUCCUUGAAGUCAAGCUGACUCUGCU UUUAGCCUCCUAAAUUAAAAGAUAGAUAGAAUAGGUCUUGUUUG CAAAAUAAAUUCAAGAUCUACUCAUCUAUCAAUAGCA |
| 580 | hsa-miR-130a-3p | CAGUGCAAUGUUAAAAGGGCAU |
| 581 | hsa-miR-7151-3p | CUACAGGCUGGAAUGGGCUCA |
| 582 | ENSG00000253065 | AGCACUUGUGUUUGCUUUUGUUUGACUUGUGGACAAAGACUUAU AGUAGACAGGCACGAAAAAAUAAAUCCUCUUUUGCAACCCAUGA GUUGUUAUACAUGCAAGAAGGAAUAUU |
| 583 | hsa-miR-146b-3p | UGCCCUGUGGACUCAGUUCUGG |
| 584 | hsa-miR-6738-3p | CUUCUGCCUGCAUUCUACUCCCAG |
| 585 | hsa-miR-98-3p | CUAUACAACUUACUACUUUCCC |
| 586 | ENSG00000251838 | CUUCUGCUAAGGUUUACACUAUAGAUGCAGGAAAAAAAAUGUCC UCACACUGUCUGUCUGAUUGUGGCAGCUGAGAUUGAAUAGAGAA AUAUAGGG |
| 587 | hsa-miR-5090 | CCGGGGCAGAUUGGUGUAGGGUG |
| 588 | SNORD115-34 | GGGUCAAUGAUGAGAACCUUAUAAUGUUCUGAAGAGAGGUGAUG ACUUAAAAAUCAUGCUCAAUAGGAUUACGCUGAGGCCC |
| 589 | MIR382 | UACUUGAAGAGAAGUUGUUCGUGGUGGAUUCGCUUUACUUAUGA CGAAUCAUUCACGGACAACACUUUUUUCAGUA |
| 590 | hsa-miR-6859-3p | UGACCCCAUGUCGCCUCUGUAG |
| 591 | hsa-miR-1184 | CCUGCAGCGACUUGAUGGCUUCC |
| 592 | hsa-miR-6811-5p | AUGCAGGCCUGUGUACAGCACU |

TABLE 3-continued

SEQ ID NOs: 561-840 Used in the HG Test Analysis

| SEQ ID NO: | Sequence Name | Sequence |
|---|---|---|
| 593 | MIR518C | GCGAGAAGAUCUCAUGCUGUGACUCUCUGGAGGGAAGCACUUUC UGUUGUCUGAAAGAAAACAAAGCGCUUCUCUUUAGAGUGUUACG GUUUGAGAAAAGC |
| 594 | hsa-miR-4504 | UGUGACAAUAGAGAUGAACAUG |
| 595 | MIR5485 | UUGCUGCAAAAAUAAUUGCAGUUUUUGCCAUUAUUUUUAAUAAU UAUAAUAAUGGCCAAAACUGCAGUUAUUUUUGCACCAA |
| 596 | MIR6761 | UCUGCUCUGAGAGAGCUCGAUGGCAGGUGCCUCCGUGUUGCCGA ACCCUCCUACGCUGCUCUCUCACUCCAG |
| 597 | hsa-miR-1282 | UCGUUUGCCUUUUUCUGCUU |
| 598 | hsa-miR-4439 | GUGACUGAUACCUUGGAGGCAU |
| 599 | MIR126 | CGCUGGCGACGGGACAUUAUUACUUUUGGUACGCGCUGUGACAC UUCAAACUCGUACCGUGAGUAAUAAUGCGCCGUCCACGGCA |
| 600 | ENSG00000221125 | AAGAUGACACUUUGAGGCAUCGUGUCUAUGGUUCAUUACUACAG AAGCUUCUCUGGAUGUGUAAAGCACAGGGAAACCAGGCAGGAGG GCACAGGGUGCUCUCCAGAACGAGAAGCCAGCUCCUGGAGUUGU UUGCUGCAACUGCCAUUCCCCGUUGAUGACCAUGCUCUUCCUUCA GAAGAGGGAGAGUGAGAGGACCAAGUCCAAGUGG |
| 601 | hsa-miR-6814-5p | UCCCAAGGGUGAGAUGCUGCCA |
| 602 | hsa-miR-4657 | AAUGUGGAAGUGGUCUGAGGCAU |
| 603 | MIR31 | GGAGAGGAGGCAAGAUGCUGGCAUAGCUGUUGAACUGGGAACCU GCUAUGCCAACAUAUUGCCAUCUUUCC |
| 604 | MIR6754 | GGCUGCCAGGGAGGCUGGUUUGGAGGAGUCUGGUGGCCUGUUCU CUUCACCUGCCUCUGCCUGCAG |
| 605 | MIR376A2 | GGUAUUUUAAAGGUAGAUUUUCCUUCUAUGGUUACGUGUUUGAU GGUUAAUCAUAGAGGAAAAUCCACGUUUUCAGUAUC |
| 606 | hsa-miR-200a-3p | UAACACUGUCUGGUAACGAUGU |
| 607 | hsa-miR-3671 | AUCAAAUAAGGACUAGUCUGCA |
| 608 | hsa-miR-6775-3p | AGGCCCUGUCCUCUGCCCCAG |
| 609 | hsa-miR-6862-3p | CCUCACCCAGCUCUCUGGCCCUCU |
| 610 | ENSG00000238368 | AUCCUUUUGUGGUUCAUAAGCAUGAUGAUUAGAUUUUCAUGCUA UUGGGUGAGAUAUGCCUUCCUCAGACUUUGUUACAGCAUAGGCA CAUUACAACCUGUCUGAUA |
| 611 | MIR183 | CCGCAGAGUGUGACUCCUGUUCUGUGUAUGGCACUGGUAGAAUU CACUGUGAACAGUCUCAGUCAGUGUAUUACCGAAGGGCCAUAAA CAGAGCAGAGACAGAUCCACGA |
| 612 | hsa-miR-423-3p | AGCUCGGUCUGAGGCCCCUCAGU |
| 613 | hsa-miR-4306 | UGGAGAGAAAGGCAGUA |
| 614 | ENSG00000252128 | ACUCCAUGAUGAACCCAAAAUGCCAAGUAUAUGACUGAACUUAC AAGUGAUACCAUCUUACGACUGAAGAGU |

TABLE 3-continued

SEQ ID NOs: 561-840 Used in the HG Test Analysis

| SEQ ID NO: | Sequence Name | Sequence |
|---|---|---|
| 615 | ENSG000002 38932 | AUCCUUUUGUAGUUCAUGAGGAUGAUGGUUGGGUGUUUCACACA UGUGUGUGAAAUGUACCACCCUCAAACCUUGUUACAAUGUCAGC ACAUUACCUGCCUGACC |
| 616 | MIR96 | UGGCCGAUUUUGGCACUAGCACAUUUUUGCUUGUGUCUCUCCGC UCUGAGCAAUCAUGUGCAGUGCCAAUAUGGGAAA |
| 617 | hsa-miR-3925-3p | ACUCCAGUUUUAGUUCUCUUG |
| 618 | hsa-miR-3065-3p | UCAGCACCAGGAUAUUGUUGGAG |
| 619 | ENSG000002 00026 | UCGAUGGGUGGGAUAAUCCUUACCUGUUCCUCGUUUUGGAGGGC AGAUAGAACAUGAUGAUUGGAGAUGCAUGAAAUGUGAUUAAUGC CUCUGCCUAAUCAGGACUUGCAACACCCUGAGUACUCCUCUCUGA U |
| 620 | 39155 ENSG000002 | AUCCUUUUGUAGUUCAUAAGUGUGAUGAUUAGGUUUUCACAUUU GUGUGUGAGAUGUAUCUCCCUCAAACAUUUUAUGACAUCGGCAU AUUAUCCUUCUGAUG |
| 621 | hsa-miR-337-3p | CUCCUAUAUGAUGCCUUUCUUC |
| 622 | hsa-miR-559 | UAAAGUAAAUAUGCACCAAAA |
| 623 | hsa-miR-580-3p | UUGAGAAUGAUGAAUCAUUAGG |
| 624 | ENSG000002 00318 | AAGACUAUACUUUCAGGGAUCAUUUGUAUAGUUCGUUACUAGAG AAUUUUCUCUGAAUGUGUAGAACACCAGAAACCACAAGGAGGAG GCGCAGCGUUCUCUCCUGAGCGUGAAGCCGGGUCCUGGUGUUGC UUCACUGCAACUGCCAUUUGCCAUUGAUGAUUGUUCUUCUCUUC CUUUGGGAGAGUAAGAGGCAAAGGAUGCAGUCUGAAUGG |
| 625 | hsa-miR-181c-3p | AACCAUCGACCGUUGAGUGGAC |
| 626 | MIR6808 | GGGGCCAGGCAGGGAGGUGGGACCAUGGGGGCCUUGCUGUGUGA CCACCGUUCCUGCAG |
| 627 | ENSG000002 38775 | AUCUUUUGUAGUUCAUAAGCAUGAUGAUUAUGUUUUUACAUUC AUGUGUAAGAUGUGCCUCCCUCAAACCUUGUUAUGAUGUCAGCA UAUUACCUGUCUGAUG |
| 628 | hsa-miR-3660 | ACUGACAGGAGAGCAUUUUGA |
| 629 | SNORA33 | AAGCCAGCCAAUGAAUCUGCUUACCUGAUUGUGUUUGUGCAGAC AUACUUUAAAAACUGGCAAUAGUAAAGCCAUGUUACGAGCCUUA AGGACAUUGAAGUCGUUAAGGUCCCUGAGAAUGGCUAUAACAAA U |
| 630 | hsa-miR-630 | AGUAUUCUGUACCAGGGAAGGU |
| 631 | ENSG000002 53028 | UCCAUCUGUUUGGCAGACCUGGAGCAGUUAGUGUCUGCUGCUAA GGUUUCCAUUACAGAUGUGAGAAAAAAAGUGUUCUUCUGCUUU CUGUCUGUCUCAGUGGCAACCAAGAUUGAAUGGGGGAUAUGAGA G |
| 632 | ENSG000002 38618 | AUUCUUUUGUAAUUCAUAAGCAUGAUGACUCGGUAUUCACGUGC AUGUGUGAGAUGUGCCACCCUGGAACCUUGUUGCAACGUCAGCA CAUUAUGGGUCUGACA |
| 633 | ENSG000002 52844 | AUGACCAAUGGUGAGAGUGUAUCAUGAAGCAAGGAAUGUGAUUA AUCUCAGUUCUGUAAACCCAAGUUCCAGU |
| 634 | hsa-miR-6079 | UUGGAAGCUUGGACCAACUAGCUG |

TABLE 3-continued

SEQ ID NOs: 561-840 Used in the HG Test Analysis

| SEQ ID NO: | Sequence Name | Sequence |
|---|---|---|
| 635 | ENSG00000238552 | AUCCUUUUGUAGUUCAUGAGCAUGACCAUCGAGUGUUUACAUGCAUGUGUGAGAUAUGACACCUUCUGAACCUUGUUACGGAGUUGGCAUGUUACCCAUCUAACC |
| 636 | ENSG00000212165 | AAGAUUAUAUUUUCAGGGAUCAUUUCUAUAGUUUUGUCACUAGGGAAGUUCCUCUGAAUGUGUAGAGCACCAGAAACAUGAGGAAGAGGCACAGGGUUCUCUCCUGAGUGUGAAGCUGGCUCUUGGCGCUGCUUUCCUGCAACUGCUAUUUGCCAUUCGUGAUUGUGGAGAGUCAGAGGGAGAGGAUGAUGCAGUCUGAGUGG |
| 637 | ENSG00000238752 | AUCCUUUUGUAGUUCAUGAGCAUGAUGAUUGGGUGUUCACGUGCAUGUGUGAGAUGUGACACCCUUGCACAUUACUCGCCUGACC |
| 638 | hsa-miR-504-5p | AGACCCUGGUCUGCACUCUAUC |
| 639 | hsa-miR-5688 | UAACAAACACCUGUAAAACAGC |
| 640 | SNORD23 | UGCCCAGUGAUGACACCAUCCUUGCUCCCCGUGCCCCCAGGGGCUAUGGGCGACACCAUGGCUGCCCCUGGGCUGGGCCAGUGGGGCCAAUGCCCAGGGGCUGAGGGCA |
| 641 | MIR6797 | CAGCCAGGAGGGAAGGGGCUGAGAACAGGACCUGUGCUCACUGGGGCCUGCAUGACCCUUCCCUCCCCACAG |
| 642 | ENSG00000252682 | ACUCACUGAUGAGUAGCUUCUGACUUUCAUUCUGAGUUUGCUGAACCCAGAUGCCAUUCCUGGGAAGG |
| 643 | ENSG00000238914 | AUCCUUUUGUGGUUCAUUAGCUUGAUAUUGGGUUUUCACACUAUUCUAUGAGAUGUGCCUCCCUCAAAAACUUGUUACAACAUUGACACAUUACCCUUCUGAUG |
| 644 | MIR3202-1 | UAUUAAUAUGGAAGGGAGAAGAGCUUUAAUGAUUGGAGUCAUUUUCAGAGCAUUAAAGCUCUUCUCCCUUCCAUAUUAAUG |
| 645 | MIR520F | UCUCAGGCUGUGACCCUCUAAAGGGAAGCGCUUUCUGUGGUCAGAAAGAAAAGCAAGUGCUUCCUUUUAGAGGGUUACCGUUUGGGA |
| 646 | hsa-miR-6844 | UUCUUUGUUUUUAAUUCACAG |
| 647 | hsa-miR-7856-5p | UUUUAAGGACACUGAGGGAUC |
| 648 | MIR6739 | GAAUGUGGGAAAGAGAAAGAACAAGUAAAAGGAAUUUUCAUUUUCCAGCCCCUAAUUGUUCUGUCUUUCUCCCAG |
| 649 | MIR4521 | UCGGCUAAGGAAGUCCUGUGCUCAGUUUUGUAGCAUCAAAACUAGGAUUUCUCUUGUUAC |
| 650 | SNORD114-28 | UGGAUCGAUGAUGACUGCUGGUGGCGUAUGAGUCAUAUGCGAUGAAUACGUGUCUAGAACUCUGAGGUCCA |
| 651 | MIR6867 | CCCGGUGUGUGUGUAGAGGAAGAAGGGAAGCUGGGAACCUGACUGCCUCUCCCUCUUUACCCACUAG |
| 652 | hsa-miR-1244 | AAGUAGUUGGUUUGUAUGAGAUGGUU |
| 653 | hsa-miR-23a-3p | AUCACAUUGCCAGGGAUUUCC |
| 654 | ENSG00000238889 | AUUCUUUUGUAGUUCUUAGGCACGAUGAUUGGGUGUUCAUGUGCAUGUUUGAGAUGUGCCUCCCUCAAACCUUGUUCUUACAUCAGCACCUUACACGUCUAACA |
| 655 | hsa-miR-4272 | CAUUCAACUAGUGAUUGU |
| 656 | MIR320E | GCCUUCUCUUCCCAGUUCUUCCUGGAGUCGGGGAAAAGCUGGGUUGAGAAGGU |

TABLE 3-continued

SEQ ID NOs: 561-840 Used in the HG Test Analysis

| SEQ ID NO: | Sequence Name | Sequence |
|---|---|---|
| 657 | ENSG00000238642 | AGUUUUCAUAGUUCAUAAGCAUGAUGAGUGGGUUUUCAUGUUC AUGUGUGAGGUGUGCCUCCCUCAAACCUUGUUAUGAUGUCAACA CAUUGCCCAUCUGAUG |
| 658 | ENSG00000266834 | UGCAGAUGAUGUAAAAGAAUAUUUGCUAUCUGAGAGAUGGUGAU GACAUUUUAAACCACCAAGAUCGCUGAUGCA |
| 659 | hsa-miR-3130-3p | GCUGCACCGGAGACUGGGUAA |
| 660 | hsa-miR-7848-3p | CUACCCUCGGUCUGCUUACCACA |
| 661 | MIR4699 | AGCAAUUGGAGAAGAUUGCAGAGUAAGUUCCUGAUUAAGAAAUG GAAUUUACUCUGCAAUCUUCUCCAAUUGCU |
| 662 | MIR770 | AGGAGCCACCUUCCGAGCCUCCAGUACCACGUGUCAGGGCCACAU GAGCUGGGCCUCGUGGGCCUGAUGUGGUGCUGGGGCCUCAGGGG UCUGCUCUU |
| 663 | MIR3686 | CUCACCUCAUUCAUUUACCUUCUCUUACAGAUCACUUUUCUGCAC UGGACAGUGAUCUGUAAGAGAAAGUAAAUGAAAGAGGUGAG |
| 664 | hsa-miR-548ar-5p | AAAAGUAAUUGCAGUUUUUGC |
| 665 | MIR1203 | UCCUCCCCGGAGCCAGGAUGCAGCUCAAGCCACAGCAGGGUGUUU AGCGCUCUUCAGUGGCUCCAGAUUGUGGCGCUGGUGCAGG |
| 666 | SNORD115-33 | GGGUCAAUGAUGAGAACCGUAUAUUGUCCUGAAGAGCGGUGAUG ACUUAAAAAUAAUGCUCAAUAGGAUUACGCUGAGGCCC |
| 667 | hsa-miR-6134 | UGAGGUGGUAGGAUGUAGA |
| 668 | ENSG00000252526 | AAGACCCUUCAGCUGCAAACAACAGCUUCCUUGGUAGUUUAUGC AGCCUGUUUCUUGUAUGGGCUGCUCUAAGGGACCAUGGAGACAG GC |
| 669 | hsa-miR-1537-5p | AGCUGUAAUUAGUCAGUUUUCU |
| 670 | MIR7977 | UUCCCAGCCAACGCACCAAAAAUGAUAUGGGUCUGUUGUCUGGA GAAAC |
| 671 | ENSG00000238843 | AUACUUUUGUAGGUCAUAAGCUGAGGAUGGGGUUUUCAUGCUCU UGUGUGAGAUAUGCUUCUCAAACCUUCUGACCUGGGCACAUU ACCCAGCUAAUG |
| 672 | hsa-miR-4520a-5p | CCUGCGUGUUUUCUGUCCAA |
| 673 | ENSG00000238772 | UUCCUGUUGGUUCCUAAGUGUGAUGAUUGGGUUUUCACAUUCAU GUGUGACAUGUGCCUCCCUCAAAUCUUGUGAUGAUGUCGGCACG UGACCCAUCUGACG |
| 674 | MIR593 | CCCCCAGAAUCUGUCAGGCACCAGCCAGGCAUUGCUCAGCCCGUU UCCCUCUGGGGGAGCAAGGAGUGGUGCUGGGUUUGUCUCUGCUG GGGUUUCUCCU |
| 675 | hsa-miR-554 | GCUAGUCCUGACUCAGCCAGU |
| 676 | SNORD87 | ACAAUGAUGACUUAAAUUACUUUUUGCCGUUUACCCAGCUGAGG UUGUCUUUGAAGAAAUAAUUUUAAGACUGAGA |
| 677 | hsa-miR-624-3p | CACAAGGUAUUGGUAUUACCU |
| 678 | ENSG00000252777 | UGGACAUUUAUUUUUAUUCAGUUUUUUCUCAAGGUGAAGGUAAC UGUUUGUAGAUGUCCUAGAGAAAUAUUGUAGCUUUCUGUUCACC CUUUGCAACUAAAAAGCAUGGACUGUUCCACUACUGAGAUUU |

TABLE 3-continued

SEQ ID NOs: 561-840 Used in the HG Test Analysis

| SEQ ID NO: | Sequence Name | Sequence |
|---|---|---|
| 679 | ENSG00000206649 | CUUCCCAUUUAUUUGCUGCUAUAGUCUCAUAAUGAUACAAGCAG UUAUAUGCAUGGGAUAAAAUAAUAUUGGGACAUUGUAAAUUGAA AUGAAGUAACCAUUUUCAUCUUUUCUGCAUGGACAAGACAUUG |
| 680 | MIR4534 | UGUGAAUGACCCCCUUCCAGAGCCAAAAUCACCAGGGAUGGAGG AGGGGUCUUGGGUACU |
| 681 | hsa-miR-4709-3p | UUGAAGAGGAGGUGCUCUGUAGC |
| 682 | MIR548F4 | GAGUUCUAACGUAUUAGGUUGGUGCAAAAGUAAUAGUGGUUUUU GCCAUUAAAAGUAAUGACAAAAACUGUAAUUACUUUUGGAACAA UAUUAAUAGAAUUUCAG |
| 683 | ENSG00000200422 | GGUCAAUGAUGUAAUGGCAUGUAUUAGCUGAAUCCAAAGUUGAA GUGAAUUCUAAAAUUACACCAAGACCUU |
| 684 | MIR16-1 | GUCAGCAGUGCCUUAGCAGCACGUAAAUAUUGGCGUUAAGAUUC UAAAAUUAUCUCCAGUAUUAACUGUGCUGCUGAAGUAAGGUUGA C |
| 685 | ENSG00000212391 | UGUUCUGACAUGGGAAGAGUAGCUUCUGGUUGGUGGAGCCCAUC UCACAUUAGCCAGAGACAAAGCAACACCUUGUUUUAUCCCGGCUU GGCUUUUGGCCUGUGUCCAUGACUGGUCCAUACCUUGGACACAU GG |
| 686 | ENSG00000238983 | AUCCCUUUGUAGUUCAUAAGCGUGAUGAUUGGGUGUUCAUGCUC AUACAUGAGCUGUGCCUCCCUCAAGCUUUGUUGUGACAUCAUCA UAUUACCUGUCCGAUG |
| 687 | hsa-miR-4722-3p | ACCUGCCAGCACCUCCCUGCAG |
| 688 | MIR6802 | GAGGGCUAGGUGGGGGGCUUGAAGCCCCGAGAUGCCUCACGUCU UCACCCCUCUCACCUAAGCAG |
| 689 | hsa-miR-141-5p | CAUCUUCCAGUACAGUGUUGGA |
| 690 | MIR3124 | GCGGGCUUCGCGGGCGAAGGCAAAGUCGAUUUCCAAAAGUGACU UUCCUCACUCCCGUGAAGUCGGC |
| 691 | hsa-miR-569 | AGUUAAUGAAUCCUGGAAAGU |
| 692 | ENSG00000212604 | UGCCCCUGACCUGGGAAGAGAGGGGCCUGGCUGGUGGUAUCCAU CUCAUACCAGCUAGGGAUGAAGAAACCGCUUGCUCAUCCCAGCCU GGCUCCUGGUCUAUGCCCAUGCCUGGUUCGUGCCUUGGACAUAUC A |
| 693 | hsa-miR-4487 | AGAGCUGGCUGAAGGGCAG |
| 694 | MIR2110 | CAGGGGUUUGGGGAAACGGCCGCUGAGUGAGGCGUCGGCUGUGU UUCUCACCGCGGUCUUUUCCUCCCACUCUUG |
| 695 | MIR5010 | GAUCCAGGGAACCCUAGAGCAGGGGGAUGGCAGAGCAAAAUUCA UGGCCUACAGCUGCCUCUUGCCAAACUGCACUGGAUUUUGUGUC UCCCAUUCCCCAGAGCUGUCUGAGGUGCUUUG |
| 696 | ENSG00000251715 | UUCACAAUGUCUAUUGAAGGAUCUCAUCACCUUUAGAGAGCUGU GGUCAUGCCCCUUAAAGUGAAUUUGGAGGUUUUUAUACCC |
| 697 | MIR640 | GUGACCCUGGGCAAGUUCCUGAAGAUCAGACACAUCAGAUCCCU UAUCUGUAAAAUGGGCAUGAUCCAGGAACCUGCCUCUACGGUUG CCUUGGGG |
| 698 | MIR4424 | CUUACAUCACACACAGAGUUAACUCAAAAUGGACUAAUUUUUCC ACUAGUUAGUCCAUUUCAAGUUAACUCUGUGUGUGAUGUAGU |
| 699 | ENSG00000238685 | AUUACUUGAAAAUCACUCCCAGGCUUUGGCCAUGGCAGCAGGUG AGAUUCAAGGCCCAGAGCCUCCAGGGCCUCAGCUCACCGCACACU GCCCCGUGUGUGGUGGGGAAACCCAGACCCCAACAGGU |

TABLE 3-continued

SEQ ID NOs: 561-840 Used in the HG Test Analysis

| SEQ ID NO: | Sequence Name | Sequence |
|---|---|---|
| 700 | hsa-miR-370-5p | CAGGUCACGUCUCUGCAGUUAC |
| 701 | MIR1307 | CAUCAAGACCCAGCUGAGUCACUGUCACUGCCUACCAAUCUCGAC CGGACCUCGACCGGCUCGUCUGUGUUGCCAAUCGACUCGGCGUGG CGUCGGUCGUGGUAGAUAGGCGGUCAUGCAUACGAAUUUUCAGC UCUUGUUCUGGUGAC |
| 702 | ENSG00000252699 | CCUCUUCUCAGAACACUUCCUGGGUCUGAUUGGUGGCCCAGGGA GCUGUCAGAGAAGAGCAGAGCAAAUGGCCUUCACUUUGUAGAUG AGAUGGCAGGAGGGUGGAUUGUUGGUCUCAGUCAGUGGUGGGAC AGAC |
| 703 | hsa-miR-433-3p | AUCAUGAUGGGCUCCUCGGUGU |
| 704 | ENSG00000201448 | AAGCAGGAUUCAGACUACAAUAUAGCUGUUAAGUGCUGUAUUGU CAUUCCCCUGCUCAAAUUAAAGUUGUUUCUUAACUAUACCCAUC UGCUAUUCUGUAGCAGCCAGGGAUGCUUGGUCACAUACAU |
| 705 | SNORA43 | GCUGUCCUGGACCUGUUGGCACCACAGACAGUUGCUCUGCUGUGC CUGUGGCCUCGGGGCAAAGAGAAAGUGGCGAUUUCUACACUCAG UGCUCGGGAACCAGUGGGCACUGAGAAUGGUUUAUGGCCUGACA UUA |
| 706 | ENSG00000201398 | UCGUCAGGUGGGAGAAUUCUUACAUGUUCCUCCUUUUGCAAGGC AGAUUAGAACAUGAUGAUUGGGGUUCGCAUAUAUGUGAUUAAC GUUUCUGUGUAAUCAGGACUUGCAACAUCCCGAAUGCCCUUACC UGAC |
| 707 | ENSG00000252740 | UGGAUCAAUGAUGACAAAGUAUCAUGAAUGAGGGAUUGUGAAUA AUCUAUUUUUAUGAACCUGUGGUCAAAU |
| 708 | hsa-miR-654-3p | UAUGUCUGCUGACCAUCACCUU |
| 709 | MIR3667 | UGAGGAUGAAAGACCCAUUGAGGAGAAGGUUCUGCUGGCUGAGA ACCUUCCUCUCCAUGGGUCUUUCAUCCUCA |
| 710 | ENSG00000238978 | AUCCUUUUGUGGUUCAUAAGAAUAGGGAUUGGGAUUUCACACUC AUGUGUGAGAUGUGCCUCCCUUAAACCUUAAGAUGUUGGCACAU UACCUAUUUGAUG |
| 711 | ENSG00000238494 | AUCCUUUUGUAGUUCAUUAGCAUAAUGAUUGGGUUUUCACACUC AGGCGUGAGAUGUGCCUCUCUCAAACCUUGCUACGAUGUUGGCA CAUUGCCUAUCUGGCA |
| 712 | hsa-miR-3606-3p | AAAAUUUCUUUCACUACUUAG |
| 713 | hsa-miR-335-3p | UUUUUCAUUAUUGCUCCUGACC |
| 714 | ENSG00000252458 | CUCAUACCUAAACCCAAGAAUCACUUUCUUAUAGUGAUGAUUUA AACAGAUGCAAACAGCGAGCACAUCUUGUCACCUUUGCGGGACU GUGGCUGUGCCCCUCGCAGUAAAUUUGGAGGUUCUACAUCC |
| 715 | MIR1297 | UGUUUAUCUCUAGGGUUGAUCUAUUAGAAUUACUUAUCUGAGCC AAAGUAAUUCAAGUAAUUCAGGUGUAGUGAAAC |
| 716 | ENSG00000201329 | AAUGCUAUACUUUCAUGGGUCAUUUCUAUAGUUUGUUAUUAGAG AAGUUUCUCUGAAUGUGUUGAGCACCAGAAACCACGAGGAGAUG CAGCAUUCUCUCCUGAACGGGAAGCCAGCUUUUGGCAUUGCUUU GAUGCAACUACCAUUUGCCAUUGAUGGCAAUGCAUCGCUUCCUC UAGGAGUGUAAGAGGGAGUGGAUGCAGUCAGAGUGG |
| 717 | MIR30B | ACCAAGUUUCAGUUCAUGUAAACAUCCUACACUCAGCUGUAAUA CAUGGAUUGGCUGGGAGGUGGAUGUUUACUUCAGCUGACUUGGA |
| 718 | ENSG00000251778 | UUCAAAAAGACCAUAUAUCCUUGAAGAGUAACUGCUGAACUUA UUCACUGGCAGUGGGCCUUAUAGCACAGUGAAUGACCAGGUUAG AGACAUGC |
| 719 | hsa-miR-544a | AUUCUGCAUUUUUAGCAAGUUC |

TABLE 3-continued

SEQ ID NOs: 561-840 Used in the HG Test Analysis

| SEQ ID NO: | Sequence Name | Sequence |
|---|---|---|
| 720 | ENSG00000201388 | UUCUCACCUAAACCCAAGAAUCACUGUUUCUUAUAGCGGUGGUU UAAACAGAGGUGCAAACAGCAAGUGAAUCUCGUCGCCUUUGCGG GGCUGUGGCCAUGCCCCUCAAAGGAAAUUUGGAGGCUCUACAGC C |
| 721 | MIR767 | GCUUUUAUAUUGUAGGUUUUUGCUCAUGCACCAUGGUUGUCUGA GCAUGCAGCAUGCUUGUCUGCUCAUACCCCAUGGUUUCUGAGCA GGAACCUUCAUUGUCUACUGC |
| 722 | MIR642A | AUCUGAGUUGGGAGGGUCCCUCUCCAAAUGUGUCUGGGGUGGG GGAUCAAGACACAUUUGGAGAGGGAACCUCCCAACUCGGCCUCU GCCAUCAUU |
| 723 | MIR454 | UCUGUUUAUCACCAGAUCCUAGAACCCUAUCAAUAUUGUCUCUG CUGUGUAAAUAGUUCUGAGUAGUGCAAUAUUGCUUAUAGGGUUU UGGUGUUUGGAAAGAACAAUGGGCAGG |
| 724 | ENSG00000207094 | AUCCAAGGCGAUUCCCUCUCCAAGGGGACAUCUAGUGCCCCUCUC AGGAAAGUAGCAACUUGGAAUAGAAUCUGGCAUGCCUAAGGUCU UUGAGGAACAGGGAUGCUUAUUUCCUCUGCCUUCCUUGGCUGCC UACAUAG |
| 725 | MIR4645 | UGAUAGGGAAACCAGGCAAGAAAUAUUGUCUCCUCAAGUUGCGA CGAGACAGUAGUUCUUGCCUGGUUUCUCUAUCA |
| 726 | MIR3155B | CCACUGCAGAGCCUGGGAAGGGAGCUGUCCGGCUCCCCAGGCUCU GCAGUGGGAGG |
| 727 | SNORD96B | CCUGGUGAUGACAGACGACAUUGUCAGCCAAUCCCCAUGUGGUA GUGAGGACAUGUCCUGCAGUUCUGAAGG |
| 728 | ENSG00000212587 | UGCACUUAUGUAUGUUUUUGUUUAACUUGUGGACAAAGACUUUA GGAAAGGUGCAAAAAAUAAAUCUUCUUUUGCAACCCAGAACUCA UUGUUCAGUAUGAGUUUUGAUACAUAUCAGAAUGGAUACU |
| 729 | hsa-miR-3186-3p | UCACGCGGAGAGAUGGCUUUG |
| 730 | ENSG00000212490 | UGCCCCUUUUAAGGUUGACACAGUGCAUUAAGCAGAAGGGUUAA GUAAGUCUCCAUAAAACCCAGAGAAGAGAAUGUAAAGCUCCUCU UUGGAGGAGCUAGACUCCUGUCUGGAGUCACAGCU |
| 731 | MIR3622B | AGUGAUAUAAUAGAGGGUGCACAGGCAUGGGAGGUCAGGUGAGC UCAGCUCCCUGCCUCACCUGAGCUCCCGUGCCUGUGCACCCUCUA UUGGCU |
| 732 | hsa-miR-6762-5p | CGGGGCCAUGGAGCAGCCUGUGU |
| 733 | MIR3938 | AGGAAUUUUUAACCCGAUCACUAGAUUAUCUACAAGGGAAUUUU UUUUUAAUUUAAAAAAUUCCCUUGUAGAUAAACCCGGUGGUCAGG UUGGAUGGCUCCAUG |
| 734 | ENSG00000207100 | UGCACUGCGUGGUAUCUGCACUCAGCAGUUUACUCCUGCUAGGG UGUUCAAAGGUCAGUGCCAUAGAAAUCCAGUAUCUGGUUUCAUU GGUUUUCUUGGCUUUGUGCUUGUUAAACCUGGUAUUUCUAUUGA UACAGCA |
| 735 | hsa-miR-3122 | GUUGGGACAAGAGGACGGUCUU |
| 736 | hsa-miR-548az-3p | AAAAACUGCAAUCACUUUUGC |
| 737 | hsa-miR-3165 | AGGUGGAUGCAAUGUGACCUCA |
| 738 | MIR2277 | GUGCUUCCUGCGGGCUGAGCGCGGGCUGAGCGCUGCCAGUCAGCG CUCACAUUAAGGCUGACAGCGCCCUGCCUGGCUCGGCCGGCGAAG CUC |
| 739 | MIR519C | UCUCAGCCUGUGACCCUCUAGAGGGAAGCGCUUUCUGUUGUCUG AAAGAAAAGAAAGUGCAUCUUUUUAGAGGAUUACAGUUUGAGA |

TABLE 3-continued

SEQ ID NOs: 561-840 Used in the HG Test Analysis

| SEQ ID NO: | Sequence Name | Sequence |
|---|---|---|
| 740 | hsa-miR-891b | UGCAACUUACCUGAGUCAUUGA |
| 741 | hsa-miR-4676-3p | CACUGUUUCACCACUGGCUCUU |
| 742 | MIR5692C1 | UAUAACAUUGUAUAUACCCACUGUGAUAUUAAGAGUAAUAGCUC UCUAGGUUAUUAUGAAUAAUAUCACAGUAGGUGUACACAAUGUU GUA |
| 743 | SCARNA15 | CUGGAGACUAAGAAAAUAGAGUCCUUGAAAUCAAGCUGACUCUG CUUUUAGCCUCCUAAAUGAAAAGGUAGAUAGAACAGGUCUUGUU UGCAAAAUAAAUUCAAGACCUACUUAUCUACCAACAGCA |
| 744 | MIR3972 | GCCCAUUUGCCUUGGCUUGGGGUGGCAGUCCUGUGGGAAUGAGA GAUGCCAAACUGGACCUGCCAGCCCCGUUCCAGGGCACAGCAU |
| 745 | ENSG00000201348 | CCAAUGUGGAUACACCCAGGAGGUCACUCUCUCCCAGGCUGUGU CCAAGUAGCAUAGGGGAGCACAGGGCUCUGUCCCCAUGAUGUAC UGUCCUUUUCCAUGACAUUGGAGAUGAAGCUGGACCUCAACUCU GCACAUGCAUAUUCCUACAACUUCUCAGAGUCCUGUGGAUAAUG ACGGAGGAGAGAAACCAUGCAGGAAACAGCC |
| 746 | ENSG00000252040 | UGAGAUGAGAUCAUGCCAUUGCACUCCAGCCUGGACGACAGAGC GAGACUUCAUCUCAAAAAAAAAAAAGGAUCCUCAGGGCUGCCAA CCUUAUAGUAGAAGUUGAGGUGGUAGUGGAUUUCUCCUACACAA |
| 747 | MIR8074 | CCAGUUCCUGAGUUUAUGCAAGAUGCCCAUGGGAGCCCAGAGAC GUCCUAUGGCGAGACUGGCAUGUACUCACACAACUGA |
| 748 | hsa-miR-3152-5p | AUUGCCUCUGUUCUAACACAAG |
| 749 | MIR619 | CGCCCACCUCAGCCUCCCAAAAUGCUGGGAUUACAGGCAUGAGCC ACUGCGGUCGACCAUGACCUGGACAUGUUUGUGCCCAGUACUGU CAGUUUGCAG |
| 750 | ENSG00000202275 | AUUGUUACAUUGAUAAAAUCAAAUCACCAUCUUUUAGCUAAGCU UGUGCUGGAUUUGCUUUUUUUCUGAUAAAGAUG |
| 751 | hsa-miR-759 | GCAGAGUGCAAACAAUUUUGAC |
| 752 | MIR514A1 | AACAUGUUGUCUGUGGUACCCUACUCUGGAGAGUGACAAUCAUG UAUAAUUAAAUUUGAUUGACACUUCUGUGAGUAGAGUAACGCAU GACACGUACG |
| 753 | MIRLET7A3 | GGGUGAGGUAGUAGGUUGUAUAGUUUGGGGCUCUGCCCUGCUAU GGGAUAACUAUACAAUCUACUGUCUUUCCU |
| 754 | hsa-miR-519a-3p | AAAGUGCAUCCUUUUAGAGUGU |
| 755 | hsa-miR-106b-3p | CCGCACUGUGGGUACUUGCUGC |
| 756 | SNORD116-20 | UGGAUCGAUGAUGACUUCCAUAUAUACAUUCCUUGGAAAGCUGA ACAAAAUGAGUGAAAACUCUAUACUGUCAUCCUCGUCGAACUGA GGUCCA |
| 757 | hsa-miR-4677-3p | UCUGUGAGACCAAAGAACUACU |
| 758 | ENSG00000252298 | UGGACAAAUGAUUAGAUUAGAUUGUGUUAUAAACCAAAGAUUAU AGUUAUUCCAAUUAUGUGCAUUUGAGAUCCACU |
| 759 | MIR493 | CUGGCCUCCAGGGCUUUGUACAUGGUAGGCUUUCAUUCAUUCGU UUGCACAUUCGGUGAAGGUCUACUGUGUGCCAGGCCCUGUGCCA G |
| 760 | hsa-miR-4538 | GAGCUUGGAUGAGCUGGGCUGA |

TABLE 3-continued

SEQ ID NOs: 561-840 Used in the HG Test Analysis

| SEQ ID NO: | Sequence Name | Sequence |
|---|---|---|
| 761 | ENSG00000212284 | UCAAUAAUGAAAUCUUCUGAUUUGGUGAGAAAUAAUGCCUUAAAAUUACACUCAAUAGGAUUAUGCUGAGG |
| 762 | hsa-miR-3913-3p | AGACAUCAAGAUCAGUCCCAAA |
| 763 | MIR4714 | AUUUUGGCCAACUCUGACCCCUUAGGUUGAUGUCAGAAUGAGGUGUACCAACCUAGGUGGUCAGAGUUGGCCAAAAU |
| 764 | hsa-miR-6838-3p | AAGUCCUGCUUCUGUUGCAG |
| 765 | hsa-miR-4531 | AUGGAGAAGGCUUCUGA |
| 766 | hsa-miR-5481 | AAAAGUAUUUGCGGGUUUUGUC |
| 767 | hsa-miR-326 | CCUCUGGGCCCUUCCUCCAG |
| 768 | hsa-miR-6830-5p | CCAAGGAAGGAGGCUGGACAUC |
| 769 | MIR6780A | GACACUUGGGAGGGAAGACAGCUGGAGAGUAUGGUCACAGCAGCAUCCUCCUCUGUUUUCUUUCCUAG |
| 770 | hsa-miR-4747-5p | AGGGAAGGAGGCUUGGUCUUAG |
| 771 | hsa-miR-4756-3p | CCAGAGAUGGUUGCCUUCCUAU |
| 772 | hsa-miR-517a-3p | AUCGUGCAUCCCUUUAGAGUGU |
| 773 | MIR3160-2 | ACCUGCCCUGGGCUUUCUAGUCUCAGCUCUCCUGACCAGCUGAGCUGGAGGAGAGCUGAGACUAGAAAGCCCAGGGCAGGU |
| 774 | hsa-miR-103a-3p | AGCAGCAUUGUACAGGGCUAUGA |
| 775 | hsa-miR-588 | UUGGCCACAAUGGGUUAGAAC |
| 776 | ENSG00000212378 | AUGUAAUAAUGUUCAUCAAAUGUCUGACCUGAAAUGAGCAUGUAGACAAGUUAAUUUAACACUGAAGAA |
| 777 | MIR548BA | AAAGGUAACUGUGAUUUUUGCUAUUAGAAAGUAAUGGCAAAAACUGCAAUUACUUU |
| 778 | hsa-miR-1251-3p | CGCUUUGCUCAGCCAGUGUAG |
| 779 | ENSG00000238995 | AACCAUGAAUGCAAGAAGCGUAUGAUUGGGUUUUCAUGCUCACGUGUGAAAUGGACCACCCUCAAACCUGGUUAUGCUAUCAGCACAUUACCUGUCUGAUG |
| 780 | SNORA64 | ACUCUCUCGGCUCUGCAUAGUUGCACUUGGCUUCACCCGUGUGACUUUCGUAACGGGGAGAGAGAGAAAAGAUCUCCUCAGGACCUCGGAUGGGCCUUACUGUGGCCUCUCUUUCCUUGAGGGGUGCAACAGGC |
| 781 | hsa-miR-206 | UGGAAUGUAAGGAAGUGUGUGG |
| 782 | MIR5708 | AUUACAGACAUGAGCGACUGUGCCUGACCAAAAGUCAACAUUAAACAACAAAUCUUGGCCAGGCACAGUGGCUCAUGCCUGUAAU |
| 783 | hsa-miR-146a-3p | CCUCUGAAAUUCAGUUCUUCAG |
| 784 | ENSG00000238488 | AUCAUUUGCAGCUUAUACAUGUGAUGACUGGGUUUUUAACUCAUAAGUGAGAUGUGCCUUUCUUACAUCUUAUUAUGACAUUAGUACAUUACCCAUUUGAUA |

TABLE 3-continued

SEQ ID NOs: 561-840 Used in the HG Test Analysis

| SEQ ID NO: | Sequence Name | Sequence |
|---|---|---|
| 785 | MIR519D | UCCCAUGCUGUGACCCUCCAAAGGGAAGCGCUUUCUGUUUGUUU UCUCUUAAACAAAGUGCCUCCCUUUAGAGUGUUACCGUUUGGGA |
| 786 | ENSG00000202498 | AGAUCAUUGAUGACUUCCAUAUAUCCAUUCCUUGGAAAGCUGAA CAACAUGAGUGAAAACUCUACUGAAAAAAGAAAAGAAAUGGGAG GCCG |
| 787 | hsa-miR-429 | UAAUACUGUCUGGUAAAACCGU |
| 788 | MIR5687 | CCUCACUUAUCUGACUCUGAAAUCUUCUAAAUGGUACCCACUUU AUUUAGAACGUUUUAGGGUCAAAUAAGUACAGG |
| 789 | hsa-miR-3922-5p | UCAAGGCCAGAGGUCCCACAGCA |
| 790 | hsa-miR-6499-5p | UCGGGCGCAAGAGCACUGCAGU |
| 791 | MIR3683 | GGGUGUACACCCCUGCGACAUUGGAAGUAGUAUCAUCUCUCCCU UGGAUGCUACGAACAAUAUCACAGAAGGUGUACACCC |
| 792 | hsa-miR-4515 | AGGACUGGACUCCCGGCAGCCC |
| 793 | hsa-miR-6884-5p | AGAGGCUGAGAAGGUGAUGUUG |
| 794 | ENSG00000202023 | CAAAUACAUGAUGAUCUCACCUCAGUUUGAACUCUCUCACUGAU CACUUGAUGACAAUAAAAGAUCUGAUAUUGUG |
| 795 | SNORA17 | ACUGCCCCUAGAGGCGUUGCAGCUGUGGCUGCCGUGUCACAUCUG UGUCAUUAGGUGGCAGAGAUUAGAGAGGCUAUGUCUACGCUCAG CGUUCUGCCCCGUGAACGUUUGAAUGUUUGAUAGUCUCACACUC |
| 796 | ENSG00000201811 | GUCUGCAUUUGAAAGUGAUCAUCAGCUAGCCUGUGUCUUCGUCA UCGAUAGUACAGGCCGGUGAACUGCGCAAAGCAUUUUCUGCAUU UGGAGGGUCCAUCUCUAUCCUUGGAAAUGCUAGUGCUUUUCUCA CA |
| 797 | MIR3926-1 | AAAAUGGAGCUGGCCAAAAAGCAGGCAGAGACUUUAAAAGCGUC UCUGCCUGCUUUUUGGCCAGCUCCGUUUU |
| 798 | ENSG00000200398 | CAGUCAGUGUCGAGAACCUUAUAUUGUUCUGAAGAGAGGUGGUG ACUUAAAAAUCAUGCUCAAUAGGAUUACGCUGAGGCCC |
| 799 | MIR1298 | AGACGAGGAGUUAAGAGUUCAUUCGGCUGUCCAGAUGUAUCCAA GUACCCUGUGUUAUUUGGCAAUAAAUACAUCUGGGCAACUGACU GAACUUUUCACUUUUCAUGACUCA |
| 800 | hsa-miR-1973 | ACCGUGCAAAGGUAGCAUA |
| 801 | ENSG00000238464 | AUCCUUUUGUAAGUCAUAAGUGUGAUUGGGUUUUCAUGCUCUUG UGUCAAAUGUGCCUCCCUCAAACCUUGUUACGAAGUGGGCACAC UACCCACCUGAUG |
| 802 | SNORD114-10 | AAGAUCAAUGAUGACUACUGUUAGUGUAUGAGUUACACAUGAUG AAUACAUGUCUGAAACUCUGAGGUCCA |
| 803 | MIR6856 | UGGAAAAGAGAGGAGCAGUGGUGCUGUGGCAGUGGCAGAGGUCG CUACAGCCCUGUGAUCUUUCCAG |
| 804 | ENSG00000239111 | AACAUUUAAAAAAUGUAUCAAGGCGUGGUGAUUAGGUUUUCAC ACUCAUGUGUGAGAUGUGCCUCCCUUGAACUUUGUUACAUUGGC ACUUUACCCAUUUGACA |
| 805 | hsa-miR-98-5p | UGAGGUAGUAAGUUGUAUUGUU |
| 806 | MIR1262 | AUCUACAAUGGUGAUGGGUGAAUUUGUAGAAGGAUGAAAGUCAA AGAAUCCUUCUCGGGAACUAAUUUUUUGGCCUUCAACAAGAAUUGU GAUAU |

TABLE 3-continued

SEQ ID NOs: 561-840 Used in the HG Test Analysis

| SEQ ID NO: | Sequence Name | Sequence |
|---|---|---|
| 807 | ENSG00000199262 | GUGCAUGUGAUGAAGCAAAUCAGUAUGAAUGAAUUCAUGAUACUGUAAACGCUUUCUGAUGUA |
| 808 | MIR548AY | AGAAGAUGCUUACUACUAGGUUGGUGCAAAAGUAAUUGUGGUUUUUGCAUUUAAAGUAAUGGCCAAAACCGCGAUUACUCUUGCACGAACCUAACGGUAACACUUCU |
| 809 | MIR4754 | ACGCGCCUGAUGCGGACCUGGGUUAGCGGAGUGAGGCCCAGUGGUCACCGCCGCCCUCCGCAGGUCCAGGUUGCCGUGCGCAUGUGCCU |
| 810 | MIR2113 | UUUUCAAAGCAAUGUGUGACAGGUACAGGGACAAAUCCCGUUAAUAAGUAAGAGGAUUUGUGCUUGGCUCUGUCACAUGCCACUUUGAAAA |
| 811 | MIR144 | UGGGGCCCUGGCUGGGAUAUCAUCAUAUACUGUAAGUUUGCGAUGAGACACUACAGUAUAGAUGAUGUACUAGUCCGGGCACCCCC |
| 812 | ENSG00000212211 | AAGAUUAUAUUUCCAGGGGUCAUUUCUGUGGUUCAUUACUUAAAGGAGUUUCCCCAAGUGUGUAGAGCACUGGAAACCACAGGAAGAUAUGCAAUGUUCUCUCCCGAGCACGAAGCUCGUUCUUGGUGUUGCUUCAUUGCAACUGCCAUUUGCCAUUGAUCAUUGUUUUUUCUUCCUUUGGGGAGAUUAAGAGGAAGAGGACACAGUCUGAGUGA |
| 813 | MIR3135A | UCACUUUGGUGCCUAGGCUGAGACUGCAGUGGUGCAAUCUCAGUUCACUGCAGCCUUGACCUCCUGGGCUCAGGUGA |
| 814 | ENSG00000207130 | CUCCAUGUGUCUUUGGAACCUGUCAGCUGUGGCAGUUGCCCUUCCUAGCCAUGGAAGAGUAAGUAUAUUCUUGUUUAUUGGCAAAGCUGUCACCAUUUCAUUGGUAUCAGAUUCUGACUUGCACAAGUAACAUUC |
| 815 | ENSG00000238440 | AUCCUUUUGAAGUUCAUAAGCAUGGUGAUUGGGUUUUCACACUCAUGUGUGAGAUGUACCACCCUUAAAGCUUGUUUAUGAUGUAGGCACAUUACCCAUCUGACA |
| 816 | MIR128-1 | UGAGCUGUUGGAUUCGGGGCCGUAGCACUGUCUGAGAGGUUUACAUUUCUCACAGUGAACCGGUCUCUUUUUCAGCUGCUUC |
| 817 | SCARNA5 | AGGUCGAUGAUGAUUGGUAAAAGGUCUGAUUGCACUGAAUGUCACGGUCCCUUUGUUGCCCUCAACUCCCAGCAGCCCAUUUUUUCCCUCCCGUCACAUUUAAGUCAUGUGUAUGGGAUCAUGGAGCAGCUGAUAAUUUGGGAUUCUGUCAGUGUGUGUUUCUGAGAGUGAUCGGCUCACAGCUGACGAGUAUCCAACAAAACCAGUUACACAGGAGACUGACGAGUGGCAGUCAUGGGUGUGAUGGUGCAUGAUCUCAAGUUUUCAAUCUGAGACCU |
| 818 | MIR4432 | GCAUCUUGCAGAGCCGUUCCAAUGCGACACCUCUAGAGUGUCAUCCCUAGAAUGUCACCUUGGAAAGACUCUGCAAGAUGCCU |
| 819 | MIR569 | GGUAUUGUUAGAUUAAUUUUGUGGGACAUUAACAACAGCAUCAGAAGCAACAUCAGCUUUAGUUAAUGAAUCCUGGAAAGUUAAGUGACUUUAUUU |
| 820 | hsa-miR-586 | UAUGCAUUGUAUUUUUAGGUCC |
| 821 | hsa-miR-4670-3p | UGAAGUUACAUCAUGGUCGCUU |
| 822 | ENSG00000212620 | GACUUCUCACUGAGCUUCUUUCUGUCUGUUGCUGGCAGCUUAUGGAUUCAUAUGAGCAGAGAGAAUCACAGAACUAGCAUUACUUUUGUCUUUACAGGAGUAUAUUUGGCUGUCUUGUGAGAUAUUA |
| 823 | SNORD114-27 | UGGUUCAGUGUUGACUACUGGUGUCGUGUGAGUCAUACAAUGAAUACAUGUCUGGAACUCUGAGGCCCA |
| 824 | ENSG00000251737 | AUCCUUUUGCGGUUCAUAAAGAACCAAGAUGACUGGGUUUCAUGCUAAUGCAUGACAUGUGCCUCCCUCAAAUCAUGUUGCCUCAUGGGCUUAUUGGCACAUUACCGUCUGAGG |
| 825 | hsa-miR-4472 | GGUGGGGGGUGUUGUUUU |
| 826 | hsa-miR-5580-5p | UGCUGGCUCAUUUCAUAUGUGU |

TABLE 3-continued

SEQ ID NOs: 561-840 Used in the HG Test Analysis

| SEQ ID NO: | Sequence Name | Sequence |
|---|---|---|
| 827 | hsa-miR-548n | CAAAAGUAAUUGUGGAUUUUGU |
| 828 | MIR6841 | GUGUUUAGGGUACUCAGAGCAAGUUGUGAAACACAGGUGUUUUUUAACCUCACCUUGCAUCUGCAUCCCCAG |
| 829 | MIR4434 | UCACUUUAGGAGAAGUAAAGUAGAACUUUGGUUUUCAACUUUUCCUACAGUGU |
| 830 | ENSG00000212558 | GUGCCUAAGGUUAACACAGCGCCUUAAGAGGCUAACACAGAAGGGCAAAGUAAGUCUCCAUAAAACCCAGAGAAGACUGUGAACCCCUCUCUGGAUCCUGUCUGGAGUCACAGCU |
| 831 | ENSG00000252517 | CCUCAUUGAUUAGUAGCUUCUGACUUUUGUUCUGAGUUUGCUGAAGCUAGAUGCCAUUCCAGAUAAGA |
| 832 | hsa-miR-6731-5p | UGGGAGAGCAGGGUAUUGUGGA |
| 833 | ENSG00000212270 | GUUCAUGAUAAGUAACAUUUCUUCAAUUUGACCUGAUGUGUAUUGAAGAAAACCAGCAUCUGAGG |
| 834 | hsa-miR-200c-5p | CGUCUUACCCAGCAGUGUUUGG |
| 835 | hsa-miR-6514-5p | UAUGGAGUGGACUUUCAGCUGGC |
| 836 | SNORD115-48 | GGGUCAAUGAUGAGAUGUUACCUUGAAGAGAAAUGAUGACGUAAAAAUUAAGUUCAGUUGGAUUACGCUGAGGCCC |
| 837 | MIR6779 | GAGCUCUGGGAGGGGCUGGGUUUGGCAGGACAGUUUCCAAGCCCUGUCUCCUCCCAUCUUCCAG |
| 838 | hsa-miR-4659b-5p | UUGCCAUGUCUAAGAAGAA |
| 839 | MIR1915 | UGAGAGGCCGCACCUUGCCUUGCUGCCCGGGCCGUGCACCCGUGGGCCCCAGGGCGACGCGGCGGGGCGGCCCUAGCGA |
| 840 | MIR573 | UUUAGCGGUUUCUCCCUGAAGUGAUGUGUAACUGAUCAGGAUCUACUCAUGUCGUCUUUGGUAAAGUUAUGUCGCUUGUCAGGGUGAGGAGAGUUUUUG |

The selection of the sncRNAs in the Sentinel™ PCa, CS and HG Tests is independent of PSA, Gleason Score, or biological pathway analysis, and as such is entirely unbiased. Because the algorithm was validated using sncRNA levels obtained from an independent training set made up of a cohort of participants whose core needle biopsy is positive or negative (PCa Test), or patients labeled as either having advanced disease (GG3-5) or not (No evidence of PCa or GG1-1) for the CS Test. (see Table 4, [000103]-[000104] and Table 5 [000109]-[000110]), this statistical methodology minimizes both Type 1 error (false negative) and Type 2 error (false positive), which ensure that the tests rigorously distinguish between none and low-grade cancer, low and intermediate grade cancer and between intermediate and high-grade disease. Based on the algorithm used in the analysis, the described invention has no false negatives and a very low (<5%) false positive rate.

Based on the three tests described above, the OpenArray™ platform sequentially interrogates the informative RNA entities present in a single sample of sncRNA extracted from urinary exosomes without compromising sensitivity and specificity of the three tests.

In one aspect, the disclosure provides a method for diagnosing prostate cancer comprising a platform that allows one to distinguish between clinically significant tumors and indolent tumors and in putting the data based on a subset sncRNAs interrogated into an algorithm that has been validated based on an independent training data set.

In one aspect, the method for diagnosing prostate cancer in a male patient comprising (1) obtaining a biological sample from the patient, (2) detecting the aggregate expression profile of a collection of signature small non-coding RNAs (sncRNAs) that bind to a plurality of nucleic acids or hybridizing probes selected from the group consisting of SEQ ID NOs: 1-280; and (3) correlating the aggregate expression profile of the collection of signature sncRNAs using the PCa test to determine whether the patient is at risk for prostate cancer, i.e., having no evidence of prostate cancer or having prostate cancer.

In another aspect, the disclosure provides a method for screening prostate cancer using the same. In yet another aspect, the disclosure provides a method for predicting the probability of prostate in a subject.

For patients identified to be at risk for prostate cancer (i.e., determined to have prostate cancer), the samples are re-analyzed using the Sentinel™ Clinical Significant (CS) Test to distinguish patients with clinically significant or aggressive prostate cancer (GG2-GG5) from patients with clinically insignificant or indolent (GG1) prostate cancer. In one embodiment, the patient is identified as having aggressive prostate cancer when the aggregate or combined expression profile of a plurality or a collection of signature sncRNAs is higher than or equal to the aggregate expression profile in a prostate cancer biological sample, or identifying the subject as having low-grade prostate cancer when the aggregate expression profile of a collection of signature sncRNAs is less than or equal to the aggregate expression profile in a low-grade prostate cancer biological sample.

In one embodiment the biological sample includes, but is not limited to, prostate tissue, blood, plasma, serum, urine, urine supernatant, urine cell pellet, cerebrospinal fluid, semen, prostatic secretions, and prostate cells. In some embodiments, the biological sample is a urine sample. In yet another embodiment, the samples are exosomes isolated from the urine sample. In a preferred embodiment, the sample is sncRNAs isolated from exosomes derived from the urinary sample.

Exosomes are small extracellular vesicles (EV) that originate in the endosomal compartment of eukaryotic cells. They are found in biological fluids including blood, urine, semen and cerebrospinal fluid. The biogenesis of exosomes is not well-understood; however, it is generally accepted that they arise at the point at which the early endosomal pathway bifurcates to form late endosomes and multi-vesicle endosomes, the first stages of the exosomal pathway. Exosomes contain sncRNAs including miRNAs and small nucleolar RNAs (snoRNAs) which are derived from the cytoplasm and nucleolar region of the cell respectively. The presence of exosomes and EVs in the tumor microenvironment have been associated with malignancy in a number of tumor types including prostate cancer and other cancers.

In certain embodiments, sncRNAs isolated from exosomes are derived from semen, blood, prostatic secretions and cerebral spinal fluid. In further embodiments, the exosomes are isolated from the cancer cells including prostate cancer cells, lymphocytes, and cells from prostate tissues.

The method for isolating exosomes is well known in the art and can be carried out using kits such as the Exosome RNA Isolation Kits (Norgen Biotek Corp., Ontario, Calif.). sncRNA yields can be quantified by fluorimetry (Qubit, Thermo Fisher Scientific), and the quality of the sncRNAs isolated is assessed using an Agilent 2100 bioanalyzer.

The RNAs extracted from the isolated exosomes are a mixture of small RNAs referred collectively as small non-coding RNAs (sncRNAs), which include miRNA, snoRNA, scaRNA, siRNA, snRNA, and exRNA. Due to their size (<200 nucleotides), the sncRNAs are readily extracted from biological samples, including, for example, Formalin-Fixed Paraffin-Embedded (FFPE) tissue or urine. The sncRNAs are not degraded during fixation or extraction, obviating the problems intrinsic in extraction of mRNA from FFPE tissues. Yield of sncRNAs of about 10 ng from the biological samples is sufficient for multiple analyses using the Exosome RNA Isolation Kits of Norgen disclosed above.

The extracted sncRNAs are reversed transcribed into cDNAs, which are more stable than RNA, thus allowing for longer storage. The resulting cDNAs are hybridized against a selected set or collection of signature sncRNAs probes or genome array or micro-array chips, such as the miR 4.0 arrays (ThermoFisher Scientific) for further analysis. The selection of the informative set of sncRNA probes is independent of PSA, Gleason Score or biological pathways. The selected set or collection of signature sncRNAs comprises SEQ ID NOs: 1-280, 281-560 and 561-840. The number of sncRNA sequences or probes in the set range from 145-196, preferably not more than 280 sncRNA sequences for in putting in the Sentinel™ PCa, Sentinel™ CS and Sentinel™ HG Tests. The tests are more precise with up to 280 sncRNA sequences added to the algorithm. Addition of more than 280 sncRNA sequences in the analysis does not increase the precision of the assay.

Real time-PCR or RT-PCR, often known as qPCR or RT-qPCR, is conducted to quantify the absolute amount of a target sequence or to compare relative amounts of a target sequence between samples. The RT-qPCR monitors amplification of the target in real-time via a target-specific (probes) fluorescent signal emitted during amplification. Because background fluorescence occurs during most RT-qPCR reactions despite the use of sequence specific probes against the targets, the issue of background fluorescence signal can be addressed by considering two values in real-time PCR: (1) the threshold line ($C_t$) and (2) the cycle quantification ($C_q$). value. The threshold line ($C_t$) is the level of detection when a reaction reaches a fluorescent intensity that is above background levels, that is a point where the reaction curve begins the exponential phase (inflexion point). The $C_q$ or cycle quantification value is the PCR cycle number at which the sample's reaction curve intersects the threshold line. The $C_q$, value therefore, indicates how many cycles it took to detect a real signal from the samples, i.e., time to event, where the event is the saturation of the fluorescence, indicating the maximum level of detection. Because RT-qPCR runs provide a reaction curve for each sample, there will be many $C_q$ values. The software in the PCR cycler will calculate and chart the $C_q$ value for each of the samples. Values are inverse to the amount of target nucleic acid in the sample, and correlate to the number of target copies in the sample. Lower $C_q$ values (typically below 29 cycles) indicate high amounts of target sequence. Conversely, higher $C_q$ values (above 38 cycles) indicate lower amounts of the target nucleic acid in the sample. However, the time to event value can be obtained when the slope of the reaction curve becomes zero, rather than using the $C_q$ when the slope is at a maximum. In one embodiment, the sncRNAs are interrogated using RT-qPCR. In another embodiment, the sncRNAs are interrogated using qPCR. In a further embodiment, the sncRNAs isolated from the urinary exosomes are interrogated using the Affymetrix GeneChip™ miRNA 4.0 Array following manufacturer's instructions.

These informative sequences obtained from the training set (usually 280 sequences) are then transferred to the OpenArray platform. Patient samples of unknown status are then interrogated on the OpenArray platform and the Sentinel Score is determined using the Classification Algorithm. The status of the patient is determined from the Sentinel Score.

In one embodiment, the sncRNAs levels from a patient of unknown prostate cancer status are interrogated on the OpenArray platform and Sentinel score from a patient of unknown disease status can then be compared to that of the training set to determine the status of the patient In one embodiment, the data obtained from the analysis of sncRNAs levels in the test sample from a patient of unknown prostate disease status (test sample) using, for example, by RT-qPCR on the Affymetrix GeneChip™ miRNA 4.0 Array can be compared to those from healthy patients (no evidence of cancer) or healthy cells obtained from the subject with prostate cancer. The data obtained from the analysis of sncRNA levels from the test sample can also be compared to clinical baselines established by analyzing healthy (no cancer) and non-healthy (with genitourinary cancer) patients, and the non-healthy patients be further categorized into different specific cancer types, which can be further categorized into different stages or severity of the specific cancer type (for example, prostate cancer, etc.) and different stages of the specific disease. In one embodiment, the data obtained from the analysis of sncRNAs expression in the test sample using RT-qPCR on the Affymetrix GeneChip™ miRNA 4.0 Array are compared to those from healthy patients (no evidence of cancer) or the data can also be compared to clinical baselines established by analyzing healthy (no cancer) and non-healthy (with having prostate cancer) patients, and the non-healthy patients be further categorized into different stages of prostate cancer (GG1 and GG2-GG5 or GG1+2 and GG3-GG5).

In some embodiments, the method uses an OpenArray™ technology (ThermoFisher Scientific) to interrogate a panel of sncRNAs (e.g., miRNAs, snoRNAs). The OpenArray™ technology uses a microscope slide-sized plate having 48 subarrays. Each subarray has 64 through-holes, and each hole is 300 µm in diameter and 300 µm deep. The holes are treated with hydrophilic and hydrophobic coatings in order to retain reagents in the through-holes via surface tension. The OpenArray™ technology, with its 3,072 through-hole (48×64), provides a system for streamlining real-time PCR studies that use large number of samples, assays or both. The system thus allows processing of samples for gene expression in large number in short time periods using microquantities of samples and reagents. The method employs an algorithm that relies on the expression level of each of the sncRNAs and the grading of the biopsies (at least 12 core needle biopsies). In the case of prostate cancer, the methodology is independent of serum Prostate Specific Antigen (PSA) levels, Gleason Score (neither of which are meaningful markers of tumor progression), or patient age. The methodology is also independent of any analyses of biological pathways. The present method uses sncRNAs isolated from the subject (e.g., urinary sample, urinary exosome, or prostate tissue samples) to stratify men into those that have prostate cancer (both indolent (clinically insignificant) or aggressive (clinically significant)) and those that do not. This methodology can replace serum PSA as the major screening assay for prostate cancer.

In one aspect, the disclosure provides a method that distinguishes clinically significant prostate cancer based on the aggregate expression profile of a collection of signature sncRNAs interrogated that is subjected to a classification algorithm that is independent of pathology (Gleason Score), tumor volume or PSA. The RNA extracted from biological samples of patients with known cancer outcomes are reverse-transcribed and hybridized against a full-genome array (e.g., Affymetrix GeneChip miR 4.0) containing sncRNAs. Small non-coding RNAs that are differentially regulated in clinically significant prostate tumors are identified. In one embodiment, the absolute value of the signal from the Open Array identifying the sncRNAs that hybridize to the probes for SEQ ID NOs: 281-561, is compared to the aggregate expression profile found in clinically significant (GG2-5) prostate cancer tumors. In another embodiment, the aggregate value of the signal from the Open Array identifying the sncRNAs that hybridize to the probes for SEQ ID NOs: 561-840, is compared to the absolute expression profile found in clinically low and favorable intermediate grade (GG1+GG2) versus unfavorable intermediate and high grade (GG3-GG5) prostate cancer tumors.

The disclosed method provides a robust and accurate determination of prostate cancer prognosis in 72-96 hours from the time when the urine sample is received to obtaining a Sentinel Score. In another embodiment, the aggregate expression profile of the identified sncRNAs that bind to SEQ ID NOs: 281-560 and 561-840 is compared to the aggregate expression profile of sncRNAs in clinically significant prostate cancer. In another embodiment, the aggregate expression profile of the identified sncRNAs interrogated that bind to SEQ ID NOs: 281-560 and 561-840 is compared to the aggregate expression profile of sncRNA in clinically significant prostate cancer. In a further embodiment, the aggregate expression profile of the identified sncRNAs that bind to SEQ ID NOs: 281-560 and 561-840 is compared to the aggregate expression profile of sncRNA in clinically significant prostate cancer sample. As a result, appropriate treatment options (or the lack thereof) can be initiated.

The terms relative aggregate expression profile are used interchangeably. The aggregate expression profile of at least a plurality of sncRNAs are combined and compared to the same aggregate expression profile in clinically significant prostate cancer tissue. In some embodiments at least 40 sncRNAs are combined and compared to the same aggregate expression profile in clinically significant prostate cancer tissue. In some embodiments at least 90 sncRNAs are combined and compared to the same aggregate expression profile in clinically significant prostate cancer tissue. In some embodiments at least 150 sncRNAs are combined and compared to the same aggregate expression profile in clinically significant prostate cancer tissue. In some embodiments at least 200 sncRNAs are combined and compared to the same aggregate expression profile in clinically significant prostate cancer tissue. In a preferred embodiment, at least 224 sncRNAs and not more than 280 sncRNAs are combined and compared to the same aggregate expression profile in clinically significantly prostate cancer tissue. In certain embodiments, a higher aggregate expression profile as compared to the aggregate expression profile in a low-grade prostate cancer tissue indicates the patient has aggressive prostate cancer and treatment is required. In other embodiments, an aggregate expression profile equal to or lower than the aggregate expression profile in a low-grade prostate cancer tissue indicates the patient does not have aggressive prostate cancer and monitoring but not treatment may be required.

In some embodiments, the aggregate expression profile of selected sncRNAs is an aggregation of various types of modulated expression of the sncRNAs. The modulated expression can be decreased or increased expression profile relative to the same sncRNA in other tissue/tumor types, such as healthy prostate tissue, low-grade prostate cancer tissue, or high-grade prostate cancer tissue.

In other embodiments, the aggregate expression profile of selected sncRNAs can be an aggregation of the decreased aggregate expression profile of certain sncRNAs as well as an aggregation of the increased aggregate expression profile of other sncRNAs in the same tissue sample. For example, a progression score, or aggregate expression profile of a collection of signature sncRNAs may include one or more sncRNAs with decreased aggregate expression profiles relative to another tissue type or other sncRNAs in the same tissue sample, while one or more of the remaining sncRNAs exhibit increased aggregate expression levels relative to another tissue type or other sncRNAs in the same tissue sample. The aggregate expression profile of the collection of differently modulated sncRNAs provides a sophisticated, unbiased, indication of whether a prostate tumor is clinically significant. Unlike other methods that merely evaluate the presence or absence, or simple increase or decrease of individual target molecules, as compared to normal tissue, the methods disclosed provide a truly unbiased, independent, and multi-variable analysis of a prostate tissue sample thereby allowing for a surprisingly accurate diagnosis of whether a prostate cancer tumor is clinically significant.

In some aspect, the method provides for the use of the aggregate expression profile of the collection of signature sncRNAs for monitoring metastasis and cancer staging.

In another aspect, the disclosure provides a method for detecting a urological malignancy based on the aggregate expression profile of the collection of signature sncRNAs interrogated and subject to analysis using the classification algorithm disclosed. In some embodiments the malignancy is cancer of the prostate.

The present disclosure provides an algorithm-based molecular diagnostic assay for predicting a clinical outcome for a patient with prostate cancer. The expression level of one or more sncRNAs may be used alone or arranged into functional gene subsets to calculate a quantitative score that can be used to predict the likelihood of a clinical outcome.

A "quantitative score" is an arithmetically or mathematically calculated numerical value for aiding in simplifying or disclosing or informing the analysis of more complex quantitative information, such as the correlation of certain expression profile of the disclosed sncRNAs or sncRNAs subsets to a likelihood of a clinical outcome of a prostate cancer patient. A quantitative score may be determined by the application of a specific algorithm. The algorithm used to calculate the quantitative score in the methods disclosed may group the expression profile values of the sncRNAs. The grouping of sncRNAs may be performed at least in part based on knowledge of the relative contribution of the sncRNAs according to physiologic functions or component cellular characteristics, such as in the groups discussed herein. A quantitative score may be determined for a sncRNA group ("sncRNA group score" or the Sentinel™ Score). The formation of groups, in addition, can facilitate the mathematical weighting of the contribution of various aggregate expression profile of genes or gene subsets to the quantitative score. The weighting of a sncRNA or sncRNAs group representing a physiological process or component cellular characteristic can reflect the contribution of that process or characteristic to the pathology of the cancer and clinical outcome, such as recurrence or upgrading/upstaging of the cancer. The present invention provides a number of algorithms for calculating the quantitative scores. For example, the Classification algorithm in the present disclosure works the same way for developing the Sentinel Scores for distinguishing different disease states. The Classification algorithm selects different sncRNA sequences from the training data set for clinically significant and insignificant disease states.

On the other hand, the Selection algorithm test how well the aggregate expression profile of the urinary exosomal sncRNAs correlate with pathological stage of the disease (cancer/no cancer) in a large population of participants with known pathology. The Selection algorithm individually assessed how well each of the 6,599 sncRNAs interrogated on the miR4.0 arrays correlates the known pathology of the participant. It then iteratively assesses all combinations of 2 sncRNAs, 3 sncRNAs or 4 sncRNAs of the 6,599 sncRNAs interrogated by the miR 4.0 Arrays, followed by examination of each individual sncRNA using a leave-one-out strategy to assess the importance of each individual sncRNA in the pathology of the disease. The Sentinel Score for a patient with unknown disease status is then determined by interrogating selected sncRNAs using the Open Array and the clinical status is determined by comparing the score to that from the training data sets. In an embodiment of the invention, an increase in the quantitative score indicates an increased likelihood of a negative clinical outcome.

Based on the quantitative score and cumulative or absolute or aggregate expression profile, methods of treatment can also be decided. The methods of treating prostate cancer include surgery for complete surgical removal of prostate tissue, administering an effective dose of radiation, and administering a therapeutically effective amount of a medication for the treatment of prostate cancer, or a combination of the above.

The algorithm-based assay and associated information provided by the practice of the methods of the present invention facilitate optimal treatment decision-making in prostate cancer. For example, such a clinical tool would enable physicians to identify patients who have a low likelihood of having an aggressive cancer and therefore would require no further medical intervention except for a routine follow-up or active surveillance every 3 months, 6 months or 12 months. Patients with no cancer do not require medical intervention return for follow-up once every year. Patients at risk for developing aggressive cancer require medical intervention, which includes but is not limited to treatment with one or more chemotherapeutic agents (e.g., taxotere, cabazitaxel, docetaxel, mitoxantrone, epirubicin, paclitaxel and estramustine, etc.), hormone therapy (e.g., lutenizing hormone releasing hormone agonists to prevent production of testosterone such as leuprorelin, goserelin and triptorelin or anti-androgen drugs that prevent testosterone from reaching the cancer cells, e.g., bicalutaminde and nilutamide), immunotherapeutics, radiation, cryotherapy, surgery or a combination thereof.

Patients who undergo treatment are monitored using the disclosed method to determine the patients' response to treatment. In one aspect, the disclosure provide a method for determining the patient's response to treatment comprising: (i) obtaining a biological sample from a patient, (ii) detecting the aggregate expression profile of a signature collection of small non-coding RNAs (sncRNAs) from the biological sample wherein the collection of sncRNAs comprises SEQ ID NOs: 1-280, 281-560 and 561-840 (iii) correlating the aggregate expression profile of sncRNAs of SEQ ID NOs: 1-280, 281-560 and 561-840 from the subject after treatment by comparing the aggregate expression profile of SEQ ID NOs: 1-280, 281-560 and 561-840 to that prior to treatment, (iv) determining if the patient is responsive to the treatment, and if there is a need for modification of the treatment. In one embodiment, the method further compares the resulting aggregate expression profiles of a signature collection of sncRNA from (iii) above is then compared to the aggregate expression profile of a signature collection of sncRNA for the large training data set from a target population having prostate cancer with known Grade groups to determine if the (a) patient prostate cancer is stable (no apparent change compared to the Grade group), (b) the patient is responsive to the treatment, i.e., patient gets better (the results show tumors that resembles tumors with lower grade group) or (c) the patient is non-responsive (patient gets worse when the results show tumors that resembles tumor of higher Grade group) based on the aggregate expression profile of a collection of signature sncRNAs and Sentinel Score for that Grade group, and if there is a need for modification of the treatment. Treatment modification includes but not limited to adjusting the concentration or amounts of chemotherapeutic agents, radiation, immunotherapeutic or hormone administered, adding or removing one or more of agents used.

In another aspect, the disclosure provides a method for determining the disease recurrence, disease progression or likelihood of survival based on the aggregate expression profile of a collection of signature sncRNAs comprising SEQ. ID. NOs: 1-280, 281-560 and 561-840 by comparing the aggregate expression profile of SEQ. ID. NOs: 1-280, 281-560 and 561-840 in a training dataset and the patient's earlier profile.

In another aspect, the disclosure provides a system for determining whether a patient has no cancer or has cancer and classifying the subject with cancer as (i) indolent (low grade, GG1), (ii) intermediate or high grade (GG2-GG5), (iii) low/intermediate risk (GG1-GG2) or (iv) aggressive (high grade, GG3-GG5) prostate cancer comprising at least three processors configured to (a) interrogate sncRNA sequences for informative sequences, (b) determine and compare a Sentinel Score to determine if the subject has prostate cancer or no prostate cancer and to classify subject determined to have cancer to the various Grade groups, e.g., low grade, intermediate/high grade, low/intermediate risk or aggressive grade cancer. Subjects determined to have no evidence of cancer do not require medical intervention and would return for follow-up once every year. Subjects determined to have low grade or low/intermediate grade prostate cancer would require no medical intervention except for a routine follow-up or active surveillance every 3, 6, or 12 months, and subjects determined to have intermediate/high grade or aggressive prostate cancer require medical intervention.

EXAMPLES

This and other aspects of the present invention are further illustrated by the following non-limiting examples.

Example 1

Study Populations

Two independent patient cohorts were used for the development and validation of the Sentinel™ PCa and Sentinel™ CS Tests. The clinical and demographic characteristics of the 233 participants used to develop the Sentinel™ PCa to classify patients as having cancer or no cancer was based on the statistical analysis of a collection of signatures snRNAs. For patients classified as having cancer, patients with GG1 (indolent, low risk cancer) are distinguished from GG2-5 (respectively as intermediate, high-risk and aggressive cancers) using the Sentinel™ CS Tests, which is also based on the statistical analysis of another collection of signatures the sncRNAs using a second Classification algorithm to classify tumors into GG1 versus GG2-5. The sncRNAs in both tests are interrogated by the Affymetrix miR 4.0 array.

Urine Collection and Processing

Urine samples for the development of the Sentinel™ PCa and CS Tests and the US-based cohort of the retrospective study were collected on the day of visit for clinical workup at two clinical sites: Albany Medical Center (Albany, N.Y., USA) and SUNY Downstate Medical Center (Brooklyn, N.Y., USA). Remaining samples for the retrospective study were retrieved from the GUBioBank, University Health Network, Toronto Calif. and shipped frozen at −20° C. in bulk to the miR Scientific laboratories. Patient information was collected and anonymized as approved by Institutional Review Board at each participating site. Prostate cancer diagnosis was obtained by histopathological grading of core-needle biopsies; the percentage of tumor per core and number of positive cores were used to assess the grade group (GG).

Urine samples were centrifuged to remove free cells and debris. RNA was extracted using Exosome RNA Isolation Kits (Norgen Biotek, ON) according to the manufacturer's instructions. sncRNA yields were quantified by fluorimetry (Qubit, Thermo Fisher Scientific) and RNA samples were stored at −80° C. until analysis.

Microarray Analysis of Total Exosomal sncRNAs sncRNAs were interrogated using the Affymetrix GeneChip™ miR 4.0 Array following the manufacturer's instructions. MAIME-compliant raw data files for the 235 patients analyzed on these arrays have been deposited in NCBI's Gene Expression Omnibus. (Edgar R et al. *Gene Expression Omnibus: NCBI gene expression and hybridization array data repository. Nucleic Acid Res* 2002 30:207). Six thousand five hundred and ninety-nine sncRNAs in the training set were interrogated on the Affymetrix GeneChip™ miRNA 4.0 Array.

The small non-coding RNA entities interrogated for each participant were analyzed using proprietary Selection and Classification Algorithms. The most informative sequences for distinguishing between cancer and non-cancer subjects (SEQ ID NOs: 1-280) and between Grade Group 1 and Grade Group 2-5 patients were identified. (SEQ ID NOs: 281-842)

QuantStudio OpenArray™-Based Interrogation of Exosomal sncRNAs cDNA synthesis, pre-amplification of selected miRNAs: For analysis of exosomal miRNA, total sncRNA was reverse transcribed in separate reactions with three specific miRNA stem-loop primer pools with the TaqMan™ MicroRNA Reverse Transcription Kit (Thermo Fisher Scientific) as recommended by the manufacturer. The miRNA cDNA pools were enriched individually with Pre-Amp primer pools for 16 cycles (95° C. for 10 min, 55° C. for 2 min, 72° C. for 2 min, 95° C. for 15 sec and 60° C. for 4 min repeated 16 cycles, 99.9° C. for 10 min), and interrogated on the QuantStudio OpenArray™ on three 56-entity sub-arrays following the manufacturer's recommendations.

cDNA Synthesis, Pre-Amplification and Interrogation of Selected snoRNAs:

Total sncRNA was reverse transcribed with High-Capacity cDNA Reverse Transcription Kit with a single Pre-Amp primer pool (Thermo Fisher Scientific) as recommended by the manufacturer. snoRNA cDNA products were enriched by preamplification (95° C. for 10 min, 95° C. for 15 sec and 60° C. for 4 min repeated for 14 and 18 cycles respectively, and 99° C. for 10 min) and interrogated on two 56-entity sub-arrays.

Statistical Analysis:

The Sentinel™ PCa Test is based on Classification Algorithm that has been trained on a cohort of participants whose core-needle biopsy is positive or negative. The Classification Algorithm takes as input the sncRNA expression signature for a participant with unknown disease status and produces a Sentinel™ Score; the participant is classified by comparing the Sentinel™ PCa Score to the pre-determined cutoff value that maintains the sensitivity for classifying a future patient with unknown disease status (but known expression signature), at a user-defined level (95% or greater). A second classification algorithm, the Sentinel™ CS Test operates analogously to the Sentinel™ PCa Test. However, the classification algorithm for the Sentinel™ CS Test is trained on a cohort of patients labeled as low grade (GG1) and a second cohort of patients labeled as favorable intermediate to high grade prostate cancer (GG2-GG5). The third classification algorithm, the Sentinel™ HG Test is trained on a cohort of patients determined to be low- and favorable intermediate-risk (GG1+GG2) prostate cancer and a second cohort characterized as unfavorable intermediate risk and high-risk (GG3-GG5)

Figure 4:
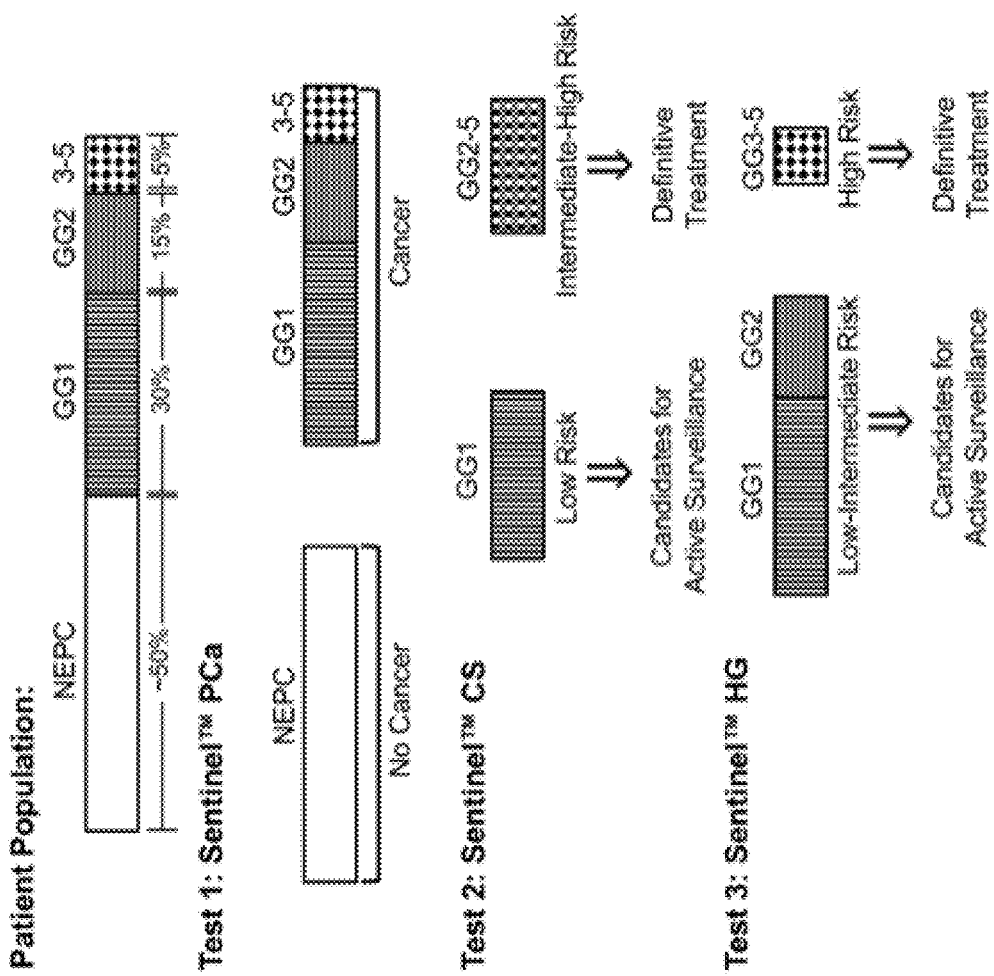
FIG. 4 shows a schematic for screening and diagnosis of a patient suspected of having prostate cancer.

The Sentinel™ Testing paradigm operates in two or three layers. First, it uses the sncRNA signature from the participant's urine to input to the classification rule of the Sentinel™ PCa Test to determine if cancer is present; second, for those patients diagnosed with cancer, the Sentinel™ CS Test determines whether the cancer is low risk (GG1) or not; thirdly the Sentinel™ HG Test determine whether the tumor is unfavorable intermediate or high risk (GG3-GG5) or not. (See FIG. 4.)

The statistical analysis used is based on the ability to identify sequences that have hidden associations with outcome that is only observed after conditioning on other sequences. Of the 400-600 informative sncRNA sequences, 280 sncRNA sequences were used in the Classification algorithm as a basis to define an expression signature for the Discovery PCa Test (FIGS. 5A-5B), and Discovery HG Test (FIGS. 7A-7B) and Discovery CS Test (FIGS. 6A-6B). The subset of informative sncRNAs considered to be of the highest importance were then identified for each Test (FIGS. 5B, 7B and 6B, respectively).

These 280 sncRNAs were combined to design an OpenArray™ platform that provides the basis for the Sentinel™ PCa and CS Tests. The Sentinel™ PCa Test incorporates the aggregate expression profiles of 84 unique sncRNAs: 60 miRNAs and 24 snoRNAs, for classifying a subject with unknown disease status as having prostate cancer or no

TABLE 4

Demographics and Clinical Characteristics of Cohort Used to Develop Classification Algorithm.

|  | Control (%) | Cancer (%) | | | | |
| --- | --- | --- | --- | --- | --- | --- |
|  |  | GG1 | GG2 | GG3 | GG4 | GG5 |
| Total | 89 (37.9%) | 90 (38.3%) | 34 (14.5%) | 9 (3.8%) | 7 (3.0%) | 6 (2.5%) |
| Age |  |  |  |  |  |  |
| Range | 23-89 | 53-83 | 50-81 | 60-81 | 51-74 | 59-74 |
| Mean ± SD | 65.6 ± 13.0 | 67.3 ± 6.7 | 66.3 ± 6.6 | 72.1 ± 6.6 | 63.0 ± 7.5 | 67.2 ± 5.5 |
| BMI |  |  |  |  |  |  |
| Range | 18.9-54.1 | 20.7-53.3 | 22.0-44.1 | 26.1-36.1 | 16.0-44.1 | 27.5-41.2 |
| Mean ± SD | 29.3 ± 5.6 | 28.4 ± 4.9 | 28.2 ± 3.8 | 30.1 ± 3.3 | 29.2 ± 8.5 | 32.7 ± 5.2 |
| Race |  |  |  |  |  |  |
| NHW | 72 | 78 | 30 | 7 | 7 | 6 |
| NHB | 3 | 7 | 4 | 1 | 0 | 0 |
| not reported | 14 | 5 | 0 | 1 | 0 | 0 |
| PSA |  |  |  |  |  |  |
| Range | N/A | 0.55-28.2 | 2.1-49.9 | 5.6-28.2 | 6.9-40.8 | 5.5-17.8 |
| Mean ± SD |  | 6.3 ± 4.0 | 7.7 ± 7.9 | 10.5 ± 7.4 | 18.8 ± 10.7 | 8.7 ± 4.6 |

*Under exempt study status, PSA levels were not available for patients with no evidence of cancer.

Table 4 established the training datasets used to develop the Sentinel™ tests. Of the 235 patients, patients included in the "no cancer" cohort (89 patients) were carefully selected from age-matched men who were seen at urology clinics for issues unrelated to urological oncology (n=58), and from men who had one or more 12-needle diagnostic core needle biopsies that showed no evidence of prostate cancer (n=30).

Patients in the "cancer" cohort (n=146) were selected based on the histopathology of the core needle biopsies. Of the 146 "cancer" cohort, 90 patients were classified as GG1 cancer, 56 patients were classified as GG2-5.

Of the 6,599 microarray sequences from the training data set interrogated using the proprietary Selection Algorithm to separate that are "informative" for the outcome versus those that are not, only 400-600 are informative. By outcome, it is meant that sncRNA sequences that impact the algorithm when each sequence is added to predict whether the subject of unknown disease status has or has no prostate cancer and the stages of the cancer (indolent versus aggressive).

prostate cancer. Similarly, the Sentinel™ CS Test utilizes 135 unique sncRNAs: 105 miRNA and 30 snoRNAs for classifying a subject having prostate cancer as having GG1 (indolent) prostate cancer or GG2-GG5 (aggressive) prostate cancer. In addition, 61 sncRNAs (25 miRNAs and 36 snoRNAs) are informative in both Tests. The OpenArray™ platform sequentially interrogates the informative RNA entities present in a single sample of sncRNA extracted from urinary exosomes without compromising sensitivity and specificity of the two tests.

Example 2

Validation of the Sentinel™ PCa, Sentinel™ CS and Sentinel™ HG Tests in a Case Control Patient Cohort The performance characteristics of the Sentinel™ PCa and Sentinel™ CS Tests using the OpenArray™ platform was established in a case control study of 1436 patients (Table 5).

TABLE 5

Demographics and Clinical Characteristics of Case-Control Sample Used to Validate the Sentinel™ PCa and Sentinel™ HG Tests.

|  | NEPC (%) | Cancer (%) | | | | |
|---|---|---|---|---|---|---|
|  |  | GG1 | GG2 | GG3 | GG4 | GG5 |
| Total | 568 (39.5%) | 437 (30.4%) | 162 (11.3%) | 131 (9.1%) | 66 (4.6%) | 72 (5.0%) |
| Age |  |  |  |  |  |  |
| Range | 23-90 | 46-93 | 50-96 | 49-95 | 50-93 | 54-91 |
| Mean ± SD | 65.8 ± 9.0 | 70.3 ± 8.8 | 71.1 ± 8.2 | 74.2 ± 8.7 | 72.4 ± 9.7 | 72.7 ± 9.5 |
| Race |  |  |  |  |  |  |
| NHW | 458 | 233 | 96 | 47 | 26 | 36 |
| NHB | 61 | 20 | 11 | 5 | 9 | 3 |
| not reported | 49 | 184 | 55 | 79 | 31 | 33 |
| PSA |  |  |  |  |  |  |
| Range | N/A | 0.21-108 | 1.24-32.0 | 1.67-138 | 1.93-1400 | 1.98-199 |
| Mean ± SD |  | 6.4 ± 6.2 | 7.4 ± 4.7 | 14.0 ± 19.4 | 57.6 ± 194.0 | 25.9 ± 36.0 |

*Under exempt study status, PSA levels were not available for individual patients with no evidence of cancer, all were less than 3.0 ng/mL.

The performance characteristics of the Sentinel™ PCa Test were determined in case control cohort of 600 men whose demographics are shown in Table 5. The scatter plot of the Sentinel™ PCa Scores is shown in FIGS. 8A-8B, with the corresponding Receiver Operator curve (ROC) curve in FIG. 8C. As summarized in Table 6, the Sentinel™ PCa Test correctly classifies 281/300 patients as having cancer and 275/300 patients as having no cancer (Sensitivity 93.7%, Specificity 91.7%).

The performance characteristics of the Sentinel™ CS Test were determined in a testing cohort of 600 men. The scatter plot of the Sentinel™ CS Scores is shown in FIGS. 9A-9B, with the corresponding Receiver Operator curve (ROC) curve in FIG. 9C. As summarized in Table 6, the Sentinel™ CS Test correctly classifies 143/154 patients as high grade (GG3-GG5) and 132/143 as not high grade (Sensitivity 92.9%, Specificity 90.4%).

The performance characteristics of the Sentinel™ HG Test were determined in a testing cohort of 600 men. The scatter plot of the Sentinel™ HG Scores is shown in FIGS. 10A-10B, with the corresponding Receiver Operator curve (ROC) curve in FIG. 10C. As summarized in Table 6, the Sentinel™ CS Test correctly classifies 94/100 patients as high grade (GG3-GG5) and 191/200 as not high grade (GG1+GG2) (Sensitivity 94%, Specificity 95.5%).

TABLE 6

Empirical Sensitivity, Specificity, PPV and NPV for Sentinel™ PCa, Sentinel™ CS and Sentinel™ HG Tests

| 1-Error Rate | Numerator | Denominator | Proportion | 95% lower CI | 95% upper CI |
|---|---|---|---|---|---|
| Sentinel™ PCa |  |  |  |  |  |
| Sensitivity | 281 | 300 | 0.937 | 0.905 | 0.960 |
| Specificity | 275 | 300 | 0.917 | 0.882 | 0.944 |
| PPV | 281 | 306 | 0.918 | 0.884 | 0.945 |
| NPV | 275 | 294 | 0.935 | 0.903 | 0.959 |
| Sentinel™ CS |  |  |  |  |  |
| Sensitivity | 143 | 154 | 0.929 | 0.880 | 0.962 |
| Specificity | 132 | 146 | 0.904 | 0.848 | 0.944 |
| PPV | 143 | 157 | 0.911 | 0.859 | 0.948 |
| NPV | 132 | 143 | 0.923 | 0.871 | 0.959 |
| Sentinel™ HG |  |  |  |  |  |
| Sensitivity | 94 | 100 | 0.940 | 0.880 | 0.975 |
| Specificity | 191 | 200 | 0.955 | 0.919 | 0.978 |
| PPV | 94 | 103 | 0.913 | 0.846 | 0.956 |
| NPV | 191 | 197 | 0.970 | 0.938 | 0.987 |

*NPV or Negative Predictive Value is the probability that following a negative test result, that individual will not have that specific disease.

$$NPV = \frac{\text{True Negative}}{\text{True Negative} + \text{False Negative}}$$

**Sensitivity of a test is the proportion of people who test positive among all those who actually have the disease.

$$\text{Sensitivity} = \frac{\text{True Positive}}{\text{True Positive} + \text{False Negative}}$$

***The specificity of a test is the proportion of people who test negative among all those who actually have that disease.

$$\text{Sensitivity} = \frac{\text{True Negative}}{\text{True Negative} + \text{False Positive}}$$

****PPV or Positive Predictive Value is the probability that following a positive test result, that individual will truly have the specific disease.

$$PPV = \frac{\text{True Positive}}{\text{True Positive} + \text{False Positive}}$$

Example 3

Safety and Scientific Validity Study to Identify Clinically Insignificant PCa with Sceintific Sentinel™ Platform.

The purpose the clinical study is to validate the performance characteristics of the Scientific Sentinel™ PCa Test and the Scientific Sentinel™ CS Test to (1) identify patients with prostate cancer in men of age 50-80 years with suspicion of prostate cancer for whom needle biopsy is performed, and (2) to distinguish men of ages 50-80 years with clinically significant prostate cancer (Grade 2 or above) from men with clinically insignificant prostate cancer (Grade Group 1). These classifications will be compared to the results of core needle biopsies, and of radical prostatectomy (where available). The sensitivity, specificity, positive and negative predictive values will be established. This study is a prospective, observational and non-interventional study. The informed participants will provide two or more urine samples over the course of the study and consent to share relevant anonymized clinical data with the study team.

Participants between the age of 50 and 80 years with suspicion of prostate cancer for whom a core-needle biopsy is performed, and otherwise meeting the inclusion and exclusion criteria, will be enrolled and will provide urine samples for the Sentinel™ PCa/CS Tests. The study will evaluate the properties of the Sentinel™ PCa Test and the Sentinel™ CS Test that is based on the disclosed method using Classification Algorithms to identify future patients with prostate cancer and to classify prostate cancer as clinically significant or clinically insignificant.

The "gold standard" assessment of cancer will be made from the results of core needle biopsies: participants with no positive cores will be designated "cancer-free"; participants with cancer in one or more cores will be designated as having "Clinically Insignificant" prostate cancer provided all cores with cancer have no greater than Grade Group 1 histopathology; participants will be designated as having "Clinically Significant" prostate cancer if any cores have Grade Groups 2-5.

Each study participant enrolled will be followed for one year. Participants will provide urine samples during each visit, and all relevant clinical data, including re-biopsies, PSA results and pathology report from radical prostatectomy (if administered as part of clinical care) will be obtained. The follow-up results, if available will be used for outcome analysis. For each urine sample provided, the Sentinel™ PCa and CS tests will be determined and compared with the available 1 year follow up outcome data to inform the sensitivity, specificity, positive and negative predictive values of the tests.

The Classification Algorithm employed functions by controlling sensitivity at, or above, a pre-specified level, denoted $1-\alpha$; for example, the value that has been assumed in this design is $\alpha=0.05$, so that sensitivity is at least 95% in the population. Note that the value of $\alpha$ represents the false-negative rate of the test, i.e., the test is (incorrectly) negative for a patient who is truly positive.

To describe how the cutoff the Sentinel™ PCa Score is calculated to control sensitivity, for each participant in the training dataset, the Sentinel™ PCa Score will be calculated using the remaining members of the training dataset and only his small non-coding RNA (sncRNA) sequence; that is, the true disease status of each patient in the training dataset will be blinded, thereby mimicking the setting for classification of a future patient. The cutoff used in the Sentinel™ PCa Test is then calculated so that the empirical sensitivity over patients in the training dataset with prostate cancer corresponds to the value that provides an upper one-sided 95% confidence interval for population sensitivity for a future patient of at least $1-\alpha$.

With this cutoff for the Sentinel™ PCa Score determined from the training dataset a priori, the corresponding values of sensitivity, specificity, positive and negative predictive values will be calculated, along with a corresponding upper 95% confidence interval, on the prospective participants data accrued in this proposed study, with each biopsy result blinded, i.e., using only the participant's sncRNA sequence. Note that these error rates refer to the classification of a future patient with unknown disease status.

Any patent, patent application publication, or scientific publication, cited in this application, is incorporated by reference in its entirety.

The invention claimed is:

1. A method for classifying a male human subject as having prostate cancer or having no prostate cancer, the method comprising:
   (i) obtaining a prostate-derived biological sample from the male human subject;
   (ii) detecting the aggregate expression profiles of a signature collection of cDNAs derived from total small non-coding RNAs (sncRNAs) extracted from the prostate-derived biological sample,
      comprising in a first high throughput microarray, a panel of hybridizing probes specific for each of the cDNA derived from sncRNAs obtained from the prostate-derived biological sample,
      wherein the hybridizing probes detect at least SEQ ID NOs 2, 6, 14, 20, 31, 56, 64, 67, 68, 69, 79, 82, 91, 92, and 161;
   (iii) correlating the aggregate expression profiles comprising at least SEQ ID NOs: 2, 6, 14, 20, 31, 56, 64, 67, 68, 69, 79, 82, 91, 92, and 161 from the prostate-derived biological sample by comparing the aggregate expression profiles of at least SEQ ID NOs: 2, 6, 14, 20, 31, 56, 64, 67, 68, 69, 79, 82, 91, 92, and 161 in a training data set from a target population having no prostate cancer and a training data set from a target population having prostate cancer; and
   (iv) determining with at least 90-95% specificity the likelihood
      that the subject has prostate cancer when the aggregate expression profile comprising at least SEQ ID NOs: 2, 6, 14, 20, 31, 56, 64, 67, 68, 69, 79, 82, 91, 92, and 161 of the prostate-derived biological sample from the subject is statistically greater than or equal to the aggregate expression profile comprising at least SEQ ID NOs: 2, 6, 14, 20, 31, 56, 64, 67, 68, 69, 79, 82, 91, 92, and 161 in the training data set from a target population having prostate cancer, wherein the subject determined to have prostate cancer requires further testing to determine if the subject has indolent/low grade (GG1) or intermediate/high grade prostate cancer (GG2-GG5), or
      that the subject has no prostate cancer when the aggregate expression profile comprising at least SEQ ID NOs: 2, 6, 14, 20, 31, 56, 64, 67, 68, 69, 79, 82, 91, 92, and 161 of the prostate-derived biological sample from the subject is statistically less than or equal to the aggregate expression profile comprising at least SEQ ID NOs: 2, 6, 14, 20, 31, 56, 64, 67, 68, 69, 79, 82, 91, 92, and 161 in the training data set from a target population having no prostate cancer, wherein the subject determined to have no prostate cancer requires monitoring.

2. The method of claim 1, wherein the expression of sncRNAs in the male human subject determined to have prostate cancer is re-analyzed to classify if the male human subject has either indolent (low grade, GG1) or intermediate or high grade, (GG2-GG5) prostate cancer, comprising:
   (i) detecting in a second high throughput microarray a second panel of hybridizing probes the aggregate expression profile of a second signature collection of cDNAs derived from sncRNAs extracted from the prostate-derived biological sample of the male subject identified to be at risk for prostate cancer,
      wherein the second panel of hybridizing probes further includes SEQ ID NOs: 22, 281, 283, 284, 285, 286, 287, 313, 316, 321, 336, 337, 340, 363, and 371;
   (ii) correlating the aggregate expression profiles of at least SEQ ID NOs: 22, 281, 283, 284, 285, 286, 287, 313, 316, 321, 336, 337, 340, 363, and 371 in a training data set from a target population with indolent (low grade, GG1) and a training data set from a target population with intermediate or high grade (GG2-GG5) prostate cancer; and
   (iii) determining with at least 90-95% specificity the likelihood that
      the subject as having indolent (low grade, GG1) when the aggregate expression profile that further includes SEQ ID NOs: 22, 281, 283, 284, 285, 286, 287, 313, 316, 321, 336, 337, 340, 363, and 371 of the prostate-derived biological sample from the subject is statistically lower than or equal to the aggregate expression profile that further includes SEQ ID NOs: 22, 281, 283, 284, 285, 286, 287, 313, 316, 321, 336, 337, 340, 363, and 371 in the training data set from a target population having indolent cancer (low grade, GG1), wherein the subject determined to have indolent (low grade GG1) prostate cancer requires monitoring; or
      the subject as having intermediate or high grade (GG2-GG5) prostate cancer when the aggregate expression profile that further includes SEQ ID NOs: 22, 281, 283, 284, 285, 286, 287, 313, 316, 321, 336, 337, 340, 363, and 371 of the prostate-derived biological sample from the subject is statistically greater than or equal to the aggregate expression profile that further includes SEQ ID NOs: 22, 281, 283, 284, 285, 286, 287, 313, 316, 321, 336, 337, 340, 363, and 371 in the training data set from a target population having intermediate or high grade (GG2-GG5) prostate cancer, wherein the subject determined to have intermediate or high grade (GG2-GG5) prostate cancer requires further testing to determine if the subject has low/intermediate risk (GG1-GG2) or aggressive (high grade, GG3-GG5) prostate cancer.

3. The method of claim 2, wherein the expression of sncRNAs in the subject determined to have intermediate or high grade, (GG2-GG5) prostate cancer is re-analyzed to classify if the male human subject has either low/intermediate grade (GG1-GG2) or aggressive (high grade, GG3-GG5) prostate cancer comprising:
   (i) detecting in a third high throughput microarray a third panel of hybridizing probes the aggregate expression profile of a third signature collection of cDNAs derived from sncRNAs extracted from the prostate-derived biological sample, wherein the third panel of hybridizing probes further includes SEQ ID NOs: 111, 178, 291, 318, 346, 347, 389, 503, 580, 620, 704, 708, 766, 791, and 797;

(ii) correlating the aggregate expression profiles of at least SEQ ID NOs: 111, 178, 291, 318, 346, 347, 389, 503, 580, 620, 704, 708, 766, 791, and 797 in a training set from a target population with low/intermediate risk (GG1-GG2) and a training set from a target population with aggressive (high grade, GG3-GG5) prostate cancer; and (iii) determining with at least 90-95% specificity the likelihood that the subject as having low/intermediate grade (GG1-GG2) prostate cancer when the aggregate expression profile that further includes SEQ ID NOs: 111, 178, 291, 318, 346, 347, 389, 503, 580, 620, 704, 708, 766, 791, and 797 of the prostate-derived biological sample from the subject is statistically less than or equal to the aggregate expression profile that further includes SEQ ID NOs: 111, 178, 291, 318, 346, 347, 389, 503, 580, 620, 704, 708, 766, 791, and 797 in the training data set from a target population having low/intermediate grade (GG1-GG2) prostate cancer, wherein the subject determined to have low/intermediate grade (GG1-GG2) prostate cancer requires monitoring; or the subject as having aggressive (high grade, GG3-GG5) prostate cancer when the aggregate expression profile that further includes SEQ ID NOs: 111, 178, 291, 318, 346, 347, 389, 503, 580, 620, 704, 708, 766, 791, and 797 of the prostate-derived biological sample from the subject is statistically greater than or equal to the aggregate expression profile that further includes SEQ ID NOs: 111, 178, 291, 318, 346, 347, 389, 503, 580, 620, 704, 708, 766, 791, and 797 in the training data set from a target population having aggressive (high grade, GG3-GG5) prostate cancer, wherein the subject determined to have aggressive (high grade, GG3-GG5) prostate cancer requires treatment.

4. The method of claim 3, wherein the subject classified as having aggressive (intermediate or high grade, GG2-GG5) prostate cancer is treated with one or more of radical prostatectomy, brachytherapy of the prostate, radiotherapy of the prostate, neoadjuvant hormone therapy and adjuvant hormone therapy.

5. The method of claim 1, wherein the prostate-derived biological sample comprises sncRNAs extracted from urinary exosomes isolated from the cell free urine.

6. The method of claim 5, wherein the sncRNAs comprises miRNA, C/D box snoRNA, and H/ACA box snoRNA.

7. The method of claim 6, wherein the sncRNA comprises a miRNA and a snoRNA.

8. The method of any of claim 1, 2, or 3, wherein the step of detecting comprises a reverse transcription polymerase chain reaction, a polymerase chain reaction, a nucleic acid hybridization, and a micro-array assay.

* * * * *